US008367629B2

(12) United States Patent
Purschke et al.

(10) Patent No.: US 8,367,629 B2
(45) Date of Patent: Feb. 5, 2013

(54) MCP-1 BINDING NUCLEIC ACIDS AND USE THEREOF

(75) Inventors: Werner Purschke, Berlin (DE); Florian Jarosch, Berlin (DE); Dirk Eulberg, Berlin (DE); Sven Klussmann, Berlin (DE); Klaus Buchner, Berlin (DE); Christian Maasch, Berlin (DE)

(73) Assignee: NOXXON Pharma AG, Berlin (DE)

( * ) Notice: Subject to any disclaimer, the term of this patent is extended or adjusted under 35 U.S.C. 154(b) by 499 days.

(21) Appl. No.: 12/325,180

(22) Filed: Nov. 29, 2008

(65) Prior Publication Data

US 2009/0156542 A1 Jun. 18, 2009

Related U.S. Application Data

(63) Continuation-in-part of application No. 12/279,183, filed as application No. PCT/EP2007/001294 on Feb. 14, 2007, now Pat. No. 8,193,159.

(30) Foreign Application Priority Data

| | | |
|---|---|---|
| Feb. 14, 2006 | (EP) | 06002935 |
| Nov. 22, 2006 | (EP) | 06024202 |
| Nov. 30, 2007 | (EP) | 07023267 |

(51) Int. Cl.

| | |
|---|---|
| ***A61K 31/70*** | (2006.01) |
| ***A61K 48/00*** | (2006.01) |
| ***C07H 21/02*** | (2006.01) |
| ***C07H 21/04*** | (2006.01) |
| *C12Q 1/68* | (2006.01) |

(52) U.S. Cl. .................... 514/44 A; 536/23.1; 536/24.1; 536/24.5; 435/375; 435/377

(58) Field of Classification Search ........................ None
See application file for complete search history.

(56) References Cited

U.S. PATENT DOCUMENTS

| | | | |
|---|---|---|---|
| 6,524,581 | B1 | 2/2003 | Adamis |
| 6,670,321 | B1 | 12/2003 | Adamis |
| 7,629,456 | B2 | 12/2009 | Lange et al. |
| 7,750,140 | B2 | 7/2010 | Helmling et al. |
| 2006/0003326 | A1 | 1/2006 | Lange et al. |
| 2006/0030535 | A1 | 2/2006 | Healy et al. |
| 2006/0257867 | A1 | 11/2006 | Helmling et al. |
| 2009/0156542 | A1 | 6/2009 | Purschke |
| 2010/0284961 | A1 | 11/2010 | Purschke |

FOREIGN PATENT DOCUMENTS

| | | |
|---|---|---|
| EP | 1386972 | 2/2004 |
| WO | 2005108431 | 11/2005 |
| WO | 2007093409 | 8/2007 |

OTHER PUBLICATIONS

Helmling et al., PNAS 101(36)13174-13179, 2004.
Drolet et al., Pharm Res 17(12)1503-1510, 2000.
Eulberg & Klussmann, ChemBioChem 4, 979-983, 2003.
Rhodes et al., FEBS Lett 506:85-90, 2001.
Eulberg et al., Nucl Acids Res 33(4)e45, 2005.
Anders et al., Naunyn-Sch Arch Pharm 375(Supp 1)53, 2007, Abstract 241.
Kulkarni et al., J Pharmacol Exp Ther DOI:10.1124/jpet.108.142711, Nov. 2008.
Kulkarni et al., J Am Soc Nephrol 18(8)2350-2358, 2007.

*Primary Examiner* — Sean McGarry
(74) *Attorney, Agent, or Firm* — MDIP LLC

(57) ABSTRACT

The present invention is related to a nucleic acid molecule capable of binding to MCP-1, whereby the nucleic acid molecule is for use as a medicament for the treatment and/or prevention of a chronic disease or chronic disorder, preferably selected from the group consisting of chronic respiratory disease, chronic kidney disease and systemic lupus erythematosus.

14 Claims, 63 Drawing Sheets

Type 1A

| | | | | | | | | Length (nt) | Pull-down | $IC_{50}$ $Ca^{++}$-Assay [nM] |
|---|---|---|---|---|---|---|---|---|---|---|
| 169-B1trc | AGCGUG | CCCGGA | *GUG* | GCA | GGGGGACGCGACC | **UGCAAUAAUG** | CACGCU | 47 | >> E10trc | 8 |
| 169-F3trc | AGCGUG | CCCGGA | *GUG* | GCA | GGGGGACGCGACC | **UGCAAUUG** | CACGCU | 45 | >> E10trc | 10 |
| 169-C1trc | AGCGUG | CCCGGA | *GUG* | GCA | GGGGGACGCGACC | **UGUAAUAAUG** | CACGCU | 47 | >> E10trc | |
| 169-A3trc | AGCGUG | CCCGGU | *GUG* | GCA | GGGGGACGCGACC | **UGCAAUAAUG** | CGCGCU | 47 | >> E10trc | |
| 169-B2trc | AGCGUG | CCCGGA | *GUA* | GCA | GGGGGGCGCGACC | **UGCAAUAAUG** | CACGCU | 47 | >> E10trc | |
| 176-B12trc | AGCGUG | CCCGGU | *GUG* | GUA | GGGGGGCGCGAUC | **UACAAUUG** | CACGCU | 45 | >> E10trc | |
| 176-D9trc | AGCGUG | CCCGGU | *GUG* | ACA | GGGGGGCGCGACC | **UGCAUUUG** | CACGCU | 45 | >> E10trc | |
| 176-B10trc | AGCGUG | CCCGGU | *GUG* | GCA | GGGGGGCGCGACC | **UGUAUUUG** | CACGCU | 45 | > E10trc | |
| 169-F2trc | AGCGUG | CCCGGA | *GUG* | GCA | GGGGGGCGCGACC | **UGCAAUAAUG** | CACGCU | 47 | > E10trc | 14 |
| 176-B9trc | AGCGUG | CCCGGU | *GUG* | GCA | GGGGGGCGCGACC | **UGCAAUUG** | CACGCU | 45 | > E10trc | |
| 176-H9trc | AGCAUG | CCCGGU | *GUG* | GCA | GGGGGGCGCGACC | **UGCAUUUG** | CAUGCU | 45 | > E10trc | |
| 176-E10trc | AGCGUG | CCCGGU | *GUG* | GUA | GGGGGGCGCGACC | **UACAUUUG** | CACGCU | 45 | 5 nM | 4-5 |
| Boxes | B1A | B2 | *B3* | B4 | B5 | **B6** | B1B | | | |

> E10trc, weaker binding than 176-E10trc as determined in competition assay
>> E10trc, much weaker binding than 176-E10trc as determined in competition assay

Fig. 1

Type 1B

| | | | | | | | | Length (nt) | Pull-down | $IC_{50}$ $Ca^{++}$-Assay [nM] |
|---|---|---|---|---|---|---|---|---|---|---|
| 176-G9trc | AGUGUG | CCAGCU | *GUG* | AUG | GGGGGGCGCGACC | **CAUUUUA** | CACACU | 44 | > C9trc | |
| 176-F9trc | AGUGUG | CCAGC | *GUG* | AUG | GGGGGGCGCGACC | **CAUUUUA** | CACACU | 43 | > C9trc | 6 |
| 176-C11trc | AGUGUG | CGAGC | *GUG* | AUG | GGGGGGCGCGACC | **CAUUUUA** | CAUACU | 43 | > C9trc | |
| 176-E11trc | AGUGUG | CCAGC | *GUG* | AUG | GGGGGGCGCGACC | **CAUUUUA** | CAUACU | 43 | > C9trc | |
| 176-D10trc | AGUAUG | CCAGC | *GUG* | AUG | GGGGGGCGCGACC | **CAUUUA** | CAUACU | 42 | > C9trc | 30 |
| 176-H10trc | AGUGUG | CCAG U | *GUG* | AUG | GGGGGGCGCGACC | **CAUUUUA** | CACACU | 43 | = C9trc | 6 |
| 176-C9trc | AGCGUG | CCAG U | *GUG* | AUG | GGGGGGCGCGACC | **CAUUUUA** | CACGCU | 43 | 5 nM | 4-5 |
| Boxes | B1A | B2 | *B3* | B4 | B5 | **B6** | B1B | | | |

= C9trc, similar binding as 176-C9trc as determined in competition assay
> C9trc, weaker binding than 176-C9trc as determined in competition assay

Fig. 2

Type 2

| | | | | Length (nt) | Pull-down | $IC_{50}$ $Ca^{++}$-Assay | $IC_{50}$ Chemotaxis |
|---|---|---|---|---|---|---|---|
| 180-B1-001 | ACGCA | CGUCCCUCACCGGUGCAAGUGAAGCCGCGGCUC | UGCGU | 43 | > D1-002 | | |
| 180-A4-002 | ACGCA | CCUCCCUCACCGGUGCAAGUGAAGCCGUGGCUC | UGCGC | 43 | > D1-002 | | |
| 180-D1-002 | ACGCA | CGUCCCUCACCGGUGCAAGUGAAGCCGUGGCUC | UGCGU | 43 | 0.7 nM | 5 nM | < 1 nM |
| Boxes | B1A | B2 | B1B | | | | |

Derivatives of 180-D1-002

| | | | | Length (nt) | Pull-down | $IC_{50}$ $Ca^{++}$-Assay | $IC_{50}$ Chemotaxis |
|---|---|---|---|---|---|---|---|
| 180-D1-011 | GCA | CGUCCCUCACCGGUGCAAGUGAAGCCGUGGCUC | UGCGU | 41 | = D1-002 | 5 nM | 1.2 nM |
| 180-D1-012 | ACGCA | CGUCCCUCACCGGUGCAAGUGAAGCCGUGGCUC | UGC | 41 | = D1-002 | 6 nM | 2.6 nM |
| 180-D1-018 | GCA | CGUCCCUCACCGGUGCAAGUGAAGCCGUGGCUC | UGC | 39 | > D1-002 | <10 nM | 2 nM |
| 180-D1-034 | CGCA | CGUCCCUCACCGGUGCAAGUGAAGCCGUGGCUC | UGCGU | 42 | > D1-002 | | |
| 180-D1-035 | CGCA | CGUCCCUCACCGGUGCAAGUGAAGCCGUGGCUC | UGCG | 41 | = D1-002 | | |
| 180-D1-036 | GCA | CGUCCCUCACCGGUGCAAGUGAAGCCGUGGCUC | UGCG | 40 | = D1-002 | 3-4 nM | 0.5 nM |
| Boxes | B1A | B2 | B1B | | | | |

= D1-002, similar binding as 180-D1-002 as determined in competition assay
> D1-002, weaker binding than 180-D1-002 as determined in competition assay

Fig. 3

Type 3

| | | | | | | | | | | length (nt) | Pull-down | $IC_{50}$ Chemotaxis [nM] |
|---|---|---|---|---|---|---|---|---|---|---|---|---|
| 178-A8 | GUGCUGC | GUAGU | *GGAAG* | ACUAC | CUAAUGA | **CAGC** | CGAAU | **GCUG** | GCAGCAC | 49 | > 178-D5 | |
| 178-F7 | GUGCUGC | GUAGU | *GGAAG* | ACUAC | CUAAUGA | **CAGC** | CUAAU | **GCUG** | GCAGCAC | 49 | > 178-D5 | |
| 178-G7 | GUGCUGC | GUAGU | *GGAAG* | ACUAC | CUUAUGA | **CAGC** | CGAAU | **GCUG** | GCAGCAC | 49 | > 178-D5 | |
| 178-C6 | GUGCUGC | GUAGU | *GAAAA* | ACUAC | UGCCAGUG | **GGU** | CAGA | **GCUA** | GCAGCAC | 48 | > 178-D5 | |
| 178-E7 | GUGCUGC | GGAGU | *UAAAA* | ACUCC | CUAAGACA | **GGC** | CAGA | **GCCG** | GCAGCAC | 48 | > 178-D5 | |
| 178-G6 | GUGCUGC | GGAGU | *UGAAA* | ACUCC | CUAAGACA | **GGC** | CAGA | **GCCG** | GCAGCAC | 48 | > 178-D5 | |
| 178-A7 | GUGCUGC | GUAGU | *GGAAG* | ACUAC | CUAUGA | **CAGC** | CUAAU | **GCUG** | GCAGCAC | 48 | > 178-D5 | |
| 178-C7 | GUGCUGC | GGAGU | *UAAAA* | ACUCC | CUAAGACA | **GGC** | UAGA | **GCCG** | GCAGCAC | 48 | > 178-D5 | |
| 178-E5 | GUGCUGC | GGCGU | *GAAAA* | ACGCC | CUGCGA | **CUGC** | CCUUUAU | **GCAG** | GCAGCAC | 48 | 4 | |
| 181-F1 | GUGCUGC | GUAGU | *GAAAA* | ACUAC | CAACGACU | **GGC** | UAGA | **GCCG** | GCAGCAC | 48 | = 178-D5 | |
| 181-B2 | GUGCUGC | GUAGU | *GAAAG* | ACUAC | CUGUGA | **CAGC** | CGAAU | **GCUG** | GCAGCAC | 48 | = 178-D5 | |
| 181-C2 | GUACUGC | GUAGU | *UAAAA* | ACUAC | CAACGACU | **GGC** | UAGA | **GCCG** | GCAGCAC | 48 | = 178-D5 | |
| 178-A6 | GUGCUGC | GUAGU | *UAAAA* | ACUAC | CAACGACU | **GGC** | UAGA | **GCCG** | GCAGCAC | 48 | = 178-D5 | 0.5 |
| 178-D6 | GUGCUGC | GUAGU | *UAAAA* | ACUAC | CAGCGACA | **GGC** | UAGA | **GCCG** | GCAGCAC | 48 | 0.5 nM | |
| 178-D5 | GUGCUGC | GUAGU | *UAAAA* | ACUAC | CAGCGACU | **GGC** | UAGA | **GCCG** | GCAGCAC | 48 | 0.5 nM | 0.5 |
| 181-A2 | GUGCUGC | GUAGU | *GAGAA* | ACUAC | CAACGACU | **GGC** | UAGA | **GCCG** | GCAGCAC | 48 | 0.1 nM | 0.5 |
| Boxes | B1A | B2A | *B3* | B2B | B4 | **B5A** | B6 | **B5B** | B1B | | | |

= 178-D5, similar binding as 178-D5 as determined in competition assay
> 178-D5, weaker binding than 178-D5 as determined in competition assay

Fig. 4

Derivatives of 178-D5 and 181-A2

| | | | | | | | | | | length (nt) | Pull-down | Biacore |
|---|---|---|---|---|---|---|---|---|---|---|---|---|
| 178-D5-020 | GGCUGC | GUAGU | UAAAA | ACUAC | CAGCGACU | GGC | UAGA | GCCG | GCAGCC | 46 | 1.5 nM | |
| 178-D5-027 | GGCGC | GUAGU | UAAAA | ACUAC | CAGCGACU | GGC | UAGA | GCCG | GCGCC | 44 | 27 nM | |
| 178-D5-030 | GUGCGC | GUAGU | UAAAA | ACUAC | CAGCGACU | GGC | UAGA | GCCG | GCGCAC | 46 | = 178-D5 | |
| 181-A2 | GUGCUGC | GUAGU | GAGAA | ACUAC | CAACGACU | GGC | UAGA | GCCG | GCAGCAC | 48 | | 0.37 nM |
| 181-A2-002 | GUGCGC | GUAGU | GAGAA | ACUAC | CAACGACU | GGC | UAGA | GCCG | GCGCAC | 46 | | = 181-A2 |
| 181-A2-004 | GUGCC | GUAGU | GAGAA | ACUAC | CAACGACU | GGC | UAGA | GCCG | GGCAC | 44 | | = 181-A2 |
| 181-A2-005 | GUGGC | GUAGU | GAGAA | ACUAC | CAACGACU | GGC | UAGA | GCCG | GCCAC | 44 | | = 181-A2 |
| 181-A2-006 | GUCGC | GUAGU | GAGAA | ACUAC | CAACGACU | GGC | UAGA | GCCG | GCGAC | 44 | | = 181-A2 |
| 181-A2-007 | UGCGC | GUAGU | GAGAA | ACUAC | CAACGACU | GGC | UAGA | GCCG | GCGCA | 44 | | = 181-A2 |
| 181-A2-008 | UGCGC | GUAGU | GAGAA | ACUAC | CAACGACU | GGC | UAGA | GCCG | GCAGC | 44 | | > 181-A2 |
| 181-A2-011 | GCUGC | GUAGU | GAGAA | ACUAC | CAACGACU | GGC | UAGA | GCCG | GCAGC | 44 | | > 181-A2 |
| 181-A2-012 | GGUGC | GUAGU | GAGAA | ACUAC | CAACGACU | GGC | UAGA | GCCG | GCACC | 44 | | > 181-A2 |
| 181-A2-015 | UGGC | GUAGU | GAGAA | ACUAC | CAACGACU | GGC | UAGA | GCCG | GCCA | 42 | | > 181-A2 |
| 181-A2-016 | GCGC | GUAGU | GAGAA | ACUAC | CAACGACU | GGC | UAGA | GCCG | GCGC | 42 | | > 181-A2 |
| 181-A2-017 | GUGC | GUAGU | GAGAA | ACUAC | CAACGACU | GGC | UAGA | GCCG | GCAC | 42 | | = 181-A2 |
| 181-A2-018 | GGGC | GUAGU | GAGAA | ACUAC | CAACGACU | GGC | UAGA | GCCG | GCCC | 42 | | = 181-A2 |
| 181-A2-019 | GAGC | GUAGU | GAGAA | ACUAC | CAACGACU | GGC | UAGA | GCCG | GCUC | 42 | | = 181-A2 |
| 181-A2-020 | CGGC | GUAGU | GAGAA | ACUAC | CAACGACU | GGC | UAGA | GCCG | GCCG | 42 | | = 181-A2 |
| 181-A2-021 | CCGC | GUAGU | GAGAA | ACUAC | CAACGACU | GGC | UAGA | GCCG | GCGG | 42 | | = 181-A2 |
| 181-A2-022 | CAGC | GUAGU | GAGAA | ACUAC | CAACGACU | GGC | UAGA | GCCG | GCUG | 42 | | > 181-A2 |
| 181-A2-023 | CUGC | GUAGU | GAGAA | ACUAC | CAACGACU | GGC | UAGA | GCCG | GCAG | 42 | | = 181-A2 |
| Boxes | B1A | B2A | B3 | B2B | B4 | B5A | B6 | B5B | B1B | | | |

= 178-D5, similar binding as 178-D5 as determined in competition assay

= 181-A2, similar binding as 181-A2 in Biacore measurement

\> 181-A2, weaker binding than 181-A2 in Biacore measurement

Fig. 5

Type 4

| | | | | length (nt) | Pull-down [nM] | $IC_{50}$ $Ca^{++}$-Assay [nM] | $IC_{50}$ Chemotaxis [nM] |
|---|---|---|---|---|---|---|---|
| 184-B8trc | AGCGUGUU | AGUGAAGUGGGUGGCAGGUAAAG | GACACGCU | 39 | 48 | | |
| 184-C6trc | AGCGUGGU | AGCGGUGUGGGUGGUAGGUAAAG | GCCACGCU | 39 | 56 | | |
| 184-H5trc | AGCGUGAU | AGAAGAGCGGGUGGUAGGUAAAG | GUCAGGCU | 39 | 69 | | |
| 184-A7trc | AGCGUGUU | AGGUAGGGUGGUAGUAAGUAAAG | GACACGCU | 39 | 29 | | |
| 174-D4-004 | CCGCUU | AGGU-GGGUGGUAGUAAGUAAAG | GGGCGG | 34 | 2-4 | 2-5 | 2 |
| 166-A4-002 | GCGCGAG | CAGGU-GGGUGGUAGAAUGUAAAGA | CUCGCGUC | 39 | | 3-5 | |
| 187-A5trc | AGCGUGUU | AGGU-GGGUGGUAGUAAGUAAAG | GACACGCU | 38 | 20 | | |
| 187-A5-001 | CGUGUU | AGGU-GGGUGGUAGUAAGUAAAG | GACACG | 34 | 23 | | |
| 187-A5-002 | GUGUU | AGGU-GGGUGGUAGUAAGUAAAG | GACAC | 32 | 26 | | |
| 187-H5trc | AGCGUGUU | AGGU-GGGUGGUAGUAAGUAAAG | GGCACGCU | 38 | 16 | | |
| 187-H5-002 | CGUGUU | AGGU-GGGUGGUAGUAAGUAAAG | GGCACG | 34 | 15 | | |
| 187-H5-003 | GUGUU | AGGU-GGGUGGUAGUAAGUAAAG | GGCAC | 32 | 17 | | |
| 187-H5-004 | UGUU | AGGU-GGGUGGUAGUAAGUAAAG | GGCA | 30 | 40 | | |
| Boxes | B1A | B2 | B1B | | | | |

Fig. 6

Other sequences

| | | length (nt) | Pull-down | Biacore | $IC_{50}$ $Ca^{++}$-Assay | $IC_{50}$ Chemotaxis |
|---|---|---|---|---|---|---|
| 177-B3 | GGACGAGAGUGACAAAUGAUAUAACCUCCUGACUAACGCUGCGGGCGACAGG | 52 | 12 nM | > 178-D5 | | |
| 177-C1 | GGACCUAUCGCUAAGACAACGCGCAGUCUACGGGACAUUCUCCGCGGACAGG | 52 | > 178-D5 | | | |
| 177-C2 | GGACAAUUGUUACCCCCGAGAGAGACAAAUGAGACAACCUCCUGAAGACAGG | 52 | 9 | > 178-D5 | | |
| 177-E3 | GGACGAAAGUGAGAAAUGAUACAACCUCCUGUUGCUGCGAAUCCGGACAGG | 51 | > 178-D5 | | | |
| 177-D1 | GGACGUAAAAGACGCUACCCGAAAGAAUGUCAGGAGGGUAGACCGACAGG | 50 | > 178-D5 | | | |
| 177-E1 | GGACUAGAAACUACAAUAGCGGCCAGUUGCACCGCGUUAUCAACGACAGG | 50 | > 178-D5 | | | |
| 177-A1 | GGACUAGUCAGCCAGUGUGUAUAUCGGACGCGGGUUUAUUUACUGACAGG | 50 | > 178-D5 | | | |
| 177-G3 | GGACUGUCCGGAGUGUGAAACUCCCCGAGACCGCCAGAAGCGGGGACAGG | 50 | 5 nM | > 178-D5 | | |
| 177-C3 | GGACUUCUAUCCAGGUGGGUGGUAGUAUGUAAAGAGAUAGAAGUGACAGG | 50 | 5 nM | > 178-D5 | | |
| 177-A2 | GGACGAGAGCGAACAAUGAUAUAACCUCCUGACGGAAAGAGAUCGACAGG | 50 | 13 nM | > 178-D5 | | |
| 170-E4trc | CCUGUGCUACACGCAGUAAGAAGUGAACGUUCAGUAUGUGUGCACAGG | 48 | | | 20 nM | |
| 166-D2trc | CGUGAGCCAGGCACCGAGGGCGUUAACUGGCUGAUUGGACACGACACG | 48 | | | + | |
| 174-A2trc | CGUGAACAUGCAAGCUAAGCGGGGCUGUUGGUUGCUUGGCCCGCCACG | 48 | | | + | |
| 174-E2trc | CGUGCAGAGAGAGACCAACCACGUAAAAUCAACCUAAUGGGCCGCACG | 48 | | | + | |
| 183-G3trc | CGUGCAGAGAGAGACCAACCACGUAAAAUCAACCUAAUGGGCCGCACG | 48 | 2-5 nM | | 2-3 nM | + |
| 183-B2trc | CGUGAACAUUCAAGCUAAGCGGGGCUGUUGGUUGCUUGGCCCGCCACG | 48 | 5-10 nM | | 2-6 nM | + |
| 166-B2trc | CGUGCCGAGGCGGCGACCAGCGUUACUUAGAGAGGCUUUGGCACCACG | 48 | 25 nM | | 2-15 nM | |
| 166-G3trc | CGUGAUAACAGCCGUCGGUCAAGAAAACAAAGUUCGGGCGGCGCACG | 47 | | | + | |
| 166-D1trc | CGUGGGUGGCGCACCGAGGGCGAAAAGCCACCAGUAAAGAUAGACCG | 47 | | | + | |
| 183-H2trc | CGUGUGAUCUCCUUUGGGGUGAUUAGCUUAGAGACUUCCCACACG | 45 | 2-5 nM | | 10 nM | + |
| 167-A7trc | GCACCUUCGCCUAAUACACGUGCCGGCUAGCUAAUACUCGUCCGC | 45 | | 180 nM | 150 nM | |
| 167-C7trc | GCACGACUUGGGCGACCAGUGAUACUUAGAGAGCAAGUCGUCGGC | 45 | | 5 nM | + | |
| 167-B5trc | GCGCGCGCUCAGUAAGAAAUUGAAAGUUCAGAAUGUCGUCGCGC | 44 | | | + | |
| 184-D7trc | AGUGUGUGGCAGGCUAAGGAGAUAUUCCGAGACCACGCU | 39 | 800 nM | | | |
| 184-D6trc | AGUGUGUGGCAGACUAUGGAUAGACUCCGAGACCACGCU | 39 | 650 nM | | | |
| 184-E5trc | AGCGUGAGGCGACCAGCGGAUUACUUAGAGAGUCACGCU | 39 | 100 nM | | | |
| 184-G6trc | AGCGUGAAGGGGACCAGCGUUACUUACAGAGUUCACGCU | 39 | 160 nM | | | |
| 184-B7trc | AGCGUGUGAUGUAUGUAGCACCGUAUCAGAGGACACGCU | 39 | 27 nM | | | |
| 184-B6trc | AGCGUGAGGCGACCCGUGUUUCGUAGAGAGUCACGCU | 37 | 60 nM | | | |

+, substance active in assay; no $IC_{50}$ determined

> 178-D5, weaker binding than 178-D5 as determined in competition assay

Fig. 7

Murine-Specific Spiegelmers

188-A3-001 and Derivatives

| | | Length (nt) | Pull-down | $IC_{50}$ $Ca^{++}$-Assay [nM] | $IC_{50}$ Chemotaxis [nM] |
|---|---|---|---|---|---|
| 188-A3-001 | GAGAUGGCGACAUUGGUUGGGCAUGAGGCGAGGCCCUUUGAUGAAUCCGCGGCCAUUC | 58 | < 1 nM | | |
| 188-A3-004 | GAUGGCGACAUUGGUUGGGCAUGAGGCGAGGCCCUUUGAUGAAUCCGCGGCCAUUC | 56 | < 1 nM | | |
| 188-A3-005 | GGCGACAUUGGUUGGGCAUGAGGCGAGGCCCUUUGAUGAAUCCGCGGCCAUUC | 53 | < 1 nM | | |
| 188-A3-006 | GGCGACAUUGGUUGGGCAUGAGGCGAGGCCCUUUGAUGAAUCCGCGGCCAUU | 52 | < 1 nM | 12 | 4 |
| 188-A3-007 = mNOX-E36 | GGCGACAUUGGUUGGGCAUGAGGCGAGGCCCUUUGAUGAAUCCGCGGCCA | 50 | ~0.2 nM | 12 | 7 |

189-G7-001 and Derivatives

| | | Length (nt) | Pull-down | $IC_{50}$ $Ca^{++}$-Assay [nM] | $IC_{50}$ Chemotaxis [nM] |
|---|---|---|---|---|---|
| 189-G7-001 | GCUGGUUACCGAGGGGGCGUCGUUGGAGUUUGGUUGGUUGUCACCAGC | 48 | < 1 nM | 20-30 | |
| 189-G7-002 | CUGGUUACCGAGGGGGCGUCGUUGGAGUUUGGUUGGUUGUCACCAG | 46 | < 1 nM | 40-50 | 6.5 |
| 189-G7-003 | UGGUUACCGAGGGGGCGUCGUUGGAGUUUGGUUGGUUGUCACCA | 44 | < 1 nM | | |
| 189-G7-007 | GCCGGUUACCGAGGGGGCGUCGUUGGAGUUUGGUUGGUUGUCACCGGC | 48 | | 20 | |
| 189-G7-008 | GCCGGCUACCGAGGGGGCGUCGUUGGAGUUUGGUUGGUUGUCGCCGGC | 48 | ~ 1 nM | 12 | 5 |
| 189-G7-010 | GCGCGUACCGAGGGGGCGUCGUUGGAGUUUGGUUGGUUGUCCGCGC | 46 | | 40 | |
| 189-G7-012 | GGGCCUACCGAGGGGGCGUCGUUGGAGUUUGGUUGGUUGUCGGCCC | 46 | | > 50 | |

Fig. 8 full circles, KD at 37°C 890 ± 65 pM
hollow circles, KD at room temperature, 146 ± 13 pM Kinetics of SpiegelmerNOX-E36 binding to human MCP-1

Fig. 18 Spiegelmer NOX-E36 binding to human MCP- family proteins and eotaxin

Spiegelmer NOX-E36 binding to MCP-1 from different species

Kinetics of Spiegelmer 181-A2-018 binding human MCP-1

Spiegelmer 181-A2-018 binding to human MCP- family proteins and eotaxin

Spiegelmer 181-A2-018 binding to MCP-1 from different species

1 QPDAINAPVTCCYNFTNRKISVQRLASYRRITSSKCPKEAVIFKTIVAKEICADPKQKWVQDSMDHLDKQTQTPKT
2 QPDAINAPVTCCYNFTNRKISVQRLASYRRITSSKCPKEAVIFKTIVAKEICADPKQKWVQDSMDHLDKQIQTPKP
3 QPDAINSPVTCCYTLTSKKISMQRLMSYRRVTSSKCPKEAVIFKTIAGKEICAEPKQKWVQDSISHLDKKNQTPKP
4 QPDAINSPVTCCYTFTGKKISSQRLGSYKRVTSSKCPKEAVIFKTILAKEICADPEQKWVQDAVKQLDKKAQTPKP
5 QPDAIISPVTCCYTLTNKKISIQRLASYKRVTSSKCPKEAVIFKTVLNKEICADPKQKWVQDSMAHLDKKSQTQTA
6 QPDAVNSPVTCCYTFTNKTISVKRLMSYRRINSTKCPKEAVIFMTKLAKGICADPKQKWVQDAIANLDKKMQTPKT
7 QPDAINSQVACCYTFNSKKISMQRLMNYRRVTSSKCPKEAVIFKTILGKELCADPKQKWVQDSINYLNKKNQTPKP
8 QPVGINTSTTCCYRFINKKIPKQRLESYRRTTSSHCPREAVIFKTKLDKEICADPTQKWVQDFMKHLDKKTQTPKL
9 GP--ASVPTTCCFNLANRKIPLQRLESYRRITSGKCPQKAVIFKTKLAKDICADPKKKWVQDSMKYLDQKSPTPKP
10 QPDSVSIPITCCFNVINRKIPIQRLESYTRITNIQCPKEAVIFKTKRGKEVCADPKERWVRDSMKHLDQIFQNLKP
11 QPDAVNAPLTCCYSFTSKMIPMSRLESYKRITSSRCPKEAVVFVTKLKREVCADPKKEWVQTYIKNLDRNQMRSEP
12 QPDAVNAPLTCCYSFTGKMIPMSRLENYKRITSSRCPKEAVVFVTKLKREICADPNKEWVQKYIRKLDQNQVRSET

| | **Protein** | **% identity with human MCP-1** |
|---|---|---|
| 1 | *Homo sapiens* MCP-1 | 100% |
| 2 | *Macaca mulatta* (Rhesus monkey) MCP-1 | 97% |
| 3 | *Sus scrofa* (Pig) MCP-1 | 79% |
| 4 | *Equus caballus* (Horse) | 78% |
| 5 | *Canis familiaris* (Dog) MCP-1 | 76% |
| 6 | *Oryctolagus cuniculus* (Rabbit) MCP-1 | 75% |
| 7 | *Bos Taurus* (Bovine) | 72% |
| 8 | *Homo sapiens* MCP-3 | 71% |
| 9 | *Homo sapiens* Eotaxin | 64% |
| 10 | *Homo sapiens* MCP-2 | 62% |
| 11 | *Mus musculus* (Mouse) MCP-1 | 55% |
| 12 | *Rattus norvegicus* (Rat) MCP-1 | 55% |

Fig. 23

Specificity of NOX-E36 and 181-A2-018

| | NOX-E-036 $K_D$ [nM] | 181-A2-018 $K_D$ [nM] |
|---|---|---|
| hMCP-1 | 0.89 | 0.37-0.6 |
| hMCP-2 | 5-10 | 10 |
| hMCP-3 | - | 10 |
| eotaxin | 5-10 | 10-20 |
| monkey MCP-1 | 0.90 | 0.6 |
| porcine MCP-1 | 0.82 | > 1000 |
| canine MCP-1 | 1.2 | > 1000 |
| rabbit MCP-1 | - | > 1000 |
| rat MCP-1 | - | - |
| mouse MCP-1 | - | - |

-, not binding

Fig. 24A

| Chemokine/synonym | binding |
|---|---|
| CCL1/I-309 | - |
| CCL2/MCP-1 | + |
| CCL3/MIP-1α | + |
| CCL4/MIP-1β | - |
| CCL5/RANTES | -* |
| CCL7/MCP-3 | - |
| CCL8/MCP-2 | + |
| CCL11/eotaxin | + |
| CCL13/MCP-4 | (+) |
| CCL14/HCC-1 | - |
| CXCL1/GROα | - |
| CXCL2/GROβ | - |
| CXCL3/GROγ | - |
| CXCL4/PF4 | -** |
| CXCL5/ENA-78 | - |
| CXCL6/GCP-2 | -** |
| CXCL7/NAP-2 | + |
| CXCL8/IL-8 | - |
| CXCL9/MIG | -* |
| CXCL10/IP-10 | - |
| CXCL11/I-TAC | -** |
| CXCL12α/SDF-1α | - |
| CXCL12β/SDF-1β | - |
| $CX_3CL1$/Fractalkine | - |
| XCL1/Lymphotactin | - |

Binding was classified as follows:

+, specific binding < 10 nM;

(+), NOX-E36 specific binding > 1 μM;

-, no interaction measurable;

-*, unspecific polyanion (PoC or dextran matrix) binding > 250 nM;

-**, unspecific polyanion (PoC or dextran matrix) binding > 10 μM.

Fig. 24 B

| | Association rate constant $k_a$ [$M^{-1}s^{-1}$] | Dissociation rate constant $k_d$ [$s^{-1}$] | Dissociation constant $K_D$ [nM] |
|---|---|---|---|
| CCL2/MCP-1 | $1.8 \pm 0.4 \times 10^5$ | $1.9 \pm 0.1 \times 10^{-4}$ | $1.1 \pm 0.2$ |
| CCL3/MIP-1α | $1.6 \pm 0.3 \times 10^5$ | $6.4 \pm 1.1 \times 10^{-4}$ | $4.1 \pm 1.3$ |
| CCL7/MCP-3 | — | — | — |
| CCL8/MCP-2 | $2.0 \pm 0.7 \times 10^5$ | $6.7 \pm 2.0 \times 10^{-4}$ | $4.2 \pm 2.5$ |
| CCL11/Eotaxin | $1.6 \pm 0.4 \times 10^5$ | $1.1 \pm 0.6 \times 10^{-3}$ | $7.7 \pm 5.2$ |
| CCL13/MCP-4 | — | — | > 1,000 |
| CXCL7/NAP-2 | $1.8 \pm 0.5 \times 10^5$ | $4.1 \pm 0.4 \times 10^{-4}$ | $2.5 \pm 0.9$ |

Fig. 24 C

Kinetics of D-mNOX-E36 binding to murine D-MCP-1

D-mNOX-E36 binding to murine and human D-MCP-1

| | Vehicle | PoC | mNOX-E36 | PoC-PEG | mNOX-E36-3'PEG |
|---|---|---|---|---|---|
| **Renal disease** | | | | | |
| **GFR** [µl/min] | 179 ± 41 | 200 ± 49 | 245 ± 69 | 157 ± 74 | 293 ± 72 |
| **U albumin/creatinin ratio** | 15.6 ± 10.1 | 4.3 ± 1.4 | 6.8 ± 1.8 | 3.8 ± 0.5 | 2.4 ± 0.7 |
| **$IgG_1$** [glom. score] | 1.5 ± 0.4 | 1.6 ± 0.2 | 1.6 ± 0.5 | 1.7 ± 0.2 | 1.7 ± 0.5 |
| **$IgG_{2a}$** [glom. score] | 0.9 ± 0.3 | 1.0 ± 0.3 | 1.0 ± 0.3 | 1.1 ± 0.3 | 1.0 ± 0.3 |
| **Activity index** [score] | 17.4 ± 4.9 | 17.8 ± 4.2 | 10.3 ± 5.0* | 17.4 ± 2.7 | 9.4 ± 4.2* |
| **Chronicity index** [score] | 6.0 ± 2.0 | 7.2 ± 2.6 | 2.6 ± 2.5 | 5.4 ± 1.0 | 1.6 ± 1.8* |
| **Mac-2+** [cells/glom] | 13.4 ± 2.0 | 12.6 ± 0.9 | 8.5 ± 2.3* | 13.6 ± 2.3 | 8.2 ± 3.5* |
| **Mac-2+** [cells/hpf] | 20.3 ± 8.1 | 20.6 ± 6.7 | 10.8 ± 5.1 | 19.3 ± 3.7 | 7.7 ± 4.0* |
| **CD3+** [cells/hpf] | 44.6±14.7 | 39.4 ± 7.5 | 23.8±10.2 | 36.2 ± 3.1 | 19.0 ± 8.0* |
| **Lung injury** [score] | 1.6 ± 0.8 | 1.6 ± 0.4 | 0.6 ± 0.5* | 1.4 ± 0.4 | 0.4 ± 0.5* |
| **Skin lesions** [% of mice] | 60 | 60 | 28 | 80 | 28 |

U albumin/creatinin ratio = urinary albumin/creatinine ratio in µg/mg, values are means ± SEM; * $p < 0.05$ Spiegelmer vs. respective PoC control.

Fig. 35

| | Vehicle | PoC | mNOX-E36 | PoC-PEG | mNOX-E36-3'PEG |
|---|---|---|---|---|---|
| **Lymphoproliferation** | | | | | |
| **Spleen weight** [% BW] | 1.8 ± 0.4 | 2.0 ± 0.2 | 1.6 ± 0.4 | 1.7 ± 0.1 | 1.6 ± 0.3 |
| **LN weight** [% BW] | 2.3 ± 0.7 | 1.8 ± 0.1 | 1.7 ± 0.3 | 1.7 ± 0.2 | 1.7 ± 0.7 |
| **Serum anti dsDNA** | | | | | |
| **$IgG_1$** [µg/ml] | 11.7 ± 3.6 | 7.5 ± 2.8 | 11.7 ± 3.4 | 8.2 ± 1.2 | 6.6 ± 1.2 |
| **$IgG_{2a}$** [µg/ml] | 2.0 ± 0.3 | 1.9 ± 0.3 | 2.1 ± 0.1 | 2.0 ± 0.2 | 1.9 ± 0.2 |
| **$IgG_{2b}$** [µg/ml] | 17.6 ± 5.6 | 18.9 ± 5.2 | 22.6 ± 3.3 | 28.3 ± 2.5 | 20.6 ± 3.8 |

LN = bulk of mesenterial lymph nodes, values are means ± SEM

Fig. 41

| | | 2K | | 1K | | |
|---|---|---|---|---|---|---|
| | | Wildtype nil | db/db nil | db/db nil | db/db PoC-PEG | db/db mNOX-E36-3'PEG |
| **Cellular response** [cells/glomerulus or hpf] | | | | | | |
| Glomerular | Mac-2+ cells | 0.3 ± 0.1 | 1.8 ± 0.2 | 5.0 ± 0.7* | 5.9 ± 0.4 | 3.5 ± 0.3# |
| | Ki-67+ cells | 0.7 ± 0.1 | 0.9 ± 0.2 | 2.4 ± 0.2* | 3.1 ± 0.3 | 1.1 ± 0.2# |
| Interstitial | Mac-2+ cells | 3.2 ± 0.3 | 8.6 ± 1.0 | 19.2 ± 2.8* | 23.8 ± 3.3 | 12.3 ± 1.2# |

Values are means ± SEM; *, $p < 0.05$ 1K db/db vs 2K db/db; #, $p < 0.05$ mNOX-E36-3'PEG vs. PoC-PEG

Fig. 45

SEQUENCE LISTING

<160> NUMBER OF SEQ ID NOS: 296

<210> SEQ ID NO 1
<211> LENGTH: 76
<212> TYPE: PRT
<213> ORGANISM: Homo sapiens

<400> SEQUENCE: 1

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

```
Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75


<210> SEQ ID NO 2
<211> LENGTH: 125
<212> TYPE: PRT
<213> ORGANISM: Mus musculus

<400> SEQUENCE: 2

Gln Pro Asp Ala Val Asn Ala Pro Leu Thr Cys Cys Tyr Ser Phe Thr
1               5                   10                  15

Ser Lys Met Ile Pro Met Ser Arg Leu Glu Ser Tyr Lys Arg Ile Thr
            20                  25                  30

Ser Ser Arg Cys Pro Lys Glu Ala Val Val Phe Val Thr Lys Leu Lys
        35                  40                  45

Arg Glu Val Cys Ala Asp Pro Lys Lys Glu Trp Val Gln Thr Tyr Ile
    50                  55                  60

Lys Asn Leu Asp Arg Asn Gln Met Arg Ser Glu Pro Thr Thr Leu Phe
65                  70                  75                  80

Lys Thr Ala Ser Ala Leu Arg Ser Ser Ala Pro Leu Asn Val Lys Leu
                85                  90                  95

Thr Arg Lys Ser Glu Ala Asn Ala Ser Thr Thr Phe Ser Thr Thr Thr
            100                 105                 110

Ser Ser Thr Ser Val Gly Val Thr Ser Val Thr Val Asn
        115                 120                 125


<210> SEQ ID NO 3
<211> LENGTH: 76
<212> TYPE: PRT
<213> ORGANISM: Maca mulatta

<400> SEQUENCE: 3

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Ile Gln Thr Pro Lys Pro
65                  70                  75


<210> SEQ ID NO 4
<211> LENGTH: 76
<212> TYPE: PRT
<213> ORGANISM: Sus scrofa

<400> SEQUENCE: 4

Gln Pro Asp Ala Ile Asn Ser Pro Val Thr Cys Cys Tyr Thr Leu Thr
1               5                   10                  15

Ser Lys Lys Ile Ser Met Gln Arg Leu Met Ser Tyr Arg Arg Val Thr
            20                  25                  30

Ser Ser Lys Cys Pro Lys Glu Ala Val Ile Phe Lys Thr Ile Ala Gly
        35                  40                  45

Lys Glu Ile Cys Ala Glu Pro Lys Gln Lys Trp Val Gln Asp Ser Ile
    50                  55                  60
```

```
Ser His Leu Asp Lys Lys Asn Gln Thr Pro Lys Pro
65                  70                  75


<210> SEQ ID NO 5
<211> LENGTH: 76
<212> TYPE: PRT
<213> ORGANISM: Canis familiaris

<400> SEQUENCE: 5

Gln Pro Asp Ala Ile Ile Ser Pro Val Thr Cys Cys Tyr Thr Leu Thr
1               5                   10                  15

Asn Lys Lys Ile Ser Ile Gln Arg Leu Ala Ser Tyr Lys Arg Val Thr
            20                  25                  30

Ser Ser Lys Cys Pro Lys Glu Ala Val Ile Phe Lys Thr Val Leu Asn
        35                  40                  45

Lys Glu Ile Cys Ala Asp Pro Lys Gln Lys Trp Val Gln Asp Ser Met
    50                  55                  60

Ala His Leu Asp Lys Lys Ser Gln Thr Gln Thr Ala
65                  70                  75


<210> SEQ ID NO 6
<211> LENGTH: 102
<212> TYPE: PRT
<213> ORGANISM: Oryctolagus cuniculus

<400> SEQUENCE: 6

Gln Pro Asp Ala Val Asn Ser Pro Val Thr Cys Cys Tyr Thr Phe Thr
1               5                   10                  15

Asn Lys Thr Ile Ser Val Lys Arg Leu Met Ser Tyr Arg Arg Ile Asn
            20                  25                  30

Ser Thr Lys Cys Pro Lys Glu Ala Val Ile Phe Met Thr Lys Leu Ala
        35                  40                  45

Lys Gly Ile Cys Ala Asp Pro Lys Gln Lys Trp Val Gln Asp Ala Ile
    50                  55                  60

Ala Asn Leu Asp Lys Lys Met Gln Thr Pro Lys Thr Leu Thr Ser Tyr
65                  70                  75                  80

Ser Thr Thr Gln Glu His Thr Thr Asn Leu Ser Ser Thr Arg Thr Pro
                85                  90                  95

Ser Thr Thr Thr Ser Leu
            100


<210> SEQ ID NO 7
<211> LENGTH: 76
<212> TYPE: PRT
<213> ORGANISM: Homo sapiens

<400> SEQUENCE: 7

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75
```

<210> SEQ ID NO 8
<211> LENGTH: 74
<212> TYPE: PRT
<213> ORGANISM: Homo sapiens

<400> SEQUENCE: 8

```
Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
        35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Lys Pro
65                  70
```

<210> SEQ ID NO 9
<211> LENGTH: 76
<212> TYPE: PRT
<213> ORGANISM: Homo sapiens

<400> SEQUENCE: 9

```
Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75
```

<210> SEQ ID NO 10
<211> LENGTH: 47
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 10
agcgugcccg gaguggcagg gggacgcgac cugcaauaau gcacgcu 47

<210> SEQ ID NO 11
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 11
agcgugcccg gaguggcagg gggacgcgac cugcaauugc acgcu 45

<210> SEQ ID NO 12
<211> LENGTH: 47
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 12
agcgugcccg gaguggcagg gggacgcgac cuguaauaau gcacgcu 47

<210> SEQ ID NO 13
<211> LENGTH: 47
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 13
agcgugcccg guguggcagg gggacgcgac cugcaauaau gcgcgcu 47

<210> SEQ ID NO 14
<211> LENGTH: 47
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 14
agcgugcccg gaguagcagg ggggcgcgac cugcaauaau gcacgcu 47

<210> SEQ ID NO 15
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 15
agcgugcccg gugugguagg ggggcgcgau cuacaauugc acgcu 45

<210> SEQ ID NO 16
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 16
agcgugcccg gugugacagg ggggcgcgac cugcauuugc acgcu 45

<210> SEQ ID NO 17
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA -continued

<400> SEQUENCE: 17
agcgugcccg guguggcagg ggggcgcgac cuguauuugc acgcu 45

<210> SEQ ID NO 18
<211> LENGTH: 47
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 18
agcgugcccg gaguggcagg ggggcgcgac cugcaauaau gcacgcu 47

<210> SEQ ID NO 19
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 19
agcgugcccg guguggcagg ggggcgcgac cugcaauugc acgcu 45

<210> SEQ ID NO 20
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 20
agcaugcccg guguggcagg ggggcgcgac cugcauuugc augcu 45

<210> SEQ ID NO 21
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 21
agcgugcccg gugugguagg ggggcgcgac cuacauuugc acgcu 45

<210> SEQ ID NO 22
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 22
agugugccag cugugauggg ggggcgcgac ccauuuuaca cacu 44

<210> SEQ ID NO 23
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 23
agugugccag cgugaugggg gggcgcgacc cauuuuacac acu 43

<210> SEQ ID NO 24
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 24
agugugcgag cgugaugggg gggcgcgacc cauuuuacau acu 43

<210> SEQ ID NO 25
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 25
agugugccag cgugaugggg gggcgcgacc cauuuuacau acu 43

<210> SEQ ID NO 26
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 26
aguaugccag cgugaugggg gggcgcgacc cauuuacaua cu 42

<210> SEQ ID NO 27
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 27
agugugccag ugugaugggg gggcgcgacc cauuuuacac acu 43

<210> SEQ ID NO 28
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 28
agcgugccag ugugaugggg gggcgcgacc cauuuuacac gcu 43

<210> SEQ ID NO 29
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 29
acgcacgucc cucaccggug caagugaagc cgcggcucug cgu 43

<210> SEQ ID NO 30
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 30
acgcaccucc cucaccggug caagugaagc cguggcucug cgc 43

<210> SEQ ID NO 31
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 31
acgcacgucc cucaccggug caagugaagc cguggcucug cgu 43

<210> SEQ ID NO 32
<211> LENGTH: 41
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 32
gcacgucccu caccggugca agugaagccg uggcucugcg u 41

<210> SEQ ID NO 33
<211> LENGTH: 41
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

```
<400> SEQUENCE: 33

acgcacgucc cucaccggug caagugaagc cguggcucug c                41

<210> SEQ ID NO 34
<211> LENGTH: 39
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 34

gcacgucccu caccggugca agugaagccg uggcucugc                  39

<210> SEQ ID NO 35
<211> LENGTH: 42
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 35

cgcacguccc ucaccggugc aagugaagcc guggcucugc gu              42

<210> SEQ ID NO 36
<211> LENGTH: 41
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 36

cgcacguccc ucaccggugc aagugaagcc guggcucugc g               41

<210> SEQ ID NO 37
<211> LENGTH: 40
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 37

gcacgucccu caccggugca agugaagccg uggcucugcg                 40

<210> SEQ ID NO 38
<211> LENGTH: 49
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 38

gugcugcgua guggaagacu accuaaugac agccgaaugc uggcagcac       49
```

<210> SEQ ID NO 39
<211> LENGTH: 49
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 39
gugcugcgua guggaagacu accuaaugac agccuaaugc uggcagcac 49

<210> SEQ ID NO 40
<211> LENGTH: 49
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 40
gugcugcgua guggaagacu accuuaugac agccgaaugc uggcagcac 49

<210> SEQ ID NO 41
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 41
gugcugcgua gugaaaaacu acugccagug ggucagagcu agcagcac 48

<210> SEQ ID NO 42
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 42
gugcugcgga guuaaaaacu cccuaagaca ggccagagcc ggcagcac 48

<210> SEQ ID NO 43
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 43
gugcugcgga guugaaaacu cccuaagaca ggccagagcc ggcagcac 48

<210> SEQ ID NO 44
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 44
gugcugcgua guggaagacu accuaugaca gccuaaugcu ggcagcac 48

<210> SEQ ID NO 45
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 45
gugcugcgga guuaaaaacu cccuaagaca ggcuagagcc ggcagcac 48

<210> SEQ ID NO 46
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 46
gugcugcggc gugaaaaacg cccugcgacu gcccuuuaug caggcagcac 50

<210> SEQ ID NO 47
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 47
gugcugcgua gugaaaaacu accaacgacu ggcuagagcc ggcagcac 48

<210> SEQ ID NO 48
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 48
gugcugcgua gugaaagacu accugugaca gccgaaugcu ggcagcac 48

<210> SEQ ID NO 49
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 49
guacugcgua guuaaaaacu accaacgacu ggcuagagcc ggcagcac 48

<210> SEQ ID NO 50
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 50
gugcugcgua guuaaaaacu accaacgacu ggcuagagcc ggcagcac 48

<210> SEQ ID NO 51
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 51
gugcugcgua guuaaaaacu accagcgaca ggcuagagcc ggcagcac 48

<210> SEQ ID NO 52
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 52
gugcugcgua guuaaaaacu accagcgacu ggcuagagcc ggcagcac 48

<210> SEQ ID NO 53
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 53
gugcugcgua gugagaaacu accaacgacu ggcuagagcc ggcagcac 48

<210> SEQ ID NO 54
<211> LENGTH: 46
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 54
ggcugcguag uuaaaaacua ccagcgacug gcuagagccg gcagcc 46

<210> SEQ ID NO 55
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 55
ggcgcguagu uaaaaacuac cagcgacugg cuagagccgg cgcc 44

<210> SEQ ID NO 56
<211> LENGTH: 46
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 56
gugcgcguag uuaaaaacua ccagcgacug gcuagagccg gcgcac 46

<210> SEQ ID NO 57
<211> LENGTH: 46
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 57
gugcgcguag ugagaaacua ccaacgacug gcuagagccg gcgcac 46

<210> SEQ ID NO 58
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 58
gugccguagu gagaaacuac caacgacugg cuagagccgg gcac 44

<210> SEQ ID NO 59
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 59
guggcguagu gagaaacuac caacgacugg cuagagccgg ccac 44

<210> SEQ ID NO 60
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 60
gucgcguagu gagaaacuac caacgacugg cuagagccgg cgac 44

<210> SEQ ID NO 61
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 61
ugcgcguagu gagaaacuac caacgacugg cuagagccgg cgca 44

<210> SEQ ID NO 62
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 62
gcugcguagu gagaaacuac caacgacugg cuagagccgg cagc 44

<210> SEQ ID NO 63
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 63
gcugcguagu gagaaacuac caacgacugg cuagagccgg cagc 44

<210> SEQ ID NO 64
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 64
ggugcguagu gagaaacuac caacgacugg cuagagccgg cacc 44

<210> SEQ ID NO 65
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA -continued

<400> SEQUENCE: 65
uggcguagug agaaacuacc aacgacuggc uagagccggc ca 42

<210> SEQ ID NO 66
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 66
gcgcguagug agaaacuacc aacgacuggc uagagccggc gc 42

<210> SEQ ID NO 67
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 67
gugcguagug agaaacuacc aacgacuggc uagagccggc ac 42

<210> SEQ ID NO 68
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 68
gggcguagug agaaacuacc aacgacuggc uagagccggc cc 42

<210> SEQ ID NO 69
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 69
gagcguagug agaaacuacc aacgacuggc uagagccggc uc 42

<210> SEQ ID NO 70
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 70
cggcguagug agaaacuacc aacgacuggc uagagccggc cg 42

<210> SEQ ID NO 71
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 71
ccgcguagug agaaacuacc aacgacuggc uagagccggc gg 42

<210> SEQ ID NO 72
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 72
cagcguagug agaaacuacc aacgacuggc uagagccggc ug 42

<210> SEQ ID NO 73
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 73
cugcguagug agaaacuacc aacgacuggc uagagccggc ag 42

<210> SEQ ID NO 74
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 74
agcguguuag ugaagugggu ggcagguaaa ggacacgcu 39

<210> SEQ ID NO 75
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 75
agcgugguag cggugugggu gguagguaaa ggccacgcu 39

<210> SEQ ID NO 76
<211> LENGTH: 39
<212> TYPE: RNA
<213> ORGANISM: Artificial Sequence -continued
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 76
agcgugauag aagagcgggu gguagguaaa ggucaggcu 39

<210> SEQ ID NO 77
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 77
agcguguuag guaggguggu aguaaguaaa ggacacgcu 39

<210> SEQ ID NO 78
<211> LENGTH: 38
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 78
agcguguuag gugggguggua guaaguaaag gacacgcu 38

<210> SEQ ID NO 79
<211> LENGTH: 38
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 79
agcguguuag gugggguggua guaaguaaag ggcacgcu 38

<210> SEQ ID NO 80
<211> LENGTH: 34
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 80
ccgcuuaggu gggugguagu aaguaaaggg gcgg 34

<210> SEQ ID NO 81
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA -continued

<400> SEQUENCE: 81
gcgcgagcag guggguggua gaauguaaag acucgcguc 39

<210> SEQ ID NO 82
<211> LENGTH: 34
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 82
cguguuaggu gggugguagu aaguaaagga cacg 34

<210> SEQ ID NO 83
<211> LENGTH: 32
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 83
guguuaggug ggugguagua aguaaaggac ac 32

<210> SEQ ID NO 84
<211> LENGTH: 34
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 84
cguguuaggu gggugguagu aaguaaaggg cacg 34

<210> SEQ ID NO 85
<211> LENGTH: 32
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 85
guguuaggug ggugguagua aguaaagggc ac 32

<210> SEQ ID NO 86
<211> LENGTH: 30
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 86
uguuaggugg gugguaguaa guaaagggca 30

-continued

<210> SEQ ID NO 87
<211> LENGTH: 52
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 87
ggacgagagu gacaaaugau auaaccuccu gacuaacgcu gcgggcgaca gg 52

<210> SEQ ID NO 88
<211> LENGTH: 52
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 88
ggaccuaucg cuaagacaac gcgcagucua cgggacauuc uccgcggaca gg 52

<210> SEQ ID NO 89
<211> LENGTH: 52
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 89
ggacaauugu uacccccgag agagacaaau gagacaaccu ccugaagaca gg 52

<210> SEQ ID NO 90
<211> LENGTH: 51
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 90
ggacgaaagu gagaaaugau acaaccuccu guugcugcga auccggacag g 51

<210> SEQ ID NO 91
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 91
ggacguaaaa gacgcuaccc gaaagaaugu caggagggua gaccgacagg 50

<210> SEQ ID NO 92
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 92
ggacuagaaa cuacaauagc ggccaguugc accgcguuau caacgacagg 50

<210> SEQ ID NO 93
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 93
ggacuaguca gccagugugu auaucggacg cggguuuauu uacugacagg 50

<210> SEQ ID NO 94
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 94
ggacuguccg gagugugaaa cuccccgaga ccgccagaag cggggacagg 50

<210> SEQ ID NO 95
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 95
ggacuucuau ccaggugggu gguaguaugu aaagagauag aagugacagg 50

<210> SEQ ID NO 96
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 96
ggacgagagc gaacaaugau auaaccuccu gacggaaaga gaucgacagg 50

<210> SEQ ID NO 97
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 97
ccugugcuac acgcaguaag aagugaacgu ucaguaugug ugcacagg 48

<210> SEQ ID NO 98
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 98
cgugagccag gcaccgaggg cguuaacugg cugauuggac acgacacg 48

<210> SEQ ID NO 99
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 99
cgugaacaug caagcuaagc ggggcuguug guugcuuggc ccgccacg 48

<210> SEQ ID NO 100
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 100
cgugcagaga gagaccaacc acguaaaauc aaccuaaugg gccgcacg 48

<210> SEQ ID NO 101
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 101
cgugcagaga gagaccaacc acguaaaauc aaccuaaugg gccgcacg 48

<210> SEQ ID NO 102
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 102
cgugaacauu caagcuaagc ggggcuguug guugcuuggc ccgccacg 48

```
<210> SEQ ID NO 103
<211> LENGTH: 48
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 103

cgugccgagg cggcgaccag cguuacuuag agaggcuuug gcaccacg                    48

<210> SEQ ID NO 104
<211> LENGTH: 47
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 104

cgugauaaca gccgucgguc aagaaaacaa aguucgggcg gcgcacg                     47

<210> SEQ ID NO 105
<211> LENGTH: 47
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 105

cguggguggc gcaccgaggg cgaaaagcca ccaguaaaga uagaccg                     47

<210> SEQ ID NO 106
<211> LENGTH: 45
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 106

cgugugaucu ccuuuggggu gauuagcuua gagacuuccc acacg                       45

<210> SEQ ID NO 107
<211> LENGTH: 45
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 107

gcaccuucgc cuaauacacg ugccggcuag cuaauacucg uccgc                       45

<210> SEQ ID NO 108
<211> LENGTH: 45
<212> TYPE: RNA
<213> ORGANISM: Artificial Sequence
```

```
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 108

gcacgacuug ggcgaccagu gauacuuaga gagcaagucg ucggc            45

<210> SEQ ID NO 109
<211> LENGTH: 44
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 109

gcgcgcgcuc aguaagaaau ugaaaguuca gaaugucguc gcgc              44

<210> SEQ ID NO 110
<211> LENGTH: 39
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 110

aguguguggc aggcuaagga gauauuccga gaccacgcu                    39

<210> SEQ ID NO 111
<211> LENGTH: 39
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 111

aguguguggc agacuaugga uagacuccga gaccacgcu                    39

<210> SEQ ID NO 112
<211> LENGTH: 39
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 112

agcgugaggc gaccagcgga uuacuuagag agucacgcu                    39

<210> SEQ ID NO 113
<211> LENGTH: 39
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA
```

<400> SEQUENCE: 113
agcgugaagg ggaccagcgu uacuuacaga guucacgcu 39

<210> SEQ ID NO 114
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 114
agcgugugau guauguagca ccguaucaga ggacacgcu 39

<210> SEQ ID NO 115
<211> LENGTH: 37
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 115
agcgugaggc gacccguguu ucguagagag ucacgcu 37

<210> SEQ ID NO 116
<211> LENGTH: 40
<212> TYPE: RNA
<213> ORGANISM: Artificial Sequence
<220> FEATURE:
<223> OTHER INFORMATION: Description of Artificial Sequence: Synthetic
NOX-E36-5'PEG sequence
<220> FEATURE:
<223> OTHER INFORMATION: L-RNA
<220> FEATURE:
<223> OTHER INFORMATION: 5'PEG

<400> SEQUENCE: 116
gcacgucccu caccggugca agugaagccg uggcucugcg 40

<210> SEQ ID NO 117
<211> LENGTH: 40
<212> TYPE: RNA
<213> ORGANISM: Artificial Sequence
<220> FEATURE:
<223> OTHER INFORMATION: Description of Artificial Sequence: Synthetic
NOX-E36-3'PEG sequence
<220> FEATURE:
<223> OTHER INFORMATION: L-RNA
<220> FEATURE:
<223> OTHER INFORMATION: 3'PEG

<400> SEQUENCE: 117
gcacgucccu caccggugca agugaagccg uggcucugcg 40

<210> SEQ ID NO 118
<211> LENGTH: 58
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 118
gagauggcga cauugguugg gcaugaggcg aggcccuuug augaauccgc ggccauuc 58

<210> SEQ ID NO 119
<211> LENGTH: 56
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 119
gauggcgaca uugguugggc augaggcgag gcccuuugau gaauccgcgg ccauuc 56

<210> SEQ ID NO 120
<211> LENGTH: 53
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 120
ggcgacauug guugggcaug aggcgaggcc cuuugaugaa uccgcggcca uuc 53

<210> SEQ ID NO 121
<211> LENGTH: 52
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 121
ggcgacauug guugggcaug aggcgaggcc cuuugaugaa uccgcggcca uu 52

<210> SEQ ID NO 122
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 122
ggcgacauug guugggcaug aggcgaggcc cuuugaugaa uccgcggcca 50

<210> SEQ ID NO 123
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA

<400> SEQUENCE: 123
gcugguuacc gagggggcgu cguuggaguu ugguugguug ucaccagc 48

```
<210> SEQ ID NO 124
<211> LENGTH: 46
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 124

cugguuaccg agggggcguc guuggaguuu gguugguugu caccag                  46


<210> SEQ ID NO 125
<211> LENGTH: 44
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 125

ugguuaccga gggggcgucg uuggaguuug guugguuguc acca                    44


<210> SEQ ID NO 126
<211> LENGTH: 48
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 126

gccgguuacc gagggggcgu cguuggaguu ugguugguug ucaccggc                48


<210> SEQ ID NO 127
<211> LENGTH: 48
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 127

gccggcuacc gagggggcgu cguuggaguu ugguugguug ucgccggc                48


<210> SEQ ID NO 128
<211> LENGTH: 46
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA

<400> SEQUENCE: 128

gcgcguaccg agggggcguc guuggaguuu gguugguugu ccgcgc                  46


<210> SEQ ID NO 129
<211> LENGTH: 46
<212> TYPE: RNA
<213> ORGANISM: Artificial Sequence
<220> FEATURE:
```

<223> OTHER INFORMATION: Description of Artificial Sequence: Synthetic
MCP-1 binder sequence
<220> FEATURE:
<223> OTHER INFORMATION: L-RNA

<400> SEQUENCE: 129
gggccuaccg agggggcguc guuggaguuu gguugguugu cggccc 46

<210> SEQ ID NO 130
<211> LENGTH: 76
<212> TYPE: PRT
<213> ORGANISM: Artificial Sequence
<220> FEATURE:
<223> OTHER INFORMATION: Description of Artificial Sequence: Synthetic
biotinylated human D MCP-1 polypeptide
<220> FEATURE:
<223> OTHER INFORMATION: D-Protein
<220> FEATURE:
<223> OTHER INFORMATION: N-term Biotin

<400> SEQUENCE: 130

```
Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75
```

<210> SEQ ID NO 131
<211> LENGTH: 76
<212> TYPE: PRT
<213> ORGANISM: Artificial Sequence
<220> FEATURE:
<223> OTHER INFORMATION: Description of Artificial Sequence: Synthetic
biotinylated mouse D MCP-1 polypeptide
<220> FEATURE:
<223> OTHER INFORMATION: D-Protein
<220> FEATURE:
<223> OTHER INFORMATION: N-term Biotin
<220> FEATURE:
<223> OTHER INFORMATION: C-term Biotin

<400> SEQUENCE: 131

```
Gln Pro Asp Ala Val Asn Ala Pro Leu Thr Cys Cys Tyr Ser Phe Thr
1               5                   10                  15

Ser Lys Met Ile Pro Met Ser Arg Leu Glu Ser Tyr Lys Arg Ile Thr
            20                  25                  30

Ser Ser Arg Cys Pro Lys Glu Ala Val Val Phe Val Thr Lys Leu Lys
        35                  40                  45

Arg Glu Val Cys Ala Asp Pro Lys Lys Glu Trp Val Gln Thr Tyr Ile
    50                  55                  60

Lys Asn Leu Asp Arg Asn Gln Met Arg Ser Glu Pro
65                  70                  75
```

<210> SEQ ID NO 132
<211> LENGTH: 47
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:

<223> OTHER INFORMATION: D-RNA

<400> SEQUENCE: 132
agcgugcccg gaguggcagg gggacgcgac cugcaauaau gcacgcu 47

<210> SEQ ID NO 133
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 133
agcgugcccg gaguggcagg gggacgcgac cugcaauugc acgcu 45

<210> SEQ ID NO 134
<211> LENGTH: 47
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 134
agcgugcccg gaguggcagg gggacgcgac cuguaauaau gcacgcu 47

<210> SEQ ID NO 135
<211> LENGTH: 47
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 135
agcgugcccg guguggcagg gggacgcgac cugcaauaau gcgcgcu 47

<210> SEQ ID NO 136
<211> LENGTH: 47
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 136
agcgugcccg gaguagcagg ggggcgcgac cugcaauaau gcacgcu 47

<210> SEQ ID NO 137
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 137
agcgugcccg gugugguagg ggggcgcgau cuacaauugc acgcu 45

<210> SEQ ID NO 138
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 138
agcgugcccg gugugacagg ggggcgcgac cugcauuugc acgcu 45

<210> SEQ ID NO 139
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 139
agcgugcccg guguggcagg ggggcgcgac cuguauuugc acgcu 45

<210> SEQ ID NO 140
<211> LENGTH: 47
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 140
agcgugcccg gaguggcagg ggggcgcgac cugcaauaau gcacgcu 47

<210> SEQ ID NO 141
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 141
agcgugcccg guguggcagg ggggcgcgac cugcaauugc acgcu 45

<210> SEQ ID NO 142
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 142
agcaugcccg guguggcagg ggggcgcgac cugcauuugc augcu 45

<210> SEQ ID NO 143
<211> LENGTH: 45
<212> TYPE: RNA

<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 143
agcgugcccg gugugguagg ggggcgcgac cuacauuugc acgcu 45

<210> SEQ ID NO 144
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 144
agugugccag cugugauggg ggggcgcgac ccauuuuaca cacu 44

<210> SEQ ID NO 145
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 145
agugugccag cgugaugggg gggcgcgacc cauuuuacac acu 43

<210> SEQ ID NO 146
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 146
agugugcgag cgugaugggg gggcgcgacc cauuuuacau acu 43

<210> SEQ ID NO 147
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 147
agugugccag cgugaugggg gggcgcgacc cauuuuacau acu 43

<210> SEQ ID NO 148
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:

<223> OTHER INFORMATION: D-RNA

<400> SEQUENCE: 148
aguaugccag cgugaugggg gggcgcgacc cauuuacaua cu 42

<210> SEQ ID NO 149
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 149
agugugccag ugugaugggg gggcgcgacc cauuuuacac acu 43

<210> SEQ ID NO 150
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 150
agcgugccag ugugaugggg gggcgcgacc cauuuuacac gcu 43

<210> SEQ ID NO 151
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 151
acgcacgucc cucaccggug caagugaagc cgcggcucug cgu 43

<210> SEQ ID NO 152
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 152
acgcaccucc cucaccggug caagugaagc cguggcucug cgc 43

<210> SEQ ID NO 153
<211> LENGTH: 43
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 153
acgcacgucc cucaccggug caagugaagc cguggcucug cgu 43

<210> SEQ ID NO 154
<211> LENGTH: 41
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 154
gcacgucccu caccggugca agugaagccg uggcucugcg u 41

<210> SEQ ID NO 155
<211> LENGTH: 41
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 155
acgcacgucc cucaccggug caagugaagc cguggcucug c 41

<210> SEQ ID NO 156
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 156
gcacgucccu caccggugca agugaagccg uggcucugc 39

<210> SEQ ID NO 157
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 157
cgcacguccc ucaccggugc aagugaagcc guggcucugc gu 42

<210> SEQ ID NO 158
<211> LENGTH: 41
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 158
cgcacguccc ucaccggugc aagugaagcc guggcucugc g 41

<210> SEQ ID NO 159
<211> LENGTH: 40
<212> TYPE: RNA

<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 159
gcacgucccu caccggugca agugaagccg uggcucugcg 40

<210> SEQ ID NO 160
<211> LENGTH: 49
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 160
gugcugcgua guggaagacu accuaaugac agccgaaugc uggcagcac 49

<210> SEQ ID NO 161
<211> LENGTH: 49
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 161
gugcugcgua guggaagacu accuaaugac agccuaaugc uggcagcac 49

<210> SEQ ID NO 162
<211> LENGTH: 49
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 162
gugcugcgua guggaagacu accuuaugac agccgaaugc uggcagcac 49

<210> SEQ ID NO 163
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 163
gugcugcgua gugaaaaacu acugccagug ggucagagcu agcagcac 48

<210> SEQ ID NO 164
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:

<223> OTHER INFORMATION: D-RNA

<400> SEQUENCE: 164
gugcugcgga guuaaaaacu cccuaagaca ggccagagcc ggcagcac 48

<210> SEQ ID NO 165
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 165
gugcugcgga guugaaaacu cccuaagaca ggccagagcc ggcagcac 48

<210> SEQ ID NO 166
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 166
gugcugcgua guggaagacu accuaugaca gccuaaugcu ggcagcac 48

<210> SEQ ID NO 167
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 167
gugcugcgga guuaaaaacu cccuaagaca ggcuagagcc ggcagcac 48

<210> SEQ ID NO 168
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 168
gugcugcggc gugaaaaacg cccugcgacu gcccuuuaug caggcagcac 50

<210> SEQ ID NO 169
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 169
gugcugcgua gugaaaaacu accaacgacu ggcuagagcc ggcagcac 48

<210> SEQ ID NO 170
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 170
gugcugcgua gugaaagacu accugugaca gccgaaugcu ggcagcac 48

<210> SEQ ID NO 171
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 171
guacugcgua guuaaaaacu accaacgacu ggcuagagcc ggcagcac 48

<210> SEQ ID NO 172
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 172
gugcugcgua guuaaaaacu accaacgacu ggcuagagcc ggcagcac 48

<210> SEQ ID NO 173
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 173
gugcugcgua guuaaaaacu accagcgaca ggcuagagcc ggcagcac 48

<210> SEQ ID NO 174
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 174
gugcugcgua guuaaaaacu accagcgacu ggcuagagcc ggcagcac 48

<210> SEQ ID NO 175
<211> LENGTH: 48
<212> TYPE: RNA

-continued

<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 175
gugcugcgua gugagaaacu accaacgacu ggcuagagcc ggcagcac 48

<210> SEQ ID NO 176
<211> LENGTH: 46
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 176
ggcugcguag uuaaaaacua ccagcgacug gcuagagccg gcagcc 46

<210> SEQ ID NO 177
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 177
ggcgcguagu uaaaaacuac cagcgacugg cuagagccgg cgcc 44

<210> SEQ ID NO 178
<211> LENGTH: 46
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 178
gugcgcguag uuaaaaacua ccagcgacug gcuagagccg gcgcac 46

<210> SEQ ID NO 179
<211> LENGTH: 46
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 179
gugcgcguag ugagaaacua ccaacgacug gcuagagccg gcgcac 46

<210> SEQ ID NO 180
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:

-continued

<223> OTHER INFORMATION: D-RNA

<400> SEQUENCE: 180
gugccguagu gagaaacuac caacgacugg cuagagccgg gcac 44

<210> SEQ ID NO 181
<211> LENGTH: 44
<212> TYPE: RNA
<213> ORGANISM: Artificial Sequence
<220> FEATURE:
<223> OTHER INFORMATION: Description of Artificial Sequence: Synthetic MCP-1 binder sequence
<220> FEATURE:
<223> OTHER INFORMATION: D-RNA

<400> SEQUENCE: 181
guggcguagu gagaaacuac caacgacugg cuagagccgg ccac 44

<210> SEQ ID NO 182
<211> LENGTH: 44
<212> TYPE: RNA
<213> ORGANISM: Artificial Sequence
<220> FEATURE:
<223> OTHER INFORMATION: Description of Artificial Sequence: Synthetic MCP-1 binder sequence
<220> FEATURE:
<223> OTHER INFORMATION: D-RNA

<400> SEQUENCE: 182
gucgcguagu gagaaacuac caacgacugg cuagagccgg cgac 44

<210> SEQ ID NO 183
<211> LENGTH: 44
<212> TYPE: RNA
<213> ORGANISM: Artificial Sequence
<220> FEATURE:
<223> OTHER INFORMATION: Description of Artificial Sequence: Synthetic MCP-1 binder sequence
<220> FEATURE:
<223> OTHER INFORMATION: D-RNA

<400> SEQUENCE: 183
ugcgcguagu gagaaacuac caacgacugg cuagagccgg cgca 44

<210> SEQ ID NO 184
<211> LENGTH: 44
<212> TYPE: RNA
<213> ORGANISM: Artificial Sequence
<220> FEATURE:
<223> OTHER INFORMATION: Description of Artificial Sequence: Synthetic MCP-1 binder sequence
<220> FEATURE:
<223> OTHER INFORMATION: D-RNA

<400> SEQUENCE: 184
gcugcguagu gagaaacuac caacgacugg cuagagccgg cagc 44

<210> SEQ ID NO 185
<211> LENGTH: 44
<212> TYPE: RNA
<213> ORGANISM: Artificial Sequence
<220> FEATURE:
<223> OTHER INFORMATION: Description of Artificial Sequence: Synthetic MCP-1 binder sequence
<220> FEATURE:
<223> OTHER INFORMATION: D-RNA

<400> SEQUENCE: 185
gcugcguagu gagaaacuac caacgacugg cuagagccgg cagc 44

<210> SEQ ID NO 186
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 186
ggugcguagu gagaaacuac caacgacugg cuagagccgg cacc 44

<210> SEQ ID NO 187
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 187
uggcguagug agaaacuacc aacgacuggc uagagccggc ca 42

<210> SEQ ID NO 188
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 188
gcgcguagug agaaacuacc aacgacuggc uagagccggc gc 42

<210> SEQ ID NO 189
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 189
gugcguagug agaaacuacc aacgacuggc uagagccggc ac 42

<210> SEQ ID NO 190
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 190
gggcguagug agaaacuacc aacgacuggc uagagccggc cc 42

<210> SEQ ID NO 191
<211> LENGTH: 42
<212> TYPE: RNA

<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 191
gagcguagug agaaacuacc aacgacuggc uagagccggc uc 42

<210> SEQ ID NO 192
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 192
cggcguagug agaaacuacc aacgacuggc uagagccggc cg 42

<210> SEQ ID NO 193
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 193
ccgcguagug agaaacuacc aacgacuggc uagagccggc gg 42

<210> SEQ ID NO 194
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 194
cagcguagug agaaacuacc aacgacuggc uagagccggc ug 42

<210> SEQ ID NO 195
<211> LENGTH: 42
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 195
cugcguagug agaaacuacc aacgacuggc uagagccggc ag 42

<210> SEQ ID NO 196
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:

<223> OTHER INFORMATION: D-RNA

<400> SEQUENCE: 196
agcguguuag ugaagugggu ggcagguaaa ggacacgcu 39

<210> SEQ ID NO 197
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 197
agcgugguag cggugugggu gguagguaaa ggccacgcu 39

<210> SEQ ID NO 198
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 198
agcgugauag aagagcgggu gguagguaaa ggucaggcu 39

<210> SEQ ID NO 199
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 199
agcguguuag guaggguggu aguaaguaaa ggacacgcu 39

<210> SEQ ID NO 200
<211> LENGTH: 38
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 200
agcguguuag gugggugguag guaaguaaag gacacgcu 38

<210> SEQ ID NO 201
<211> LENGTH: 38
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 201
agcguguuag gugggguggua guaaguaaag ggcacgcu 38

<210> SEQ ID NO 202
<211> LENGTH: 34
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 202
ccgcuuaggu gggugguagu aaguaaaggg gcgg 34

<210> SEQ ID NO 203
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 203
gcgcgagcag gugggguggua gaauguaaag acucgcguc 39

<210> SEQ ID NO 204
<211> LENGTH: 34
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 204
cguguuaggu gggugguagu aaguaaagga cacg 34

<210> SEQ ID NO 205
<211> LENGTH: 32
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 205
guguuaggug ggugguagua aguaaaggac ac 32

<210> SEQ ID NO 206
<211> LENGTH: 34
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 206
cguguuaggu gggugguagu aaguaaaggg cacg 34

<210> SEQ ID NO 207
<211> LENGTH: 32
<212> TYPE: RNA

<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 207
guguuaggug ggugguagua aguaaagggc ac 32

<210> SEQ ID NO 208
<211> LENGTH: 30
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 208
uguuaggugg gugguaguaa guaaagggca 30

<210> SEQ ID NO 209
<211> LENGTH: 52
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 209
ggacgagagu gacaaaugau auaaccuccu gacuaacgcu gcgggcgaca gg 52

<210> SEQ ID NO 210
<211> LENGTH: 52
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 210
ggaccuaucg cuaagacaac gcgcagucua cgggacauuc uccgcggaca gg 52

<210> SEQ ID NO 211
<211> LENGTH: 52
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 211
ggacaauugu uacccccgag agagacaaau gagacaaccu ccugaagaca gg 52

<210> SEQ ID NO 212
<211> LENGTH: 51
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:

<223> OTHER INFORMATION: D-RNA

<400> SEQUENCE: 212
ggacgaaagu gagaaaugau acaaccuccu guugcugcga auccggacag g 51

<210> SEQ ID NO 213
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 213
ggacguaaaa gacgcuaccc gaaagaaugu caggagggua gaccgacagg 50

<210> SEQ ID NO 214
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 214
ggacuagaaa cuacaauagc ggccaguugc accgcguuau caacgacagg 50

<210> SEQ ID NO 215
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 215
ggacuaguca gccagugugu auaucggacg cggguuuauu uacugacagg 50

<210> SEQ ID NO 216
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 216
ggacuguccg gagugugaaa cuccccgaga ccgccagaag cggggacagg 50

<210> SEQ ID NO 217
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 217
ggacuucuau ccaggugggu gguaguaugu aaagagauag aagugacagg 50

<210> SEQ ID NO 218
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 218
ggacgagagc gaacaaugau auaaccuccu gacggaaaga gaucgacagg 50

<210> SEQ ID NO 219
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 219
ccugugcuac acgcaguaag aagugaacgu ucaguaugug ugcacagg 48

<210> SEQ ID NO 220
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 220
cgugagccag gcaccgaggg cguuaacugg cugauuggac acgacacg 48

<210> SEQ ID NO 221
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 221
cgugaacaug caagcuaagc ggggcuguug guugcuuggc ccgccacg 48

<210> SEQ ID NO 222
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 222
cgugcagaga gagaccaacc acguaaaauc aaccuaaugg gccgcacg 48

<210> SEQ ID NO 223
<211> LENGTH: 48
<212> TYPE: RNA

<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 223
cgugcagaga gagaccaacc acguaaaauc aaccuaaugg gccgcacg 48

<210> SEQ ID NO 224
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 224
cgugaacauu caagcuaagc ggggcuguug guugcuuggc ccgccacg 48

<210> SEQ ID NO 225
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 225
cgugccgagg cggcgaccag cguuacuuag agaggcuuug gcaccacg 48

<210> SEQ ID NO 226
<211> LENGTH: 47
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 226
cgugauaaca gccgucgguc aagaaaacaa aguucgggcg gcgcacg 47

<210> SEQ ID NO 227
<211> LENGTH: 47
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 227 cgugggugge gcaccgaggg cgaaaagcca ccaguaaaga uagaccg 47

<210> SEQ ID NO 228
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:

<223> OTHER INFORMATION: D-RNA

<400> SEQUENCE: 228
cgugugaucu ccuuuggggu gauuagcuua gagacuuccc acacg 45

<210> SEQ ID NO 229
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 229
gcaccuucgc cuaauacacg ugccggcuag cuaauacucg uccgc 45

<210> SEQ ID NO 230
<211> LENGTH: 45
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 230
gcacgacuug ggcgaccagu gauacuuaga gagcaagucg ucggc 45

<210> SEQ ID NO 231
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 231
gcgcgcgcuc aguaagaaau ugaaaguuca gaaugucguc gcgc 44

<210> SEQ ID NO 232
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 232 agugugugge aggcuaagga gauauuccga gaccacgcu 39

<210> SEQ ID NO 233
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 233 agugugugge agacuaugga uagacuccga gaccacgcu 39

-continued

<210> SEQ ID NO 234
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 234
agcgugaggc gaccagcgga uuacuuagag agucacgcu 39

<210> SEQ ID NO 235
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 235
agcgugaagg ggaccagcgu uacuuacaga guucacgcu 39

<210> SEQ ID NO 236
<211> LENGTH: 39
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 236
agcgugugau guauguagca ccguaucaga ggacacgcu 39

<210> SEQ ID NO 237
<211> LENGTH: 37
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 237
agcgugaggc gacccguguu ucguagagag ucacgcu 37

<210> SEQ ID NO 238
<211> LENGTH: 40
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA
<220> FEATURE:
<223> OTHER INFORMATION: 5'PEG

<400> SEQUENCE: 238
gcacgucccu caccggugca agugaagccg uggcucugcg 40

<210> SEQ ID NO 239

```
<211> LENGTH: 40
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: D-RNA
<220> FEATURE:
<223> OTHER INFORMATION: 3'PEG

<400> SEQUENCE: 239

gcacgucccu caccggugca agugaagccg uggcucugcg                           40

<210> SEQ ID NO 240
<211> LENGTH: 58
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: D-RNA

<400> SEQUENCE: 240

gagauggcga cauugguugg gcaugaggcg aggcccuuug augaauccgc ggccauuc       58

<210> SEQ ID NO 241
<211> LENGTH: 56
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: D-RNA

<400> SEQUENCE: 241

gauggcgaca uugguugggc augaggcgag gcccuuugau gaauccgcgg ccauuc         56

<210> SEQ ID NO 242
<211> LENGTH: 53
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: D-RNA

<400> SEQUENCE: 242

ggcgacauug guugggcaug aggcgaggcc cuuugaugaa uccgcggcca uuc            53

<210> SEQ ID NO 243
<211> LENGTH: 52
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: D-RNA

<400> SEQUENCE: 243

ggcgacauug guugggcaug aggcgaggcc cuuugaugaa uccgcggcca uu             52

<210> SEQ ID NO 244
<211> LENGTH: 50
<212> TYPE: RNA
<213> ORGANISM: Artificial Sequence
```

<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 244
ggcgacauug guugggcaug aggcgaggcc cuuugaugaa uccgcggcca 50

<210> SEQ ID NO 245
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 245
gcugguuacc gagggggcgu cguuggaguu ugguugguug ucaccagc 48

<210> SEQ ID NO 246
<211> LENGTH: 46
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 246
cugguuaccg agggggcguc guuggaguuu gguugguugu caccag 46

<210> SEQ ID NO 247
<211> LENGTH: 44
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 247
ugguuaccga gggggcgucg uuggaguuug guugguuguc acca 44

<210> SEQ ID NO 248
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 248
gccgguuacc gagggggcgu cguuggaguu ugguugguug ucaccggc 48

<210> SEQ ID NO 249
<211> LENGTH: 48
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 249
gccggcuacc gagggggcgu cguuggaguu ugguugguug ucgccggc 48

<210> SEQ ID NO 250
<211> LENGTH: 46
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 250
gcgcguaccg agggggcguc guuggaguuu gguugguugu ccgcgc 46

<210> SEQ ID NO 251
<211> LENGTH: 46
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: D-RNA

<400> SEQUENCE: 251
gggccuaccg agggggcguc guuggaguuu gguugguugu cggccc 46

<210> SEQ ID NO 252
<211> LENGTH: 76
<212> TYPE: PRT
<213> ORGANISM: Rattus norvegicus

<400> SEQUENCE: 252

```
Gln Pro Asp Ala Val Asn Ala Pro Leu Thr Cys Cys Tyr Ser Phe Thr
1               5                   10                  15

Gly Lys Met Ile Pro Met Ser Arg Leu Glu Asn Tyr Lys Arg Ile Thr
            20                  25                  30

Ser Ser Arg Cys Pro Lys Glu Ala Val Val Phe Val Thr Lys Leu Lys
        35                  40                  45

Arg Glu Ile Cys Ala Asp Pro Asn Lys Glu Trp Val Gln Lys Tyr Ile
    50                  55                  60

Arg Lys Leu Asp Gln Asn Gln Val Arg Ser Glu Thr
65                  70                  75
```

<210> SEQ ID NO 253
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA
<220> FEATURE:
<223> OTHER INFORMATION: 5'PEG

<400> SEQUENCE: 253
ggcgacauug guugggcaug aggcgaggcc cuuugaugaa uccgcggcca 50

<210> SEQ ID NO 254
<211> LENGTH: 50
<212> TYPE: RNA
<213> ORGANISM: Artificial Sequence
<220> FEATURE:
<223> OTHER INFORMATION: Description of Artificial Sequence: Synthetic
MCP-1 binder sequence
<220> FEATURE:
<223> OTHER INFORMATION: L-RNA
<220> FEATURE:
<223> OTHER INFORMATION: 3'PEG

<400> SEQUENCE: 254
ggcgacauug guugggcaug aggcgaggcc cuuugaugaa uccgcggcca 50

<210> SEQ ID NO 255
<211> LENGTH: 11
<212> TYPE: DNA
<213> ORGANISM: Artificial Sequence
<220> FEATURE:
<223> OTHER INFORMATION: Description of Artificial Sequence: Synthetic
NOX-E36 Capture probe
<220> FEATURE:
<223> OTHER INFORMATION: L-DNA
<220> FEATURE:
<223> OTHER INFORMATION: 3'-(Spacer18)2-NH4+

<400> SEQUENCE: 255
gagggacgtg c 11

<210> SEQ ID NO 256
<211> LENGTH: 9
<212> TYPE: DNA
<213> ORGANISM: Artificial Sequence
<220> FEATURE:
<223> OTHER INFORMATION: Description of Artificial Sequence: Synthetic
NOX-E36 Detect probe
<220> FEATURE:
<223> OTHER INFORMATION: L-DNA
<220> FEATURE:
<223> OTHER INFORMATION: 5'-Biotin-(Spacer18)2

<400> SEQUENCE: 256 cgcagagcc 9

<210> SEQ ID NO 257
<211> LENGTH: 73
<212> TYPE: PRT
<213> ORGANISM: Artificial Sequence
<220> FEATURE:
<223> OTHER INFORMATION: Description of Artificial Sequence: Synthetic
CCL1/I-309 polypeptide
<220> FEATURE:
<223> OTHER INFORMATION: L-Protein

<400> SEQUENCE: 257

```
Lys Ser Met Gln Val Pro Phe Ser Arg Cys Cys Phe Ser Phe Ala Glu
1               5                   10                  15

Gln Glu Ile Pro Leu Arg Ala Ile Leu Cys Tyr Arg Asn Thr Ser Ser
            20                  25                  30

Ile Cys Ser Asn Glu Gly Leu Ile Phe Lys Leu Lys Arg Gly Lys Glu
        35                  40                  45

Ala Cys Ala Leu Asp Thr Val Gly Trp Val Gln Arg His Arg Lys Met
    50                  55                  60

Leu Arg His Cys Pro Ser Lys Arg Lys
65                  70
```

<210> SEQ ID NO 258
<211> LENGTH: 69
<212> TYPE: PRT
<213> ORGANISM: Artificial Sequence
<220> FEATURE:

<223> OTHER INFORMATION: Description of Artificial Sequence: Synthetic
      CCL3/MIP-1 polypeptide
<220> FEATURE:
<223> OTHER INFORMATION: L-Protein

<400> SEQUENCE: 258

```
Ser Leu Ala Ala Asp Thr Pro Thr Ala Cys Cys Phe Ser Tyr Thr Ser
1               5                   10                  15

Arg Gln Ile Pro Gln Asn Phe Ile Ala Asp Tyr Phe Glu Thr Ser Ser
            20                  25                  30

Gln Cys Ser Lys Pro Gly Val Ile Phe Leu Thr Lys Arg Ser Arg Gln
        35                  40                  45

Val Cys Ala Asp Pro Ser Glu Glu Trp Val Gln Lys Tyr Val Ser Asp
    50                  55                  60

Leu Glu Leu Ser Ala
65
```

<210> SEQ ID NO 259
<211> LENGTH: 69
<212> TYPE: PRT
<213> ORGANISM: Artificial Sequence
<220> FEATURE:
<223> OTHER INFORMATION: Description of Artificial Sequence: Synthetic
      CCL4/MIP-1beta polypeptide
<220> FEATURE:
<223> OTHER INFORMATION: L-Protein

<400> SEQUENCE: 259

```
Ala Pro Met Gly Ser Asp Pro Pro Thr Ala Cys Cys Phe Ser Tyr Thr
1               5                   10                  15

Ala Arg Lys Leu Pro Arg Asn Phe Val Val Asp Tyr Tyr Glu Thr Ser
            20                  25                  30

Ser Leu Cys Ser Gln Pro Ala Val Val Phe Gln Thr Lys Arg Ser Lys
        35                  40                  45

Gln Val Cys Ala Asp Pro Ser Glu Ser Trp Val Gln Glu Tyr Val Tyr
    50                  55                  60

Asp Leu Glu Leu Asn
65
```

<210> SEQ ID NO 260
<211> LENGTH: 68
<212> TYPE: PRT
<213> ORGANISM: Artificial Sequence
<220> FEATURE:
<223> OTHER INFORMATION: Description of Artificial Sequence: Synthetic
      CCL5/RANTES polypeptide
<220> FEATURE:
<223> OTHER INFORMATION: L-Protein

<400> SEQUENCE: 260

```
Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65
```

<210> SEQ ID NO 261

<211> LENGTH: 82
<212> TYPE: PRT
<213> ORGANISM: Artificial Sequence
<220> FEATURE:
<223> OTHER INFORMATION: Description of Artificial Sequence: Synthetic
CCL13/MCP-4 polypeptide
<220> FEATURE:
<223> OTHER INFORMATION: L-Protein

<400> SEQUENCE: 261

Phe Asn Pro Gln Gly Leu Ala Gln Pro Asp Ala Leu Asn Val Pro Ser
1 5 10 15

Thr Cys Cys Phe Thr Phe Ser Ser Lys Lys Ile Ser Leu Gln Arg Leu
20 25 30

Lys Ser Tyr Val Ile Thr Thr Ser Arg Cys Pro Gln Lys Ala Val Ile
35 40 45

Phe Arg Thr Lys Leu Gly Lys Glu Ile Cys Ala Asp Pro Lys Glu Lys
50 55 60

Trp Val Gln Asn Tyr Met Lys His Leu Gly Arg Lys Ala His Thr Leu
65 70 75 80

Lys Thr

<210> SEQ ID NO 262
<211> LENGTH: 74
<212> TYPE: PRT
<213> ORGANISM: Artificial Sequence
<220> FEATURE:
<223> OTHER INFORMATION: Description of Artificial Sequence: Synthetic
CCL14/HCC-1 polypeptide
<220> FEATURE:
<223> OTHER INFORMATION: L-Protein

<400> SEQUENCE: 262

Thr Lys Thr Glu Ser Ser Ser Arg Gly Pro Tyr His Pro Ser Glu Cys
1 5 10 15

Cys Phe Thr Tyr Thr Thr Tyr Lys Ile Pro Arg Gln Arg Ile Met Asp
20 25 30

Tyr Tyr Glu Thr Asn Ser Gln Cys Ser Lys Pro Gly Ile Val Phe Ile
35 40 45

Thr Lys Arg Gly His Ser Val Cys Thr Asn Pro Ser Asp Lys Trp Val
50 55 60

Gln Asp Tyr Ile Lys Asp Met Lys Glu Asn
65 70

<210> SEQ ID NO 263
<211> LENGTH: 73
<212> TYPE: PRT
<213> ORGANISM: Artificial Sequence
<220> FEATURE:
<223> OTHER INFORMATION: Description of Artificial Sequence: Synthetic
CXCL1/GROalpha polypeptide
<220> FEATURE:
<223> OTHER INFORMATION: L-Protein

<400> SEQUENCE: 263

Ala Ser Val Ala Thr Glu Leu Arg Cys Gln Cys Leu Gln Thr Leu Gln
1 5 10 15

Gly Ile His Pro Lys Asn Ile Gln Ser Val Asn Val Lys Ser Pro Gly
20 25 30

Pro His Cys Ala Gln Thr Glu Val Ile Ala Thr Leu Lys Asn Gly Arg
35 40 45

Lys Ala Cys Leu Asn Pro Ala Ser Pro Ile Val Lys Lys Ile Ile Glu
50 55 60

Lys Met Leu Asn Ser Asp Lys Ser Asn
65 70

<210> SEQ ID NO 264
<211> LENGTH: 73
<212> TYPE: PRT
<213> ORGANISM: Artificial Sequence
<220> FEATURE:
<223> OTHER INFORMATION: Description of Artificial Sequence: Synthetic
CXCL2/GRObeta polypeptide
<220> FEATURE:
<223> OTHER INFORMATION: L-Protein

<400> SEQUENCE: 264

Ala Pro Leu Ala Thr Glu Leu Arg Cys Gln Cys Leu Gln Thr Leu Gln
1 5 10 15

Gly Ile His Leu Lys Asn Ile Gln Ser Val Lys Val Lys Ser Pro Gly
20 25 30

Pro His Cys Ala Gln Thr Glu Val Ile Ala Thr Leu Lys Asn Gly Gln
35 40 45

Lys Ala Cys Leu Asn Pro Ala Ser Pro Met Val Lys Lys Ile Ile Glu
50 55 60

Lys Met Leu Lys Asn Gly Lys Ser Asn
65 70

<210> SEQ ID NO 265
<211> LENGTH: 73
<212> TYPE: PRT
<213> ORGANISM: Artificial Sequence
<220> FEATURE:
<223> OTHER INFORMATION: Description of Artificial Sequence: Synthetic
CXCL3/GROgama polypeptide
<220> FEATURE:
<223> OTHER INFORMATION: L-Protein

<400> SEQUENCE: 265

Ala Ser Val Val Thr Glu Leu Arg Cys Gln Cys Leu Gln Thr Leu Gln
1 5 10 15

Gly Ile His Leu Lys Asn Ile Gln Ser Val Asn Val Arg Ser Pro Gly
20 25 30

Pro His Cys Ala Gln Thr Glu Val Ile Ala Thr Leu Lys Asn Gly Lys
35 40 45

Lys Ala Cys Leu Asn Pro Ala Ser Pro Met Val Gln Lys Ile Ile Glu
50 55 60

Lys Ile Leu Asn Lys Gly Ser Thr Asn
65 70

<210> SEQ ID NO 266
<211> LENGTH: 70
<212> TYPE: PRT
<213> ORGANISM: Artificial Sequence
<220> FEATURE:
<223> OTHER INFORMATION: Description of Artificial Sequence: Synthetic
CXCL4/PF4 polypeptide
<220> FEATURE:
<223> OTHER INFORMATION: L-Protein

<400> SEQUENCE: 266

Glu Ala Glu Glu Asp Gly Asp Leu Gln Cys Leu Cys Val Lys Thr Thr
1 5 10 15

Ser Gln Val Arg Pro Arg His Ile Thr Ser Leu Glu Val Ile Lys Ala
20 25 30

Gly Pro His Cys Pro Thr Ala Gln Leu Ile Ala Thr Leu Lys Asn Gly

-continued

```
        35                  40                  45

Arg Lys Ile Cys Leu Asp Leu Gln Ala Pro Leu Tyr Lys Lys Ile Ile
    50                  55                  60

Lys Lys Leu Leu Glu Ser
65                  70


<210> SEQ ID NO 267
<211> LENGTH: 77
<212> TYPE: PRT
<213> ORGANISM: Artificial Sequence
<220> FEATURE:
<223> OTHER INFORMATION: Description of Artificial Sequence: Synthetic
      CXCL5/ENA-78 polypeptide
<220> FEATURE:
<223> OTHER INFORMATION: L-Protein

<400> SEQUENCE: 267

Gly Pro Ala Ala Ala Val Leu Arg Glu Leu Arg Cys Val Cys Leu Gln
1               5                   10                  15

Thr Thr Gln Gly Val His Pro Lys Met Ile Ser Asn Leu Gln Val Phe
            20                  25                  30

Ala Ile Gly Pro Gln Cys Ser Lys Val Glu Val Val Ala Ser Leu Lys
        35                  40                  45

Asn Gly Lys Glu Ile Cys Leu Asp Pro Glu Ala Pro Phe Leu Lys Lys
    50                  55                  60

Val Ile Gln Lys Ile Leu Asp Gly Gly Asn Lys Glu Asn
65                  70                  75


<210> SEQ ID NO 268
<211> LENGTH: 77
<212> TYPE: PRT
<213> ORGANISM: Artificial Sequence
<220> FEATURE:
<223> OTHER INFORMATION: Description of Artificial Sequence: Synthetic
      CXCL6/GCP-2 polypeptide
<220> FEATURE:
<223> OTHER INFORMATION: L-Protein

<400> SEQUENCE: 268

Gly Pro Val Ser Ala Val Leu Thr Glu Leu Arg Cys Thr Cys Leu Arg
1               5                   10                  15

Val Thr Leu Arg Val Asn Pro Lys Thr Ile Gly Lys Leu Gln Val Phe
            20                  25                  30

Pro Ala Gly Pro Gln Cys Ser Lys Val Glu Val Val Ala Ser Leu Lys
        35                  40                  45

Asn Gly Lys Gln Val Cys Leu Asp Pro Glu Ala Pro Phe Leu Lys Lys
    50                  55                  60

Val Ile Gln Lys Ile Leu Asp Ser Gly Asn Lys Lys Asn
65                  70                  75


<210> SEQ ID NO 269
<211> LENGTH: 94
<212> TYPE: PRT
<213> ORGANISM: Artificial Sequence
<220> FEATURE:
<223> OTHER INFORMATION: Description of Artificial Sequence: Synthetic
      CXCL7/NAP-2 polypeptide
<220> FEATURE:
<223> OTHER INFORMATION: L-Protein

<400> SEQUENCE: 269

Ser Ser Thr Lys Gly Gln Thr Lys Arg Asn Leu Ala Lys Gly Lys Glu
1               5                   10                  15
```

```
Glu Ser Leu Asp Ser Asp Leu Tyr Ala Glu Leu Arg Cys Met Cys Ile
            20                  25                  30

Lys Thr Thr Ser Gly Ile His Pro Lys Asn Ile Gln Ser Leu Glu Val
        35                  40                  45

Ile Gly Lys Gly Thr His Cys Asn Gln Val Glu Val Ile Ala Thr Leu
    50                  55                  60

Lys Asp Gly Arg Lys Ile Cys Leu Asp Pro Asp Ala Pro Arg Ile Lys
65                  70                  75                  80

Lys Ile Val Gln Lys Lys Leu Ala Gly Asp Glu Ser Ala Asp
                85                  90


<210> SEQ ID NO 270
<211> LENGTH: 79
<212> TYPE: PRT
<213> ORGANISM: Artificial Sequence
<220> FEATURE:
<223> OTHER INFORMATION: Description of Artificial Sequence: Synthetic
      CXCL8/IL-8 polypeptide
<220> FEATURE:
<223> OTHER INFORMATION: L-Protein

<400> SEQUENCE: 270

Glu Gly Ala Val Leu Pro Arg Ser Ala Lys Glu Leu Arg Cys Gln Cys
1               5                   10                  15

Ile Lys Thr Tyr Ser Lys Pro Phe His Pro Lys Phe Ile Lys Glu Leu
            20                  25                  30

Arg Val Ile Glu Ser Gly Pro His Cys Ala Asn Thr Glu Ile Ile Val
        35                  40                  45

Lys Leu Ser Asp Gly Arg Glu Leu Cys Leu Asp Pro Lys Glu Asn Trp
    50                  55                  60

Val Gln Arg Val Val Glu Lys Phe Leu Lys Arg Ala Glu Asn Ser
65                  70                  75


<210> SEQ ID NO 271
<211> LENGTH: 103
<212> TYPE: PRT
<213> ORGANISM: Artificial Sequence
<220> FEATURE:
<223> OTHER INFORMATION: Description of Artificial Sequence: Synthetic
      CXCL9/MIG polypeptide
<220> FEATURE:
<223> OTHER INFORMATION: L-Protein

<400> SEQUENCE: 271

Thr Pro Val Val Arg Lys Gly Arg Cys Ser Cys Ile Ser Thr Asn Gln
1               5                   10                  15

Gly Thr Ile His Leu Gln Ser Leu Lys Asp Leu Lys Gln Phe Ala Pro
            20                  25                  30

Ser Pro Ser Cys Glu Lys Ile Glu Ile Ile Ala Thr Leu Lys Asn Gly
        35                  40                  45

Val Gln Thr Cys Leu Asn Pro Asp Ser Ala Asp Val Lys Glu Leu Ile
    50                  55                  60

Lys Lys Trp Glu Lys Gln Val Ser Gln Lys Lys Lys Gln Lys Asn Gly
65                  70                  75                  80

Lys Lys His Gln Lys Lys Lys Val Leu Lys Val Arg Lys Ser Gln Arg
                85                  90                  95

Ser Arg Gln Lys Lys Thr Thr
            100


<210> SEQ ID NO 272
<211> LENGTH: 77
```

```
<212> TYPE: PRT
<213> ORGANISM: Artificial Sequence
<220> FEATURE:
<223> OTHER INFORMATION: Description of Artificial Sequence: Synthetic
      CXCL10/IP-10 polypeptide
<220> FEATURE:
<223> OTHER INFORMATION: L-Protein

<400> SEQUENCE: 272

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro
65                  70                  75


<210> SEQ ID NO 273
<211> LENGTH: 73
<212> TYPE: PRT
<213> ORGANISM: Artificial Sequence
<220> FEATURE:
<223> OTHER INFORMATION: Description of Artificial Sequence: Synthetic
      CXCL11/I-TAC  polypeptide
<220> FEATURE:
<223> OTHER INFORMATION: L-Protein

<400> SEQUENCE: 273

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70


<210> SEQ ID NO 274
<211> LENGTH: 72
<212> TYPE: PRT
<213> ORGANISM: Artificial Sequence
<220> FEATURE:
<223> OTHER INFORMATION: Description of Artificial Sequence: Synthetic
      CXCL12alpha/SDF-1alpha polypeptide
<220> FEATURE:
<223> OTHER INFORMATION: L-Protein

<400> SEQUENCE: 274

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys Met
65                  70
```

```
<210> SEQ ID NO 275
<211> LENGTH: 72
<212> TYPE: PRT
<213> ORGANISM: Artificial Sequence
<220> FEATURE:
<223> OTHER INFORMATION: Description of Artificial Sequence: Synthetic
      CXCL12beta/SDF-1beta polypeptide
<220> FEATURE:
<223> OTHER INFORMATION: L-Protein

<400> SEQUENCE: 275

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys Met
65                  70


<210> SEQ ID NO 276
<211> LENGTH: 76
<212> TYPE: PRT
<213> ORGANISM: Artificial Sequence
<220> FEATURE:
<223> OTHER INFORMATION: Description of Artificial Sequence: Synthetic
      CX3CL1/Fractalkine polypeptide
<220> FEATURE:
<223> OTHER INFORMATION: L-Protein

<400> SEQUENCE: 276

Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
            20                  25                  30

Ser Cys Gly Lys Arg Ala Ile Ile Leu Glu Thr Arg Gln His Arg Leu
        35                  40                  45

Phe Cys Ala Asp Pro Lys Glu Gln Trp Val Lys Asp Ala Met Gln His
    50                  55                  60

Leu Asp Arg Gln Ala Ala Ala Leu Thr Arg Asn Gly
65                  70                  75


<210> SEQ ID NO 277
<211> LENGTH: 93
<212> TYPE: PRT
<213> ORGANISM: Artificial Sequence
<220> FEATURE:
<223> OTHER INFORMATION: Description of Artificial Sequence: Synthetic
      XCL1/Lymphotactin polypeptide
<220> FEATURE:
<223> OTHER INFORMATION: L-Protein

<400> SEQUENCE: 277

Val Gly Ser Glu Val Ser Asp Lys Arg Thr Cys Val Ser Leu Thr Thr
1               5                   10                  15

Gln Arg Leu Pro Val Ser Arg Ile Lys Thr Tyr Thr Ile Thr Glu Gly
            20                  25                  30

Ser Leu Arg Ala Val Ile Phe Ile Thr Lys Arg Gly Leu Lys Val Cys
        35                  40                  45

Ala Asp Pro Gln Ala Thr Trp Val Arg Asp Val Val Arg Ser Met Asp
```

```
    50                  55                  60

Arg Lys Ser Asn Thr Arg Asn Asn Met Ile Gln Thr Lys Pro Thr Gly
65                  70                  75                  80

Thr Gln Gln Ser Thr Asn Thr Ala Val Thr Leu Thr Gly
                85                  90


<210> SEQ ID NO 278
<211> LENGTH: 40
<212> TYPE: RNA
<213> ORGANISM: Artificial Sequence
<220> FEATURE:
<223> OTHER INFORMATION: Description of Artificial Sequence: Synthetic
      biotinylated NOX-E36 sequence
<220> FEATURE:
<223> OTHER INFORMATION: L-RNA
<220> FEATURE:
<223> OTHER INFORMATION: 5'-Biotin

<400> SEQUENCE: 278

gcacgucccu caccggugca agugaagccg uggcucugcg                           40


<210> SEQ ID NO 279
<211> LENGTH: 40
<212> TYPE: RNA
<213> ORGANISM: Artificial Sequence
<220> FEATURE:
<223> OTHER INFORMATION: Description of Artificial Sequence: Synthetic
      POC sequence
<220> FEATURE:
<223> OTHER INFORMATION: L-RNA

<400> SEQUENCE: 279

uaaggaaacu cggucugaug cgguagcgcu gugcagagcu                           40


<210> SEQ ID NO 280
<211> LENGTH: 40
<212> TYPE: RNA
<213> ORGANISM: Artificial Sequence
<220> FEATURE:
<223> OTHER INFORMATION: Description of Artificial Sequence: Synthetic
      POC-PEG sequence
<220> FEATURE:
<223> OTHER INFORMATION: L-RNA
<220> FEATURE:
<223> OTHER INFORMATION: 5'PEG

<400> SEQUENCE: 280

uaaggaaacu cggucugaug cgguagcgcu gugcagagcu                           40


<210> SEQ ID NO 281
<211> LENGTH: 11
<212> TYPE: DNA
<213> ORGANISM: Artificial Sequence
<220> FEATURE:
<223> OTHER INFORMATION: Description of Artificial Sequence: Synthetic
      mNOX-E36 Capture probe
<220> FEATURE:
<223> OTHER INFORMATION: 3'-(Spacer18)2-NH4+

<400> SEQUENCE: 281

ccaatgtcgc c                                                          11


<210> SEQ ID NO 282
<211> LENGTH: 9
<212> TYPE: DNA
<213> ORGANISM: Artificial Sequence
<220> FEATURE:
<223> OTHER INFORMATION: Description of Artificial Sequence: Synthetic
      mNOX-E36 Detect probe
```

<220> FEATURE:
<223> OTHER INFORMATION: L-DNA
<220> FEATURE:
<223> OTHER INFORMATION: 5'-Biotin-(Spacer18)2

<400> SEQUENCE: 282 cgcagagcc 9

<210> SEQ ID NO 283
<211> LENGTH: 76
<212> TYPE: PRT
<213> ORGANISM: Equus caballus

<400> SEQUENCE: 283

```
Gln Pro Asp Ala Ile Asn Ser Pro Val Thr Cys Cys Tyr Thr Phe Thr
1               5                   10                  15

Gly Lys Lys Ile Ser Ser Gln Arg Leu Gly Ser Tyr Lys Arg Val Thr
            20                  25                  30

Ser Ser Lys Cys Pro Lys Glu Ala Val Ile Phe Lys Thr Ile Leu Ala
        35                  40                  45

Lys Glu Ile Cys Ala Asp Pro Glu Gln Lys Trp Val Gln Asp Ala Val
    50                  55                  60

Lys Gln Leu Asp Lys Lys Ala Gln Thr Pro Lys Pro
65                  70                  75
```

<210> SEQ ID NO 284
<211> LENGTH: 76
<212> TYPE: PRT
<213> ORGANISM: Bos taurus

<400> SEQUENCE: 284

```
Gln Pro Asp Ala Ile Asn Ser Gln Val Ala Cys Cys Tyr Thr Phe Asn
1               5                   10                  15

Ser Lys Lys Ile Ser Met Gln Arg Leu Met Asn Tyr Arg Arg Val Thr
            20                  25                  30

Ser Ser Lys Cys Pro Lys Glu Ala Val Ile Phe Lys Thr Ile Leu Gly
        35                  40                  45

Lys Glu Leu Cys Ala Asp Pro Lys Gln Lys Trp Val Gln Asp Ser Ile
    50                  55                  60

Asn Tyr Leu Asn Lys Lys Asn Gln Thr Pro Lys Pro
65                  70                  75
```

<210> SEQ ID NO 285
<211> LENGTH: 125
<212> TYPE: PRT
<213> ORGANISM: Rattus norvegicus

<400> SEQUENCE: 285

```
Gln Pro Asp Ala Val Asn Ala Pro Leu Thr Cys Cys Tyr Ser Phe Thr
1               5                   10                  15

Gly Lys Met Ile Pro Met Ser Arg Leu Glu Asn Tyr Lys Arg Ile Thr
            20                  25                  30

Ser Ser Arg Cys Pro Lys Glu Ala Val Val Phe Val Thr Lys Leu Lys
        35                  40                  45

Arg Glu Ile Cys Ala Asp Pro Asn Lys Glu Trp Val Gln Lys Tyr Ile
    50                  55                  60

Arg Lys Leu Asp Gln Asn Gln Val Arg Ser Glu Thr Thr Val Phe Tyr
65                  70                  75                  80

Lys Ile Ala Ser Thr Leu Arg Thr Ser Ala Pro Leu Asn Val Asn Leu
                85                  90                  95
```

```
Thr His Lys Ser Glu Ala Asn Ala Ser Thr Leu Phe Ser Thr Thr Thr
            100                 105                 110

Ser Ser Thr Ser Val Glu Val Thr Ser Met Thr Glu Asn
        115                 120                 125


<210> SEQ ID NO 286
<211> LENGTH: 50
<212> TYPE: RNA
<213> ORGANISM: Artificial Sequence
<220> FEATURE:
<223> OTHER INFORMATION: Description of Artificial Sequence: Synthetic
      MCP-1 binder sequence
<220> FEATURE:
<223> OTHER INFORMATION: L-RNA
<220> FEATURE:
<223> OTHER INFORMATION: 3'PEG

<400> SEQUENCE: 286

accggcgccu aaguaguuuc ccggagcgga guacggguug guuacagcgg                50


<210> SEQ ID NO 287
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287

csucccucac cggugcaagu gaagccgygg cuc                                  33


<210> SEQ ID NO 288
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288

cgucccucac cggugcaagu gaagccgugg cuc                                  33


<210> SEQ ID NO 289
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, u, g, unknown or other

<400> SEQUENCE: 289

agndrdgbkg gurgyargua aag                                             23


<210> SEQ ID NO 290
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290

aggugggugg uaguaaguaa ag                                              22
```

<210> SEQ ID NO 291
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 291
caggugggug guagaaugua aaga 24

<210> SEQ ID NO 292
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 292
gggggrcgcg ayc 13

<210> SEQ ID NO 293
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 293
ugcaauaaug 10

<210> SEQ ID NO 294
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 294
ggggggcgcg acc 13

<210> SEQ ID NO 295
<211> LENGTH: 44
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: L-RNA

<400> SEQUENCE: 295
ugcgcguagu gagaaacuac caacgacugg cuagagccgg cagc 44

<210> SEQ ID NO 296
<211> LENGTH: 44
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: D-RNA -continued

<400> SEQUENCE: 296
ugcgcguagu gagaaacuac caacgacugg cuagagccgg cagc 44

MCP-1 BINDING NUCLEIC ACIDS AND USE THEREOF

SEQUENCE LISTING

The instant application contains a Sequence Listing which has been submitted in ASCII format via EFS-Web and is hereby incorporated by reference in its entirety. Said ASCII copy, created on Jun. 24, 2011, is named 21315862.txt and is 99,966 bytes in size.

The present invention is related to nucleic acids binding to MCP-1, and the use thereof for the manufacture of a medicament and a diagnostic agent, respectively.

Human MCP-1 (monocyte chemoattractant protein-1; alternative names, MCAF [monocyte chemoattracting and activating factor]; CCL2; SMC-CF [smooth muscle cell-colony simulating factor]; HC-11; LDCF; GDCF; TSG-8; SCYA2; A2; SwissProt accession code, P13500) was characterized by three groups independently (Matsushima 1988; Rollins 1989; Yoshimura 1989). It consists of 76 amino acids and features a heparin binding site like all chemokines. The two intramolecular disulfide bonds confer a stable, rigid structure to the molecule. Furthermore, MCP-1 carries a pyroglutamate at its amino terminus. At Thr 71, a potential O-linked glycosylation site is located. Additional MCP family members exist both in humans (MCP-2, -3, -4) and mice (MCP-2, -3, -5). The human proteins are approximately 70% homologous to human MCP-1.

The structure of MCP-1 has been solved by NMR (Handel 1996) and X-ray (Lubkowski 1997). The MCP-1 monomer has the typical chemokine fold in which the amino-terminal cysteines are followed by a long loop that leads into three antiparallel β-pleated sheets in a Greek key motif. The protein terminates in an α helix that overlies the three β sheets (PDB data accession code 1 DOK).

Although the three-dimensional structure of MCP-1 forms from different mammalian species has generally been maintained, the amino acid sequence has not particularly well been conserved during evolution. Sequence alignment results demonstrate 55% overall sequence similarity between human and murine MCP-1 (also called JE) within the first 76 amino acids. Apart from the amino acid sequence, murine MCP-1 differs from human MCP-1 in molecular size (125 amino acids) and the extent of glycosylation. Murine MCP-1 contains a 49-amino acid carboxyterminal domain that is not present in human MCP-1 and is not required for in vitro bioactivity. Human MCP-1 shares the following percentage of identical amino acids with MCP-1 from:

| | |
|---|---|
| *Macaca mulatta* (Rhesus monkey) MCP-1 | 97% |
| *Sus scrofa* (Pig) MCP-1 | 79% |
| *Equus caballus* (Horse) | 78% |
| *Canis familiaris* (Dog) MCP-1 | 76% |
| *Oryctolagus cuniculus* (Rabbit) MCP-1 | 75% |
| *Bos taurus* (Bovine) | 72% |
| *Homo sapiens* MCP-3 | 71% |
| *Homo sapiens* Eotaxin | 64% |
| *Homo sapiens* MCP-2 | 62% |
| *Mus musculus* (Mouse) MCP-1 | 55% |
| *Rattus norvegicus* (Rat) MCP-1 | 55% |

Given this high degree of divergence it may be necessary to generate antagonists of rodent MCP-1 for successful performance of pharmacological studies in rodent models.

MCP-1 is a potent attractor of monocytes/macrophages, basophils, activated T cells, and NK cells. A wide variety of cell types, such as endothelial cells, epithelial cells, fibroblasts, keratinocytes, synovial cells, mesangial cells, osteoblasts, smooth muscle cells, as well as a multitude of tumor cells express MCP-1 (Baggiolini 1994). Its expression is stimulated by several types of proinflammatory agents such as IL-1β, TNF-α, IFN-γ, LPS (lipopolysaccharide), and GM-CSF.

Rather unusual in the promiscuous chemokine network, MCP-1 is highly specific in its receptor usage, binding only to the chemokine receptor CCR2 with high affinity. Like all chemokine receptors, CCR2 is a G-protein-coupled receptor (GPCR) (Dawson 2003). CCR2 seems to be expressed in two slightly different forms due to alternative splicing of the mRNA encoding the carboxyterminal region, CCR2a and CCR2b (Charo 1994). These receptors are expressed in monocytes, myeloid precursor cells and activated T cells (Myers 1995; Qin 1996). The dissociation constant of MCP-1 to the receptor transfected into HEK-293 cells is 260 pM which is in agreement with values measured on monocytes (Myers 1995; Van Riper 1993). Activation of CCR2 b on transfected HEK-293 cells with MCP-1 inhibits adenylyl cyclase at a concentration of 90 pM, and mobilizes intracellular calcium at slightly higher concentrations, seemingly independent of phosphatidyl inositol hydrolysis. The effects on adenylyl cyclase and intracellular calcium release are strongly inhibited by pertussis toxin, implying the involvement of $G_i$ type heterotrimeric G-proteins in signal transduction (Myers 1995).

MCP-1 is involved in monocyte recruitment into inflamed tissues. There, resident macrophages release chemokines such as MCP-1 and others, and cytokines like TNF, IL-1β and others, which activate endothelial cells to express a battery of adhesion molecules. The resulting "sticky" endothelium causes monocytes in the blood vessel to roll along its surface. Here, the monocytes encounter MCP-1 presented on the endothelial surface, which binds to CCR2 on monocytes and activates them. This finally leads to firm arrest, spreading of monocytes along the endothelium, and transmigration into the surrounding tissue, where the monocytes differentiate into macrophages and migrate towards the site of maximal MCP-1 concentration.

MCP-1 is a member of the chemokine family which is a family of small (ca. 8-14 kDa) heparin-binding, mostly basic and structurally related molecules. They are formed predominantly in inflamed tissues and regulate the recruitment, activation, and proliferation of white blood cells (leukocytes) (Baggiolini 1994; Springer 1995; Schall 1994). Chemokines selectively induce chemotaxis of neutrophils, eosinophils, basophils, monocytes, macrophages, mast cells, T and B cells. In addition to their chemotactic effect, they can selectively exert other effects in responsive cells like changes in cell shape, transient increase in the concentration of free intracellular calcium ions, degranulation, upregulation of integrins, formation of bioactive lipids such as leukotrienes, prostaglandins, thromboxanes, or respiratory burst (release of reactive oxygen species for destruction of pathogenic organisms or tumor cells). Thus, by provoking the release of further proinflammatory mediators, chemotaxis and extravasation of leukocytes towards sites of infection or inflammation, chemokines trigger escalation of the inflammatory response.

Based on the arrangement of the first two of four conserved cysteine residues, the chemokines are divided into four classes: CC or β-chemokines in which the cysteines are in tandem, CXC or α-chemokines, where they are separated by one additional amino acid residue, XC or γ chemokines with lymphotactin as only representative to date, that possess only one disulfide bridge, and CX3C-chemokines which feature three amino acid residues between the cysteines, with membrane-bound fractalkin as only class member known to date (Bazan 1997).

The CXC chemokines act primarily on neutrophils, in particular those CXC chemokines that carry the amino acid sequence ELR on their amino terminus. Examples of CXC chemokines that are active on neutrophils are IL-8, GROα, -β, and -γ, NAP-2, ENA-78 and GCP-2. The CC chemokines act on a larger variety of leukocytes, such as monocytes, macrophages, eosinophils, basophils, as well as T and B lymphocytes (Oppenheim 1991; Baggiolini 1994; Miller 1992; Jose 1994; Ponath 1996a). Examples of these are 1-309; MCP-1, -2, -3, -4, MIP-1α and -β, RANTES, and eotaxin.

Chemokines act through receptors that belong to a superfamily of seven transmembrane-spanning G protein-coupled receptors (GPCRs; Murphy 2000). Generally speaking, chemokine and chemokine receptor interactions tend to be promiscuous in that one chemokine can bind many chemokine receptors and conversely a single chemokine receptor can interact with several chemokines. Some known receptors for the CC chemokines include CCR1, which binds MIP-1α and RANTES (Neote 1993; Gao 1993); CCR2, which binds chemokines including MCP-1, -2, -3, and -4 (Charo 1994; Myers 1995; Gong 1997; Garcia-Zepeda 1996); CCR3, which binds chemokines including eotaxin, RANTES, and MCP-3 (Ponath 1996b); CCR4, which has been found to signal in response to MCP-1, MIP-1α, and RANTES (Power 1995); and CCR5, which has been shown to signal in response to MIP-1α and -β, and RANTES (Boring 1996; Raport 1996; Samson 1996).

As mentioned above, all four members of the MCP family (1-4) bind to CCR2, whereas MCP-2, MCP-3, and MCP-4 can also interact with CCR1 and CCR3 (Gong 1997; Heath 1997; Uguccioni 1997) and, in the case of MCP-2, CCR5 (Ruffing 1998). Another CC chemokine showing high homology with the MCP family is eotaxin, which was originally isolated from the bronchoalveolar lavage fluid taken from allergen-challenged, sensitized guinea pigs (Jose 1994). It has been shown that eotaxin is also able to activate CCR2 (Martinelli 2001).

The problem underlying the present invention is to provide a means which specifically interacts with MCP-1 and which means is suitable for the prevention and/or treatment of a chronic disease and chronic disorder, respectively. More specifically, the problem underlying the present invention is to provide for a nucleic acid based means which specifically interacts with MCP-1 and which nucleic acid is suitable for the prevention and/or treatment of a chronic disease and chronic disorder, respectively.

A still further problem underlying the present invention is to provide a means for the manufacture of a diagnostic agent for the treatment of a disease, whereby the disease is a chronic disease and chronic disorder, respectively.

In connection with the above specified problems the chronic disease and chronic disorder, respectively, is preferably a chronic respiratory disease, a chronic kidney disease and systemic lupus erythematosus.

These and other problems underlying the present invention are solved by the subject matter of the attached independent claims. Preferred embodiments may be taken from the dependent claims.

The problem underlying the instant invention is solved by the subject matter of the independent claims. Preferred embodiments are subject to the dependent claims.

More specifically, in a first aspect which is also a first embodiment of said first aspect, the problem underlying the instant invention is solved by a nucleic acid molecule capable of binding to MCP-1, whereby the nucleic acid molecule is for use as a medicament for the treatment and/or prevention of a chronic disease or chronic disorder, preferably selected from the group consisting of chronic respiratory disease, chronic kidney disease and systemic lupus erythematosus.

In a second aspect which is also a first embodiment of said second aspect, the problem underlying the instant invention is solved by a nucleic acid molecule capable of binding to MCP-1, whereby the nucleic acid molecule is for use as a diagnostic agent for the diagnosis of a chronic disease or chronic disorder, preferably selected from the group consisting of chronic respiratory disease, chronic kidney disease and systemic lupus erythematosus.

In a second embodiment of the first and the second aspect which is also an embodiment of the first embodiment of the first aspect and the second aspect, chronic respiratory disease is selected from the group of pneumonitis, lung and pleura inflammation, pleuritis, pleural effusion, lupus pneumonitis, chronic diffuse interstitial lung disease, pulmonary emboli, pulmonary hemorrhage, shrinking lung syndrome, pulmonary hypertension and chronic obstructive pulmonary disease and combinations thereof.

In a third embodiment of the first and the second aspect which is also an embodiment of the first and the second embodiment of the first aspect and the second aspect, pulmonary hypertension is selected from the group of pulmonary hypertension associated with left heart disease, pulmonary hypertension associated with lung diseases and/or hypoxemia, pulmonary hypertension due to chronic thrombotic and/or embolic disease, pulmonary arterial hypertension, preferably idiopathic pulmonary arterial hypertension, collagenose-associated pulmonary arterial hypertension, familial pulmonary arterial hypertension, pulmonary arterial hypertension associated with other diseases, and pulmonary arterial hypertension associated with venous or capillary diseases.

In a fourth embodiment of the first and the second aspect which is also an embodiment of the first, the second and the third embodiment of the first aspect and the second aspect, chronic obstructive pulmonary disease is chronic obstructive pulmonary disease with or without pulmonary vascular involvement.

In a fifth embodiment of the first and the second aspect which is also an embodiment of the first, second, third and fourth embodiment of the first aspect and the second aspect, chronic obstructive pulmonary disease is selected from the group of chronic bronchitis and emphysema.

In a sixth embodiment of the first and the second aspect which is also an embodiment of the first embodiment of the first aspect and the second aspect, chronic kidney disease is selected from the group of lupus nephritis, membranoproliferative glomerulonephritis, membranous glomerulonephritis, IgA nephropathy, post-streptococcal glomerulonephritis, rapidly progressive glomerulonephritis, nephritic syndrome, focal segmental glomerulosclerosis, diabetic nephropathy, nephrotic syndrome, and nephrotic syndrome, preferably lupus nephritis.

In a seventh embodiment of the first and the second aspect which is also an embodiment of the first, the second, the third, the fourth, the fifth and the sixth embodiment of the first aspect and the second aspect, the nucleic acid is selected from the group comprising type 1A nucleic acids, type 1B nucleic acids, type 2 nucleic acids, type 3 nucleic acids, type 4 nucleic acids and nucleic acids having a nucleic acid sequence according to any of SEQ ID NO: 87 to 115.

In an eighth embodiment of the first and the second aspect which is also an embodiment of the seventh embodiment of the first aspect and the second aspect, the type 2 nucleic acid comprises in 5'->3' direction a first stretch Box B1A, a second stretch Box B2, and a third stretch Box B1 B, whereby the first stretch Box B1A and the third stretch Box B1B optionally hybridize with each other, whereby upon hybridization a double-stranded structure is formed, the first stretch Box B1A comprises a nucleotide sequence selected from the group comprising ACGCA, CGCA and GCA, the second stretch Box B2 comprises a nucleotide sequence of CSUCCCUCACCGGUGCAAGUGAAGCCGYGGCUC (SEQ ID NO: 287), and the third stretch Box B1B comprises a nucleotide sequence selected from the group comprising UGCGU, UGCG and UGC.

In a ninth embodiment of the first and the second aspect which is also an embodiment of the eighth embodiment of the first aspect and the second aspect, the second stretch Box B2 comprises a nucleotide sequence of CGUCCCUCACCGGUGCAAGUGAAGCCGUGGCUC (SEQ ID NO: 288).

In a tenth embodiment of the first and the second aspect which is also an embodiment of the eighth and the ninth embodiment of the first aspect and the second aspect, a) the first stretch Box B1A comprises a nucleotide sequence of ACGCA, and the third stretch Box B1B comprises a nucleotide sequence of UGCGU; or b) the first stretch Box B1A comprises a nucleotide sequence of CGCA, and the third stretch Box B1B comprises a nucleotide sequence of UGCG; or c) the first stretch Box B1A comprises a nucleotide sequence of GCA, and the third stretch Box B1B comprises a nucleotide sequence of UGC or UGCG.

In an eleventh embodiment of the first and the second aspect which is also an embodiment of the eighth, ninth and tenth embodiment of the first aspect and the second aspect, the first stretch Box B1A comprises a nucleotide sequence of GCA.

In a twelfth embodiment of the first and the second aspect which is also an embodiment of the eighth, ninth, tenth and eleventh embodiment of the first aspect and the second aspect, preferably of the eleventh embodiment of the first and the second aspect the third stretch Box B1B comprises a nucleotide sequence of UGCG.

In a 13$^{th}$ embodiment of the first and the second aspect which is also an embodiment of the eighth, ninth, tenth, eleventh and twelfth embodiment of the first aspect and the second aspect, the nucleic acid comprises a nucleic acid sequence according to SEQ ID No:37, SEQ ID NO:116, SEQ ID NO:117 and SEQ ID NO:278.

In a 14$^{th}$ embodiment of the first and the second aspect which is also an embodiment of the first, second third, fourth, fifth, sixth and seventh embodiment of the first aspect and the second aspect, the type 3 nucleic acid comprises in 5'->3' direction a first stretch Box B1A, a second stretch Box B2A, a third stretch Box B3, a fourth stretch Box B2B, a fifth stretch Box B4, a sixth stretch Box B5A, a seventh stretch Box B6, an eighth stretch Box B5B and a ninth stretch Box B1B, whereby the first stretch Box B1A and the ninth stretch Box B1B optionally hybridize with each other, whereby upon hybridization a double-stranded structure is formed, the second stretch Box B2A and the fourth Box B2B optionally hybridize with each other, whereby upon hybridization a double-stranded structure is formed, the sixth stretch Box B5A and the eighth Box B5B optionally hybridize with each other, whereby upon hybridization a double-stranded structure is formed, the first stretch Box B1A comprises a nucleotide sequence which is selected from the group comprising GURCUGC, GKSYGC, KBBSC and BNGC, the second stretch Box B2A comprises a nucleotide sequence of GKMGU, the third stretch Box B3 comprises a nucleotide sequence of KRRAR, the fourth stretch Box B2B comprises a nucleotide sequence of ACKMC, the fifth stretch Box B4 comprises a nucleotide sequence selected from the group comprising CURYGA, CUWAUGA, CWRMGACW and UGCCAGUG, the sixth stretch Box B5A comprises a nucleotide sequence selected from the group comprising GGY and CWGC, the seventh stretch Box B6 comprises a nucleotide sequence selected from the group comprising YAGA, CKAAU and CCUUUAU, the eighth stretch Box B5B comprises a nucleotide sequence selected from the group comprising GCYR and GCWG, and the ninth stretch Box B1B comprises a nucleotide sequence selected from the group comprising GCAGCAC, GCRSMC, GSVVM and GCNV.

In a 15$^{th}$ embodiment of the first and the second aspect which is also an embodiment of the 14$^{th}$ embodiment of the first aspect and the second aspect, the third stretch Box B3 comprises a nucleotide sequence of GAGAA or UAAAA In a 16$^{th}$ embodiment of the first and the second aspect which is also an embodiment of the 14$^{th}$ and the 15$^{th}$ embodiment of the first aspect and the second aspect, the fifth stretch Box B4 comprises a nucleotide sequence of CAGCGACU or CAACGACU.

In a 17$^{th}$ embodiment of the first and the second aspect which is also an embodiment of the 14$^{th}$, 15$^{th}$ and 16$^{th}$ embodiment of the first aspect and the second aspect, the fifth stretch Box B4 comprises a nucleotide sequence of CAGCGACU and Box B3 comprises a nucleotide sequence of UAAAA.

In an 18$^{th}$ embodiment of the first and the second aspect which is also an embodiment of the 14$^{th}$, 15$^{th}$, and 16$^{th}$ embodiment of the first aspect and the second aspect, the fifth stretch Box B4 comprises a nucleotide sequence of CAACGACU and the third stretch Box B3 comprises a nucleotide sequence of GAGAA.

In a 19$^{th}$ embodiment of the first and the second aspect which is also an embodiment of the 14$^{th}$, 15$^{th}$, 16$^{th}$, 17$^{th}$ and 18$^{th}$ embodiment of the first aspect and the second aspect, the seventh stretch Box B6 comprises a nucleotide sequence of UAGA.

In a 20$^{th}$ embodiment of the first and the second aspect which is also an embodiment of the 14$^{th}$, 15$^{th}$, 16$^{th}$, 17$^{th}$, 18$^{th}$ and 19$^{th}$ embodiment of the first aspect and the second aspect, a) the first stretch Box B1A comprises a nucleotide sequence of GURCUGC, and the ninth stretch Box B1B comprises a nucleotide sequence of GCAGCAC; or b) the first stretch Box B1A comprises a nucleotide sequence of GKSYGC, and the ninth stretch Box B1B comprises a nucleotide sequence of GCRSMC; or c) the first stretch Box B1A comprises a nucleotide sequence of KBBSC, and the ninth stretch Box B1B comprises a nucleotide sequence of GSVVM; or d) the first stretch Box B1A comprises a nucleotide sequence of BNGC, and the ninth stretch Box B1B comprises a nucleotide sequence of GCNV.

In a 21$^{st}$ embodiment of the first and the second aspect which is also an embodiment of the 20$^{th}$ embodiment of the first aspect and the second aspect, a) the first stretch Box B1A comprises a nucleotide sequence of GUGCUGC, and the ninth stretch Box B1B comprises a nucleotide sequence of GCAGCAC; or b) the first stretch Box B1A comprises a nucleotide sequence of GUGCGC, and the ninth stretch Box B1B comprises a nucleotide sequence of GCGCAC; or c) the first stretch Box B1A comprises a nucleotide sequence of KKSSC, and the ninth stretch Box B1B comprises a nucleotide sequence of GSSMM; or d) the first stretch Box B1A comprises a nucleotide sequence of SNGC, and the ninth stretch Box B1B comprises a nucleotide sequence of GCNS.

In a 22$^{nd}$ embodiment of the first and the second aspect which is also an embodiment of the 21st embodiment of the first aspect and the second aspect, the first stretch Box B1A comprises a nucleotide sequence of GGGC, and the ninth stretch Box B1B comprises a nucleotide sequence of GCCC.

In a 23$^{rd}$ embodiment of the first and the second aspect which is also an embodiment of the 14$^{th}$, 15$^{th}$, 16$^{th}$, 17$^{th}$, 18$^{th}$, 19$^{th}$, 20$^{th}$, 21$^{st}$ and 22$^{nd}$ embodiment of the first aspect and the second aspect, second stretch Box B2A comprises a nucleotide sequence of GKMGU and the fourth stretch Box B2B comprises a nucleotide sequence of ACKMC.

In a 24$^{th}$ embodiment of the first and the second aspect which is also an embodiment of the 23$^{rd}$ embodiment of the first aspect and the second aspect, the second stretch Box B2A comprises a nucleotide sequence of GUAGU and the fourth stretch Box B2B comprises a nucleotide sequence of ACUAC.

In a 25th embodiment of the first and the second aspect which is also an embodiment of the 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$ and 24$^{th}$ embodiment of the first aspect and the second aspect, a) the sixth stretch Box B5A comprises a nucleotide sequence of GGY, and the eighth stretch Box B5B comprises a nucleotide sequence of GCYR; or b) the sixth stretch Box B5A comprises a nucleotide sequence of CWGC, and the eighth stretch Box B5B comprises a nucleotide sequence of GCWG.

In a 26$^{th}$ embodiment of the first and the second aspect which is also an embodiment of the 25$^{th}$ embodiment of the first aspect and the second aspect, the sixth stretch Box B5A comprises a nucleotide sequence of GGC, and the eighth stretch Box B5B comprises a nucleotide sequence of GCCG.

In a 27th embodiment of the first and the second aspect which is also an embodiment of the 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24th, 25$^{th}$ and 26$^{th}$ embodiment of the first aspect and the second aspect, preferably of the 25$^{th}$ and the 26$^{th}$ embodiment of the first and the second aspect, the sixth stretch Box B5A hybridizes with the nucleotides GCY of the eighth stretch Box B5B.

In a 28th embodiment of the first and the second aspect which is also an embodiment of the 14$^{th}$, 15$^{th}$, 16$^{th}$, 17$^{th}$, and, 19$^{th}$, 20$^{th}$, 21$^{st}$, 22$^{nd}$, 23$^{rd}$, 24$^{th}$, 25$^{th}$ embodiment of the first aspect and the second aspect, the nucleic acid comprises a nucleic acid sequence according to SEQ ID NO:56.

In a 29th embodiment of the first and the second aspect which is also an embodiment of the 14$^{th}$, 15$^{th}$, 16$^{th}$, and 18$^{th}$, 19$^{th}$, 20$^{th}$, 21$^{st}$, 22$^{nd}$, 23$^{rd}$, 24th, 25$^{th}$, 26$^{th}$ and 27$^{th}$ embodiment of the first aspect and the second aspect, the nucleic acid comprises a nucleic acid sequence selected from the group comprising the nucleic acid sequences according to SEQ ID NO:57 to 61, SEQ ID NO:67 to 71 and SEQ ID NO:73.

In a 30$^{th}$ embodiment of the first and the second aspect which is also an embodiment of the first, second, third, fourth, fifth, sixth and seventh embodiment of the first aspect and the second aspect, the type 4 nucleic acid comprises in 5'->3' direction a first stretch Box B1A, a second stretch Box B2, a third stretch Box B1B whereby the first stretch Box B1A and the third stretch Box B1B optionally hybridize with each other, whereby upon hybridization a double-stranded structure is formed, the first stretch Box B1A comprises a nucleotide sequence selected from the group comprising AGCGUGDU, GCGCGAG, CSKSUU, GUGUU, and UGUU;

the second stretch Box B2 comprises a nucleotide sequence selected from the group comprising AGNDRDGBKGGURGYARGUAAAG (SEQ ID NO: 289), AGGUGGGUGGUAGUAAGUAAAG (SEQ ID NO: 290) and CAGGUGGGUGGUAGAAUGUAAAGA (SEQ ID NO: 291), and the third stretch Box B1B comprises a nucleotide sequence selected from the group comprising GNCASGCU, CUCGCGUC, GRSMSG, GRCAC, and GGCA.

In a 31$^{st}$ embodiment of the first and the second aspect which is also an embodiment of the 30$^{th}$ embodiment of the first aspect and the second aspect, a) the first stretch Box B1A comprises a nucleotide sequence of GUGUU, and the third stretch Box B1B comprises a nucleotide sequence of GRCAC;

b) the first stretch Box B1A comprises a nucleotide sequence of GCGCGAG, and the third stretch Box B1B comprises a nucleotide sequence of CUCGCGUC; or c) the first stretch Box B1A comprises a nucleotide sequence of CSKSUU, and the third stretch Box B1B comprises a nucleotide sequence of GRSMSG, or d) the first stretch Box B1A comprises a nucleotide sequence of UGUU, and the third stretch Box B1B comprises a nucleotide sequence of GGCA, or e) the first stretch Box B1A comprises a nucleotide sequence of AGCGUGDU, and the third stretch Box B1B comprises a nucleotide sequence of GNCASGCU.

In a 32$^{nd}$ embodiment of the first and the second aspect which is also an embodiment of the 31$^{st}$ embodiment of the first aspect and the second aspect, the first stretch Box B1A comprises a nucleotide sequence of CSKSUU and the third stretch Box B1B comprises a nucleotide sequence of GRSMSG.

In a 33$^{rd}$ embodiment of the first and the second aspect which is also an embodiment of the 32$^{nd}$ embodiment of the first aspect and the second aspect, the first stretch Box B1A comprises a nucleotide sequence of CCGCUU and the third stretch Box B1B comprises a nucleotide sequence of GGGCGG.

In a 34$^{th}$ embodiment of the first and the second aspect which is also an embodiment of the 30$^{th}$, 31$^{st}$, 32$^{nd}$ and 33$^{rd}$ embodiment of the first aspect and the second aspect, the second stretch Box B2 comprises a nucleotide sequence of AGGUGGGUGGUAGUAAGUAAAG (SEQ ID NO: 290).

In a 35$^{th}$ embodiment of the first and the second aspect which is also an embodiment of the 30$^{th}$, 31$^{st}$, 32$^{nd}$, 33$^{rd}$ and the 34$^{th}$ embodiment of the first aspect and the second aspect, the nucleic acid comprises a nucleic acid sequence according to SEQ ID NO:80 and SEQ ID NO:81.

In a 36$^{th}$ embodiment of the first and the second aspect which is also an embodiment of the first, second, third, fourth, fifth, sixth and seventh embodiment of the first aspect and the second aspect, the type 1A nucleic acid comprises in 5'->3' direction a first stretch Box B1A, a second stretch Box B2, a third stretch Box B3, a fourth stretch Box B4, a fifth stretch Box B5, a sixth stretch Box B6and a seventh stretch Box B1B, whereby the first stretch Box B1A and the seventh stretch Box B1B optionally hybridize with each other, whereby upon hybridization a double-stranded structure is formed, the first stretch Box B1A comprises a nucleotide sequence of AGCRUG, the second stretch Box B2comprises a nucleotide sequence of CCCGGW, the third stretch Box B3comprises a nucleotide sequence of GUR, the fourth stretch Box B4comprises a nucleotide sequence of RYA, the fifth stretch Box B5comprises a nucleotide sequence of GGGGGRCGCGAYC (SEQ ID NO: 292)

the sixth stretch Box B6comprises a nucleotide sequence of UGCAAUAAUG (SEQ ID NO: 293) or URYAWUUG, and the seventh stretch Box B1B comprises a nucleotide sequence of CRYGCU.

In a 37$^{th}$ embodiment of the first and the second aspect which is also an embodiment of the 36$^{th}$ embodiment of the first aspect and the second aspect, the first stretch Box B1A comprises a nucleotide sequence of AGCGUG.

In a 38$^{th}$ embodiment of the first and the second aspect which is also an embodiment of the 36$^{th}$ and 37$^{th}$ embodiment of the first aspect and the second aspect, the second stretch Box B2 comprises a nucleotide sequence of CCCGGU.

In a 39$^{th}$ embodiment of the first and the second aspect which is also an embodiment of the 36$^{th}$, 37$^{th}$ and 38$^{th}$ embodiment of the first aspect and the second aspect, the third stretch Box B3 comprises a nucleotide sequence of GUG.

In a 40$^{th}$ embodiment of the first and the second aspect which is also an embodiment of the 36$^{th}$, 37$^{th}$, 38$^{th}$ and 39$^{th}$ embodiment of the first and the second aspect the fourth stretch Box B4 comprises a nucleotide sequence of GUA.

In a 41$^{st}$ embodiment of the first and the second aspect which is also an embodiment of the 36$^{th}$, 37$^{th}$, 38$^{th}$, 39$^{th}$ and 40$^{th}$ embodiment of the first aspect and the second aspect, the fifth stretch Box B5 comprises a nucleotide sequence of GGGGGGCGCGACC (SEQ ID NO: 294)

In a 42$^{nd}$ embodiment of the first and the second aspect which is also an embodiment of the 36$^{th}$, 37$^{th}$, 38$^{th}$, 39$^{th}$, 40$^{th}$ and 41$^{st}$ embodiment of the first aspect and the second aspect, the sixth stretch Box B6 comprises a nucleotide sequence of UACAUUUG.

In a 43$^{rd}$ embodiment of the first and the second aspect which is also an embodiment of the 36$^{th}$, 37$^{th}$, 38$^{th}$, 39$^{th}$, 40$^{th}$, 41$^{st}$ and 42$^{nd}$ embodiment of the first aspect and the second aspect, the seventh stretch Box B1B comprises a nucleotide sequence of CACGCU.

In a 44$^{th}$ embodiment of the first and the second aspect which is also an embodiment of the 36$^{th}$, 37$^{th}$, 38$^{th}$, 39$^{th}$, 40$^{th}$, 41$^{st}$, 42$^{nd}$ and 43$^{rd}$ embodiment of the first aspect and the second aspect, the nucleic acid comprises a nucleic acid sequence according to SEQ ID NO:21.

In a 45$^{th}$ embodiment of the first and the second aspect which is also an embodiment of the first, second, third, fourth, fifth, sixth and seventh embodiment of the first aspect and the second aspect, the type 1B nucleic acid comprises in 5'->3' direction a first stretch Box B1A, a second stretch Box B2, a third stretch Box B3, a fourth stretch Box B4, a fifth stretch Box B5, a sixth stretch Box B6 and a seventh stretch Box B1B, whereby the first stretch Box B1A and the seventh stretch Box B1B optionally hybridize with each other, whereby upon hybridization a double-stranded structure is formed, the first stretch Box B1A comprises a nucleotide sequence of AGYRUG, the second stretch Box B2 comprises a nucleotide sequence of CCAGCU or CCAGY, the third stretch Box B3 comprises a nucleotide sequence of GUG, the fourth stretch Box B4 comprises a nucleotide sequence of AUG, the fifth stretch Box B5 comprises a nucleotide sequence of GGGGGGCGCGACC (SEQ ID NO: 294)

the sixth stretch Box B6 comprises a nucleotide sequence of CAUUUUA or CAUUUA, and the seventh stretch Box B1B comprises a nucleotide sequence of CAYRCU.

In a 46$^{th}$ embodiment of the first and the second aspect which is also an embodiment of the 45$^{th}$ embodiment of the first aspect and the second aspect, the first stretch Box B1A comprises a nucleotide sequence of AGCGUG.

In a $47^{th}$ embodiment of the first and the second aspect which is also an embodiment of the $45^{th}$ and $46^{th}$ embodiment of the first aspect and the second aspect, the second stretch Box B2 comprises a nucleotide sequence of CCAGU.

In a $48^{th}$ embodiment of the first and the second aspect which is also an embodiment of the $45^{th}$, $46^{th}$ and $47^{th}$ embodiment of the first aspect and the second aspect, the sixth stretch Box B6 comprises a nucleotide sequence of CAUUUUA.

In a $49^{th}$ embodiment of the first and the second aspect which is also an embodiment of the $45^{th}$, $46^{th}$, $47^{th}$, and $48^{th}$ embodiment of the first and the second aspect, the seventh stretch Box B1B comprises a nucleotide sequence of CACGCU.

In a $50^{th}$ embodiment of the first and the second aspect which is also an embodiment of the $45^{th}$, $46^{th}$, $47^{th}$, $48^{th}$ and $49^{th}$ embodiment of the first and the second aspect, the nucleic acid comprises a nucleic acid sequence according to SEQ ID NO:28 and SEQ ID NO:27.

In a $51^{st}$ embodiment of the first and the second aspect which is also an embodiment of any of the first to the $50^{th}$ embodiment of the first and the second aspect the MCP-1 is selected from the group comprising monkey MCP-1, horse MCP-1, rabbit MCP-1, bovine MCP-1, canine MCP-1, porcine MCP-1 and human MCP-1.

In a $52^{nd}$ embodiment of the first and the second aspect which is also an embodiment of any of the first to the $51^{st}$ embodiment of the first and the second aspect, the nucleic acid is capable of binding human MCP-1.

In a $53^{rd}$ embodiment of the first and the second aspect which is also an embodiment of any of the first to the $52^{nd}$ embodiment of the first and the second aspect, preferably of the $52^{nd}$ embodiment of the first and the second aspect the MCP-1 has an amino acid sequence according to SEQ ID NO:1.

In a $54^{th}$ embodiment of the first and the second aspect which is also an embodiment of any of the first to the $53^{rd}$ embodiment of the first and the second aspect, the nucleic acid comprises a modification, whereby the modification is preferably a high molecular weight moiety and/or whereby the modification preferably allows to modify the characteristics of the nucleic acid according to any of claims 1 to 54 in terms of residence time in the animal or human body, preferably the human body.

In a $55^{th}$ embodiment of the first and the second aspect which is also an embodiment of the $54^{th}$ embodiment of the first and the second aspect, the modification is selected from the group comprising a HES moiety, a PEG moiety, biodegradable modifications and combinations thereof.

In a $56^{th}$ embodiment of the first and the second aspect which is also an embodiment of the $55^{th}$ embodiment of the first and the second aspect, the modification is a PEG moiety consisting of a straight or branched PEG, whereby the molecular weight of the PEG moiety is preferably from about 20,000 to 120,000 Da, more preferably from about 30,000 to 80,000 Da and most preferably about 40,000 Da.

In a $57^{th}$ embodiment of the first and the second aspect which is also an embodiment of the $55^{th}$ embodiment of the first and the second aspect, the modification is a HES moiety, whereby preferably the molecular weight of the HES moiety is from about 10,000 to 200,000 Da, more preferably from about 30,000 to 170.000 Da and most preferably about 150,000 Da.

In a $58^{th}$ embodiment of the first and the second aspect which is also an embodiment of the $54^{th}$, $55^{th}$, $56^{th}$ and $57^{th}$ embodiment of the first and the second aspect, the modification is coupled to the nucleic acid via a linker, whereby the linker is a linker or a biodegradable linker.

In a $59^{th}$ embodiment of the first and the second aspect which is also an embodiment of the $54^{th}$, $55^{th}$, $56^{th}$, $57^{th}$ and $58^{th}$ embodiment of the first and the second aspect, the modification is coupled to the nucleic acid at its 5'-terminal nucleotide and/or its 3'-terminal nucleotide and/or to a nucleotide of the nucleic acid between the 5'-terminal nucleotide and the 3'-terminal nucleotide.

In a $60^{th}$ embodiment of the first and the second aspect which is also an embodiment of any of the first to the $59^{th}$ embodiment of the first and the second aspect, the nucleotides of or the nucleotides forming the nucleic acid are L-nucleotides.

In a $61^{st}$ embodiment of the first and the second aspect which is also an embodiment of any of the first to the $60^{th}$ embodiment of the first and the second aspect, the nucleic acid is an L-nucleic acid.

In a $62^{nd}$ embodiment of the first and the second aspect which is also an embodiment of any of the first to the $60^{th}$ embodiment of the first and the second aspect, the moiety of the nucleic acid capable of binding MCP-1 consists of L-nucleotides.

In a third aspect which is also a first embodiment of said third aspect, the problem underlying the instant invention is solved by a pharmaceutical composition comprising a nucleic acid molecule as defined in any embodiment of the first and the second aspect, and optionally a further constituent, whereby the further constituent is selected from the group comprising pharmaceutically acceptable excipients, pharmaceutically acceptable carriers and pharmaceutically active agents and whereby the pharmaceutical composition is for the treatment and/or prevention of a chronic disease or chronic disorder.

In a second embodiment of the third aspect which is also an embodiment of the first embodiment of the third aspect, the pharmaceutical composition comprises a nucleic acid molecule as defined in any embodiment of the first and the second aspect, and a pharmaceutically acceptable carrier.

In a third embodiment of the third aspect which is also an embodiment of the first and the second embodiment of the third aspect, the chronic disease or chronic disorder is as defined in any of the preceding claims.

In a fourth embodiment of the third aspect which is also an embodiment of the first, second and third embodiment of the third aspect, the pharmaceutical composition comprises a second pharmaceutically active agent, whereby such second pharmaceutically active agent is an immunosuppressive agent.

In a fifth embodiment of the third aspect which is also an embodiment of the fourth embodiment of the third aspect, the immunosuppressive agent is contained in said pharmaceutical composition as a separate dosage unit.

In a sixth embodiment of the third aspect which is also an embodiment of the fourth and the fifth embodiment of the third aspect, the pharmaceutical composition contains less of the immunosuppressive agent than a pharmaceutical composition containing the immunosuppressive agent as a monotherapy.

In a seventh embodiment of the third aspect which is also an embodiment of the fourth, fifth, and, sixth embodiment of the third aspect, dosage unit of the immunosuppressive agent contains less than the dosage unit of the immunosuppressive agent if used as a monotherapy.

In an eighth embodiment of the third aspect which is also an embodiment of the sixth and seventh embodiment of the third aspect, the reduction of the immunosuppressive agent subject to the sixth and seventh embodiment of the third aspect is at least 10%, at least 20%, at least 30%, at least 40%, at least 50%, at least 60%, at least 70%, at least 80% or at least 90%, preferably at least 75%.

In a ninth embodiment of the third aspect which is also an embodiment of the fourth, fifth, sixth, seventh and eighth embodiment of the third aspect, the immunosuppressive agent is selected from the group comprising cyclophosphamide and mycophenolate mofetil.

In a tenth embodiment of the third aspect which is also an embodiment of the first, second, third, fourth, fifth, sixth, seventh, eighth and ninth embodiment of the third aspect, more preferably of the eighth and the ninth embodiment of the third aspect, the chronic disease is lupus nephritis and/or pneumonitis.

In an eleventh embodiment of the third aspect which is also an embodiment of the first, second and third embodiment of the third aspect, the pharmaceutical composition comprises a second pharmaceutically active agent, whereby such second pharmaceutically active agent is an anti-inflammatory agent.

In a twelfth embodiment of the third aspect which is also an embodiment of the eleventh embodiment of the third aspect, the anti-inflammatory agent is contained in said pharmaceutical composition as a separate dosage unit.

In a $13^{th}$ embodiment of the third aspect which is also an embodiment of the eleventh and twelfth embodiment of the third aspect, the pharmaceutical composition contains less of the anti-inflammatory agent than a pharmaceutical composition containing the anti-inflammatory agent as a monotherapy.

In a $14^{th}$ embodiment of the third aspect which is also an embodiment of the eleventh twelfth and $13^{th}$ embodiment of the third aspect, the dosage unit of the anti-inflammatory agent contains less than the dosage unit of the immunosuppressive agent if used as a monotherapy.

In a $15^{th}$ embodiment of the third aspect which is also an embodiment of the $13^{th}$ and $14^{th}$ embodiment of the third aspect, the reduction of the immunosuppressive agent subject to the $13^{th}$ and $14^{th}$ embodiment of the third aspect is at least 10%, at least 20%, at least 30%, at least 40%, at least 50%, at least 60%, at least 70%, at least 80% or at least 90%, preferably at least 75%.

In a $16^{th}$ embodiment of the third aspect which is also an embodiment of the eleventh, twelfth, $13^{th}$, $14^{th}$ and $15^{th}$ embodiment of the third aspect, the anti-inflammatory agent is selected from the group comprising dexamethasone and roflumilast, preferably the anti-inflammatory agent is dexamethasone.

In a $17^{th}$ embodiment of the third aspect which is also an embodiment of the eleventh. Twelfth, $13^{th}$, $14^{th}$, $15^{th}$ and 16th embodiment of the third aspect, preferably of the $15^{th}$ and $16^{th}$ embodiment of the third aspect, the chronic disease is a chronic respiratory disease and more preferably COPD.

In a fourth aspect which is also a first embodiment of said fourth aspect, the problem underlying the instant invention is solved by a nucleic acid molecule as defined in any of embodiments 1 to 62 of the first and the second aspect, for use in a method for the treatment of a subject suffering from or being at risk of developing a chronic disease or chronic disorder, whereby the method comprises administering to the subject a pharmaceutically active amount of the nucleic acid molecule.

In a second embodiment of the fourth aspect the chronic disease or chronic disorder is as defined in any of the preceding claims.

In a third embodiment of the fourth aspect which is also an embodiment of the first and the second embodiment of the fourth aspect, the method further comprises the step of administering to the subject an immunosuppressive agent.

In a fourth embodiment of the fourth aspect which is also an embodiment of the third embodiment of the fourth aspect, the amount of the immunosuppressive agent administered in the course of the treatment is less than the amount of the immunosuppressive agent which would have been administered to the subject as monotherapy.

In a fifth embodiment of the fourth aspect which is also an embodiment of the fourth embodiment of the fourth aspect, the amount of the immunosuppressive agent is reduced by at least 10%, at least 20%, at least 30%, at least 40%, at least 50%, at least 60%, at least 70%, at least 80% or at least 90%, preferably at least 75%.

In a sixth embodiment of the fourth aspect which is also an embodiment of the first, second, third, fourth, and fifth embodiment of the fourth aspect, the immunosuppressive agent is selected from the group comprising cyclophosphamide and mycophenolate mofetil.

In a seventh embodiment of the fourth aspect which is also an embodiment of the first, second, third, fourth, fifth and sixth embodiment of the fourth aspect, and more specifically of the fifth and the sixth embodiment of the fourth aspect the chronic disease is a chronic kidney disease, preferably lupus nephritis, and/or pneumonitis.

In an eighth embodiment of the fourth aspect which is also an embodiment of the first, and the second embodiment of the fourth aspect the method further comprises the step of administering to the subject an anti-inflammatory agent.

In a ninth embodiment of the fourth aspect which is also an embodiment of the eighth embodiment of the fourth aspect, the amount of the anti-inflammatory agent administered in the course of the treatment is less than the amount of the immunosuppressive agent which would have been administered to the subject as monotherapy.

In a tenth embodiment of the fourth aspect which is also an embodiment of the ninth embodiment of the fourth aspect, the amount of the immunosuppressive agent is reduced by at least 10%, at least 20%, at least 30%, at least 40%, at least 50%, at least 60%, at least 70%, at least 80% or at least 90%, preferably at least 75%.

In an eleventh embodiment of the fourth aspect which is also an embodiment of the eighth, ninth and tenth embodiment of the fourth aspect, the anti-inflammatory agent is selected from the group comprising dexamethasone and roflumilast, preferably the anti-inflammatory agent is dexamethasone.

In a twelfth embodiment of the fourth aspect which is also an embodiment of the eighth, ninth, tenth and eleventh embodiment of the fourth aspect, and more specifically of the tenth and the eleventh embodiment of the fourth aspect the chronic disease is a chronic respiratory disease, preferably COPD.

In a fifth aspect which is also a first embodiment of said fifth aspect, the problem underlying the instant invention is solved by the use of a nucleic acid molecule as defined in any of embodiments 1 to 62 of the first and the second aspect, for the manufacture of a medicament for the treatment and/or prevention of a chronic disease or a chronic disorder.

In a second embodiment of the fifth aspect, the disease or disorder is one as defined in connection with any of embodiments 1 to 62 of the first and the second aspect.

In a third embodiment of the fifth aspect, which is also an embodiment of the first and the second embodiment of the fifth aspect, the medicament is for use in human medicine or for veterinary medicine.

In a sixth aspect which is also a first embodiment of said sixth aspect, the problem underlying the instant invention is solved by a method for the diagnosis of a chronic disease or a chronic disorder comprising the following steps:

contacting a sample from a subject which is to be tested whether or not to suffer from or being at risk to develop a chronic disease or chronic disorder, with a nucleic acid molecule as defined in any of embodiments 1 to 62 of the first and the second aspect; and directly or indirectly detecting whether a complex is formed comprising MCP-1 and the nucleic acid molecule.

In a second embodiment of the sixth aspect the chronic disease or chronic disorder is a chronic disorder or chronic disease as defined in connection with any of embodiments 1 to 62 of the first and the second aspect.

In a seventh aspect which is also a first embodiment of said seventh aspect, the problem underlying the instant invention is solved by the use of a nucleic acid molecule as defined in connection with any of embodiments 1 to 62 of the first and the second aspect, for the manufacture of a diagnostic agent for the diagnosis of a chronic disease or chronic disorder as defined in connection with any of embodiments 1 to 62 of the first and the second aspect.

It will be understood by a person skilled in the art that the following embodiments and features may also be realized in connection with the features and embodiments described herein, in particular in connection with the aspects and embodiments as subject to the claims attached hereto.

As used herein, the terms chronic disease and chronic disorder preferably refer to a chronic respiratory disease, a chronic kidney disease and systemic lupus erythematosus. Preferably the term chronic respiratory disease as used herein comprises pneumonitis, lung and pleura inflammation, pleuritis, pleural effusion, lupus pneumonitis, chronic diffuse interstitial lung disease, pulmonary emboli, pulmonary hemorrhage, shrinking lung syndrome, pulmonary hypertension and chronic obstructive pulmonary disease and combinations thereof. More preferably, the term pulmonary hypertension comprises pulmonary hypertension associated with left heart disease, pulmonary hypertension associated with lung diseases and/or hypoxemia, pulmonary hypertension due to chronic thrombotic and/or embolic disease, pulmonary arterial hypertension, preferably idiopathic pulmonary arterial hypertension, collagenose-associated pulmonary arterial hypertension, familial pulmonary arterial hypertension, pulmonary arterial hypertension associated with other diseases, and pulmonary arterial hypertension associated with venous or capillary diseases. Furthermore, the term chronic obstructive pulmonary disease preferably comprises chronic obstructive pulmonary disease with or without pulmonary vascular involvement. Finally, the term chronic obstructive pulmonary disease preferably comprises those selected from the group of chronic bronchitis and emphysema. Also, the term chronic kidney disease preferably comprises lupus nephritis, membranoproliferative glomerulonephritis, membranous glomerulonephritis, IgA nephropathy, post-streptococcal glomerulonephritis, rapidly progressive glomerulonephritis, nephritic syndrome, focal segmental glomerulosclerosis, diabetic nephropathy, nephrotic syndrome, and nephrotic syndrome, preferably lupus nephritis.

The features of the nucleic acid according to the present invention as described herein can be realised in any aspect of the present invention where the nucleic acid is used, either alone or in any combination.

Human as well as murine MCP-1 are basic proteins having the amino acid sequence according to SEQ ID NOs:1 and 2, respectively.

The finding that short high affinity binding nucleic acids to MCP-1 could be identified, is insofar surprising as Eaton et al. (1997) observed that the generation of aptamers, i.e. D-nucleic acids binding to a target molecule, directed to a basic protein is in general very difficult because this kind of target produces a high but non-specific signal-to-noise ratio. This high signal-to-noise ratio results from the high non-specific affinity shown by nucleic acids for basic targets such as MCP-1.

As outlined in more detail in the claims and example 1, the present inventors could more surprisingly identify a number of different MCP-1 binding nucleic acid molecules, whereby most of the nucleic acids could be characterised in terms of stretches of nucleotide which are also referred to herein as Boxes. The various MCP-1 binding nucleic acid molecules can be categorised based on said Boxes and some structural features and elements, respectively. The various categories thus defined are also referred to herein as types and more specifically as type 1A, type 1B, type 2, type 3 and type 4.

It is within the present invention that the nucleic acids according to the present invention or stretches thereof or any part(s) thereof can, in principle, hybridise with each other. Upon such hybridisation a double-stranded structure is formed. It will be acknowledged by the ones skilled in the art that such hybridisation may or may not occur, particularly under in vitro and/or in vivo conditions. Also, in case of such hybridisation, it is not necessarily the case that the hybridisation occurs over the entire length of the two stretches where, at least based on the rules for base pairing, such hybridisation and thus formation of a double-stranded structure may, in principle, occur. As preferably used herein, a double-stranded structure is a part of a molecule or a structure formed by two or more separate strands or two spatially separated stretches of a single strand, whereby at least one, preferably two or more base pairs exist which are base paired preferably in accordance with the Watson-Crick base pairing rules. It will also be acknowledged by the one skilled in the art that other base pairing such as Hoogsten base pairing may exist in or form such double-stranded structure.

In a preferred embodiment the term arrangement as used herein, means the order or sequence of structural or functional feature or elements described herein in connection with the nucleic acids disclosed herein.

It is within the present invention that the nucleic acid according to the present invention is a nucleic acid molecule. Insofar the terms nucleic acid and nucleic acid molecule are used herein in a synonymous manner if not indicated to the contrary. In one embodiment of the present application the nucleic acid and thus the nucleic acid molecule comprises a nucleic acid molecule which is characterized in that all of the consecutive nucleotides forming the nucleic acid molecule are linked with or connected to each other by one or more than one covalent bond. More specifically, each of such nucleotides is linked with or connected to two other nucleotides, preferably through phosphodiester bonds or other bonds, forming a stretch of consecutive nucleotides. In such arrangement, however, the two terminal nucleotides, i.e. preferably the nucleotide at the 5' end and at the 3' end, are each linked to a single nucleotide only under the proviso that such arrangement is a linear and not a circular arrangement and thus a linear rather than a circular molecule.

In another embodiment of the present application the nucleic acid and thus the nucleic acid molecule comprises at least two groups of consecutive nucleotides, whereby within each group of consecutive nucleotides each nucleotide is linked with or connected to two other nucleotides, preferably through phosphodiester bonds or other bonds, forming a stretch of consecutive nucleotides. In such arrangement, however, the two terminal nucleotides, i.e. preferably the nucleotide at the 5' end and at the 3' end, are each linked to a single nucleotide only. In such embodiment, the two groups of consecutive nucleotides, however, are not linked with or connected to each other through a covalent bond which links one nucleotide of one group and one nucleotide of another or the other group through a covalent bond, preferably a covalent bond formed between a sugar moiety of one of said two nucleotides and a phosphor moiety of the other of said two nucleotides or nucleosides. In an alternative embodiment, the two groups of consecutive nucleotides, however, are linked with or connected to each other through a covalent bond which links one nucleotide of one group and one nucleotide of another or the other group through a covalent bond, preferably a covalent bond formed between a sugar moiety of one of said two nucleotides and a phosphor moiety of the other of said two nucleotides or nucleosides. Preferably, the at least two groups of consecutive nucleotides are not linked through any covalent bond. In another preferred embodiment, the at least two groups are linked through a covalent bond which is different from a phosphodiester bond. In still another embodiment, the at least two groups are linked through a covalent bond which is a phosphodiester bond.

The nucleic acids according to the present invention shall also comprise nucleic acids which are essentially homologous to the particular sequences disclosed herein. The term substantially homologous shall be understood such that the homology is at least 75%, preferably 85%, more preferably 90% and most preferably more than 95%, 96%, 97%, 98% or 99%.

The actual percentage of homologous nucleotides present in the nucleic acid according to the present invention will depend on the total number of nucleotides present in the nucleic acid. The percent modification can be based upon the total number of nucleotides present in the nucleic acid.

The homology can be determined as known to the person skilled in the art. More specifically, a sequence comparison algorithm then calculates the percent sequence identity for the test sequence(s) relative to the reference sequence, based on the designated program parameters. The test sequence is preferably the sequence or nucleic acid molecule which is said to be or to be tested whether it is homologous, and if so, to what extent, to another nucleic acid molecule, whereby such another nucleic acid molecule is also referred to as the reference sequence. In an embodiment, the reference sequence is a nucleic acid molecule as described herein, more preferably a nucleic acid molecule having a sequence according to any of SEQ ID NOs:10 to 129, 132 to 256 and 278-282. Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al, 2004).

The term inventive nucleic acid or nucleic acid according to the present invention shall also comprise those nucleic acids comprising the nucleic acids sequences disclosed herein or part thereof, preferably to the extent that the nucleic acids or said parts are involved in the binding to MCP-1. The term inventive nucleic acid as preferably used herein, shall also comprise in an embodiment a nucleic acid which is suitable to bind to any molecule selected from the group comprising MCP-2, MCP-3, MCP-4, and eotaxin. It will be acknowledged by the ones skilled in the art that the individual nucleic acids according to the present invention will bind to one or several of such molecules. Such nucleic acid is, in an embodiment, one of the nucleic acid molecules described herein, or a derivative and/or a metabolite thereof, whereby such derivative and/or metabolite are preferably a truncated nucleic acid compared to the nucleic acid molecules described herein. Truncation may be related to either or both of the ends of the nucleic acids as disclosed herein. Also, truncation may be related to the inner sequence of nucleotides of the nucleic acid, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the inventive nucleic acid(s), whereby the stretch can be as little as one nucleotide long. The binding of a nucleic acid according to the present invention, preferably to a molecule selected from the group comprising MCP-1, MCP-2, MCP-3, MCP-4 and eotaxin, can be determined by the ones skilled in the art using routine experiments or by using or adopting a method as described herein, preferably as described herein in the example part. It is within an embodiment of the present invention, unless explicitly indicated to the contrary, that whenever it is referred herein to the binding of the nucleic acids according to the present invention to or with MCP-1, this applies also to the binding of the nucleic acids according to the present invention to or with any molecule selected from the group comprising MCP-2, MCP-3, MCP-4 and eotaxin.

The nucleic acids according to the present invention may be either D-nucleic acids or L-nucleic acids. Preferably, the inventive nucleic acids are L-nucleic acids. In addition it is possible that one or several parts of the nucleic acid are present as D-nucleic acids or at least one or several parts of the nucleic acids are L-nucleic acids. The term "part" of the nucleic acids shall mean as little as one nucleotide. Such nucleic acids are generally referred to herein as D- and L-nucleic acids, respectively. Therefore, in a particularly preferred embodiment, the nucleic acids according to the present invention consist of L-nucleotides and comprise at least one D-nucleotide. Such D-nucleotide is preferably attached to a part different from the stretches defining the nucleic acids according to the present invention, preferably those parts thereof, where an interaction with other parts of the nucleic acid is involved. Preferably, such D-nucleotide is attached at a terminus of any of the stretches and of any nucleic acid according to the present invention, respectively. In a further preferred embodiment, such D-nucleotides may act as a spacer or a linker, preferably attaching modifications such as PEG and HES to the nucleic acids according to the present invention.

It is also within an embodiment of the present invention that each and any of the nucleic acid molecules described herein in their entirety in terms of their nucleic acid sequence(s) are limited to the particular nucleotide sequence(s). In other words, the terms “comprising” or “comprise(s)” shall be interpreted in such embodiment in the meaning of containing or consisting of.

It is also within the present invention that the nucleic acids according to the present invention are part of a longer nucleic acid whereby this longer nucleic acid comprises several parts whereby at least one such part is a nucleic acid according to the present invention, or a part thereof. The other part(s) of these longer nucleic acids can be either one or several D-nucleic acid(s) or one or several L-nucleic acid(s). Any combination may be used in connection with the present invention. These other part(s) of the longer nucleic acid either alone or taken together, either in their entirety or in a particular combination, can exhibit a function which is different from binding, preferably from binding to MCP-1. One possible function is to allow interaction with other molecules, whereby such other molecules preferably are different from MCP-1, such as, e.g., for immobilization, cross-linking, detection or amplification. In a further embodiment of the present invention the nucleic acids according to the invention comprise, as individual or combined moieties, several of the nucleic acids of the present invention. Such nucleic acid comprising several of the nucleic acids of the present invention is also encompassed by the term longer nucleic acid.

L-nucleic acids as used herein are nucleic acids consisting of L-nucleotides, preferably consisting completely of L-nucleotides.

D-nucleic acids as used herein are nucleic acids consisting of D-nucleotides, preferably consisting completely of D-nucleotides.

The terms nucleic acid and nucleic acid molecule are used herein in an interchangeable manner if not explicitly indicated to the contrary.

Also, if not indicated to the contrary, any nucleotide sequence is set forth herein in 5'→3' direction.

Irrespective of whether the inventive nucleic acid consists of D-nucleotides, L-nucleotides or a combination of both with the combination being e.g. a random combination or a defined sequence of stretches consisting of at least one L-nucleotide and at least one D-nucleic acid, the nucleic acid may consist of desoxyribonucleotide(s), ribonucleotide(s) or combinations thereof.

Designing the inventive nucleic acids as L-nucleic acid is advantageous for several reasons. L-nucleic acids are enantiomers of naturally occurring nucleic acids. D-nucleic acids, however, are not very stable in aqueous solutions and particularly in biological systems or biological samples due to the widespread presence of nucleases. Naturally occurring nucleases, particularly nucleases from animal cells are not capable of degrading L-nucleic acids. Because of this the biological half-life of the L-nucleic acid is significantly increased in such a system, including the animal and human body. Due to the lacking degradability of L-nucleic acid no nuclease degradation products are generated and thus no side effects arising therefrom observed. This aspect delimits the L-nucleic acid of factually all other compounds which are used in the therapy of diseases and/or disorders involving the presence of MCP-1. L-nucleic acids which specifically bind to a target molecule through a mechanism different from Watson Crick base pairing, or aptamers which consists partially or completely of L-nucleotides, particularly with those parts of the aptamer being involved in the binding of the aptamer to the target molecule, are also called spiegelmers.

It is also within the present invention that the inventive nucleic acids, also referred to herein as nucleic acids according to the invention, regardless whether they are present as D-nucleic acids, L-nucleic acids or D, L-nucleic acids or whether they are DNA or RNA, may be present as single-stranded or double-stranded nucleic acids. Typically, the inventive nucleic acids are single-stranded nucleic acids which exhibit defined secondary structures due to the primary sequence and may thus also form tertiary structures. The inventive nucleic acids, however, may also be double-stranded in the meaning that two strands which are complementary or partially complementary to each other are hybridised to each other. This confers stability to the nucleic acid which, in particular, will be advantageous if the nucleic acid is present in the naturally occurring D-form rather than the L-form.

The inventive nucleic acids may be modified. Such modifications may be related to the single nucleotide of the nucleic acid and are well known in the art. Examples for such modification are described in, among others, Venkatesan (Venkatesan 2003); Kusser (Kusser 2000); Aurup (Aurup 1994); Cummins (Cummins 1995); Eaton et al. (Eaton 1995); Green et al. (Green 1995); Kawasaki et al. (Kawasaki 1993); Lesnik et al. (Lesnik 1993); and Miller & Kragel (Miller 1993). Such modification can be a H atom, a F atom or O—CH3 group or NH2-group at the 2' position of the individual nucleotide of which the nucleic acid consists. Also, the nucleic acid according to the present invention can comprise at least one LNA nucleotide. In an embodiment the nucleic acid according to the present invention consists of LNA nucleotides.

In an embodiment, the nucleic acids according to the present invention may be a multipartite nucleic acid. A multipartite nucleic acid as used herein, is a nucleic acid which consists of at least two nucleic acid strands. These at least two nucleic acid strands form a functional unit whereby the functional unit is a ligand to a target molecule. The at least two nucleic acid strands may be derived from any of the inventive nucleic acids by either cleaving the nucleic acid to generate two strands or by synthesising one nucleic acid corresponding to a first part of the inventive, i.e. overall nucleic acid and another nucleic acid corresponding to the second part of the overall nucleic acid. It is to be acknowledged that both the cleavage and the synthesis may be applied to generate a multipartite nucleic acid where there are more than two strands as exemplified above. In other words, the at least two nucleic acid strands are typically different from two strands being complementary and hybridising to each other although a certain extent of complementarity between the various nucleic acid parts may exist.

Finally it is also within the present invention that a fully closed, i.e. circular structure for the nucleic acids according to the present invention is realized, i.e. that the nucleic acids according to the present invention are closed, preferably through a covalent linkage, whereby more preferably such covalent linkage is made between the 5' end and the 3' end of the nucleic acid sequences as disclosed herein.

The present inventors have discovered that the nucleic acids according to the present invention exhibit a very favourable $K_D$ value range.

A possibility to determine the binding constant is the use of the so called Biacore device, which is also known to the one skilled in the art. Affinity as used herein was also measured by the use of the "pull-down assay" as described in the examples. An appropriate measure in order to express the intensity of the binding between the nucleic acid according to the target which is in the present case MCP-1, is the so-called $K_D$ value which as such as well the method for its determination are known to the one skilled in the art.

The nucleic acids according to the present invention are characterized by a certain $K_D$ value. Preferably, the $K_D$ value shown by the nucleic acids according to the present invention is below 1 μM. A $K_D$ value of about 1 μM is said to be characteristic for a non-specific binding of a nucleic acid to a target. As will be acknowledged by the ones in the art, the $K_D$ value of a group of compounds such as the nucleic acids according to the present invention are within a certain range. The above-mentioned $K_D$ of about 1 μM is a preferred upper limit for the $K_D$ value. The preferred lower limit for the $K_D$ of target binding nucleic acids can be about 10 picomolar or higher. It is within the present invention that the $K_D$ values of individual nucleic acids binding to MCP-1 are preferably within this range. Preferred ranges can be defined by choosing any first number within this range and any second number within this range. Preferred upper values are 250 nM and 100 nM, preferred lower values are 50 nM, 10 nM, 1 nM, 100 pM and 10 pM.

The nucleic acid molecules according to the present invention may have any length provided that they are still able to bind to the target molecule. It will be acknowledged in the art that there are preferred lengths of the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 20 to 50 nucleotides and about 30 to 50 nucleotides.

It is within the present invention that the nucleic acids disclosed herein comprise a moiety which preferably is a high molecular weight moiety and/or which preferably allows to modify the characteristics of the nucleic acid in terms of, among others, residence time in the animal body, preferably the human body. A particularly preferred embodiment of such modification is PEGylation and HESylation of the nucleic acids according to the present invention. As used herein PEG stands for poly(ethylene glycol) and HES for hydroxyethyl starch. PEGylation as preferably used herein is the modification of a nucleic acid according to the present invention whereby such modification consists of a PEG moiety which is attached to a nucleic acid according to the present invention. HESylation as preferably used herein is the modification of a nucleic acid according to the present invention whereby such modification consists of a HES moiety which is attached to a nucleic acid according to the present invention. These modifications as well as the process of modifying a nucleic acid using such modifications, are described in European patent application EP 1 306 382 and in international patent application WO2005/074993, the disclosure of which is herewith incorporated in its entirety by reference.

Preferably, the molecular weight of a modification consisting of or comprising a high molecular weight moiety is about from 2,000 to 250,000 Da, preferably 20,000 to 200,000 Da. In the case of PEG being such high molecular weight moiety, the molecular weight is preferably 20,000 to 120,000 Da, more preferably 40,000 to 80,000 Da. In the case of HES being such high molecular weight moiety, the molecular weight is preferably 20,000 to 200,000 Da, more preferably 40,000 to 150,000 Da. The process of HES modification is, e.g., described in German patent application DE 1 2004 006 249.8 and international patent application WO2002080979 the disclosure of which is herewith incorporated in its entirety by reference.

It is within the present invention that either of PEG and HES may be used as either a linear or branched from as further described in the patent applications WO2005/074993, WO2002/080979 and PCT/EP02/11950. Such modification can, in principle, be made to the nucleic acid molecules of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule.

The modification and preferably the PEG and/or HES moiety can be attached to the nucleic acid molecule of the present invention either directly or through a linker. It is also within the present invention that the nucleic acid molecule according to the present invention comprises one or more modifications, preferably one or more PEG and/or HES moiety. In an embodiment the individual linker molecule attaches more than one PEG moiety or HES moiety to a nucleic acid molecule according to the present invention. The linker used in connection with the present invention can itself be either linear or branched. This kind of linker is known to the ones skilled in the art and is further described in the patent applications WO2005/074993 and PCT/EP02/11950.

In a preferred embodiment the linker is a biodegradable linker. The biodegradable linker allows to modify the characteristics of the nucleic acid according to the present invention in terms of, among other, residence time in the animal body, preferably in the human body, due to release of the modification from the nucleic acid according to the present invention. Usage of a biodegradable linker may allow a better control of the residence time of the nucleic acid according to the present invention. A preferably embodiment of such biodegradable linker are biodegradable linker as described in but not limited to the international patent applications WO2006/052790, WO2008/034122, WO2004/092191 and WO2005/099768, whereby in the international patent applications WO2004/092191 and WO2005/099768, the linker is part of a polymeric oligonucleotide prodrug that consists of one or two modifications as described herein, a nucleic acid molecule and the biodegradable linker in between.

It is within the present invention that the modification is a biodegradable modification, whereby the biodegradable modification can be attached to the nucleic acid molecule of the present invention either directly or through a linker. The biodegradable modification allows to modify the characteristics of the nucleic acid according to the present invention in terms of, among other, residence time in the animal body, preferably in the human body, due to release of the modification from the nucleic acid according to the present invention. Usage of biodegradable modification may allow a better control of the residence time of the nucleic acid according to the present invention. A preferably embodiment of such biodegradable modification are biodegradable polymers as described in but not restricted to the international patent applications WO2002/065963, WO2003/070823, WO2004/113394 and WO2000/41647, in WO2000/41647 preferably page 18, line 4 to 24. More preferably, the biodegradable polymer is a biodegradable PEG or a biodegradable polyglycolic acid (abbr. PLGA) as described in the international patent applications WO2004/113394 and WO2000/41647, respectively.

Without wishing to be bound by any theory, it seems that by modifying the nucleic acids according to the present invention with high molecular weight moiety such as a polymer and more particularly the polymers disclosed herein, which are preferably physiologically acceptable, the excretion kinetic is changed. More particularly, it seems that due to the increased molecular weight of such modified inventive nucleic acids and due to the nucleic acids not being subject to metabolism particularly when in the L form, excretion from an animal body, preferably from a mammalian body and more preferably from a human body is decreased. As excretion typically occurs via the kidneys, the present inventors assume that the glomerular filtration rate of the thus modified nucleic acid is significantly reduced compared to the nucleic acids not having this kind of high molecular weight modification which results in an increase in the residence time in the body. In connection therewith it is particularly noteworthy that, despite such high molecular weight modification the specificity of the nucleic acid according to the present invention is not affected in a detrimental manner. Insofar, the nucleic acids according to the present invention have surprising characteristics—which normally cannot be expected from pharmaceutically active compounds—such that a pharmaceutical formulation providing for a sustained release is not necessarily required to provide for a sustained release. Rather the nucleic acids according to the present invention in their modified form comprising a high molecular weight moiety, can as such already be used as a sustained release-formulation. Insofar, the modification(s) of the nucleic acid molecules as disclosed herein and the thus modified nucleic acid molecules and any composition comprising the same may provide for a distinct, preferably controlled pharmacokinetics and biodistribution thereof. This also includes residence time in circulation and distribution to tissues. Such modifications are further described in the patent application PCT/EP02/11950.

However, it is also within the present invention that the nucleic acids disclosed herein do not comprise any modification and particularly no high molecular weight modification such as PEGylation or HESylation. Such embodiment is particularly preferred when the nucleic acid shows preferential distribution to any target organ or tissue in the body or when a fast clearance of the nucleic acids from the body after administration is desired. Nucleic acids as disclosed herein with a preferential distribution profile to any target organ or tissue in the body would allow establishment of effective local concentrations in the target tissue while keeping systemic concentration of the nucleic acids low. This would allow the use of low doses which is not only beneficial from an economic point of view, but also reduces unnecessary exposure of other tissues to the nucleic acid agent, thus reducing the potential risk of side effects. Fast clearance of the nucleic acids as disclosed herein from the body after administration might be desired in case of in vivo imaging or specific therapeutic dosing requirements using the nucleic acids or medicaments comprising the same, each according to the present invention.

The inventive nucleic acids, which are also referred to herein as the nucleic acids according to the present invention, and/or the antagonists according to the present invention may be used for the generation or manufacture of a medicament. Such medicament or a pharmaceutical composition according to the present invention contains at least one of the inventive nucleic acids, optionally together with further pharmaceutically active compounds, whereby the inventive nucleic acid preferably acts as pharmaceutically active compound itself. Such medicaments comprise in preferred embodiments at least a pharmaceutically acceptable carrier. Such carrier may be, e.g., water, buffer, PBS, glucose solution, preferably a 5% glucose salt balanced solution, starch, sugar, gelatine or any other acceptable carrier substance. Such carriers are generally known to the one skilled in the art. It will be acknowledged by the person skilled in the art that any embodiments, use and aspects of or related to the medicament of the present invention is also applicable to the pharmaceutical composition of the present invention and vice versa.

The indication, diseases and disorders for the treatment and/or prevention of which the nucleic acids, the pharmaceutical compositions and medicaments in accordance with or prepared in accordance with the present invention result from the involvement, either direct or indirect, of MCP-1 in the respective pathogenic mechanism. However, also those indications, diseases and disorders can be treated and prevented in the pathogenic mechanism of which MCP-2, MCP-3, MCP-4 and/or eotaxin are either directly or indirectly involved. It is obvious for the ones skilled in the art that particularly those nucleic acids according to the present invention can be used insofar, i.e. for the diseases involving in the broader sense MCP-2, MCP-3, MCP-4 and eotaxin, which interact and bind, respectively, to or with MCP-2, MCP-3, MCP-4 and eotaxin, respectively.

More specifically, such uses arise, among others, from the expression pattern of MCP-1 which suggests that it plays important roles in human diseases that are characterized by mononuclear cell infiltration. Such cell infiltration is present in many inflammatory and autoimmune diseases.

In animal models, MCP-1 has been shown to be expressed in the brain after focal ischemia (Kim 1995; Wang 1995) and during experimental autoimmune encephalomyelitis (Hulkower 1993; Ransohoff 1993; Banisor 2005). MCP-1 may be an important chemokine that targets mononuclear cells in the disease process illustrated by these animal models, such as stroke and multiple sclerosis.

A large body of evidence argues in favor of a unique role of the MCP-1/CCR2 axis in monocyte chemoattraction and thus chronic inflammation: (i) MCP-1- or CCR2-deficient mice show markedly reduced macrophage chemotactic response while otherwise appearing normal (Kuziel 1997; Kurihara 1997; Boring 1997; Lu 1998). (ii), despite functional redundancy with other chemokines in vitro, loss of MCP-1 effector function alone is sufficient to impair monocytic trafficking in several inflammatory models (Lloyd 1997; Furuichi 2003; Egashira 2002; Galasso 2000; Ogata 1997; Kennedy 1998; Gonzalo 1998; Kitamoto 2003). (iii), MCP-1 levels are elevated in many inflammatory diseases. In fact, MCP-1 is thought to play a role in many diseases with and without an obvious inflammatory component such as rheumatoid arthritis (Koch 1992; Hosaka 1994; Akahoshi 1993; Harigai 1993; Rollins 1996), renal disease (Wada 1996; Viedt 2002), restenosis after angioplasty (Economou 2001), allergy and asthma (Alam 1996; Holgate 1997; Gonzalo 1998), cancer (Salcedo 2000; Gordillo 2004), atherosclerosis (Nelken 1991; Yla-Herttuala 1991; Schwartz 1993; Takeya 1993; Boring 1998), psoriasis (Vestergaard 2004), inflammation of the nervous system (Huang 2001), atopic dermatitis (Kaburagi 2001), colitis (Okuno 2002), endometriosis (Jolicoeur 2001), uveitis (Tuaillon 2002), retinal disorders (Nakazawa 2007), idiopathic pulmonary fibrosis and sarcoidosis (Iyonaga 1994) and polymyositis/dermatomyositis (De Bleecker 2002).

Therapeutic intervention with anti-MCP-1 agents—or CCR2 antagonists—would affect the excess inflammatory monocyte trafficking but may spare basal trafficking of phagocytes, thereby avoiding general immunosuppression and increased risk of infections (Dawson 2003).

Additionally, based on the increasing knowledge on the molecular mechanisms of the inflammatory process and the interplay of locally secreted mediators of inflammation, new targets for the therapy of kidney diseases have been identified (Holdsworth 2000; Segerer 2000). One of those targets, for which robust data on expression and interventional studies with specific antagonists in appropriate animal models exist is MCP-1. This protein has a widely non-redundant role for immune-cell recruitment to sites of renal inflammation. Infiltration of immune cells to the kidney is thought to be a major mechanism of structural renal damage and decline of renal function in the development of various forms of kidney disease.

All types of renal cells can express chemokines including MCP-1 upon stimulation in vitro (Segerer 2000); there is a long list of stimuli that trigger MCP-1 expression in vitro including cytokines, oxygen radicals, immune complexes, and lipid mediators.

In healthy kidneys of rats and mice, MCP-1 is not expressed, but is readily upregulated during the course of acute and chronic rodent models of renal inflammation including immune complex glomerulonephritis, rapid progressive glomerulonephritis, proliferative glomerulonephritis, diabetic nephropathy, obstructive nephropathy, or acute tubular necrosis (Segerer 2000; Anders 2003). The expression data for MCP-1 in rodents do correlate well with the respective expression found in human renal biopsies (Rovin 1994; Cockwell 1998; Wada 1999). Furthermore, renal expression in human kidneys is associated with disease activity and declines when appropriate therapy induced disease remission (Amann 2003).

Glomerular mononuclear cell infiltration is associated with the development of a diffuse glomerulosclerosis in patients with diabetic nephropathy. MCP-1 plays an important role in the recruitment and accumulation of monocytes and lymphocytes within the glomerulus (Banba 2000; Morii 2003).

Locally produced MCP-1 seems to be particularly involved in the initiation and progression of tubulointerstitial damage, as documented in experiments using transgenic mice with nephrotoxic serum-induced nephritis (NSN). MCP-1 was mainly detected in vascular endothelial cells, tubular epithelial cells and infiltrated mononuclear cells in the interstitial lesions. The MCP-1 mediated activation of tubular epithelial cells is consistent with the notion that MCP-1 contributes to tubulointerstitial inflammation, a hallmark of progressive renal disease (Wada 2001; Viedt 2002)

Due to the homology between MCP-1 on the one hand and MCP-2, MCP-3, MCP-4 and eotaxin on the other hand, the nucleic acids according to the present invention, at least those of them which interact with or bind to MCP-2, MCP-3, MCP-4 and eotaxin, respectively, can typically be used for the treatment, prevention and/or diagnosis of any disease where MCP-2, MCP-3, MCP-4 and eotaxin, respectively, is either directly or indirectly involved. Involved as preferably used herein, means that if the respective molecule which is involved in the disease, is prevented from exerting one, several or all of its functions in connection with the pathogenic mechanism underlying the disease, the disease will be cured or the extent thereof decreased or the outbreak thereof prevented; at least the symptoms or any indicator of such disease will be relieved and improved, respectively, such that the symptoms and indicator, respectively, is identical or closer to the one(s) observed in a subject not suffering from the disease or not being at risk to develop such disease.

Of course, because the MCP-1 binding nucleic acids according to the present invention interact with or bind to human or murine MCP-1, a skilled person will generally understand that the MCP-1 binding nucleic acids according to the present invention can easily be used for the treatment, prevention and/or diagnosis of any disease as described herein of humans and animals.

These members of the monocyte chemoattractant protein (MCP) family, i.e. MCP-2, MCP-3, MCP-4 and eotaxin thus share a high degree of sequence similarity with MCP-1. Although not exclusively, eotaxin, MCP-2, -3, and 4 interact via CCR3, the characteristic chemokine receptor on human eosinophils (Heath 1997). The CCR3 receptor is upregulated in neoplastic conditions, such as cutaneous T-cell lymphoma (Kleinhans 2003), glioblastoma (Kouno 2004), or renal cell carcinoma (Johrer 2005).

More specifically, increased levels of eotaxin are directly associated with asthma diagnosis and compromised lung function (Nakamura 1999). Elevated expression of eotaxin at sites of allergic inflammation has been observed in both atopic and nonatopic asthmatics (Ying 1997; Ying 1999). Also, mRNAs coding for MCP-2 and -4 are constitutively expressed in a variety of tissues; their physiological functions in these contexts, however, are unknown. Plasma MCP-2 levels are elevated in sepsis together with MCP-1 (Bossink 1995); MCP-3 expression occurs in asthmatics (Humbert 1997). Finally, MCP-4 can be found at the luminal surface of atherosclerotic vessels (Berkhout 1997).

Accordingly, disease and/or disorders and/or diseased conditions for the treatment and/or prevention of which the medicament according to the present invention may be used include, but are not limited to inflammatory diseases, autoimmune diseases, autoimmune encephalomyelitis, stroke, acute and chronic multiple sclerosis, chronic inflammation, rheumatoid arthritis, renal diseases, restenosis, restenosis after angioplasty, acute and chronic allergic reactions, primary and secondary immunologic or allergic reactions, asthma, conjunctivitis, bronchitis, cancer, atherosclerosis, atherosclerotic cardiovascular heart failure or stroke, psoriasis, psoriatic arthritis, inflammation of the nervous system, atopic dermatitis, colitis, endometriosis, uveitis, retinal disorders including macular degeneration, retinal detachment, diabetic retinopathy, retinopathy of prematurity, retinitis pigmentosa, proliferative vitreoretinopathy, and central serous chorioretinopathy; idiopathic pulmonary fibrosis, idiopathic and/or collagenose-associated pulmonary arterial hypertension, sarcoidosis, polymyositis, dermatomyositis, avoidance of immunosuppression, reducing the risk of infection, sepsis, renal inflammation, glomerulonephritis, rapid progressive glomerulonephritis, proliferative glomerulonephritis, diabetic nephropathy, obstructive nephropathy, acute tubular necrosis, and diffuse glomerulosclerosis, systemic lupus erythematosus, chronic bronchitis, Behçet's disease, amyotrophic lateral sclerosis (ALS), premature atherosclerosis after Kawasaki's disease, myocardial infarction, obesity, chronic liver disease, peyronie's disease, acute spinal chord injury, lung or kidney transplantation, myocarditis, Alzheimer's disease, and neuropathy, breast carcinoma, gastric carcinoma, bladder cancer, ovarian cancer, hamartoma, colorectal carcinoma, colonic adenoma, pancreatitis, chronic obstructive pulmonary disease (COPD) with and without pulmonary vascular involvement, and inflammatory bowel diseases such as Crohn's disease or ulcerative colitis.

A particularly preferred chronic kidney disease is lupus nephritis, preferably for combination therapy.

Lupus nephritis is an inflammation of the kidney caused by systemic lupus erythematosus (abbr. SLE) and is also known as lupus glomerulonephritis, a type or form of glomerulonephritis. Glomerulonephritis, also known as glomerular nephritis, is a renal disease characterized by inflammation of the glomeruli, or small blood vessels in the kidneys.

SLE also known as lupus is a chronic autoimmune disease, resulting in inflammation and tissue damage. Apart from the kidneys, SLE can affect any part of the body, but most often harms die heart, joints, skin, lungs, blood vessels, liver, and nervous system. The damage of the lungs becomes manifest in chronic respiratory diseases such as pneumonitis, pulmonary manifestations may include lung and pleura inflammation which can cause pleuritis, pleural effusion, lupus pneumonitis, chronic diffuse interstitial lung disease, pulmonary hypertension, pulmonary emboli, pulmonary hemorrhage, and shrinking lung syndrome.

The diagnosis of lupus nephritis typically depends on blood tests, urine analysis, X-rays, ultrasound scans of the kidneys, and/or a kidney biopsy.

The World Health Organization has divided lupus nephritis into five classes based on the biopsy all of which shall be encompassed by the term lupus nephritis as used herein.

This classification was defined in 1982 and revised in 1995.

- Class I is minimal mesangial glomerulonephritis which is histologically normal on light microscopy but with mesangial deposits on electron microscopy.
- Class II is based on a finding of mesangial proliferative lupus nephritis. This form typically responds completely to treatment with corticosteroids.
- Class III is focal proliferative nephritis and often successfully responds to treatment with high doses of corticosteroids.
- Class IV is diffuse proliferative nephritis. This form is mainly treated with corticosteroids and immunosuppressant drugs.
- Class V is membranous nephritis and is characterized by extreme edema and protein loss.
- Class VI Glomerulosclerosis Other types or forms of the kidney disease glomerulonephritis are

- Membranoproliferative glomerulonephritis (abbr. MPGN), a type of glomerulonephritis caused by deposits in the kidney glomerular mesangium and basement membrane (abbr. GBM) thickening, activating complement and damaging the glomeruli;
- Membranous glomerulonephritis (abbr. MGN), also known as membranous nephropathy, a slowly progressive disease of the kidney;
- IgA nephropathy, the most common glomerulonephritis throughout the world; the disease derives its name from the deposits of Immunoglobulin A (abbr. IgA) in the blotchy pattern in the mesangium, the heart of the glomerulus.
- Post-streptococcal glomerulonephritis, a disorder of the glomeruli (glomerulonephritis), or small blood vessels in the kidneys, following streptococcal infection;
- Rapidly progressive glomerulonephritis (abbr. RPGN), a syndrome of the kidney that, if left untreated, rapidly progresses into acute renal failure and death within months. In 50% of cases, RPGN is associated with an underlying disease such as Goodpasture syndrome, systemic lupus erythematosus, or Wegener granulomatosis; the remaining cases are idiopathic;
- Nephritic syndrome (or acute nephritic syndrome), which rather means a collection of signs associated with disorders affecting the kidneys, more specifically glomerular disorders;
- Focal segmental glomerulosclerosis, a cause of nephrotic syndrome, in children and adolescents, as well as an important cause of kidney failure in adults;
- Diabetic nephropathy, also known as Kimmelstiel-Wilson syndrome and intercapillary glomerulonephritis, is a progressive kidney disease caused by angiopathy of capillaries in the kidney glomeruli. It is characterized by nephrotic syndrome and nodular glomerulosclerosis. It is due to longstanding diabetes mellitus, and is a prime cause for dialysis in many Western countries;
- Nephrotic syndrome, a nonspecific disorder in which the kidneys are damaged, causing them to leak large amounts of protein (>3.5 grams per day per 1.73 $m^2$ body surface area) into the urine;
- Interstitial nephritis (or tubulo-interstitial nephritis), a form of nephritis affecting the interstitium of the kidneys surrounding the tubules. This disease can be either acute or chronic.

There is very strong evidence that MCP-1 and its respective chemokine receptor CCR2 play a crucial role in autoimmune tissue injury such as the clinical manifestations of SLE (Gerard & Rollins 2001). For example, $MRL^{lpr/lpr}$ mice deficient either for the MCP-1 or the CCR2 gene are protected from lupus-like autoimmunity (Perez de Lema 2005, Tesch 1999). Hence, the MCP-1/CCR2 axis may represent a promising therapeutic target, e.g. for lupus nephritis.

Chronic respiratory diseases, also known as chronic pulmonary diseases or chronic lung diseases, are chronic diseases of the airways and other structures of the lung, e.g. like lung vasculature. Some of the most common chronic respiratory diseases are asthma, chronic obstructive pulmonary disease (abbr. COPD), respiratory allergies, occupational lung diseases and pulmonary hypertension.

Chronic obstructive pulmonary disease (abbr. COPD) is a lung ailment that is characterized by a persistent blockage of airflow from the lungs. It is an under-diagnosed, life-threatening lung disease that interferes with normal breathing and is not fully reversible. COPD includes a few lung diseases: the most common are chronic bronchitis and emphysema. Many people with COPD have both of these diseases. The emphysema is a damage to the air sacs at the tips of the airways what makes it hard for the body to take in the oxygen it needs. During chronic bronchitis the airways are irritated, red, and make too much sticky mucus. The walls of the airways are swollen and partly block the air from passing through.

The involvement of MCP-1 in COPD and/or COPD development has not been clear so far_De Boer and colleges found in a semi-quantitative analysis of peripheral lung tissues of current or ex-smoker with COPD 1.5-fold higher levels of MCP-1 mRNA (De Boer 2000). Based on their results, the authors assumed that MCP-1 might be involved in the recruitment of macrophages and mast cells into the airway epithelium in COPD. Traves et al (Traves 2002) found increased levels of MCP-1 in the sputum, but not in the bronchoalveolar lavage (abbr. BAL) fluid, and assumed that MCP-1 is involved in the migration of monocytes and neutrophils into the airway contributing to the increased inflammatory load associated with COPD (Traves 2002). However, in 2006 Ko et al. (Ko 2006) determined exhaled breath condensate of patients with COPD. They could not find elevated MCP-1 levels in COPD patients (Ko 2006).

Although MCP-1 is involved in the inflammation process and the recruitment of monocytes and/or neutrophils that cause inflammation, it was not absolutely clear whether MCP-1 is involved in COPD and/or development of COPD. Surprisingly, as shown in Example 11 of the present invention, in an acknowledged animal model that is widely used to screen substances for usefulness in the treatment of COPD, administration of MCP-1 binding Spiegelmer lead to a reduction of cellular infiltrate into lungs. Based on the data shown in the present application, MCP-1 binding Spiegelmers are suitable for have the use in the therapy of chronic respiratory diseases, preferably COPD, alone or one element of a combination therapy, preferably in combination therapy with a steroid drug, preferably dexamethasone Combination therapy of MCP-1 binding Spiegelmers with dexamethasone or other steroid drugs takes the advantage of two independent mode-of-action in order to treat chronic respiratory diseases such as COPD.

Alterations in pulmonary vessel structure and function are highly prevalent in patients with COPD (Peinado 2008), herein specified as COPD with pulmonary vascular involvement. Vascular abnormalities impair gas exchange and may result in pulmonary hypertension which is one of the principal factors associated with reduced survival in COPD patients (Peinado 2008). Changes in pulmonary circulation have been identified at initial disease stages, providing new insight into their pathogenesis. Endothelial cell damage and dysfunction produced by the effects of cigarette smoke products or inflammatory elements is now considered to be the primary alteration that initiates the sequence of events resulting in pulmonary hypertension (Peinado 2008).

Pulmonary hypertension (abbr. PH) is an increase in blood pressure in the pulmonary artery, pulmonary vein, or pulmonary capillaries together known as the lung vasculature, leading to shortness of breath, dizziness, fainting, and other symptoms, all of which are exacerbated by exertion. PH can be a severe disease with markedly decreased exercise tolerance and heart failure. Since 1973 a distinction between primary PH and secondary PH was made (Hatano & Strasser 1975).

Primary PH is a syndrome characterized by chronically increased pulmonary vascular resistance in the absence of known cause, which, if untreated, usually leads to death within four years (Rubin 1997).

Secondary PH results from sustained vasoconstriction and structural alterations to the pulmonary vascular bed (Hopkins 2002). The major stimuli that are responsible for these changes are chronic alveolar hypoxia, chronic inflammation and excessive shear stress (Voelker 1995).

In 2003, the 3rd World Symposium on Pulmonary Arterial Hypertension was convened in Venice to modify the classification based on new understandings of disease mechanisms. The revised system developed by this group provides the current framework for understanding pulmonary hypertension (Simonneau 2004):

- WHO Group I—Pulmonary Arterial Hypertension (Abbr. PAH)
  - Idiopathic pulmonary arterial hypertension (abbr. IPAH)
  - Familial pulmonary arterial hypertension (abbr. FPAH)
  - Pulmonary arterial hypertension associated with other diseases (abbr. APAH) whereby the other diseases are collagen vascular disease (e.g. scleroderma), congenital shunts between the systemic and pulmonary circulation, portal hypertension, HIV infection, drugs, toxins, or other diseases or disorders
  - Pulmonary arterial hypertension associated with venous or capillary disease
- WHO Group II—Pulmonary Hypertension Associated with Left Heart Disease
  - Atrial or ventricular disease
  - Valvular disease (e.g. mitral stenosis)
- WHO Group III—Pulmonary Hypertension Associated with Lung Diseases and/or Hypoxemia
  - Chronic obstructive pulmonary disease (abbr. COPD), interstitial lung disease (abbr. ILD)
  - Sleep-disordered breathing, alveolar hypoventilation
  - Chronic exposure to high altitude
  - Developmental lung abnormalities
- WHO Group IV—Pulmonary Hypertension Due to Chronic Thrombotic and/or Embolic Disease
  - Pulmonary embolism in the proximal or distal pulmonary arteries
  - Embolization of other matter, such as tumor cells or parasites
- WHO Group V—Miscellaneous A number of agents has recently been developed for primary and secondary PAH: a prostacyclin derivative such as epoprostenol, an endothelin receptor antagonist such as bosentan and a phosphodiesterase type 5 inhibitor such as sildenafil (Torres 2007).

MCP-1 levels are elevated in patients with idiopathic pulmonary arterial hypertension or primary pulmonary hypertension compared to healthy controls. These results imply a contribution of MCP-1 to the development of pulmonary hypertension (Itoh 2006,). As shown in Example 12, MCP-1 binding Spiegelmers shows positive effects on PH in an animal model that is widely used to screen substances for usefulness in the treatment of pulmonary hypertension. Hence, MCP-1 binding Spiegelmers are useable as agents for the treatment of PH.

In a further embodiment, the medicament comprises a further pharmaceutically active agent. Such further pharmaceutically active compounds are, among others but not limited thereto, those known to control blood pressure and diabetes such as angiotensin converting enzyme (ACE) inhibitors and angiotensin receptor blockers. The further pharmaceutically active compound can be, in a further embodiment, also one of those compounds which reduce infiltration of immune cells to sites of chronic inflammation or generally suppress the exuberant immune response that is present in chronic inflammatory settings and that leads to tissue damage. Such compounds can be, but are not limited to, steroids or immune suppressants and are preferably selected from the group comprising corticosteroids like prednisone, methylprednisolone, hydrocortisone, dexamethasone and general immunosuppressants such as cyclophosphamide, cyclosporine, chlorambucil, azathioprine, tacrolimus or mycophenolate mofetil. Additionally, more specific blockers of T-cell costimulation, e.g. blockers of CD154 or CD40 or CD28 or CD86 or CD80; or T- and/or B-cell depleting agents like an anti-CD20 agent are useful in further embodiments. Finally, the further pharmaceutically active agent may be a modulator of the activity of any other chemokine which can be a chemokine agonist or antagonist or a chemokine receptor agonist or antagonist. Alternatively, or additionally, such further pharmaceutically active agent is a further nucleic acid according to the present invention. Alternatively, the medicament comprises at least one more nucleic acid which binds to a target molecule different from MCP-1 or exhibits a function which is different from the one of the nucleic acids according to the present invention.

It is within the present invention that the medicament is alternatively or additionally used, in principle, for the prevention of any of the diseases disclosed in connection with the use of the medicament for the treatment of said diseases. Respective markers therefore, i.e. for the respective diseases are known to the ones skilled in the art. Preferably, the respective marker is MCP-1. Alternatively and/or additionally, the respective marker is selected from the group comprising MCP-2, MCP-3, MCP-4 and eotaxin. A still further group of markers is selected from the group comprising autoreactive antibodies in the plasma, such as, for example, anti-dsDNA antibodies or rheumatoid factor.

In one embodiment of the medicament of the present invention, such medicament is for use in combination with other treatments for any of the diseases disclosed herein, particularly those for which the medicament of the present invention is to be used.

"Combination therapy" (or "co-therapy") includes the administration of a medicament of the invention and at least a second agent as part of a specific treatment regimen intended to provide the beneficial effect from the co-action of these therapeutic agents, i.e. the medicament of the present invention and said second agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents.

In a preferred embodiment, the chronic disease is either a chronic kidney disease and more preferably lupus nephritis, or a chronic lung disease and more preferably pneumonitis, which is to be treated using a combination therapy. Such combination therapy makes use of a combination of the nucleic acid molecule as disclosed herein, and an immunosuppressive agent. Preferably the immunosuppressive agent is selected from the group comprising cyclophosphamide and mycophenolate mofetil.

Cyclophosphamide (the generic name for Cytoxan, Neosar, Revimmune), also known as cytophosphane, is a nitrogen mustard alkylating agent, from the oxazophorines group. Intravenous and oral administration of cyclophosphamide has been the standard of care for treating lupus glomerulonephritis (Steinberg 1991). Cyclophosphamide is a "prodrug" which is converted in the liver to active forms that have chemotherapeutic activity. Indeed, the use of cyclophosphamide is limited by potentially severe toxic effects including bone marrow suppression, hemorrhagic cystitis, opportunistic infections, malignant diseases, and premature gonadal failure (Boumpas 1995). Clinical trials of treatment with intermittent intravenous cyclophosphamide combined with corticosteroids show greater long-term renal survival but not overall survival, as compared with treatment with corticosteroids alone (Austin 1986; Valeri 1994; Lehman 1989; Boumpas 1992). Furthermore, failure to achieve remission, which is associated with an increased rate of progression to renal failure, is reported in 18 to 57 percent of patients who received cyclophosphamide (Korbert 2000; Gourley 1996; Ionnidis 2000; Mok 2004).

Mycophenolate mofetil is an immunosuppressive agent, whereby it is metabolized in the liver to the active moiety mycophenolic acid. It inhibits inosine monophosphate dehydrogenase, the enzyme that controls the rate of synthesis of guanine monophosphate in the de novo pathway of purine synthesis used in the proliferation of B and T lymphocytes. Mycophenolate mofetil is approved for the prevention of transplant rejection, has been used in patients with lupus nephritis that is refractory to cyclophosphamide and in patients who cannot tolerate cyclophosphamide (Dooley 1990; Gaubitz 1999; Kingdon 2001; Karim 2002). In a 4-week trial, mycophenolate mofetil was more effective than intravenous cyclophosphamide in inducing remission of lupus nephritis (Ginzler 2005).

However, each of the two drugs is associated with significant morbidity and mortality. For example, in the Aspreva Lupus Management Study (ALMS) trial mycophenolate mofetil caused serious adverse effects in 27.7% and treatment-related death in 4.9% and cyclophosphamide in 22.8% and 2.8% of treated patients, respectively (Appel 2007). Most serious adverse effects and deaths were related to infections due to the unspecific immunosuppressive effects of cyclophosphamide and mycophenolate mofetil (Appel 2007). Novel drugs specifically blocking autoimmune inflammation may allow reducing the toxicity of current treatment protocols either by replacing cyclophosphamide and mycophenolate mofetil or by allowing significant dose reductions when used in combination.

In connection with such combination therapy a significant reduction of the overall amount of the immunosuppressive agent is possible whilst still achieving a therapeutic effect. The reduction of the overall amount of the immunosuppressive agent may be either realized by reducing the amount of the immunosuppressive agent at each administration, or by reducing the frequency of the administration of the immunosuppressive agent in the treatment of the disease. Regardless of which of said two options is practiced, in any case the overall amount of the immunosuppressive agent which is administered to the patient in the course of the treatment is reduced compared to the overall amount of the immunosuppressive agent administered in the treatment of the patient if only the immunosuppressive agent rather than the combination of the immunosuppressive agent and the nucleic acid molecule according to the present invention is administered. Such administration of the immunosuppressive agent in connection with the treatment of said disease as the only pharmaceutically active agent, is also referred to herein as monotherapy. The extent of such reduction depends on the specific immunosuppressive agent and the specific disease, as well as the individual characteristics of the patient to be treated. In any case the combination therapy according to the present invention goes along with fewer side effects compared to the use of the respective immunosuppressive agent as a monotherapy.

A further preferred embodiment of a combination therapy using as one pharmaceutically active agent the nucleic acid molecule according to the present invention, is a combination therapy in connection with the treatment of chronic respiratory diseases, whereby the chronic respiratory disease is preferably COPD. The agent to be used in said combination therapy together with the nucleic acid molecule according to the present invention is an anti-inflammatory agent. Preferably, the anti-inflammatory agent is selected from the group comprising dexamethasone and roflumilast; more preferably said anti-inflammatory agent is dexamethasone.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As outlined in general terms above, the medicament according to the present invention can be administered, in principle, in any form known to the ones skilled in the art. A preferred route of administration is systemic administration, more preferably by parenteral administration, preferably by injection. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficacy.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that are well known to the ordinary skill in the art.

Furthermore, preferred medicaments of the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

The medicament of the present invention will generally comprise an effective amount of the active component(s) of the therapy, including, but not limited to, a nucleic acid molecule of the present invention, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least one of the nucleic acids according to the present invention and preferably a pharmaceutically acceptable vehicle. Such vehicle can be any vehicle or any binder used and/or known in the art. More particularly such binder or vehicle is any binder or vehicle as discussed in connection with the manufacture of the medicament disclosed herein. In a further embodiment, the pharmaceutical composition comprises a further pharmaceutically active agent.

The preparation of a medicament and a pharmaceutical composition will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, a medicament will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the individual or the subject to be treated. Specific amounts of active compound required for administration depend on the judgment of the practitioner and are peculiar to each individual.

A minimal volume of a medicament required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatin capsule), the active drug component, i.e. a nucleic acid molecule of the present invention and/or any further pharmaceutically active agent, also referred to herein as therapeutic agent(s) or active compound(s) can be combined with an oral, non-toxic, pharmaceutically acceptable inert carrier such as ethanol, glycerol, water and the like. Moreover, when desired or necessary, suitable binders, lubricants, disintegrating agents, and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes, and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol, and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The medicament of the invention can also be administered in such oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical composition or medicament may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

For solid compositions, excipients include pharmaceutical grades of mannitol, lactose, starch, magnesium stearate, sodium saccharin, talcum, cellulose, glucose, sucrose, magnesium carbonate, and the like. The active compound defined above, may be also formulated as suppositories, using for example, polyalkylene glycols, for example, propylene glycol, as the carrier. In some embodiments, suppositories are advantageously prepared from fatty emulsions or suspensions.

The medicaments and nucleic acid molecules, respectively, of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, what is well known to the ordinary skill in the art. For example, the nucleic acid molecules described herein can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic-acid associated complexes is provided in U.S. Pat. No. 6,011,020.

The medicaments and nucleic acid molecules, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the medicaments and nucleic acid molecules, respectively, of the present invention may be coupled to a class of biodegradable polymers useful in achieving controlled release of a drag, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition and medicament, respectively, to be administered may also contain minor amounts of non-toxic auxiliary substances such as wetting or emulsifying agents, pH buffering agents, and other substances such as for example, sodium acetate, and triethanolamine oleate.

The dosage regimen utilizing the nucleic acid molecules and medicaments, respectively, of the present invention is selected in accordance with a variety of factors including type, species, age, weight, sex and medical condition of the patient; the severity of the condition to be treated; the route of administration; the renal and hepatic function of the patient; and the particular aptamer or salt thereof employed.

An ordinarily skilled physician or veterinarian can readily determine and prescribe the effective amount of the drug required to prevent, counter or arrest the progress of the condition.

Effective plasma levels of the nucleic acid according to the present invention preferably range from 500 fM to 500 μM in the treatment of any of the diseases disclosed herein.

The nucleic acid molecules and medicaments, respectively, of the present invention may preferably be administered in a single daily dose, every second or third day, weekly, every second week, in a single monthly dose or every third month.

It is within the present invention that the medicament as described herein constitutes the pharmaceutical composition disclosed herein.

In a further aspect the present invention is related to a method for the treatment of a subject who is need of such treatment, whereby the method comprises the administration of a pharmaceutically active amount of at least one of the nucleic acids according to the present invention. In an embodiment, the subject suffers from a disease or is at risk to develop such disease, whereby the disease is any of those disclosed herein, particularly any of those diseases disclosed in connection with the use of any of the nucleic acids according to the present invention for the manufacture of a medicament.

It is to be understood that the nucleic acid as well as the antagonists according to the present invention can be used not only as a medicament or for the manufacture of a medicament, but also for cosmetic purposes, particularly with regard to the involvement of MCP-1 in inflamed regional skin lesions. Therefore, a further condition or disease for the treatment or prevention of which the nucleic acid, the medicament and/or the pharmaceutical composition according to the present invention can be used, is inflamed regional skin lesions.

As preferably used herein a diagnostic or diagnostic agent or diagnostic means is suitable to detect, either directly or indirectly MCP-1, preferably MCP-1 as described herein and more preferably MCP-1 as described herein in connection with the various disorders and diseases described herein. However, to the extent that the nucleic acid molecules according to the present invention are also binding to any, some or all of MCP-2, MCP-3, MCP-4 and eotaxin, such nucleic acid molecules can also be used for the diagnosis of diseases and disorders, respectively, the pathogenic mechanism is either directly or indirectly linked or associated with the over-expression or over-activity with MCP-2, MCP-3, MCP-4 and/or eotaxin. The diagnostic is suitable for the detection and/or follow-up of any of the disorders and diseases, respectively, described herein. Such detection is possible through the binding of the nucleic acids according to the present invention to MCP-1. Such binding can be either directly or indirectly be detected. The respective methods and means are known to the ones skilled in the art. Among others, the nucleic acids according to the present invention may comprise a label which allows the detection of the nucleic acids according to the present invention, preferably the nucleic acid bound to MCP-1. Such a label is preferably selected from the group comprising radioactive, enzymatic and fluorescent labels. In principle, all known assays developed for antibodies can be adopted for the nucleic acids according to the present invention whereas the target-binding antibody is substituted to a target-binding nucleic acid. In antibody-assays using unlabeled target-binding antibodies the detection is preferably done by a secondary antibody which is modified with radioactive, enzymatic and fluorescent labels and bind to the target-binding antibody at its Fc-fragment. In the case of a nucleic acid, preferably a nucleic acid according to the present invention, the nucleic acid is modified with such a label, whereby preferably such a label is selected from the group comprising biotin, Cy-3 and Cy-5, and such label is detected by an antibody directed against such label, e.g. an anti-biotin antibody, an anti-Cy3 antibody or an anti-Cy5 antibody, or—in the case that the label is biotin—the label is detected by streptavidin or avidin which naturally bind to biotin. Such antibody, streptavidin or avidin in turn is preferably modified with a respective label, e.g. a radioactive, enzymatic or fluorescent label (like a secondary antibody).

In a further embodiment the nucleic acid molecules according to the invention are detected or analysed by a second detection means, wherein the said detection means is a molecular beacon. The methodology of molecular beacon is known to persons skilled in the art. In brief, nucleic acids probes which are also referred to as molecular beacons, are a reverse complement to the nucleic acids sample to be detected and hybridise because of this to a part of the nucleic acid sample to be detected. Upon binding to the nucleic acid sample the fluorophoric groups of the molecular beacon are separated which results in a change of the fluorescence signal, preferably a change in intensity. This change correlates with the amount of nucleic acids sample present.

It will be acknowledged that the detection of MCP-1 using the nucleic acids according to the present invention will particularly allow the detection of MCP-1 as defined herein.

In connection with the detection of the MCP-1 a preferred method comprises the following steps:

(a) providing a sample which is to be tested for the presence of MCP-1, (b) providing a nucleic acid according to the present invention, (c) reacting the sample with the nucleic acid, preferably in a reaction vessel whereby step (a) can be performed prior to step (b), or step (b) can be preformed prior to step (a).

In a preferred embodiment a further step d) is provided, which consists in the detection of the reaction of the sample with the nucleic acid. Preferably, the nucleic acid of step b) is immobilised to a surface. The surface may be the surface of a reaction vessel such as a reaction tube, a well of a plate, or the surface of a device contained in such reaction vessel such as, for example, a bead. The immobilisation of the nucleic acid to the surface can be made by any means known to the ones skilled in the art including, but not limited to, non-covalent or covalent linkages. Preferably, the linkage is established via a covalent chemical bond between the surface and the nucleic acid. However, it is also within the present invention that the nucleic acid is indirectly immobilised to a surface, whereby such indirect immobilisation involves the use of a further component or a pair of interaction partners. Such further component is preferably a compound which specifically interacts with the nucleic acid to be immobilised which is also referred to as interaction partner, and thus mediates the attachment of the nucleic acid to the surface. The interaction partner is preferably selected from the group comprising nucleic acids, polypeptides, proteins and antibodies. Preferably, the interaction partner is an antibody, more preferably a monoclonal antibody. Alternatively, the interaction partner is a nucleic acid, preferably a functional nucleic acid. More preferably such functional nucleic acid is selected from the group comprising aptamers, spiegelmers, and nucleic acids which are at least partially complementary to the nucleic acid.

In a further alternative embodiment, the binding of the nucleic acid to the surface is mediated by a multi-partite interaction partner. Such multi-partite interaction partner is preferably a pair of interaction partners or an interaction partner consisting of a first member and a second member, whereby the first member is comprised by or attached to the nucleic acid and the second member is attached to or comprised by the surface. The multi-partite interaction partner is preferably selected from the group of pairs of interaction partners comprising biotin and avidin, biotin and streptavidin, and biotin and neutravidin. Preferably, the first member of the pair of interaction partners is biotin.

A preferred result of such method is the formation of an immobilised complex of MCP-1 and the nucleic acid, whereby more preferably said complex is detected. It is within an embodiment that from the complex the MCP-1 is detected.

A respective detection means which is in compliance with this requirement is, for example, any detection means which is specific for that/those part(s) of the MCP-1. A particularly preferred detection means is a detection means which is selected from the group comprising nucleic acids, polypeptides, proteins and antibodies, the generation of which is known to the ones skilled in the art.

The method for the detection of MCP-1 also comprises that the sample is removed from the reaction vessel which has preferably been used to perform step c).

The method comprises in a further embodiment also the step of immobilising an interaction partner of MCP-1 on a surface, preferably a surface as defined above, whereby the interaction partner is defined as herein and preferably as above in connection with the respective method and more preferably comprises nucleic acids, polypeptides, proteins and antibodies in their various embodiments. In this embodiment, a particularly preferred detection means is a nucleic acid according to the present invention, whereby such nucleic acid may preferably be labelled or non-labelled. In case such nucleic acid is labelled it can directly or indirectly be detected. Such detection may also involve the use of a second detection means which is, preferably, also selected from the group comprising nucleic acids, polypeptides, proteins and embodiments in the various embodiments described herein. Such detection means are preferably specific for the nucleic acid according to the present invention. In a more preferred embodiment, the second detection means is a molecular beacon. Either the nucleic acid or the second detection means or both may comprise in a preferred embodiment a detection label. The detection label is preferably selected from the group comprising biotin, a bromo-deoxyuridine label, a digoxigenin label, a fluorescence label, a UV-label, a radio-label, and a chelator molecule. Alternatively, the second detection means interacts with the detection label which is preferably contained by, comprised by or attached to the nucleic acid. Particularly preferred combinations are as follows:

the detection label is biotin and the second detection means is an antibody directed against biotin, or wherein the detection label is biotin and the second detection means is an avidin or an avidin carrying molecule, or wherein the detection label is biotin and the second detection means is a streptavidin or a streptavidin carrying molecule, or wherein the detection label is biotin and the second detection means is a neutravidin or a neutravidin carrying molecule, or wherein the detection label is a bromo-desoxyuridine and the second detection means is an antibody directed against bromo-desoxyuridine, or wherein the detection label is a digoxigenin and the second detection means is an antibody directed against digoxigenin, or wherein the detection label is a chelator and the second detection means is a radio-nuclide, whereby it is preferred that said detection label is attached to the nucleic acid. It is to be acknowledged that this kind of combination is also applicable to the embodiment where the nucleic acid is attached to the surface. In such embodiment it is preferred that the detection label is attached to the interaction partner.

Finally, it is also within the present invention that the second detection means is detected using a third detection means, preferably the third detection means is an enzyme, more preferably showing an enzymatic reaction upon detection of the second detection means, or the third detection means is a means for detecting radiation, more preferably radiation emitted by a radio-nuclide. Preferably, the third detection means is specifically detecting and/or interacting with the second detection means.

Also in the embodiment with an interaction partner of MCP-1 being immobilised on a surface and the nucleic acid according to the present invention is preferably added to the complex formed between the interaction partner and the MCP-1, the sample can be removed from the reaction, more preferably from the reaction vessel where step c) and/or d) are preformed.

In an embodiment the nucleic acid according to the present invention comprises a fluorescence moiety and whereby the fluorescence of the fluorescence moiety is different upon complex formation between the nucleic acid and MCP-1 and free MCP-1.

In a further embodiment the nucleic acid is a derivative of the nucleic acid according to the present invention, whereby the derivative of the nucleic acid comprises at least one fluorescent derivative of adenosine replacing adenosine. In a preferred embodiment the fluorescent derivative of adenosine is ethenoadenosine.

In a further embodiment the complex consisting of the derivative of the nucleic acid according to the present invention and the MCP-1 is detected using fluorescence.

In an embodiment of the method a signal is created in step (c) or step (d) and preferably the signal is correlated with the concentration of MCP-1 in the sample.

In a preferred aspect, the assays may be performed in 96-well plates, where components are immobilized in the reaction vessels as described above and the wells acting as reaction vessels.

It will be acknowledged by the ones skilled in the art that what has been said above also applies to MCP-2, MCP-3, MCP-4 and/or eotaxin, at least to the extent that the nucleic acids according to the present invention are also binding to or with MCP-2, MCP-3, MCP-4 and/or eotaxin.

It is within the present invention that the method for the detection of MCP-1 in a sample as disclosed herein, may also be applied as a method for the diagnosis of a disease such as chronic diseases and chronic disorders as described herein in more detail.

The inventive nucleic acid may further be used as starting material for drug design. Basically there are two possible approaches. One approach is the screening of compound libraries whereas such compound libraries are preferably low molecular weight compound libraries. In an embodiment, the screening is a high throughput screening. Preferably, high throughput screening is the fast, efficient, trial-and-error evaluation of compounds in a target based assay. In best case the analysis are carried by a colorimetric measurement. Libraries as used in connection therewith are known to the one skilled in the art.

Alternatively, the nucleic acid according to the present invention may be used for rational design of drugs. Preferably, rational drug design is the design of a pharmaceutical lead structure. Starting from the 3-dimensional structure of the target which is typically identified by methods such as X-ray crystallography or nuclear magnetic resonance spectroscopy, computer programs are used to search through databases containing structures of many different chemical compounds. The selection is done by a computer, the identified compounds can subsequently be tested in the laboratory.

The rational design of drugs may start from any of the nucleic acid according to the present invention and involves a structure, preferably a three dimensional structure, which is similar to the structure of the inventive nucleic acids or identical to the binding mediating parts of the structure of the inventive nucleic acids. In any case such structure still shows the same or a similar binding characteristic as the inventive nucleic acids. In either a further step or as an alternative step in the rational design of drugs the preferably three dimensional structure of those parts of the nucleic acids binding to the neurotransmitter are mimicked by chemical groups which are different from nucleotides and nucleic acids. By this mimicry a compound different from the nucleic acids can be designed. Such compound is preferably a small molecule or a peptide.

In case of screening of compound libraries, such as by using a competitive assay which is known to the one skilled in the arts, appropriate MCP-1 analogues, MCP-1 agonists or MCP-1 antagonists may be found. Such competitive assays may be set up as follows. The inventive nucleic acid, preferably a spiegelmer which is a target binding L-nucleic acid, is coupled to a solid phase. In order to identify MCP-1 analogues labelled MCP-1 may be added to the assay. A potential analogue would compete with the MCP-1 molecules binding to the spiegelmer which would go along with a decrease in the signal obtained by the respective label. Screening for agonists or antagonists may involve the use of a cell culture assay as known to the ones skilled in the art.

The kit according to the present invention may comprise at least one or several of the inventive nucleic acids. Additionally, the kit may comprise at least one or several positive or negative controls. A positive control may, for example, be MCP-1, particularly the one against which the inventive nucleic acid is selected or to which it binds, preferably, in liquid form. A negative control may, e.g., be a peptide which is defined in terms of biophysical properties similar to MCP-1, but which is not recognized by the inventive nucleic acids. Furthermore, said kit may comprise one or several buffers. The various ingredients may be contained in the kit in dried or lyophilised form or solved in a liquid. The kit may comprise one or several containers which in turn may contain one or several ingredients of the kit. In a further embodiment, the kit comprises an instruction or instruction leaflet which provides to the user information on how to use the kit and its various ingredients. It will be understood that this kind of kit is also and in particular suitable for the diagnosis and detection of a chronic disease and chronic disorder as described herein.

The pharmaceutical and bioanalytical determination of the nucleic acid according to the present invention is elementarily for the assessment of its pharmacokinetic and biodynamic profile in several humours, tissues and organs of the human and non-human body. For such purpose, any of the detection methods disclosed herein or known to a person skilled in the art may be used. In a further aspect of the present invention a sandwich hybridisation assay for the detection of the nucleic acid according to the present invention is provided. Within the detection assay a capture probe and a detection probe are used. The capture probe is complementary to the first part and the detection probe to the second part of the nucleic acid according to the present invention. Both capture and detection probe can be formed by DNA nucleotides, modified DNA nucleotides, modified RNA nucleotides, RNA nucleotides, LNA nucleotides and/or PNA nucleotides.

Hence, the capture probe comprise a sequence stretch complementary to the 5'-end of the nucleic acid according to the present invention and the detection probe comprise a sequence stretch complementary to the 3'-end of the nucleic acid according to the present invention. In this case the capture probe is immobilised to a surface or matrix via its 5'-end whereby the capture probe can be immobilised directly at its 5'-end or via a linker between of its 5'-end and the surface or matrix. However, in principle the linker can be linked to each nucleotide of the capture probe. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

Alternatively, the capture probe comprises a sequence stretch complementary to the 3'-end of the nucleic acid according to the present invention and the detection probe comprise a sequence stretch complementary to the 5'-end of the nucleic acid according to the present invention. In this case the capture probe is immobilised to a surface or matrix via its 3'-end whereby the capture probe can be immobilised directly at its 3'-end or via a linker between of its 3'-end and the surface or matrix. However, in principle, the linker can be linked to each nucleotide of the sequence stretch that is complementary to the nucleic acid according to the present invention. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

The number of nucleotides of the capture and detection probe that may hybridise to the nucleic acid according to the present invention is variable and can be dependent from the number of nucleotides of the capture and/or the detection probe and/or the nucleic acid according to the present invention itself. The total number of nucleotides of the capture and the detection probe that may hybridise to the nucleic acid according to the present invention should be maximal the number of nucleotides that are comprised by the nucleic acid according to the present invention. The minimal number of nucleotides (2 to 10 nucleotides) of the detection and capture probe should allow hybridisation to the 5'-end or 3'-end, respectively, of the nucleic acid according to the present invention. In order to realize high specificity and selectivity between the nucleic acid according to the present invention and other nucleic acids occurring in samples that are analyzed the total number of nucleotides of the capture and detection probe should be or maximal the number of nucleotides that are comprised by the nucleic acid according to the present invention.

Moreover the detection probe preferably carries a marker molecule or label that can be detected as previously described herein. The label or marker molecule can in principle be linked to each nucleotide of the detection probe. Preferably, the label or marker is located at the 5'-end or 3'-end of the detection probe, whereby between the nucleotides within the detection probe that are complementary to the nucleic acid according to the present invention, and the label a linker can be inserted. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

The detection of the nucleic acid according to the present invention can be carried out as follows:

The nucleic acid according to the present invention hybridises with one of its ends to the capture probe and with the other end to the detection probe. Afterwards unbound detection probe is removed by, e.g., one or several washing steps. The amount of bound detection probe which preferably carries a label or marker molecule, can be measured subsequently as, for example, outlined in more detail in WO/2008/052774 which is incorporated herein by reference.

As preferably used herein, the term treatment comprises in a preferred embodiment additionally or alternatively prevention and/or follow-up.

As preferably used herein, the terms disease and disorder shall be used in an interchangeable manner, if not indicated to the contrary.

As used herein, the term comprise is preferably not intended to limit the subject matter followed or described by such term. However, in an alternative embodiment the term comprises shall be understood in the meaning of containing and thus as limiting the subject matter followed or described by such term.

The various SEQ ID NOs., the chemical nature of the nucleic acid molecules according to the present invention and the target molecules MCP-1 as used herein, the actual sequence thereof and the internal reference number is summarized in the following table.

| Seq.-ID | 1. RNA/ Peptide | Sequence | 2. Internal Reference |
|---|---|---|---|
| 1 | L-protein | QPDAINAPVTCCYNFTNRKISVQRLASYRRITSSKCPKEAVIFKTIVAKEICADPK QKWVQDSMDHLDKQTQTPKT | human MCP-1, huMCP-1, CCL2 |
| 2 | L-protein | QPDAVNAPLTCCYSFTSKMIPMSRLESYKRITSSRCPKEAVVFVTKLKREVCADPK KEWVQTYIKNLDRNQMRSEPTTLFKTASALRSSAPLNVKLTRKSEANASTTFSTTT SSTSVGVTSVTVN | mouse MCP-1, mCCL2, mMCP-1, murine MCP-1 (Mus musculus) |
| 3 | L-protein | QPDAINAPVTCCYNFTNRKISVQRLASYRRITSSKCPKEAVTFKTTVAKEICADPK QKWVQDSMDHLDKQIQTPKP | monkey MCP-1 (*Macaca mulatta*) |

-continued

| | | | |
|---|---|---|---|
| 4 | L-protein | QPDAINSPVTCCYTLTSKKISMQRLMSYRRVTSSKCPKEAVIFKTIAGKEICAEPK QKWVQDSISHLDKKNQTPKP | pig MCP-1 (*Sus scrofa*) |
| 5 | L-protein | QPDAIISPVTCCYTLTNKKISIQRLASYKRVTSSKCPKEAVIFKTVLNKEICADPK QKWVQDSMAHLDKKSQTQTA | dog MCP-1 (*Canis familiaris*) |
| 6 | L-protein | QPDAVNSPVTCCYTFTNKTISVKRLMSYRRINSTKCPKEAVIFMTKLAKGICADPK QKWVQDAIANLDKKMQTPKTLTSYSTTQEHTTNLSSTRTPSTTTSL | rabbit MCP-1 (*Oryctolagus cuniculus*) |
| 7 | L-protein | QPVGINTSTTCCYRFINKKIPKQRLESYRRTTSSHCPREAVIFKTKLDKEICADPT QKWVQDFMKHLDKKTQTPKL | human MCP-3, CCL7, huMCP-3 |
| 8 | L-protein | GPASVPTTCCFNLANRKIPLQRLESYRRITSGKCPQKAVIEKTKLAKDICADPKKK WVQDSMKYLDQKSPTPKP | human eotaxin/CCL11 |
| 9 | L-protein | QPDSVSIPITCCFNVTNRKIPIQRLESYTRITNIQCPKEAVIFKTKRGKEVCADPK ERWVRDSMKHLDQIFQNLKP | human MCP-2, CCL8, huMCP-2 |
| 10 | L-RNA | AGCGUGCCCGGAGUGGCAGGGGGACGCGACCUGCAAUAAUGCACGCU | 169-B1trc |
| 11 | L-RNA | AGCGUGCCCGGAGUGGCAGGGGGACGCGACCUGCAAUUGCACGCU | 169-F3trc |
| 12 | 1. L-RNA | AGCGUGCCCGGAGUGGCAGGGGGACGCGACCUGUAAUAAUGCACGCU | 2. 169-C1trc |

| Seq.-ID | 3. RNA/ Peptide | Sequence | 4. Internal Reference |
|---|---|---|---|
| 13 | L-RNA | AGCGUGCCCGGUGUGGCAGGGGGACGCGACCUGGAAUAAUGCGCGCU | 169-A3trc |
| 14 | L-RNA | AGCGUGCCCGGAGUAGCAGGGGGGCGCGACCUGCAAUAAUGCACGCU | 169-B2trc |
| 15 | L-RNA | AGCGUGCCCGGUGUGGUAGGGGGGCGCGAUCUACAAUUGCACGCU | 176-B12trc |
| 16 | L-RNA | AGCGUGCCCGGUGUGACAGGGGGGCGCGACCUGCAUUUGCACGCU | 176-D9trc |
| 17 | L-RNA | AGCGUGCCGGGUGUGGCAGGGGGGCGCGACCUGUAUUUGCACGCU | 176-B10trc |
| 18 | L-RNA | AGCGUGCCCGGAGUGGCAGGGGGGCGCGACCUGCAAUAAUGCACGCU | 169-F2trc |
| 19 | L-RNA | AGCGUGCCCGGUGUGGCAGGGGGGCGCGACCUGCAAUUGCACGCU | 176-B9trc |
| 20 | L-RNA | AGCAUGCCCGGUGUGGGAGGGGGGCGCGACCUGCAUUUGCAUGCU | 176-H9trc |
| 21 | L-RNA | AGCGUGCCCGGUGUGGUAGGGGGGCGCGACGUACAUUUGCACGCU | 176-E10trc |
| 22 | L-RNA | AGUGUGCCAGCUGUGAUGGGGGGGCGCGACCCAUUUUACACACU | 176-G9trc |
| 23 | L-RNA | AGUGUGCCAGCGUGAUGGGGGGGCGCGACCCAUUUUACACACU | 176-F9trc |
| 24 | L-RNA | AGUGUGCGAGCGUGAUGGGGGGGCGCGACCCAUUUUACAUACU | 176-C11trc |
| 25 | L-RNA | AGUGUGCCAGCGUGAUGGGGGGGCGCGACCCAUUUUACAUACU | 176-E11trc |
| 26 | L-RNA | AGUAUGCCAGCGUGAUGGGGGGGCGCGACCCAUUUUACAUACU | 176-D10trc |
| 27 | L-RNA | AGUGUGCCAGUGUGAUGGGGGGGCGCGACCCAUUUUACACACU | 176-H10trc |
| 28 | L-RNA | AGCGUGCCAGUGUGAUGGGGGGGCGCGAGCGAUUUUAGACGCU | 176-C9trc |
| 29 | L-RNA | ACGCACGUCCCUCACCGGUGCAAGUGAAGCCGCGGCUCUGCGU | 180-B1-001 |

| Seq.-ID | 5. RNA/ Peptide | Sequence | 6. Internal Reference |
|---|---|---|---|
| 30 | L-RNA | ACGCACCUCCCUCACCGGUGCAAGUGAAGCCGUGGCUCUGCGC | 180-A4-002 |
| 31 | L-RNA | ACGCACGUCCCUCACCGGUGCAAGUGAAGCCGUGGCUCUGCGU | 180-D1-002 |
| 32 | L-RNA | GCACGUCCCUCACCGGUGCAAGUGAAGCCGUGGCUCUGCGU | 180-D1-011 |
| 33 | L-RNA | ACGCACGUCCCUCACCGGUGCAAGUGAAGCCGUGGCUCUGC | 180-D1-012 |
| 34 | L-RNA | GCACGUCCCUCACCGGUGCAAGUGAAGCCGUGGCUGUGC | 180-D1-018 |
| 35 | L-RNA | CGCACGUCCCUCACCGGUGCAAGUGAAGCCGUGGCUCUGCGU | 180-D1-034 |
| 36 | L-RNA | CGCACGUCCCUCACCGGUGCAAGUGAAGCCGUGGCUCUGCG | 180-D1-035 |
| 37 | L-RNA | GCACGUCCCUCACCGGUGCAAGUGAAGCCGUGGCUCUGCG | 180-D1-036 = NOX-E36 |

-continued

| | | | |
|---|---|---|---|
| 38 | L-RNA | GUGCUGCGUAGUGGAAGACUACCUAAUGACAGCCGAAUGCUGGCAGCAC | 178-A8 |
| 39 | L-RNA | GUGCUGCGUAGUGGAAGACUACCUAAUGACAGCCUAAUGCUGGCAGCAC | 178-F7 |
| 40 | L-RNA | GUGCUGCGUAGUGGAAGACUACCUUAUGACAGCCGAAUGCUGGCAGCAC | 178-G7 |
| 41 | L-RNA | GUGCUGCGUAGUGAAAAACUACUGCCAGUGGGUCAGAGCUAGCAGCAC | 178-C6 |
| 42 | L-RNA | GUGCUGCGGAGUUAAAAACUCCCUAAGACAGGCCAGAGCCGGCAGCAC | 178-E7 |
| 43 | L-RNA | GUGCUGCGGAGUUGAAAACUCCCUAAGACAGGCCAGAGCCGGCAGCAC | 178-G6 |
| 44 | L-RNA | GUGCUGCGUAGUGGAAGACUACCUAUGACAGCCUAAUGCUGGCAGCAC | 178-A7 |
| 45 | L-RNA | GUGCUGCGGAGUUAAAAACUCCCUAAGACAGGCUAGAGCCGGCAGCAC | 178-C7 |

| Seq.-ID | 7. RNA/ Peptide | Sequence | 8. Internal Reference |
|---|---|---|---|
| 46 | L-RNA | GUGCUGCGGCGUGAAAAACGCCCUGCGACUGCCCUUUAUGCAGGGAGCAC | 178-E5 |
| 47 | L-RNA | GUGCUGCGUAGUGAAAAACUACCAACGACUGGCUAGAGCCGGCAGCAC | 181-F1 |
| 48 | L-RNA | GUGCUGCGUAGUGAAAGACUACCUGUGACAGCCGAAUGCUGGCAGCAC | 181-B2 |
| 49 | L-RNA | GUACUGCGUAGUUAAAAACUACCAACGACUGGCUAGAGCCGGCAGCAC | 181-02 |
| 50 | L-RNA | GUGCUGCGUAGUUAAAAACUACCAACGACUGGCUAGAGCCGGCAGCAC | 178-A6 |
| 51 | L-RNA | GUGCUGCGUAGUUAAAAACUACCAGCGACAGGCUAGAGCCGGCAGCAC | 178-D6 |
| 52 | L-RNA | GUGCUGCGUAGUUAAAAACUACCAGCGACUGGCUAGAGCCGGCAGCAC | 178-D5 |
| 53 | L-RNA | GUGCUGCGUAGUGAGAAACUACCAACGACUGGCUAGAGCCGGCAGCAC | 181-A2 |
| 54 | L-RNA | GGCUGCGUAGUUAAAAACUACCAGCGACUGGCUAGAGCCGGCAGCC | 178-D5-020 |
| 55 | L-RNA | GGCGCGUAGUUAAAAACUACCAGCGACUGGCUAGAGCCGGCGCC | 178-D5-027 |
| 56 | L-RNA | GUGCGCGUAGUUAAAAACUACCAGCGACUGGCUAGAGCCGGCGCAC | 178-D5-030 |
| 57 | L-RNA | GUGCGCGUAGUGAGAAACUACCAACGACUGGCUAGAGCCGGCGCAC | 181-A2-002 |
| 58 | L-RNA | GUGCCGUAGUGAGAAACUACCAACGACUGGCUAGAGCCGGGCAC | 181-A2-004 |
| 59 | L-RNA | GUGGCGUAGUGAGAAACUACCAACGACUGGCUAGAGCCGGCCAC | 181-A2-005 |
| 60 | L-RNA | GUCGCGUAGUGAGAAACUACCAACGACUGGCUAGAGCCGGCGAC | 181-A2-006 |
| 61 | L-RNA | UGCGCGUAGUGAGAAACUACCAACGACUGGCUAGAGCCGGCGCA | 181-A2-007 |
| 62 | L-RNA | GCUGCGUAGUGAGAAACUACCAACGACUGGCUAGAGCCGGCAGC | 181-A2-008 |

| Seq.-ID | 9. RNA/ Peptide | Sequence | 10. Internal Reference |
|---|---|---|---|
| 63 | L-RNA | GCUGCGUAGUGAGAAACUACCAACGACUGGCUAGAGCCGGCAGC | 181-A2-011 |
| 64 | L-RNA | GGUGCGUAGUGAGAAACUACCAACGACUGGCUAGAGCCGGCACC | 181-A2-012 |
| 65 | L-RNA | UGGCGUAGUGAGAAACUACCAACGACUGGCUAGAGCCGGC-CA | 181-A2-015 |
| 66 | L-RNA | GCGCGUAGUGAGAAACUACCAACGACUGGCUAGAGCCGGCGC | 181-A2-016 |
| 67 | L-RNA | GUGCGUAGUGAGAAACUACCAACGACUGGCUAGAGCCGGCAC | 181-A2-017 |
| 68 | L-RNA | GG-GCGUAGUGAGAAACUACCAACGACUGGCUAGAGCCGGCCC | 181-A2-018 |
| 69 | L-RNA | GAGCGUAGUGAGAAACUACCAACGACUGGCUAGAGCCGGCUC | 181-A2-019 |
| 70 | L-RNA | CGGCGUAGUGAGAAACUACCAACGACUGGGUAGAGCCGGCCG | 181-A2-020 |
| 71 | L-RNA | CCGCGUAGUGAGAAACUACCAACGACUGGCUAGAGCCGGCGG | 181-A2-021 |
| 72 | L-RNA | CAGCGUAGUGAGAAACUACCAACGACUGGCUAGAGCCGGCUG | 181-A2-022 |
| 73 | L-RNA | CUGCGUAGUGAGAAACUACCAACGACUGGCUAGAGCCGGCAG | 181-A2-023 |
| 74 | L-RNA | AGCGUGUUAGUGAAGUGGGUGGCAGGUAAAGGACACGCU | 184-B8trc |

-continued

| | | | |
|---|---|---|---|
| 75 | L-RNA | AGCGUGGUAGCGGUGUGGGUGGUAGGUAAAGGCCACGCU | 184-C6trc |
| 76 | L-RNA | AGCGUGAUAGAAGAGCGGGUGGUAGGUAAAGGUCAGGCU | 184-H5trc |
| 77 | L-RNA | AGCGUGUUAGGUAGGGUGGUAGUAAGUAAAGGACACGCU | 184-A7trc |
| 78 | L-RNA | AGCGUGUUAGGUGGGUGGUAGUAAGUAAAGGACACGCU | 187-A5trc |
| 79 | L-RNA | AGCGUGUUAGGUGGGUGGUAGUAAGUAAAGGGCACGCU | 187-H5trc |

| Seq.-ID | 11. RNA/ Peptide | Sequence | 12. Internal Reference |
|---|---|---|---|
| 80 | L-RNA | CCGCUUAGGUGGGUGGUAGUAAGUAAAGGGGCGG | 174-D4-004 |
| 81 | L-RNA | GCGCGAGCAGGUGGGUGGUAGAAUGUAAAGACUCGCGUC | 166-A4-002 |
| 82 | L-RNA | CGUGUUAGGUGGGUGGUAGUAAGUAAAGGACACG | 187-A5trc-001 |
| 83 | L-RNA | GUGUUAGGUGGGUGGUAGUAAGUAAAGGACAC | 187-A5trc-002 |
| 84 | L-RNA | CGUGUUAGGUGGGUGGUAGUAAGUAAAGGGCACG | 187-H5trc-002 |
| 85 | L-RNA | GUGUUAGGUGGGUGGUAGUAAGUAAAGGGCAC | 187-H5trc-003 |
| 86 | L-RNA | UGUUAGGUGGGUGGUAGUAAGUAAAGGGCA | 187-H5trc-004 |
| 87 | L-RNA | GGACGAGAGUGACAAAUGAUAUAACCUCCUGACUAACGCUGCGGGCGACAGG | 177-B3 |
| 88 | L-RNA | GGACCUAUCGCUAAGACAACGCGCAGUCUACGGGACAUUCUCCGCGGACAGG | 177-C1 |
| 89 | L-RNA | GGACAAUUGUUACCCCCGAGAGAGACAAAUGAGACAACCUCCUGAAGACAGG | 177-C2 |
| 90 | L-RNA | GGACGAAAGUGAGAAAUGAUACAACCUCCUGUUGCUGCGAAUCCGGACAGG | 177-E3 |
| 91 | L-RNA | GGACGUAAAAGACGCUACCCGAAAGAAUGUCAGGAGGGUAGACCGACAGG | 177-D1 |
| 92 | L-RNA | GGACUAGAAACUACAAUAGCGGCCAGUUGCACCGCGUUAUCAACGACAGG | 177-E1 |
| 93 | L-RNA | GGACUAGUCAGCCAGUGUGUAUAUCGGACGCGGGUUUAUUUACUGACAGG | 177-A1 |
| 94 | L-RNA | GGACUGUCCGGAGUGUGAAACUCCCCGAGACCGCCAGAAGCGGGGACAGG | 177-G3 |
| 95 | L-RNA | GGACUUCUAUCCAGGUGGGUGGUAGUAUGUAAAGAGAUAGAAGUGACAGG | 177-C3 |
| 96 | L-RNA | GGACGAGAGCGAACAAUGAUAUAACCUCCUGACGGAAAGAGAUCGACAGG | 177-A2 |
| 97 | L-RNA | CCUGUGCUACACGCAGUAAGAAGUGAACGUUCAGUAUGUGUGCACAGG | 170-E4trc |

| Seq.-ID | 13. RNA/ Peptide | Sequence | 14. Internal Reference |
|---|---|---|---|
| 98 | L-RNA | CGUGAGCCAGGCACCGAGGGCGUUAACUGGCUGAUUGGACACGACACG | 166-D2trc |
| 99 | L-RNA | CGUGAACAUGCAAGCUAAGCGGGGCUGUUGGUUGCUUGGCCCGCCACG | 174-A2trc |
| 100 | L-RNA | CGUGCAGAGAGAGACCAACCACGUAAAAUCAACCUAAUGGGCCGCACG | 174-E2trc |
| 101 | L-RNA | CGUGCAGAGAGAGACCAACCACGUAAAAUCAACCUAAUGGGCCGCACG | 183-G3trc |
| 102 | L-RNA | CGUGAACAUUCAAGCUAAGCGGGGCUGUUGGUUGCUUGGCCCGCCACG | 183-B2trc |
| 103 | L-RNA | CGUGCCGAGGCGGCGACCAGCGUUACUUAGAGAGGCUUUGGCACCACG | 166-B2trc |
| 104 | L-RNA | CGUGAUAACAGCCGUCGGUCAAGAAAACAAAGUUCGGGCGGCGCACG | 166-G3trc |
| 105 | L-RNA | CGUGGGUGGCGCACCGAGGGCGAAAAGCCACCAGUAAAGAUAGACCG | 166-D1trc |
| 106 | L-RNA | CGUGUGAUCUCCUUUGGGGUGAUUAGCUUAGAGACUUCCCACACG | 183-H2trc |
| 107 | L-RNA | GCACCUUCGCCUAAUACACGUGCCGGCUAGCUAAUACUCGUCCGC | 167-A7trc |
| 108 | L-RNA | GCACGACUUGGGCGACCAGUGAUACUUAGAGAGCAAGUCGUCGGC | 167-C7trc |
| 109 | L-RNA | GCGCGCGCUCAGUAAGAAAUUGAAAGUUCAGAAUGUCGUCGCGC | 167-B5trc |
| 110 | L-RNA | AGUGUGUGGCAGGCUAAGGAGAUAUUCCGAGACCACGCU | 184-D7trc |
| 111 | L-RNA | AGUGUGUGGCAGACUAUGGAUAGACUCCGAGACCACGCU | 184-D6trc |

-continued

| | | | |
|---|---|---|---|
| 112 | L-RNA | AGCGUGAGGCGACCAGCGGAUUACUUAGAGAGUCACGCU | 184-E5trc |
| 113 | L-RNA | AGCGUGAAGGGGACCAGCGUUACUUACAGAGUUCACGCU | 184-G6trc |
| 114 | L-RNA | AGCGUGUGAUGUAUGUAGCACCGUAUCAGAGGACACGCU | 184-B7trc |
| 115 | L-RNA | AGCGUGAGGCGACCCGUGUUUCGUAGAGAGUCACGCU | 184-B6trc |

| Seq.-ID | 15. RNA/ Peptide | Sequence | 16. Internal Reference |
|---|---|---|---|
| 116 | L-RNA | 5'PEG-GCACGUCCCUCACCGGUGCAAGUGAAGCCGUGGCUCUGCG | NOX-E36-5'PEG |
| 117 | L-RNA | GCACGUCCCUCACCGGUGCAAGUGAAGCCGUGGCUCUGCG-3'PEG | NOX-E36-3'PEG |
| 118 | L-RNA | GAGAUGGCGACAUUGGUUGGGCAUGAGGCGAGGCCCUUUGAUGAAUCCGCGGCCAUUC | 188-A3-001 |
| 119 | L-RNA | GAUGGCGACAUUGGUUGGGCAUGAGGCGAGGCCCUUUGAUGAAUCCGCGGCCAUUC | 188-A3-004 |
| 120 | L-RNA | GGCGACAUUGGUUGGGCAUGAGGCGAGGCCCUUUGAUGAAUCCGCGGCCAUUC | 188-A3-005 |
| 121 | L-RNA | GGCGACAUUGGUUGGGCAUGAGGCGAGGCCCUUUGAUGAAUCCGCGGCCAUU | 188-A3-006 |
| 122 | L-RNA | GGCGACAUUGGUUGGGCAUGAGGCGAGGCCCUUUGAUGAAUCCGCGGCCA | 188-A3-007 = mNOX-E36 |
| 123 | L-RNA | GCUGGUUACCGAGGGGGCGUCGUUGGAGUUUGGUUGGUUGUCACCAGC | 189-G7-001 |
| 124 | L-RNA | CUGGUUACCGAGGGGGCGUCGUUGGAGUUUGGUUGGUUGUCACCAG | 189-G7-002 |
| 125 | L-RNA | UGGUUACCGAGGGGGCGUCGUUGGAGUUUGGUUGGUUGUCACCA | 189-G7-003 |
| 126 | L-RNA | GCCGGUUACCGAGGGGGCGUCGUUGGAGUUUGGUUGGUUGUCACCGGC | 189-G7-007 |
| 127 | L-RNA | GCCGGCUACCGAGGGGGCGUCGUUGGAGUUUGGUUGGUUGUCGCCGGC | 189-G7-008 |
| 128 | L-RNA | GCGCGUACCGAGGGGGCGUCGUUGGAGUUUGGUUGGUUGUCCGCGC | 189-G7-010 |
| 129 | L-RNA | GGGCCUACCGAGGGGGCGUCGUUGGAGUUUGGUUGGUUGUCGGCCC | 189-G7-012 |

| Seq.-ID | 17. RNA/ Peptide | Sequence | 18. Internal Reference |
|---|---|---|---|
| 130 | D-protein | Btiotin-QPDAINAPVTCCYNFTNRKISVQRLASYRRITSSKCPKEAVIFKTIVAKEI CADPKQKWVQDSMDHLDKQTQTPKT | biotinylated human D-MCP-1 |
| 131 | 3. D-protein | Biotin-QPDAVNAPLTCCYSFTSKMIPMSRLESYKRITSSRCPKEAVVFVTKLKREQT YIKNLDRNQMRSEP-Biotin | 4. biotiny lated mouse D-MCP-1 |
| 132 | D-RNA | AGCGUGCCCGGAGUGGCAGGGGGACGCGACCUGCAAUAAUGCACGCU | 169-B1Trc |
| 133 | D-RNA | AGCGUGCCCGGAGUGGCAGGGGGACGCGACCUGCAAUUGCACGCU | 169-F3trc |
| 134 | 5. D-RNA | AGCGUGCCCGGAGUGGCAGGGGGACGCGACCUGUAAUAAUGCACGCU | 6. 169-C1trc |
| 135 | D-RNA | AGCGUGCCCGGUGUGGCAGGGGGAGGCGACCUGCAAUAAUGCGCGCU | 169-A3trc |
| 136 | D-RNA | AGCGUGCCCGGAGUAGCAGGGGGGCGCGACCUGCAAUAAUGCACGCU | 169-B2trc |
| 137 | D-RNA | AGCGUGCCCGGUGUGGUAGGGGGGCGCGAUCUACAAUUGCACGCU | 176-B12trc |
| 138 | D-RNA | AGCGUGCCCGGUGUGACAGGGGGGCGCGACCUGCAUUUGCACGCU | 176-D9trc |
| 139 | D-RNA | AGCGUGCCCGGUGUGGCAGGGGGGCGCGACCUGUAUUUGCACGCU | 176-B10trc |

| Seq.-ID | 19. RNA/ Peptide | Sequence | 20. Internal Reference |
|---|---|---|---|
| 140 | D-RNA | AGCGUGCCCGGAGUGGCAGGGGGGCGCGACCUGCAAUAAUGCACGCU | 169-F2trc |
| 141 | D-RNA | AGCGUGCCCGGUGUGGCAGGGGGGCGCGACCUGCAAUUGCACGCU | 176-B9trc |
| 142 | D-RNA | AGCAUGCCCGGUGUGGCAGGGGGGCGCGACCUGCAUUUGCAUGCU | 176-H9trc |
| 143 | D-RNA | AGCGUGCCCGGUGUGGUAGGGGCGCGCGACCUACAUUUGCACGCU | 176-E10trc |
| 144 | D-RNA | AGUGUGCCAGCUGUGAUGGGGGGGCGCGACCCAUUUUACACACU | 176-G9trc |
| 145 | D-RNA | AGUGUGCCAGCGUGAUGGGGGGGCGCGACCCAUUUUACACACU | 176-F9trc |

-continued

| | | | |
|---|---|---|---|
| 146 | D-RNA | AGUGUGCGAGCGUGAUGGGGGGGCGCGACCCAUUUUACAUACU | 176-C11trc |
| 147 | D-RNA | AGUGUGCCAGCGUGAUGGGGGGGCGCGACCCAUUUUACAUACU | 176-E11trc |
| 148 | D-RNA | AGUAUGCCAGCGUGAUGGGGGGGCGCGACCCAUUUACAUACU | 176-D10trc |
| 149 | D-RNA | AGUGUGCCAGUGUGAUGGGGGGGCGCGACCCAUUUUACACACU | 176-H10trc |
| 150 | D-RNA | AGCGUGCCAGUGUGAUGGGGGGGCGCGACCCAUUUUACACGCU | 176-C9trc |
| 151 | D-RNA | ACGCACGUCCCUCACCGGUGCAAGUGAAGCCGCGGCUCUGCGU | 180-B1-001 |
| 152 | D-RNA | ACGCACCUCCCUCACCGGUGCAAGUGAAGCCGUGGCUCUGCGC | 180-A4-002 |
| 153 | D-RNA | ACGCACGUCCCUCACCGGUGCAAGUGAAGCCGUGGCUCUGCGU | 180-D1-002 |
| 154 | D-RNA | GCACGUCCCUCACCGGUGCAAGUGAAGCCGUGGCUCUGCGU | 180-D1-011 |

| Seq.-ID | 21. RNA/ Peptide | Sequence | 22. Internal Reference |
|---|---|---|---|
| 155 | D-RNA | ACGCACGUCCCUCACCGGUGCAAGUGAAGCCGUGGCUCUGC | 180-D1-012 |
| 156 | D-RNA | GCACGUCCCUCACCGGUGCAAGUGAAGCCGUGGCUCUGC | 180-D1-018 |
| 157 | D-RNA | CGCACGUCCCUCACCGGUGCAAGUGAAGCCGUGGCUCUGCGU | 180-D1-034 |
| 158 | D-RNA | CGCACGUCCCUCACCGGUGCAAGUGAAGCCGUGGCUCUGCG | 180-D1-035 |
| 159 | D-RNA | GCACGUCCCUCACCGGUGCAAGUGAAGCCGUGGCUCUGCG | (D-) 180-D1-036, (D-) NOX-E36 |
| 160 | D-RNA | GUGCUGCGUAGUGGAACACUACCUAAUGACAGCCGAAUGCUGGCAGCAC | 178-A8 |
| 161 | D-RNA | GUGCUGCGUAGUGGAAGACUACCUAAUGACAGCCUAAUGCUGGCAGCAC | 178-F7 |
| 162 | D-RNA | GUGCUGCGUAGUGGAAGACUACCUUAUGACAGCCGAAUGCUGGCAGCAC | 178-G7 |
| 163 | D-RNA | GUGCUGCGUAGUGAAAAACUACUGCCAGUGGGUCAGAGCUAGCAGCAC | 178-C6 |
| 164 | D-RNA | GUGCUGCGGAGUUAAAAACUCCCUAAGACAGGCCAGAGCCGGCAGCAC | 178-E7 |
| 165 | D-RNA | GUGCUGCGGAGUUGAAAACUCCCUAAGACAGGCCAGAGCCGGCAGCAC | 178-G6 |
| 166 | D-RNA | GUGCUGCGUAGUGGAAGACUACCUAUGACAGCCUAAUGCUGGCAGCAC | 178-A7 |
| 167 | D-RNA | GUGCUGCGGAGUUAAAAACUCCCUAAGACAGGCUAGAGCCGGCAGCAC | 178-C7 |
| 168 | D-RNA | GUGCUGCGGCGUGAAAAACGCCCUGCGACUGCCCUUUAUGCAGGCAGCAC | 178-E5 |
| 169 | D-RNA | GUGCUGCGUAGUGAAAAACUACCAACGACUGGCUAGAGCCGGCAGCAC | 181-F1 |
| 170 | D-RNA | GUGCUGCGUAGUGAAAGACUACCUGUGACAGCCGAAUGCUGGCAGCAC | 181-B2 |

| Seq.-ID | 23. RNA/ Peptide | Sequence | 27. Internal Reference |
|---|---|---|---|
| 171 | D-RNA | GUACUGCGUAGUUAAAAACUACCAACGACUGGCUAGAGCCGGCAGCAC | 181-C2 |
| 172 | D-RNA | GUGCUGCGUAGUUAAAAACUACCAACGACUGGCUAGAGCCGGCAGCAC | 178-A6 |
| 173 | D-RNA | GUGCUGCCUAGUUAAAAACUACCAGCGACAGGCUAGAGCCGGCAGCAC | 178-D6 |
| 174 | D-RNA | GUGCUGCGUAGUUAAAAACUACCAGCGACUGGCUAGAGCCGGCAGCAC | 178-D5 |
| 175 | D-RNA | GUGCUGCGUAGUGAGAAACUACCAACGACUGGCUAGAGCCGGCAGCAC | 181-A2 |
| 176 | D-RNA | GGCUGCGUAGUUAAAAACUACCAGCGACUGGCUAGAGCCGGCAGCC | 178-D5-020 |
| 177 | D-RNA | GGCGCGUAGUUAAAAACUACCAGCGACUGGCUAGAGCCGGCGCC | 178-D5-027 |
| 178 | D-RNA | GUGCGCGUAGUUAAAAACUACCAGCGAGUGGCUAGAGCCGGCGCAC | 178-D5-030 |
| 179 | D-RNA | GUGCGCGUAGUGAGAAACUACCAACGACUGGCUAGAGCCGGCGCAC | 181-A2-002 |
| 180 | D-RNA | GUGCCGUAGUGAGAAACUACCAACGACUGGCUAGAGCCGGGCAC | 181-A2-004 |
| 181 | D-RNA | GUGGCGUAGUGAGAAACUACCAACGACUGGCUAGAGCCGGCCAC | 181-A2-005 |
| 182 | D-RNA | GUCGCGUAGUGAGAAACUACCAACGACUGGCUAGAGCCGGCGAC | 181-A2-006 |

-continued

| Seq.-ID | 25. RNA/ Peptide | Sequence | 2. Internal Reference |
|---|---|---|---|
| 183 | D-RNA | UGCGCGUAGUGAGAAACUACCAACGACUGGCUAGAGCCGGCGCA | 181-A2-007 |
| 184 | D-RNA | GCUGCGUAGUGAGAAACUACCAACGACUGGCUAGAGCCGGCAGC | 181-A2-008 |
| 185 | D-RNA | GCUGCGUAGUGAGAAACUACCAACGACUGGCUAGAGCCGGCAGC | 181-A2-011 |
| 186 | D-RNA | GGUGCGUAGUGAGAAACUACCAACGACUGGCUAGAGCCGGCACC | 181-A2-012 |
| 187 | D-RNA | UGGCGUAGUGAGAAACUACCAACGACUGGCUAGAGCCGGC-CA | 181-A2-015 |
| 188 | D-RNA | GCGCGUAGUGAGAAACUACCAACGACUGGCUAGAGCCGGCGC | 181-A2-016 |
| 189 | D-RNA | GUGCGUAGUGAGAAACUACCAACGACUGGCUAGAGCCGGCAC | 181-A2-017 |
| 190 | D-RNA | GG-GCGUAGUGAGAAACUACCAACGACUGGCUAGAGCCGGCCC | 181-A2-018 |
| 191 | D-RNA | GAGCGUAGUGAGAAACUACCAACGACUGGCUAGAGCCGGCUC | 181-A2-019 |
| 192 | D-RNA | CGGCGUAGUGAGAAACUACCAACGACUGGCUAGAGCCGGCCG | 181-A2-020 |
| 193 | D-RNA | CCGCGUAGUGAGAAACUACCAACGACUGGCUAGAGCCGGCGG | 181-A2-022 |
| 194 | D-RNA | CAGCGUAGUGAGAAACUACCAACGACUGGCUAGAGCCGGCUG | 181-A2-022 |
| 195 | D-RNA | CUGCGUAGUGAGAAACUACCAACGACUGGCUAGAGCCGGCAG | 181-A2-023 |
| 196 | D-RNA | AGCGUGUUAGUGAAGUGGGUGGCAGGUAAAGGACACGCU | 184-B8trc |
| 197 | D-RNA | AGCGUGGUAGCGGUGUGGGUGGUAGGUAAAGGCCACGCU | 184-C6trc |
| 198 | D-RNA | AGCGUGAUAGAAGAGCGGGUGGUAGGUAAAGGUCAGGCU | 184-H5trc |
| 199 | D-RNA | AGCGUGUUAGGUAGGGUGGUAGUAAGUAAAGGACACGCU | 184-A7trc |
| 200 | D-RNA | AGCGUGUUAGGUGGGUGGUAGUAAGUAAAGGACACGCU | 187-A5trc |
| 201 | D-RNA | AGCGUGUUAGGUGGGUGGUAGUAAGUAAAGGGCACGCU | 187-H5trc |
| 202 | D-RNA | CCGCUUAGGUGGGUGGUAGUAAGUAAAGGGGCGG | 174-D4-004 |
| 203 | D-RNA | GCGCGAGCAGGUGGGUGGUAGAAUGUAAAGACUCGCGUC | 166-A4-002 |
| 204 | D-RNA | CGUGUUAGGUGGGUGGUAGUAAGUAAAGGACACG | 187-A5trc-001 |
| 205 | D-RNA | GUGUUAGGUGGGUGGUAGUAAGUAAAGGACAC | 187-A5trc-002 |
| 206 | D-RNA | CGUGUUAGGUGGGUGGUAGUAAGUAAAGGGCACG | 187-H5trc-002 |

| Seq.-ID | 27. RNA/ Peptide | Sequence | 28. Internal Reference |
|---|---|---|---|
| 207 | D-RNA | GUGUUAGGUGGGUGGUAGUAAGUAAAGGGCAC | 187-H5trc-003 |
| 208 | D-RNA | UGUUAGGUGGGUGGUAGUAAGUAAAGGGCA | 187-H5trc-004 |
| 209 | D-RNA | GGACGAGAGUGACAAAUGAUAUAACCUCCUGACUAACGCUGCGGGCGACAGG | 177-B3 |
| 210 | D-RNA | GGACCUAUCGCUAAGACAACGCGCAGUCUACGGGACAUUCUCCGCGGACAGG | 177-C1 |
| 211 | D-RNA | GGACAAUUGUUACCCCCGAGAGAGACAAAUGAGACAACCUCCUGAAGACAGG | 177-C2 |
| 212 | D-RNA | GGACGAAAGUGAGAAAUGAUACAACCUCCUGUUGCUGCGAAUCCGGACAGG | 177-E3 |
| 213 | D-RNA | GGACGUAAAAGACGCUACCCGAAAGAAUGUCAGGAGGGUAGACCGACAGG | 177-D1 |
| 214 | D-RNA | GGACUAGAAACUACAAUAGCGGCCAGUUGCACCGCGUUAUCAACGACAGG | 177-E1 |
| 215 | D-RNA | GGACUAGUCAGCCACUGUGUAUAUCGGACGCGGGUUUAUUUACUGACAGG | 177-A1 |
| 216 | D-RNA | GGACUGUCCGGAGUGUGAAACUCCCCGAGACCGCCAGAAGCGGGGACAGG | 177-G3 |
| 217 | D-RNA | GGACUUCUAUCCAGGUGGGUGGUAGUAUGUAAAGAGAUAGAAGUGACAGG | 177-C3 |
| 218 | D-RNA | GGACGAGAGCGAACAAUGAUAUAACCUCCUGACGGAAAGAGAUCGACAGG | 177-A2 |

-continued

| | | | |
|---|---|---|---|
| 219 | D-RNA | CCUGUGCUACACGCAGUAAGAAGUGAACGUUCAGUAUGUGUGCACAGG | 170-E4trc |
| 220 | D-RNA | CGUGAGCCAGGCACCGAGGGCGUUAACUGGCUGAUUGGACACGACACG | 166-D2trc |
| 221 | D-RNA | CGUGAACAUGCAAGCUAAGCGGGGCUGUUGGUUGCUUGGCCCGCCACG | 174-A2trc |
| 222 | D-RNA | CGUGCAGAGAGAGACCAACCACGUAAAAUCAACCUAAUGGGGCGCACG | 174-E2trc |
| 223 | D-RNA | CGUGCAGAGAGAGACCAACCACGUAAAAUCAACCUAAUGGGCCGCACG | 183-G3trc |

| Seq.-ID | 29. RNA/ Peptide | Sequence | 30. Internal Reference |
|---|---|---|---|
| 224 | D-RNA | CGUGAACAUUCAAGCUAAGCGGGGCUGUUGGUUGCUUGGCCCGCCACG | 183-B2trc |
| 225 | D-RNA | CGUGCCGAGGCGGCGACCAGCGUUACUUAGAGAGGCUUUGGCACCACG | 166-B2trc |
| 226 | D-RNA | CGUGAUAACAGCCGUCGGUCAAGAAAACAAAGUUCGGGCGGCGCACG | 166-G3trc |
| 227 | D-RNA | CGUGGGUGGCGCACCGAGGGCGAAAAGCCACCAGUAAAGAUAGACCG | 166-D1trc |
| 228 | D-RNA | CGUGUGAUCUCCUUUGGGGUGAUUAGCUUAGAGACUUCCCACACG | 183-H2trc |
| 229 | D-RNA | GCACCUUCGCCUAAUACACGUGCCGGCUAGCUAAUACUCGUCCGC | 167-A7trc |
| 230 | D-RNA | GCACGACUUGGGCGACCAGUGAUACUUAGAGAGCAAGUCGUCGGC | 167-C7trc |
| 231 | D-RNA | GCGCGCGCUGAGUAAGAAAUUGAAAGUUCAGAAUGUCGUCGCGC | 167-B5trc |
| 232 | D-RNA | AGUGUGUGGCAGGCUAAGGAGAUAUUCCGAGACCACGCU | 184-D7trc |
| 233 | D-RNA | AGUGUGUGGCAGACUAUGGAUAGACUCCGAGACCACGCU | 184-D6trc |
| 234 | D-RNA | AGCGUGAGGCGACCAGCGGAUUACUUAGAGAGUCACGCU | 184-E5trc |
| 235 | D-RNA | AGCGUGAAGGGGACCAGCGUUACUUACAGAGUUCACGCU | 184-G6trc |
| 236 | D-RNA | AGCGUGUGAUGUAUGUAGCACCGUAUCAGAGGACACGCU | 184-B7trc |
| 237 | D-RNA | AGCGUGAGGCGACCCGUGUUUCGUAGAGAGUCACGCU | 184-B6trc |
| 238 | D-RNA | 5'PEG-GCACGUCCCUCACCGGUGCAAGUGAAGCCGUGGCUCUGCG | NOX-E36-5'PEG |
| 239 | D-RNA | GCACGUCCCUCACCGGUGCAAGUGAAGCCGUGGCUCUGCG-3'PEG | NOX-E36-3'PEG |

| Seq.-ID | 31. RNA/ Peptide | Sequence | 32. Internal Reference |
|---|---|---|---|
| 240 | D-RNA | GAGAUGGCGACAUUGGUUGGGCAUGAGGCGAGGCCCUUUGAUGAAUCCGCGGCCAUUC | 188-A3-001 |
| 241 | D-RNA | GAUGGCGACAUUGGUUGGGCAUGAGGCGAGGCCCUUUGAUGAAUCCGCGGGCAUUC | 188-A3-004 |
| 242 | D-RNA | GGCGACAUUGGUUGGGCAUGAGGCGAGGCCCUUUGAUGAAUCCGCGGCCAUUC | 188-A3-005 |
| 243 | D-RNA | GGCGACAUUGGUUGGGCAUGAGGCGAGGCCCUUUGAUGAAUCCGCGGCCAUU | 188-A3-006 |
| 244 | D-RNA | GGCGACAUUGGUUGGGCAUGAGGCGAGGCCCUUUGAUGAAUCCGCGGCCA | (D-) 188-A3-007 = (D) mNOX-E36 |
| 245 | D-RNA | GCUGGUUACCGAGGGGGCGUCGUUGGAGUUUGGUUGGUUGUCACCAGC | 189-G7-001 |
| 246 | D-RNA | CUGGUUACCGAGGGGGCGUCGUUGGAGUUUGGUUGGUUGUCACCAG | 189-G7-002 |
| 247 | D-RNA | UGGUUACCGAGGGGGCGUCGUUGGAGUUUGGUUGGUUGUCACCA | 189-G7-003 |
| 248 | D-RNA | GCCGGUUACCGAGGGGGCGUCGUUGGAGUUUGGUUGGUUGUCACCGGC | 189-G7-007 |
| 249 | D-RNA | GCCGGCUACCGAGGGGGCGUCGUUGGAGUUUGGUUGGUUGUCGCCGGC | 189-G7-008 |
| 250 | D-RNA | GCGCGUACCGAGGGGGCGUCGUUGGAGUUUGGUUGGUUGUCCGCGC | 189-G7-010 |
| 251 | D-RNA | GGGCCUACCGAGGGGGCGUCGUUGGAGUUUGGUUGGUUGUCGGCCC | 189-G7-012 |
| 252 | L-protein | QPDAVNAPLTCCYSFTGKMIPMSRLENYKRITSSRCPKEAVVFVTKLKREICAD PNKEWVQKYIRKLDQNQVRSET | rat MCP-1 |

-continued

| Seq.-ID | 33. RNA/ Peptide | Sequence | 34. Internal Reference |
|---|---|---|---|
| 253 | L-RNA | 5'PEG-GGCGACAUUGGUUGGGCAUGAGGCGAGGCCCUUUGAUGAAUCCGCGGCCA | mNOX-E36-5'PEG |
| 254 | L-RNA | GGCGACAUUGGUUGGGCAUGAGGCGAGGCCCUUUGAUGAAUCCGCGGCCA-3'PEG | mNOX-E36-3'PEG |
| 255 | L-DNA | 5'-GAGGGACGTGC-(Spacer18)$_2$-NH4$^+$-3' | NOX-E36 Capture probe |
| 256 | L-DNA | 5'-Biotin-(Spacer18)$_2$-GGCAGAGCC | NOX-E36 Detect (-ion) probe |
| 257 | L-Protein | KSMQVPFSRCCFSFAEQEIPLRATLCYRNTSSICSNEGLIFKLKRGKEACALDTV GWVQRHRKMLRHCPSKRK | CCL1/I-309 |
| 258 | L-Protein | SLAADTPTACCFSYTSRQIPQNFIADYFETSSQCSKPGVIFLTKRSRQVCADPSE EWVQKYUSDLELSA | CCL3/MTP-1α |
| 259 | L-Protein | APMGSDPPTACCFSYTARKLPRNFVVDYYETSSLCSQPAVVFQTKRSKQVCADPS ESWVQEYVYDLELN | CCL4/MIP-1β |
| 260 | L-Protein | SPYSSDTTPCCFAYIARPLPRAETKEYFYTSGKCSNPAVVFVTRKNRQVCANPEK KWVREYTNSLEMS | CCL5/RANTES |
| 261 | L-Protein | FNPQGLAQPDALNVPSTCCFTFSSKKISLQRLKSYVITTSRCPQKAVIFRTKLGK EICADPKEKWVQNYMKHLGRKAHTLKT | CCL13/MCP-4 |
| 262 | L-Protein | TKTESSSRGPYHPSECCFTYTTYKIPRQRTMDYYETNSQCSKPGICFITKRGHSV CTNPSDKWCQDYIKDMKEN | CCL14/HCC-1 |
| 263 | L-Protein | ASVATELRCQGLQTLQGIHPKNIQSVNVKSPGPHCAQTEVIATLKNGRKACLNPA SPIVKKIIEKMLNSDKSN | CXCL1/GROα |

| Seq.-ID | 35. RNA/ Peptide | Sequence | 36. Internal Reference |
|---|---|---|---|
| 264 | L-Protein | APLATELRCQCLQTLQCIHLKNIQSVKVKSPGPHCAQTEVIATLKNGQKACLNPAS PMVKKITEKMLKNGKSN | CXCL2/GROβ |
| 265 | L-Protein | ASVVTELRCQCLQTLQGIBLKNTQSVNVRSPGPHCAQTEVIATLKNGKKACLNPAS PMVQKTIEKILNKGSTN | CXCL3/GROγ |
| 266 | L-Protein | EAEEDGDLQCLCVKTTSQVRPRHTTSLEVIKAGPRCPTAQLIATLKNGRKICLDLQ APLYKKIIKKLLES | CXCL4/PF4 |
| 267 | L-Protein | GPAAAVLP.ELRCVCLQTTQGVHPKMISNLQVFAIGPQCSKVEVVASLKNGKEICLD PEAPFLKKVTQKILDGGNKEN | CXCL5/ENA-78 |
| 268 | L-Protein | GPVSAVLTELRCTCLRVTLRVNPKTIGKLQVFPAGPQCSKVEVVASLKNGKQVCLD PEAPFLKKVIQKILDSGNKKN | CXCL6/GCP-2 |
| 269 | L-Protein | SSTKGQTKRNLAKGKEESLDSDLYAELRCMCIKTTSGIHPKNTQSLEVTGKGTHCN QVEVIATLKDGRKICLDPDAPRIKKIVQKKLAGDESAD | CXCL7/NAP-2 |
| 270 | L-Protein | EGAVLPRSAKELRCQCTKTYSKPFHPKFTKELRVIESGPHCANTEIIVKLSDGREL CLDPKENWVQRVVEKFLKRAENS | CXCL8/IL-8 |
| 271 | L-Protein | TPVVRKGRCSGISTNQGTIHLQSLKDLKQFAPSPSCEKIEI IATLKNGVQTCLNPD SADVKELIKKWEKQVSQKKKQKNGKKHQKKKVLKVRKSQRSRQKKTT | CXCL9/MIG |
| 272 | L-Protein | VPLSRTVRCTCISISNQPVNPRSLEKLEITPASQFCPRVETIATMKKKGEKRCLNP ESKAIKNLLKAVSKERSKRSP | CXCL10/IP-10 |

| Seq.-ID | 37. RNA/ Peptide | Sequence | 38. Internal Reference |
|---|---|---|---|
| 273 | L-Protein | FPMFKRGRCLCIGPGVKAVKVADIEKASIMYPSNNGDKIEVIITLKENKGQRCLNP KSKQARLIIKKVERKNF | CXCL11/I-TAC |
| 274 | L-Protein | KPVSLSYRCPCRFFESHVARANVKHLKTLNTPNCALQIVARLKNNNRQVCTDPKLK WIQEYLEKALNKRFKM | CXCL12α/SDF-1α |
| 275 | L-Proteifl | KPVSLSYRCPCRFFESHVARANVKHLKILNTPNCALQIVARLKNNNRQVCTDPKLK WIQEYLEKALNKRFKN | CXCL12β/SDF-1β |
| 276 | L-Protein | QHHGVTKCNITCSKMTSKIPVALLIHYQQNQASCGKRAIILETRQHRLFCADPKEQ WVKDAMQHLDRQAAALTRNG | GX$_3$CL1/Fractalkine |

-continued

| | | | |
|---|---|---|---|
| 277 | L-Protein | VGSEVSDKRTCVSLTTQRLPVSRIKTYTTTEGSLRAVIFITKRGLKVCADPQATWV RDVVRSMDRKSNTRNNMIQTKPTGTQQSTNTAVTLTG | XCL1/Lymphotactin |
| 278 | L-RNA | 5'-Biotin-GCACGUCCCUCACCGGUGCAAGUGAAGCCGUGGCUCUGCG | biotinylated NOZ-E36 |
| 279 | L-RNA | 5'-UAAGGAAACUCGGUCUGAUGCGGU AGCGCUGUGCAGAGCU | POC |
| 280 | L-RNA | 5'-PEG-UAAGGAAACUCGGUGUGAUGCGGU AGCGCUGUGCAGAGCU-3' | POC-PEG |
| 281 | L-DNA | 5'-CCAATGTCGCC-(Spacer18)$_2$-NH4$^+$-3' | mNOX-E36 Capture probe |

| Seq.-ID | 39. RNA/ Peptide | Sequence | 40. Internal Reference |
|---|---|---|---|
| 282 | L-DNA | 5'-Biotin-(Spacer18)$_{2}$-*CGCAGAGCC* | mNOX-E36 Detect (-ion) probe |
| 283 | L-protein | QPDAINSPVTCCYTFTGKKISSQRLGSYKRVTSSKCPKEAVIFKTILAKEICADPE QKWVQDAVKQLDKKAQTPKP | horse MCP-1 (*Equus caballus*) |
| 284 | L-protein | QPDAINSQVACCYTFNSKKISMQRLMNYRRVTSSKCPKEAVIFKTILGKELCADPK QKWVQDSINYLNKKNQTPKP | bovine MCP-1 (*Bos Taurus*) |
| 285 | L-protein | QPDAVNAPLTCCYSFTGKMIPMSRLENYKRITSSRCPKEAVVFVTKLKREICADPN KEWVQKYTRKLDQNQVRSETTVFYKIASTLRTSAPLNVNLTHKSEANASTLFSTTT SSTSVEVTSMTEN | rat MCP-1 (*Rattus norvegicus*) norvegicus) |
| 286 | 1-RNA | 5'-ACCGGCGCCUAAGUAGUUUCCCGGAGCGGAGUACGGGUUGGUUACAGCGG-3'PEG | revmNOX-E36-3'-PEG |

The present invention is further illustrated by the figures, examples and the sequence listing from which further features, embodiments and advantages may be taken, wherein FIG. 1 shows an alignment of sequences of related RNA ligands binding to human MCP-1 indicating the sequence motif ("Type 1A") that is in a preferred embodiment in its entirety essential for binding to human MCP-1 (FIG. 1 discloses L-RNA sequences as SEQ ID NOS 10-21, respectively, in order of appearance, and the corresponding D-RNA sequences as SEQ ID NOS 132-143, respectively);

FIG. 2 shows an alignment of sequences of related RNA ligands binding to human MCP-1 indicating the sequence motif ("Type 1B") that is in a preferred embodiment in its entirety essential for binding to human MCP-1 and derivatives of RNA ligands 180-D1-002 (FIG. 2 discloses L-RNA sequences as SEQ ID NOS 22-28, respectively, in order of appearance, and the corresponding D-RNA sequences as SEQ ID NOS 144-150, respectively);

FIG. 3 shows an alignment of sequences of related RNA ligands binding to human MCP-1 indicating the sequence motif ("Type 2") that is in a preferred embodiment in its entirety essential for binding to human MCP-1 (FIG. 3 discloses L-RNA sequences as SEQ ID NOS 29-37, respectively, in order of appearance, and the corresponding D-RNA sequences as SEQ ID NOS 151-159, respectively);

FIG. 4 shows an alignment of sequences of related RNA ligands binding to human MCP-1 indicating the sequence motif ("Type 3") that is in a preferred embodiment in its entirety essential for binding to human MCP-1 (FIG. 4 discloses L-RNA sequences as SEQ ID NOS 38-53, respectively, in order of appearance, and the corresponding D-RNA sequences as SEQ ID NOS 160-175, respectively);

Figure 9:
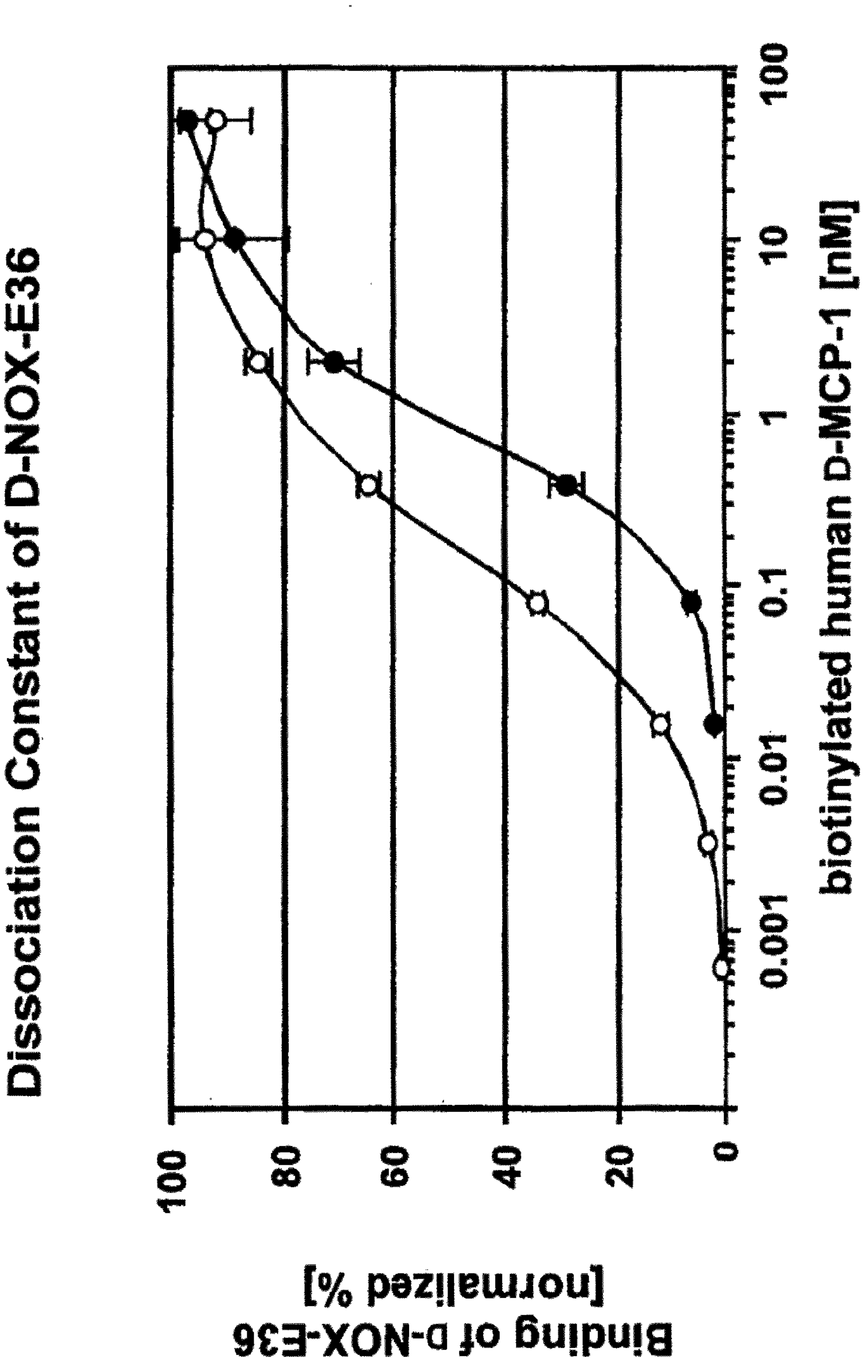
Figure 10:
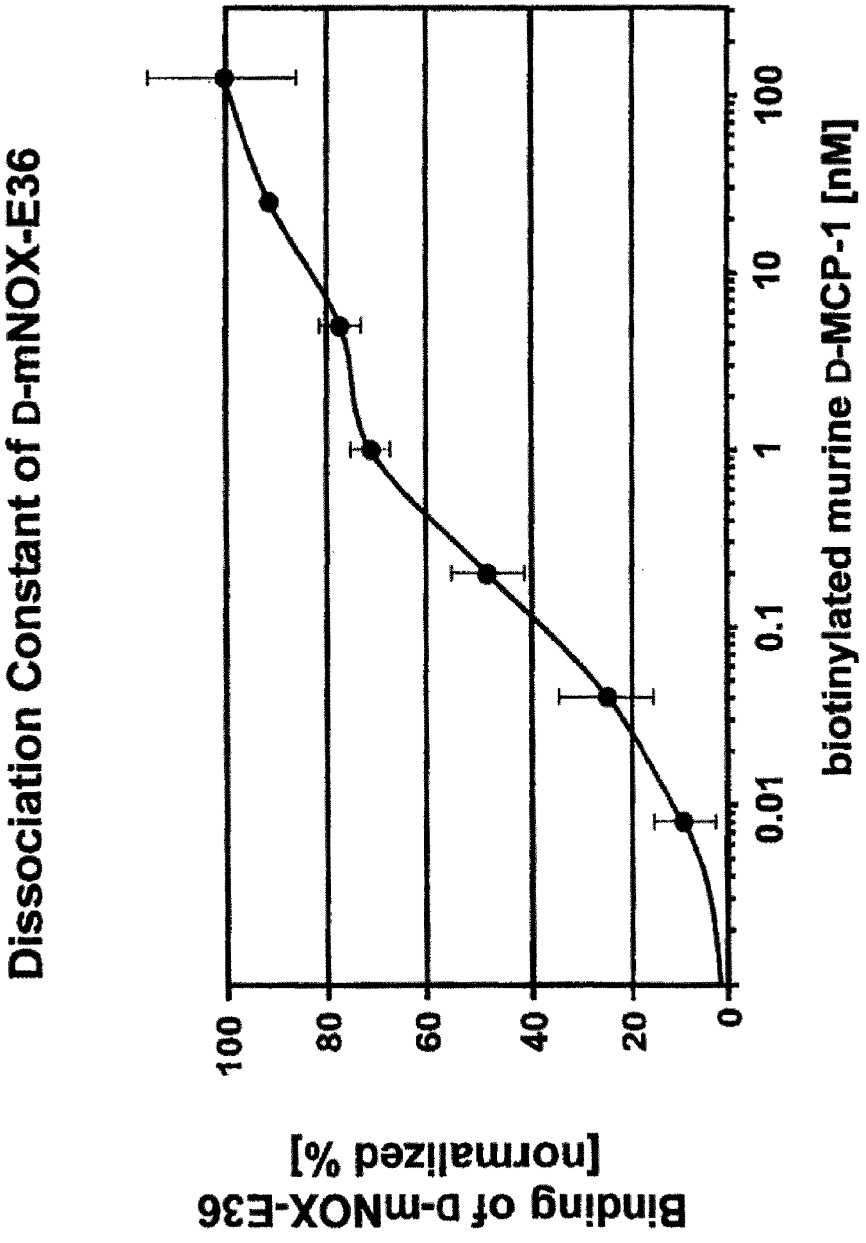
Figure 11:
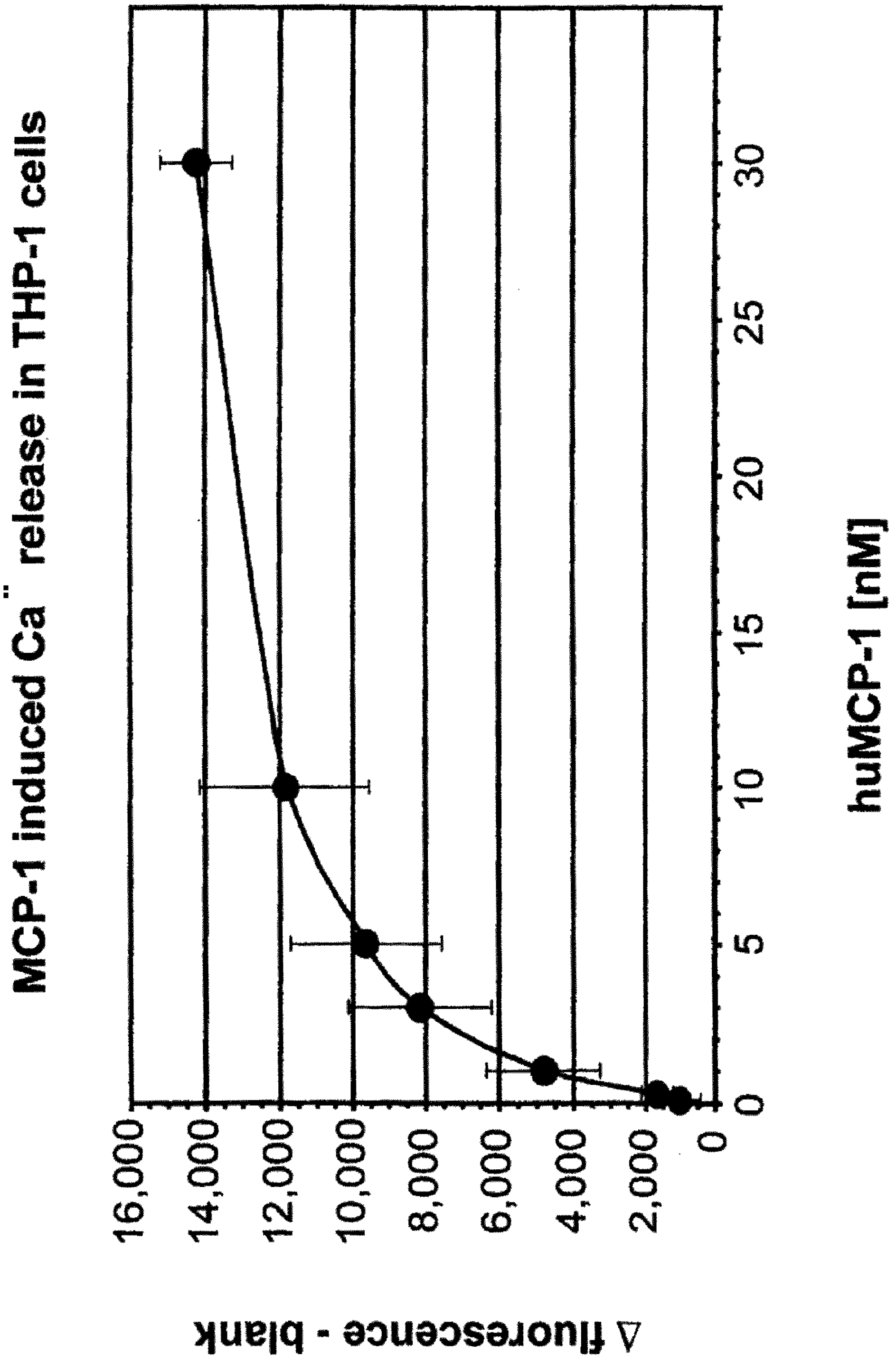
Figure 12:
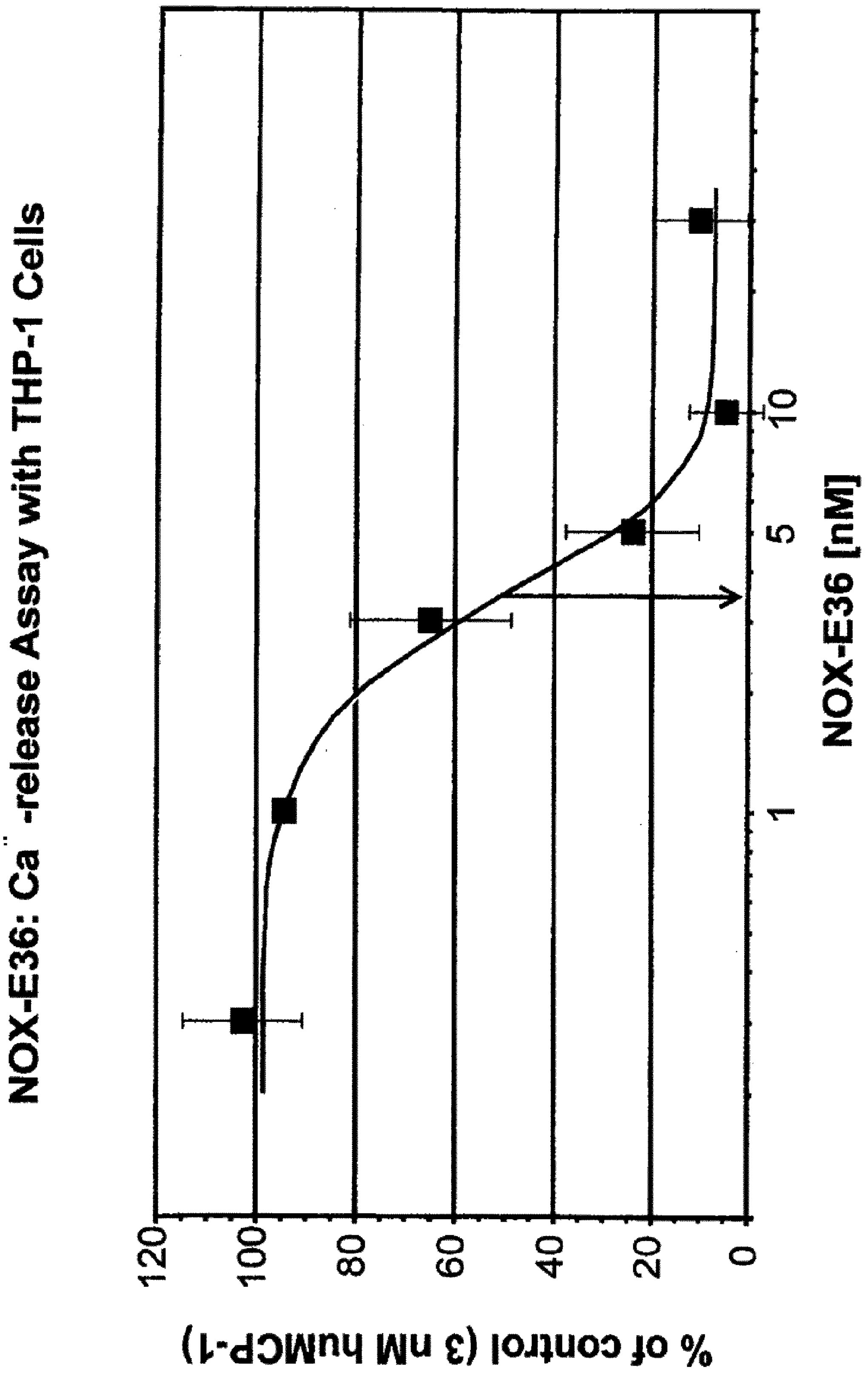
Figure 13:
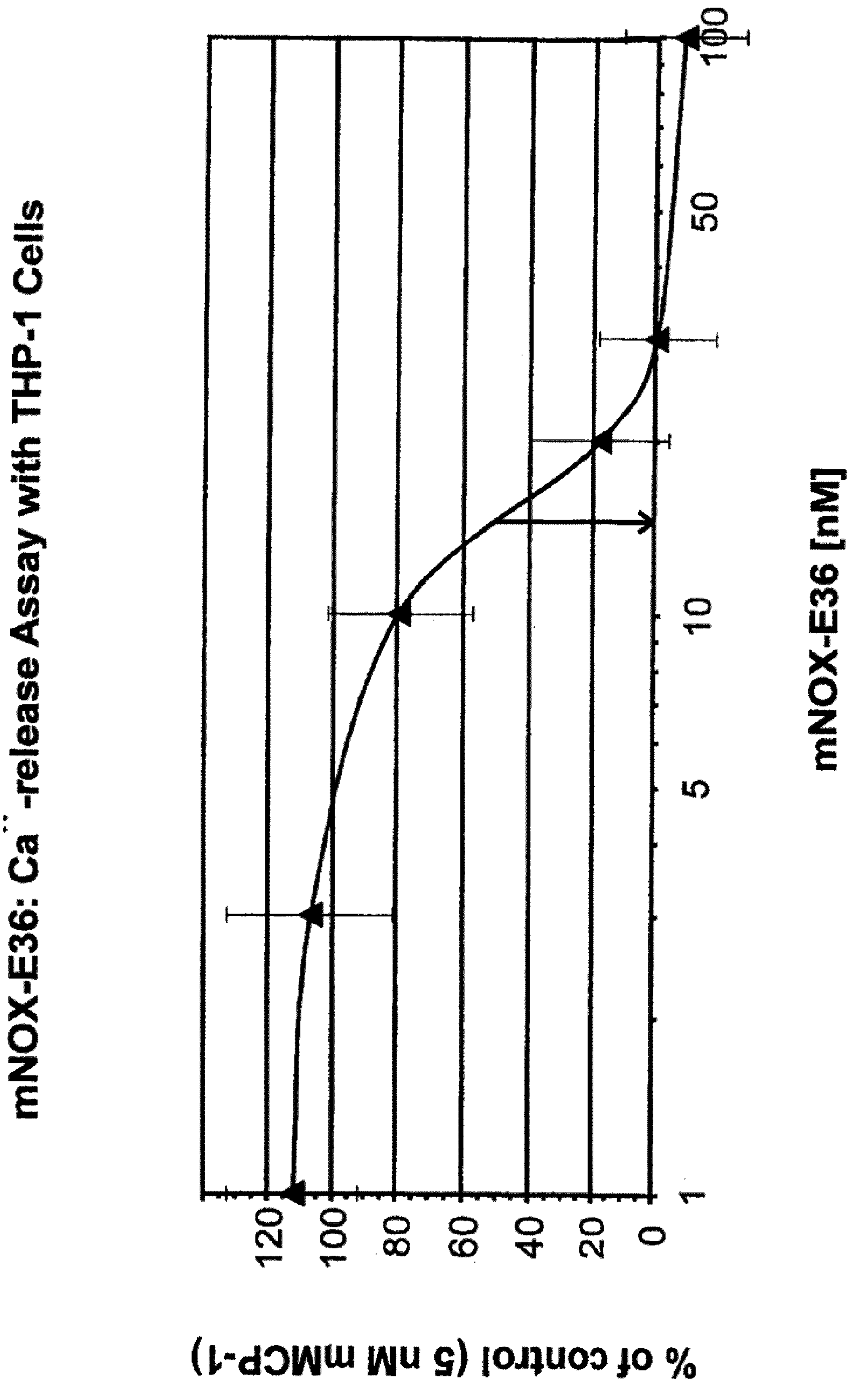
Figure 14:
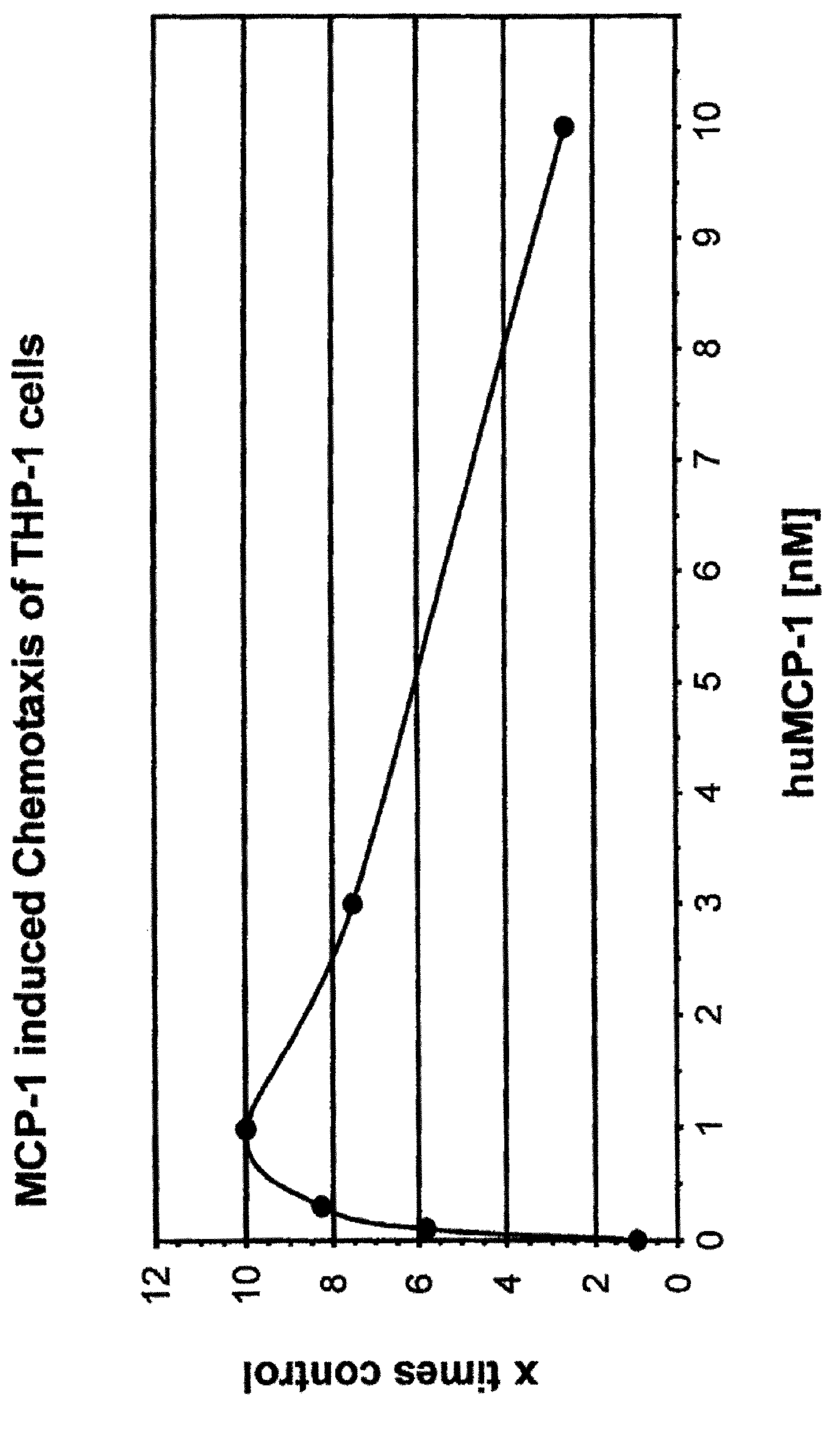
Figure 15:
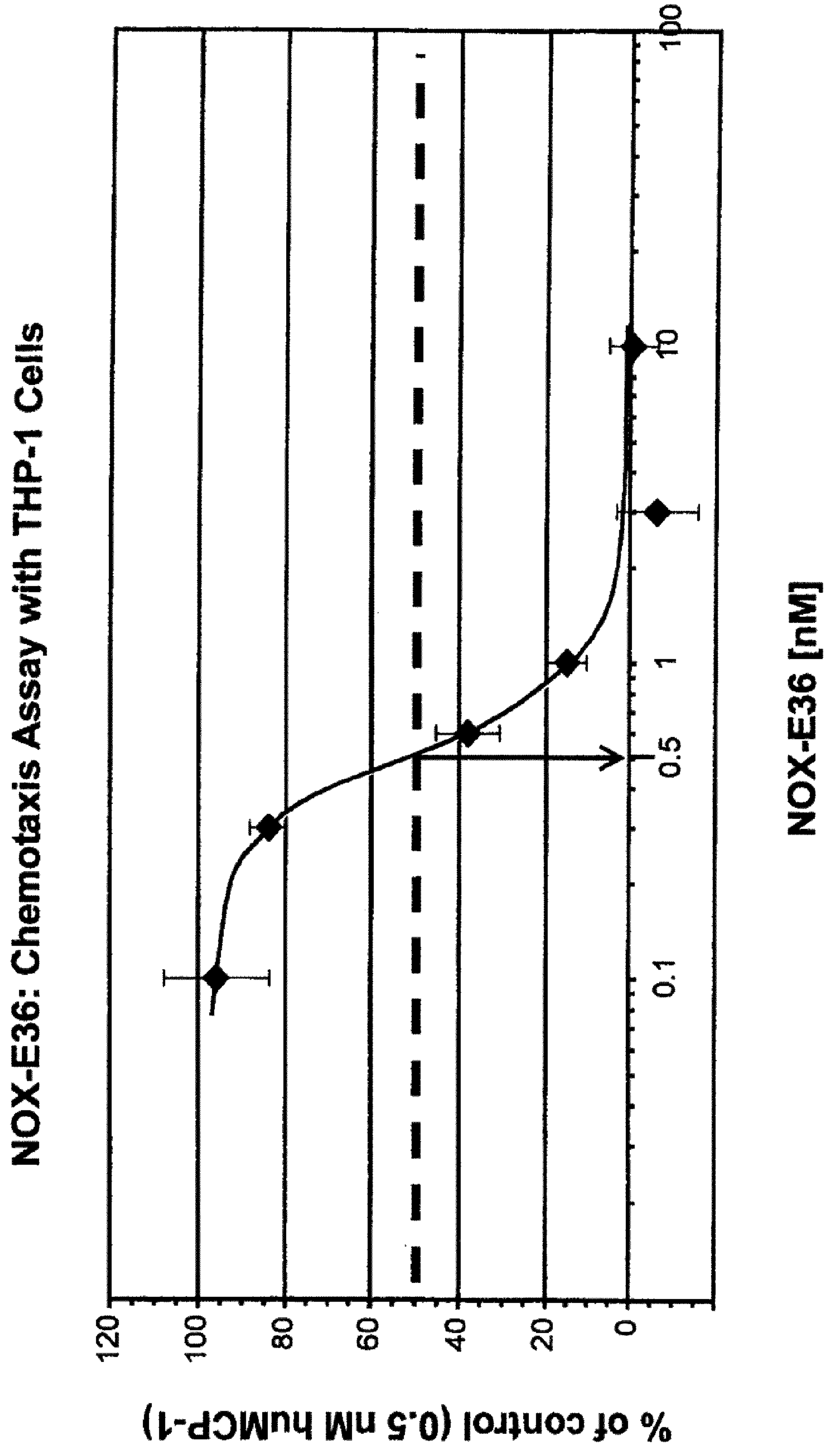
Figure 16:
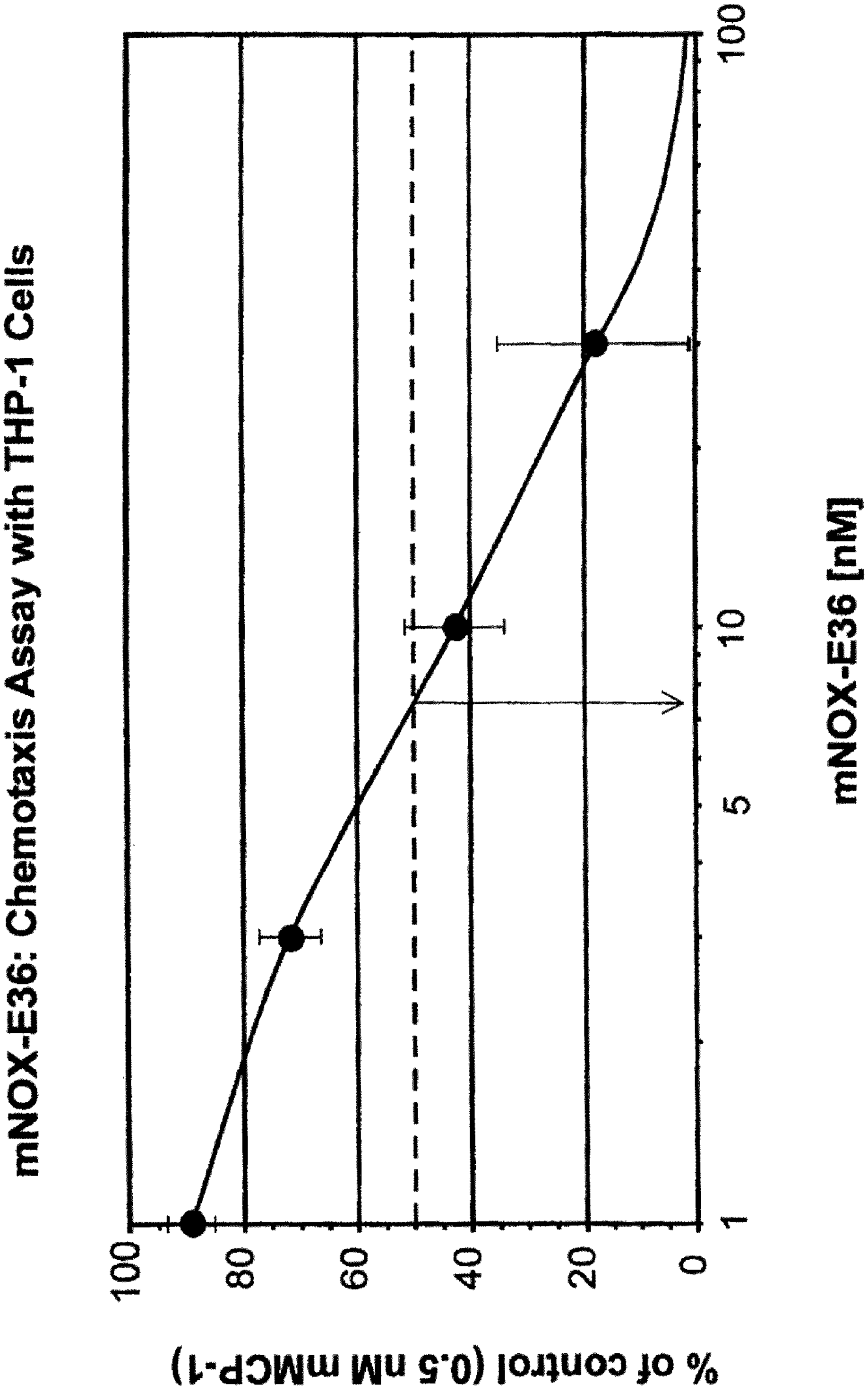
Figure 17:
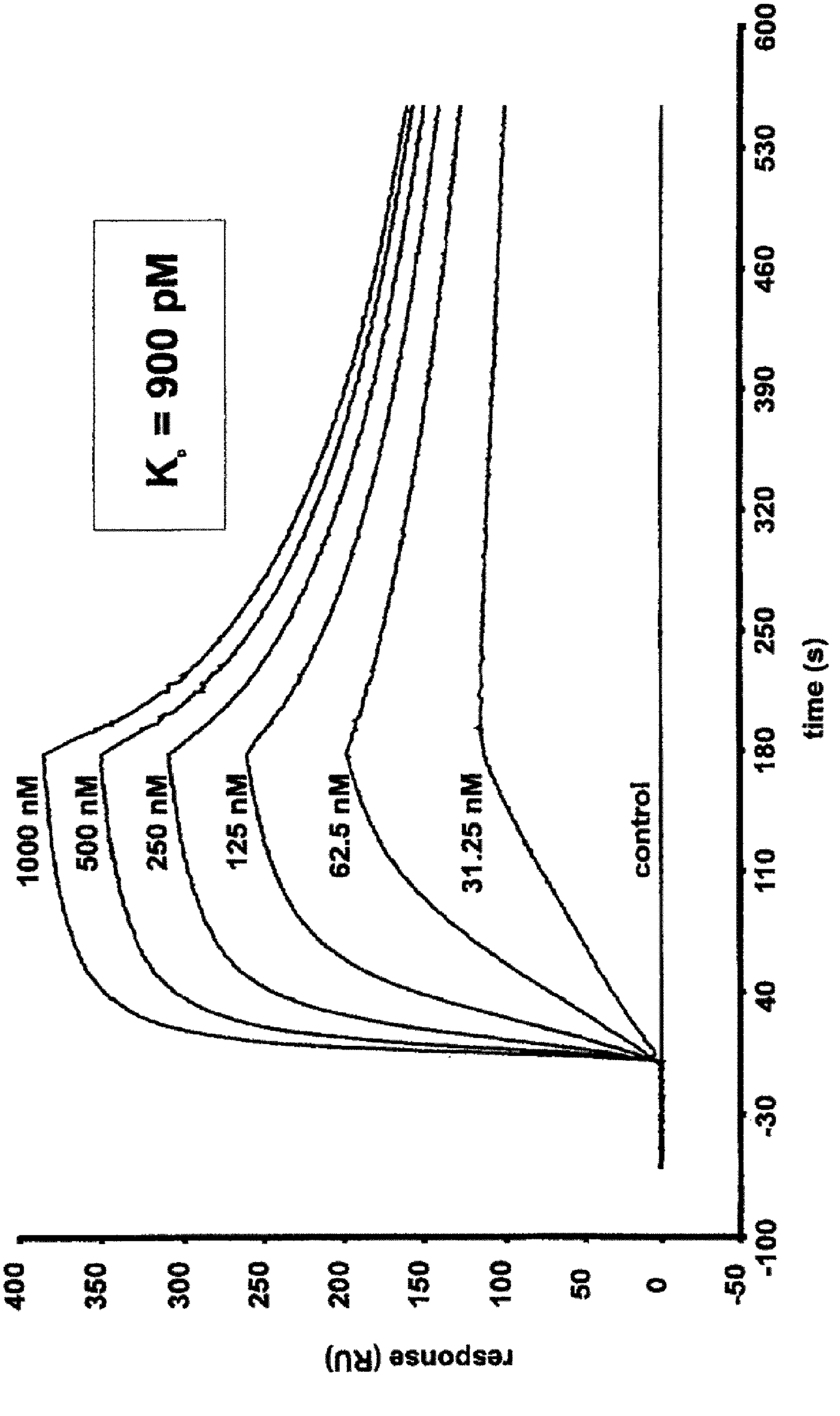
Figure 18:
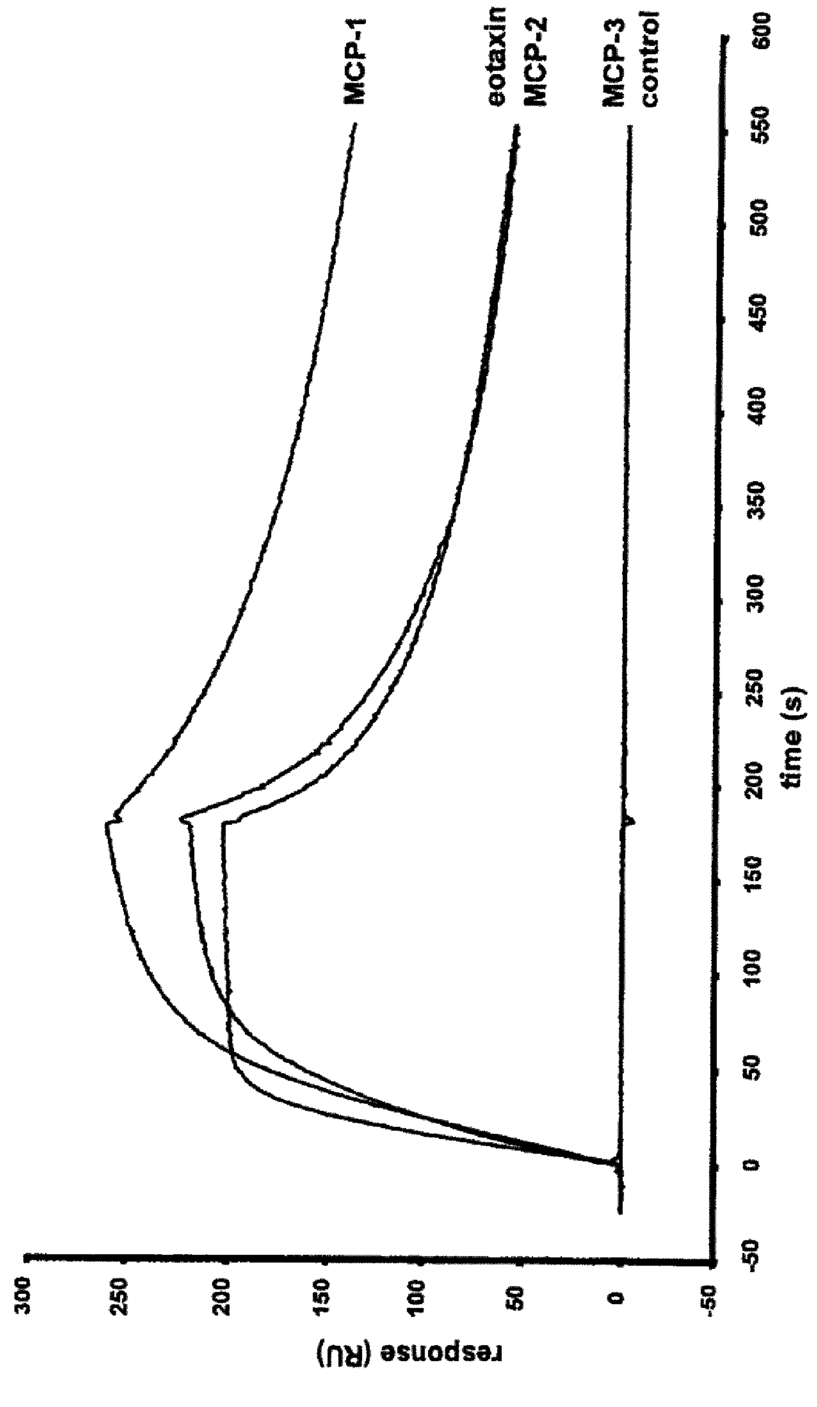
Figure 19:
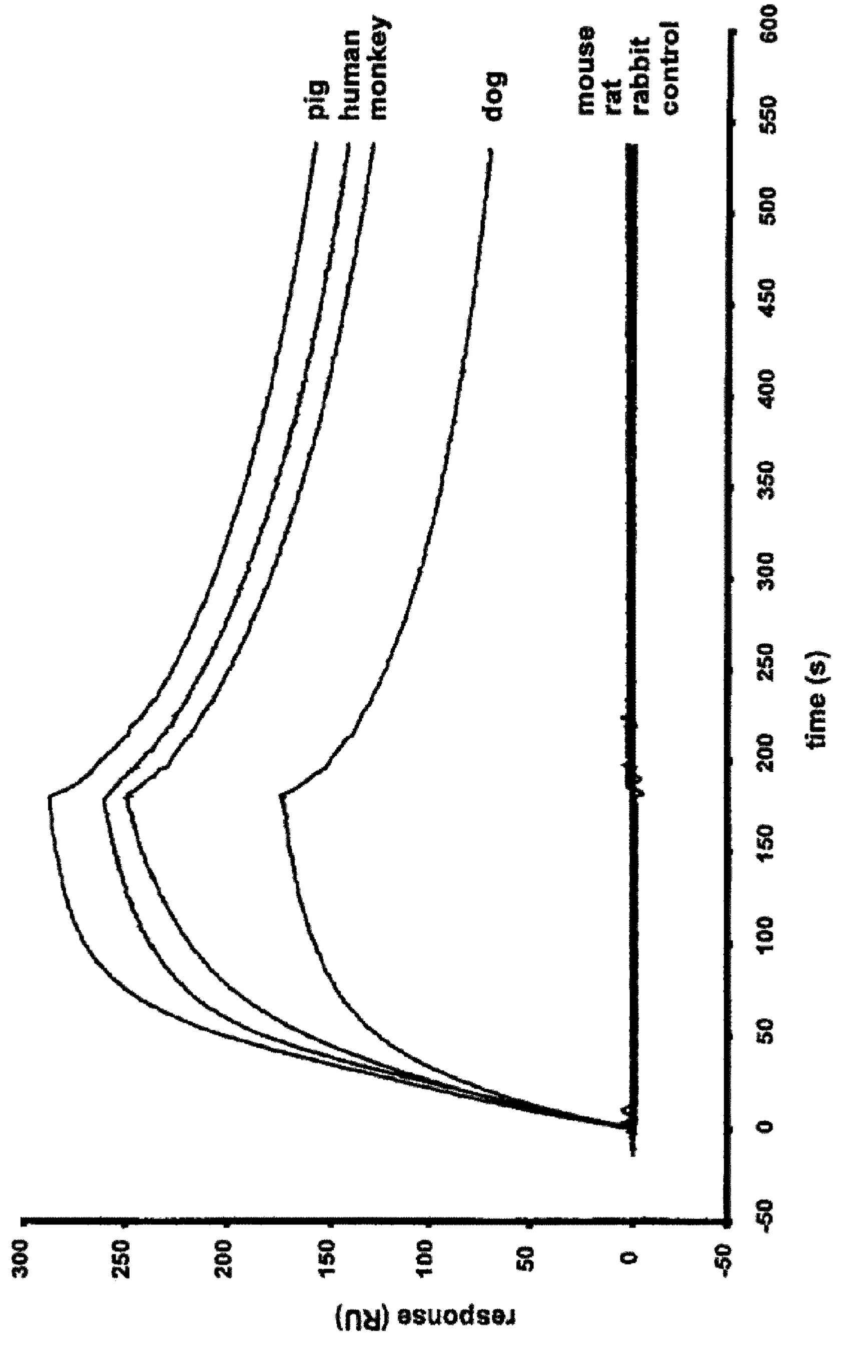
Figure 20:
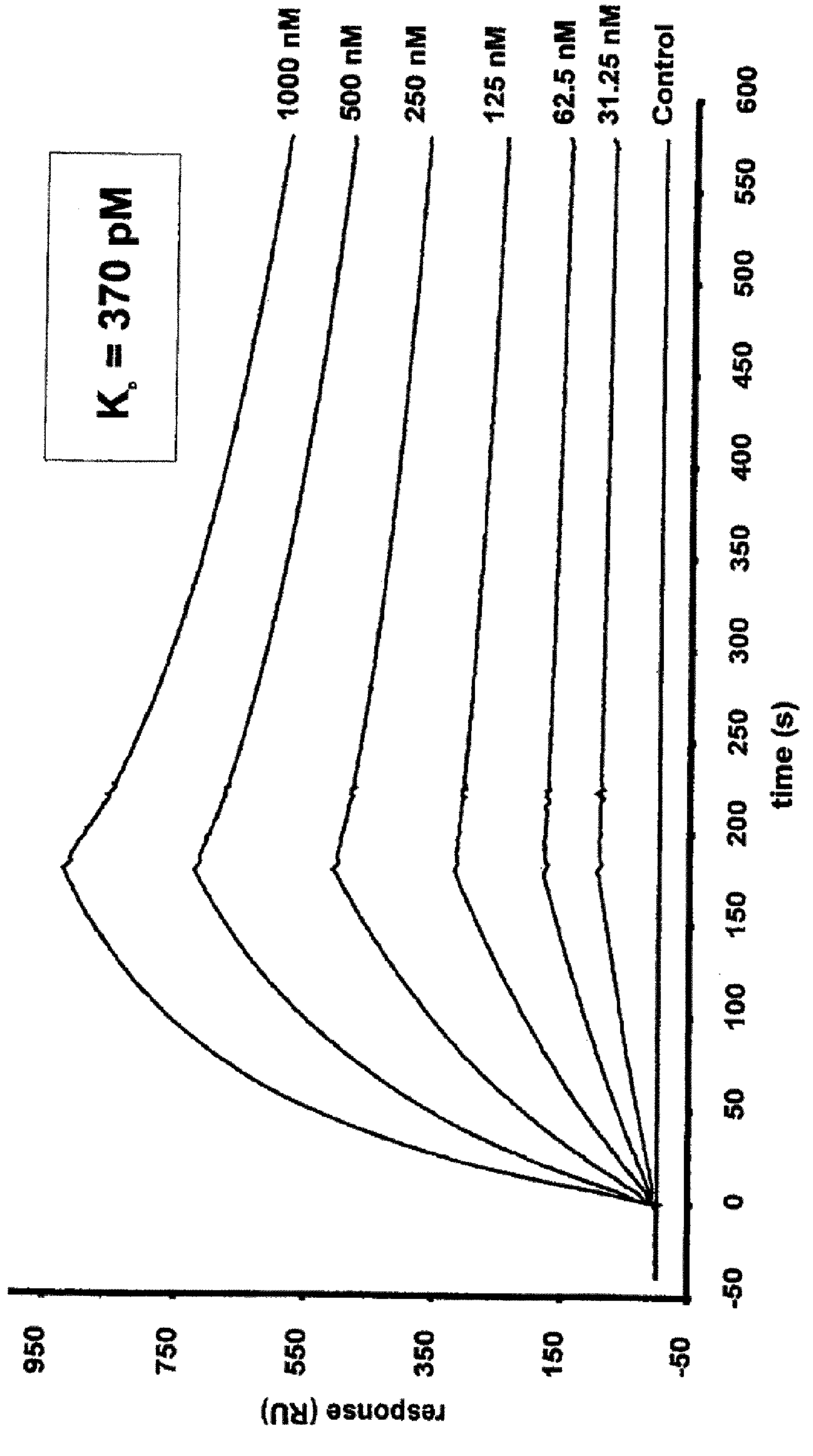
Figure 21:
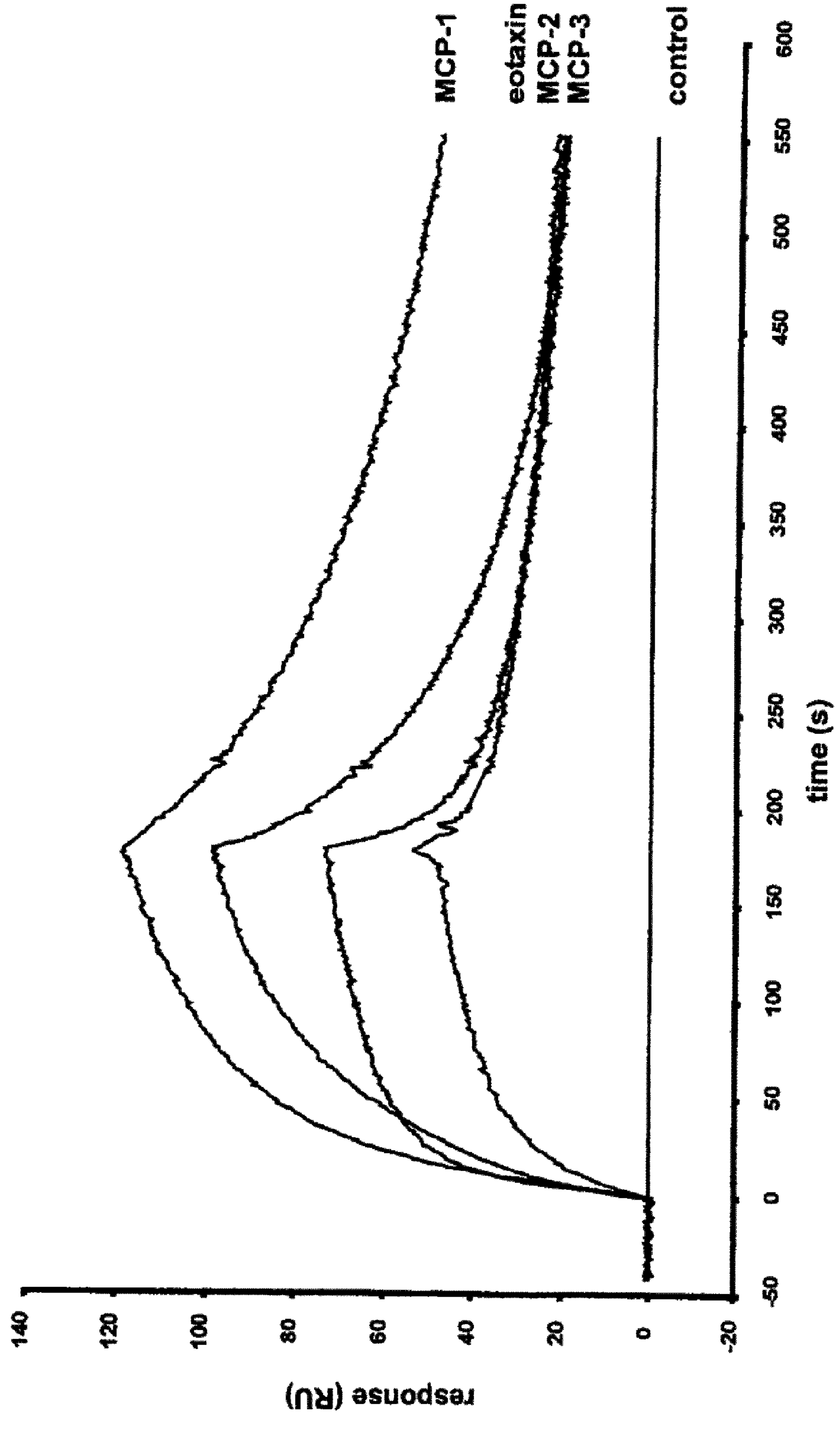
Figure 22:
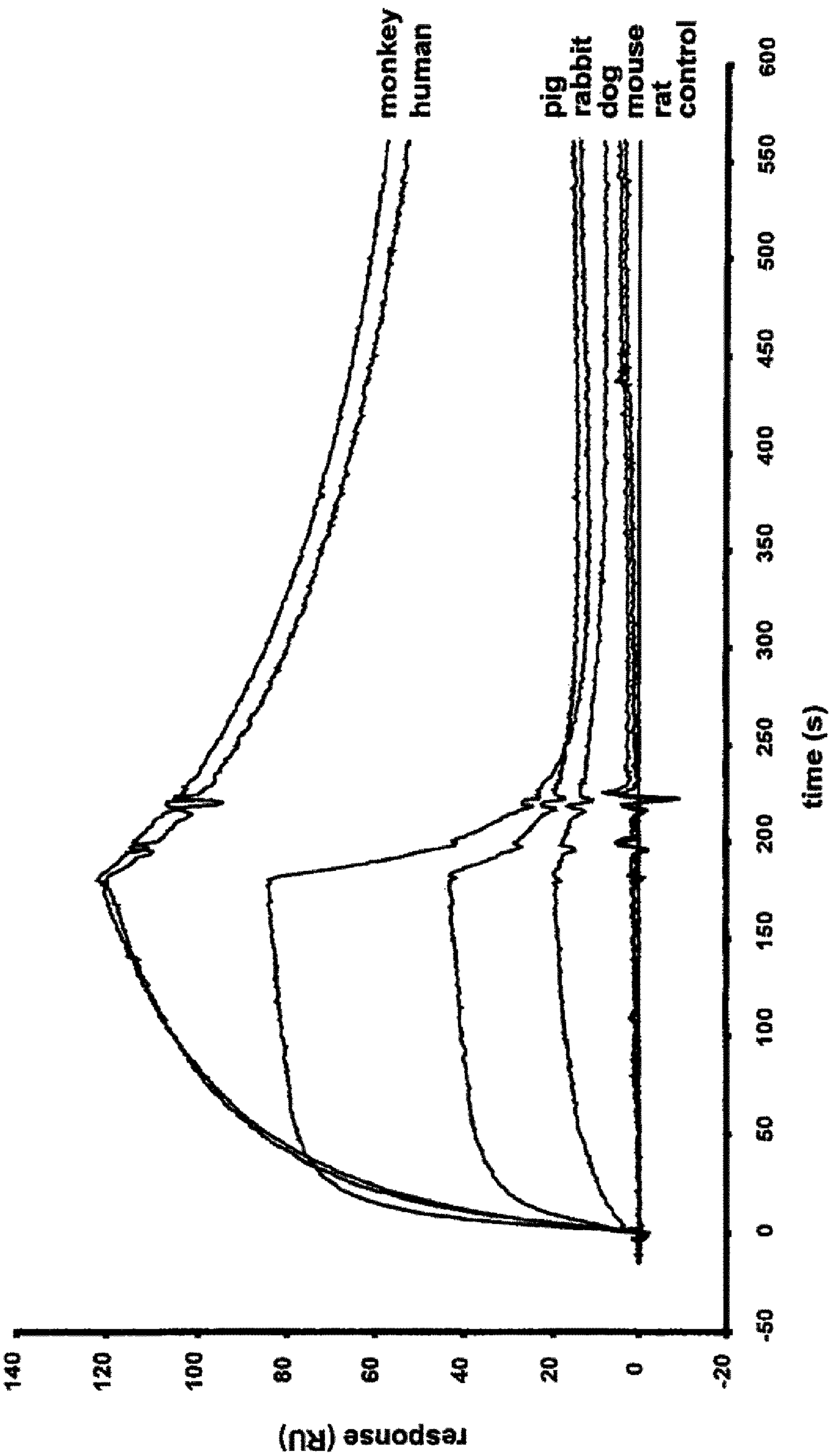
Figure 24:
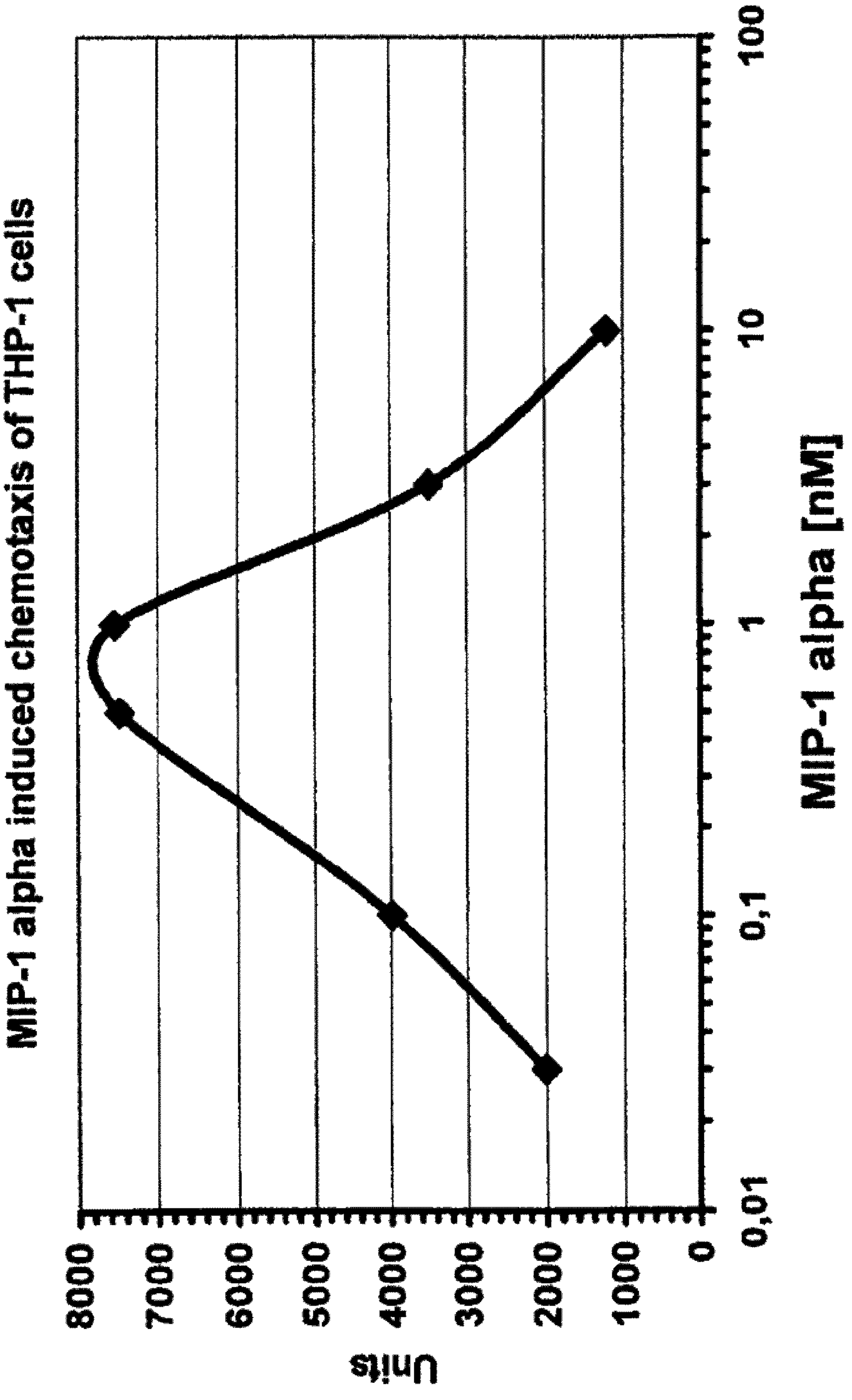
Figure 24:
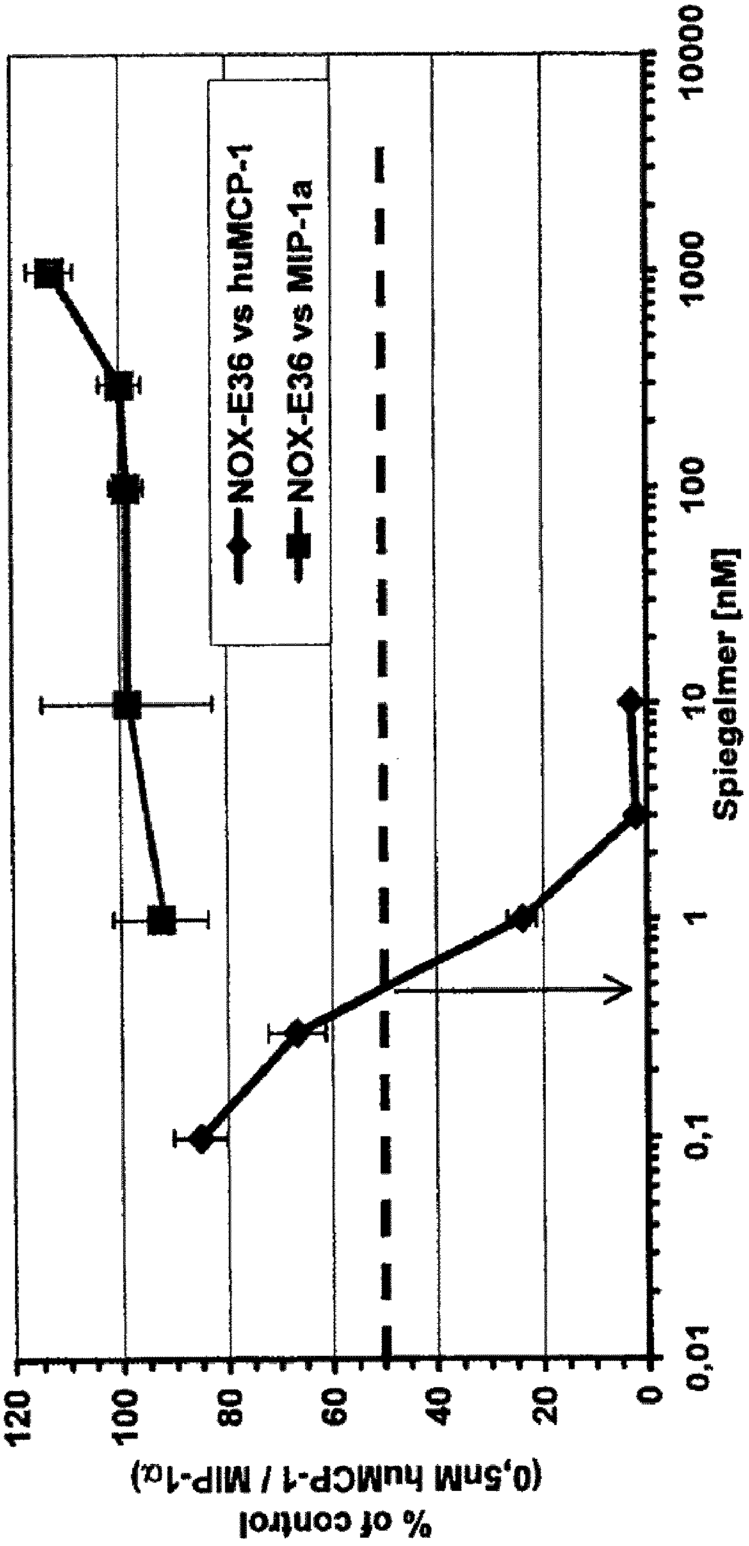
Figure 25:
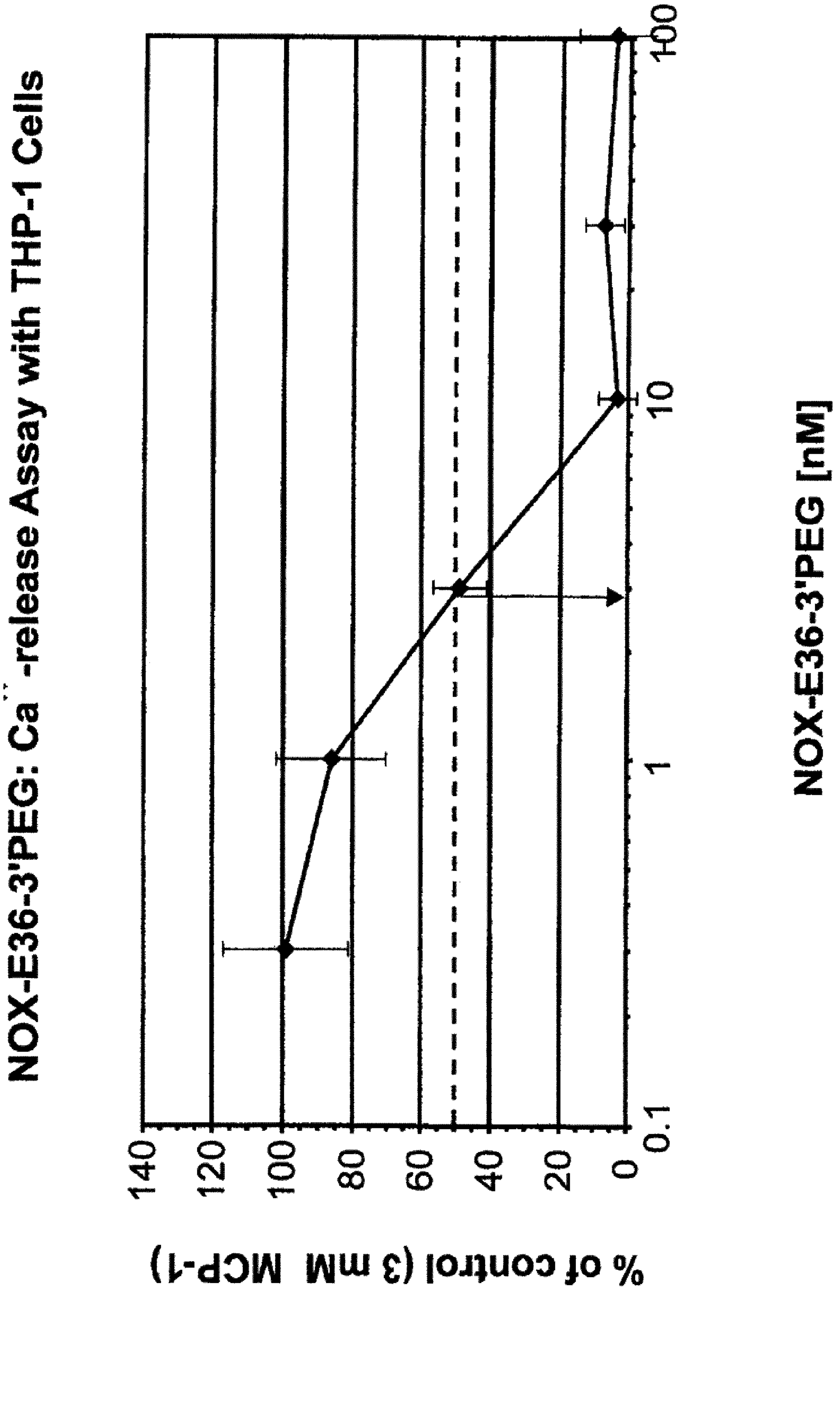
Figure 26:
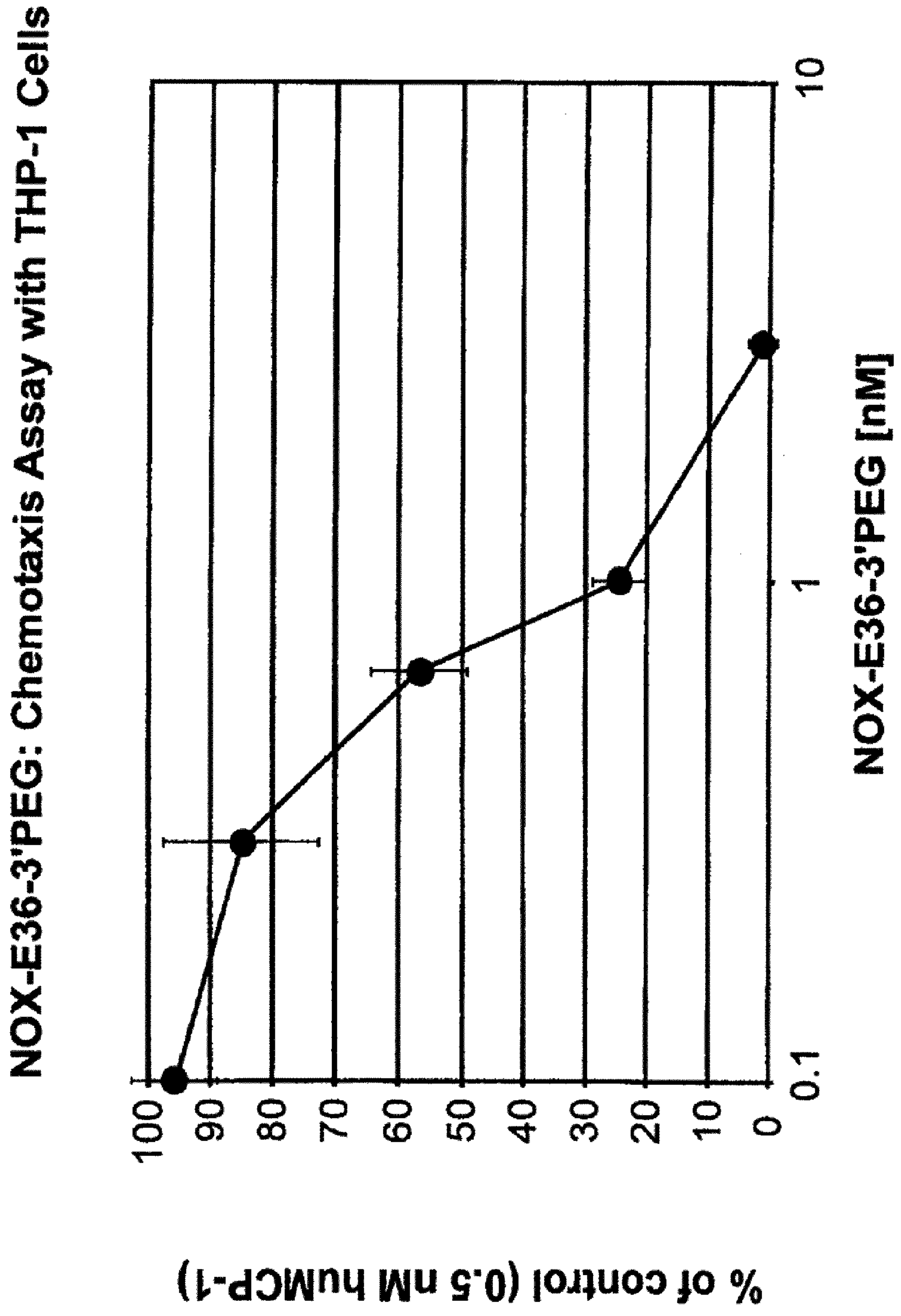
Figure 27A:
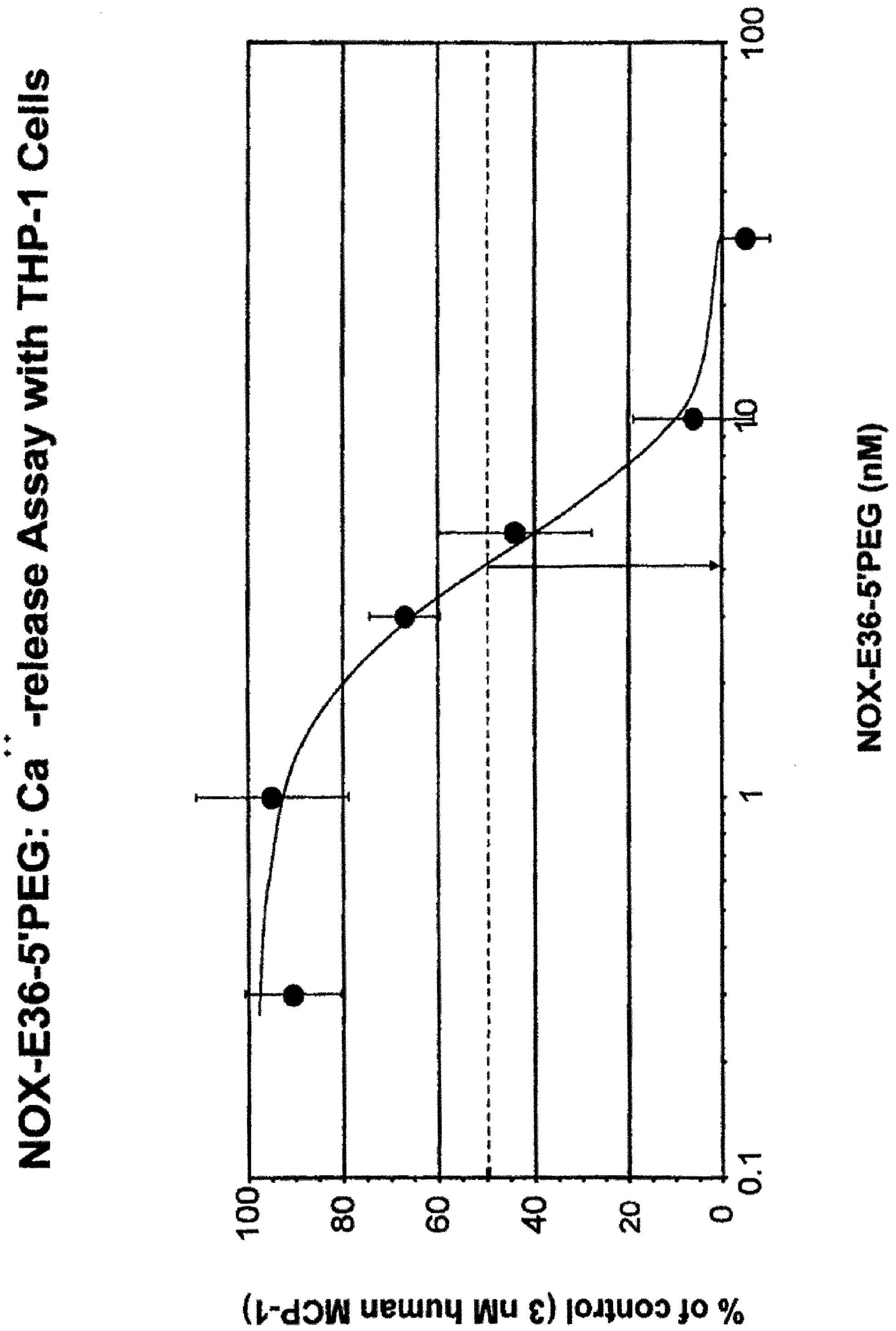
Figure 27B:
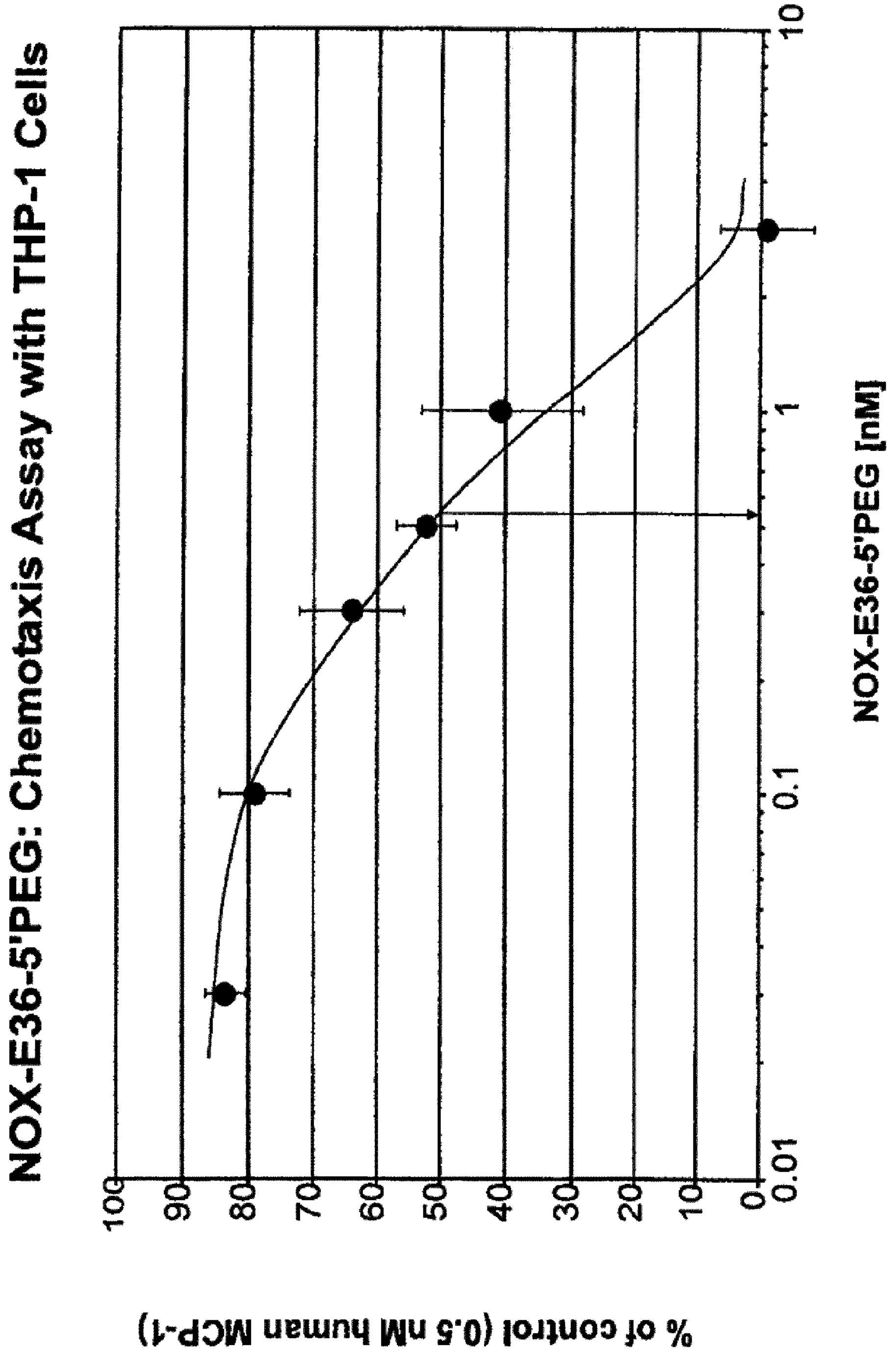
Figure 28:
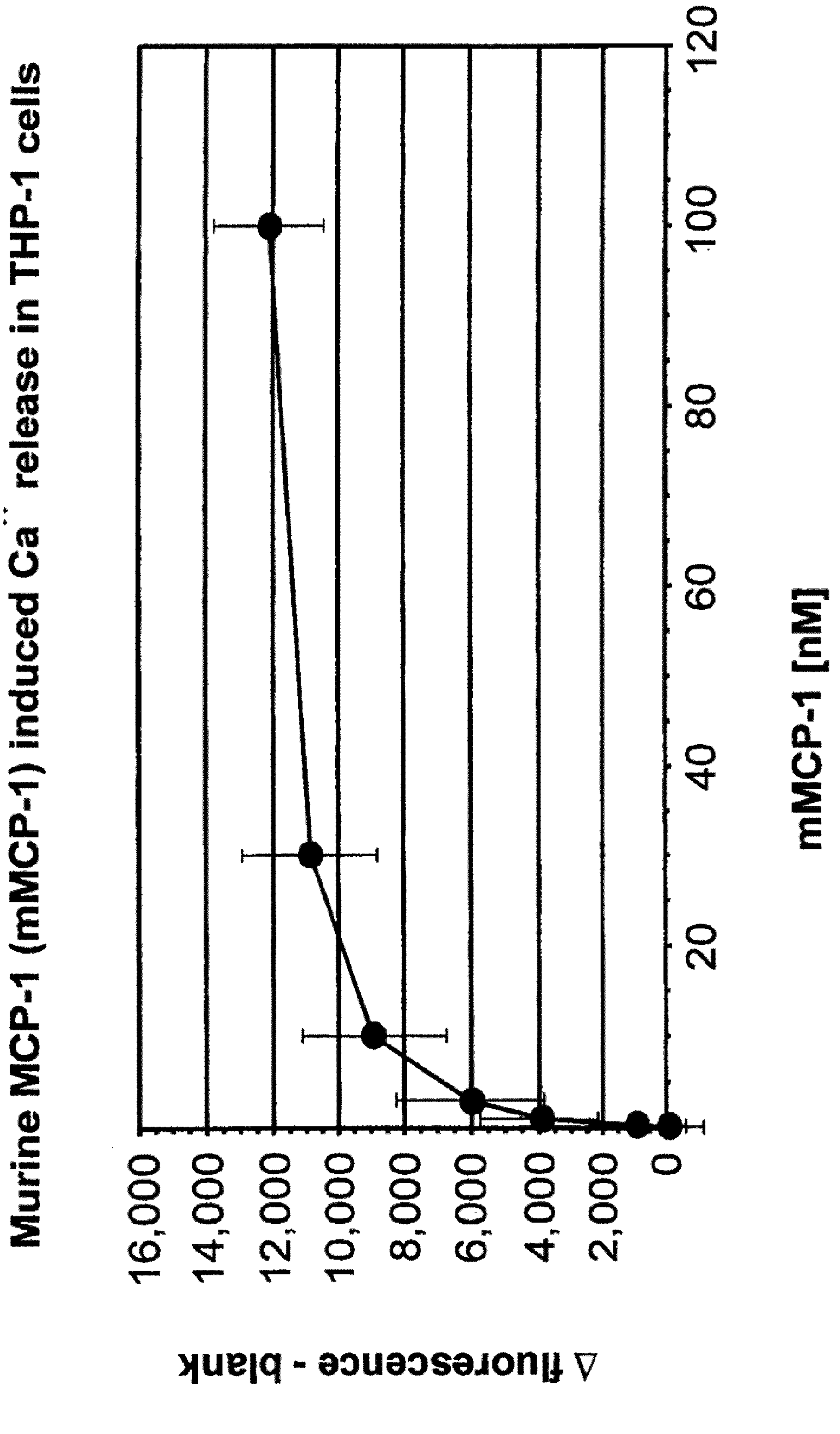
Figure 29:
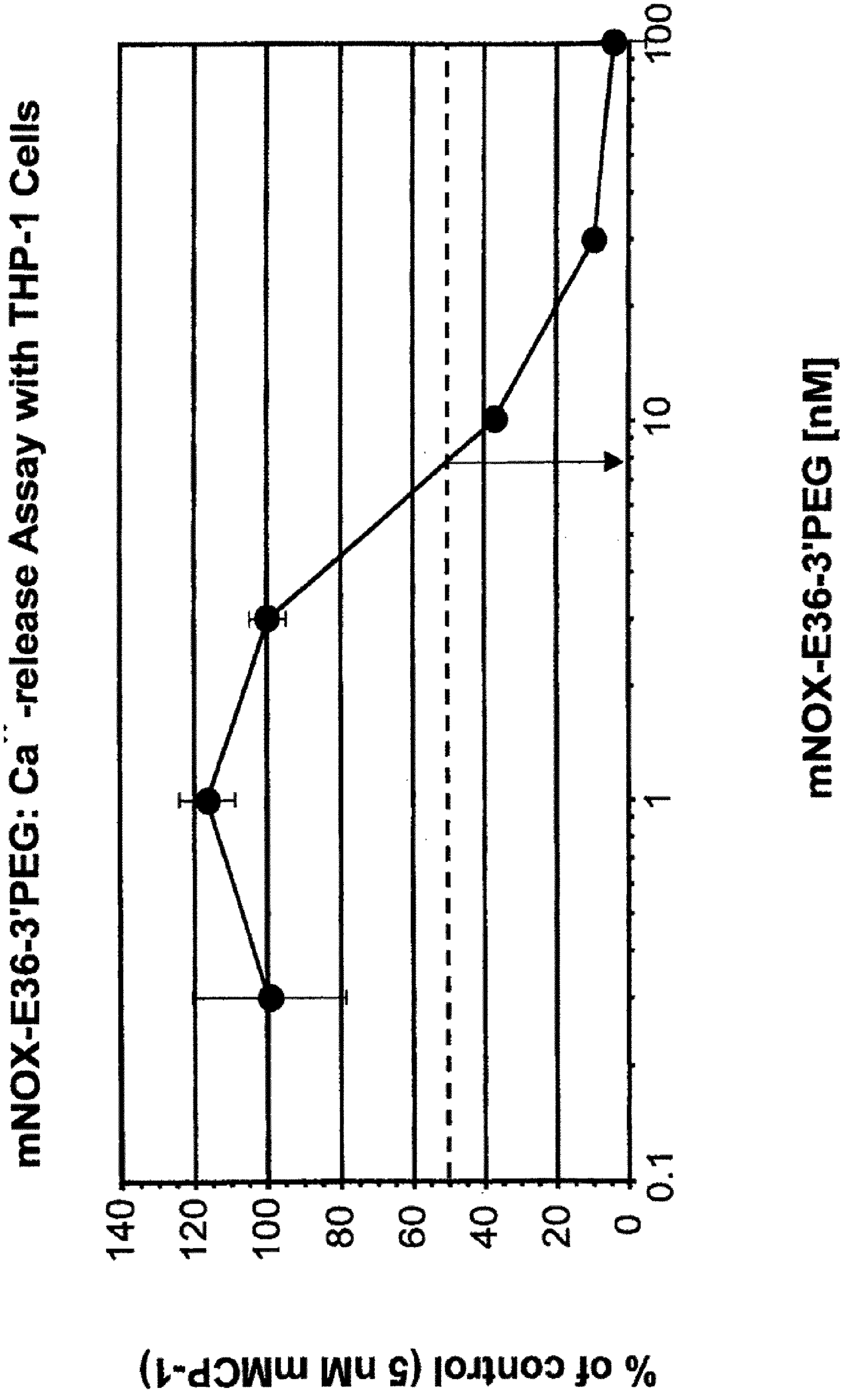
Figure 30:
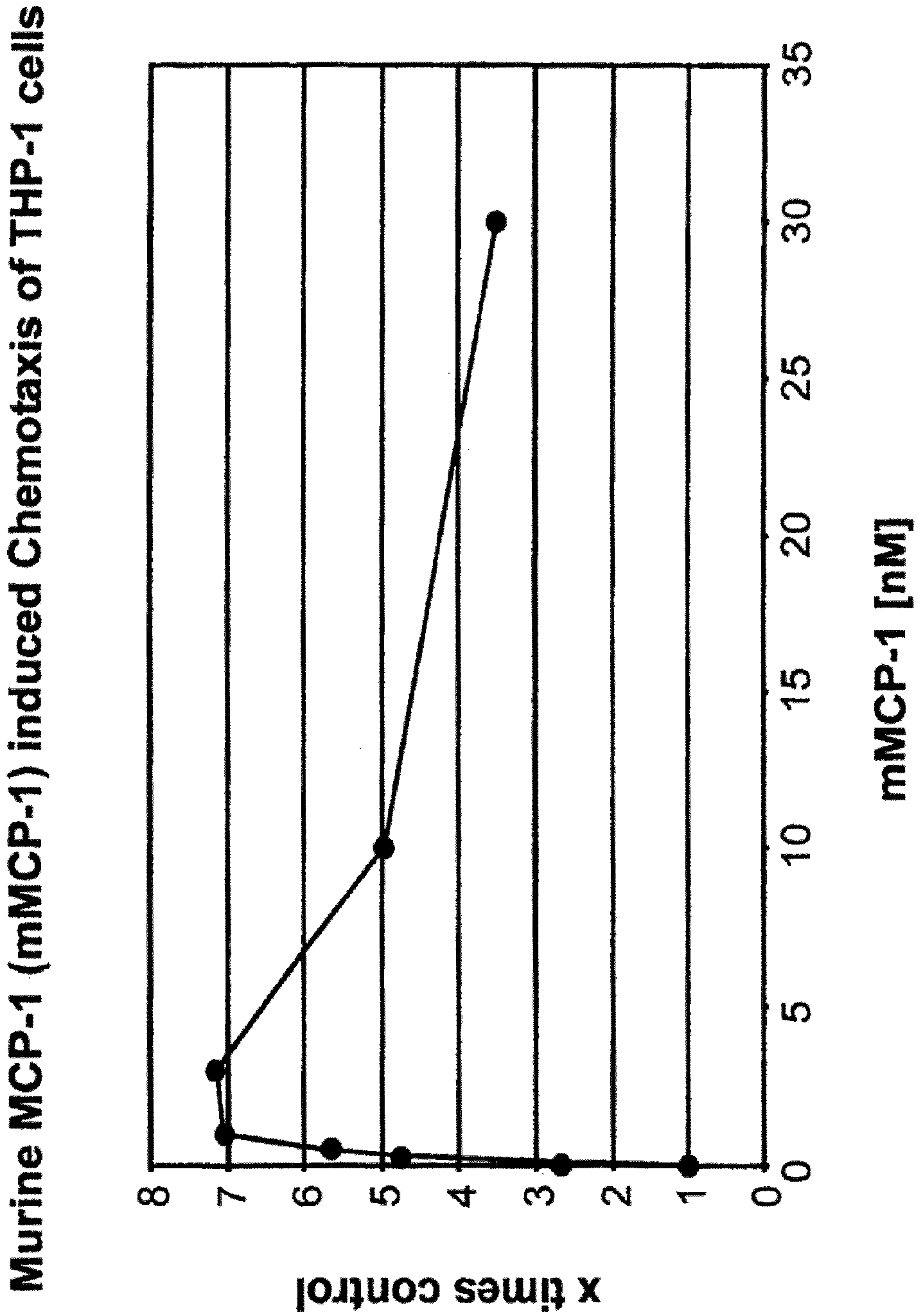
Figure 31:
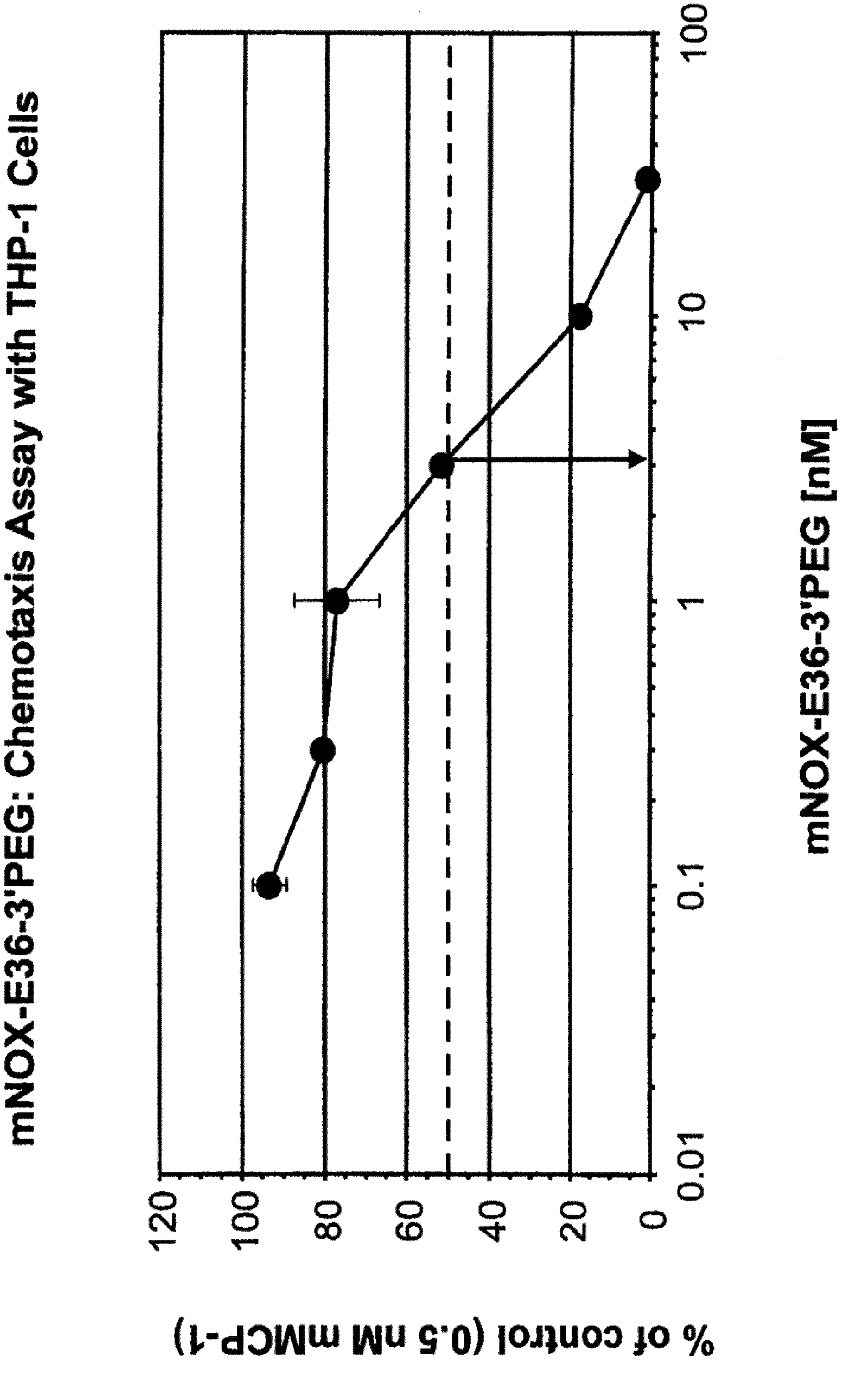
Figure 32:
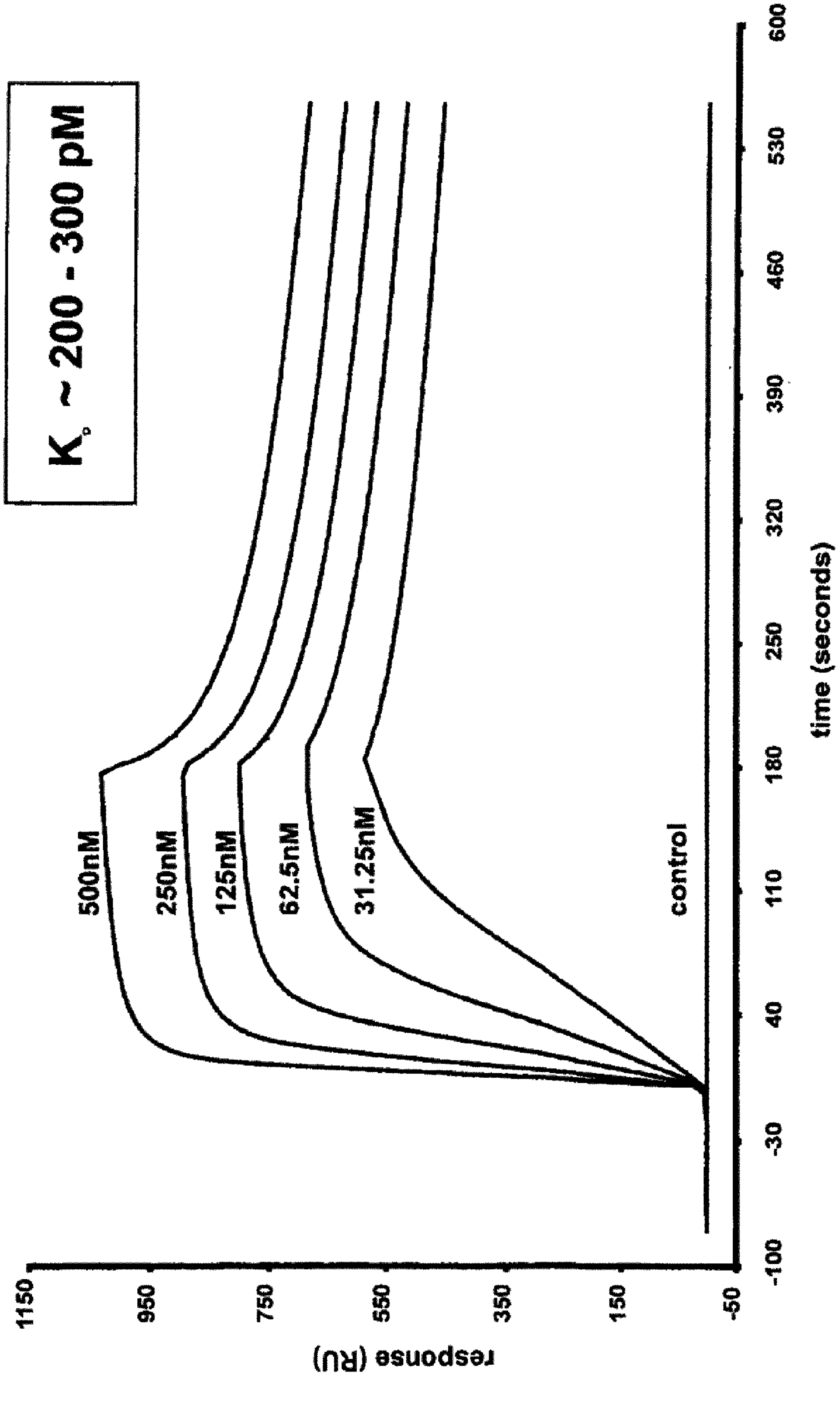
Figure 33:
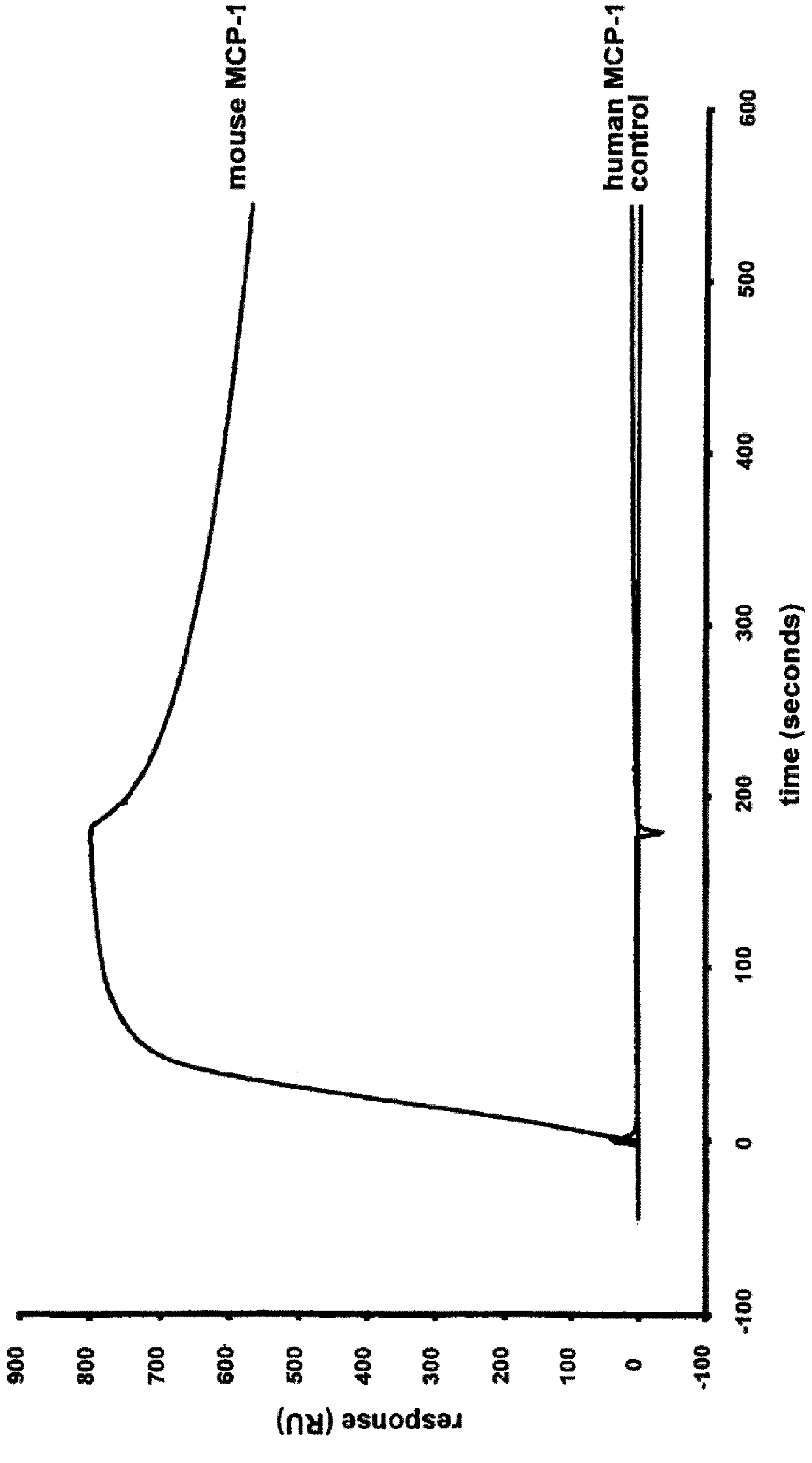
Figure 34:
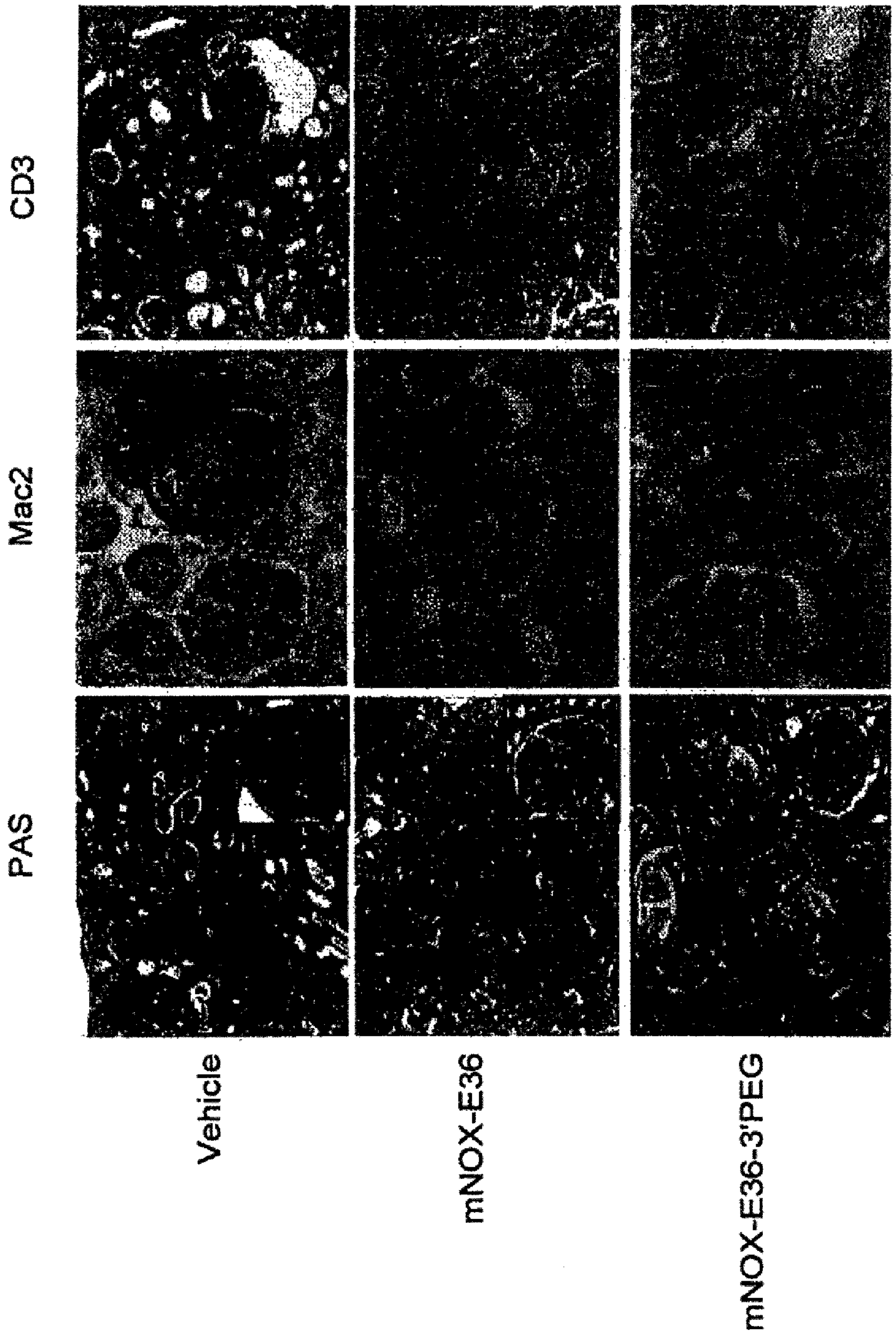
Figure 36:
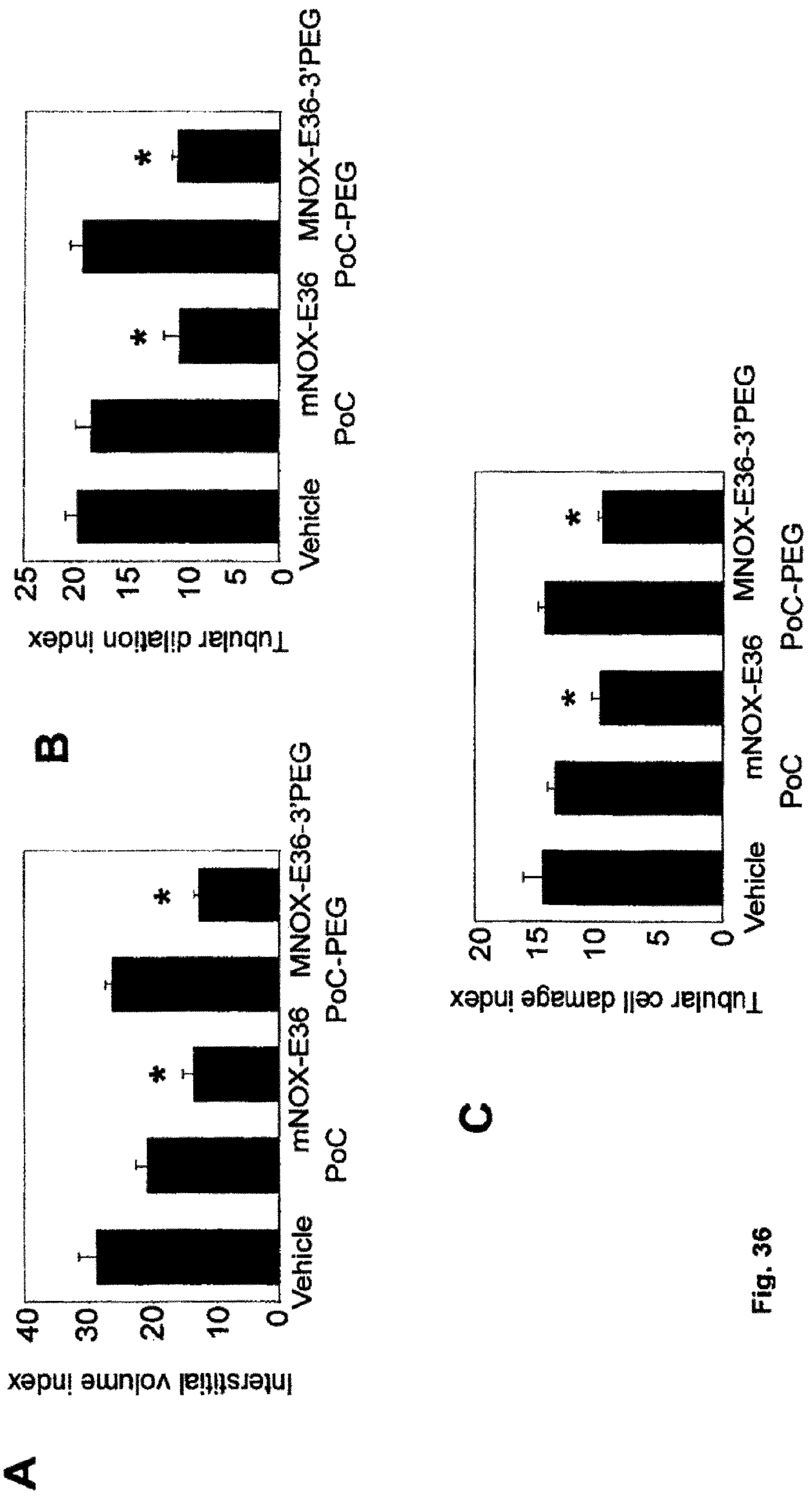
Figure 37:
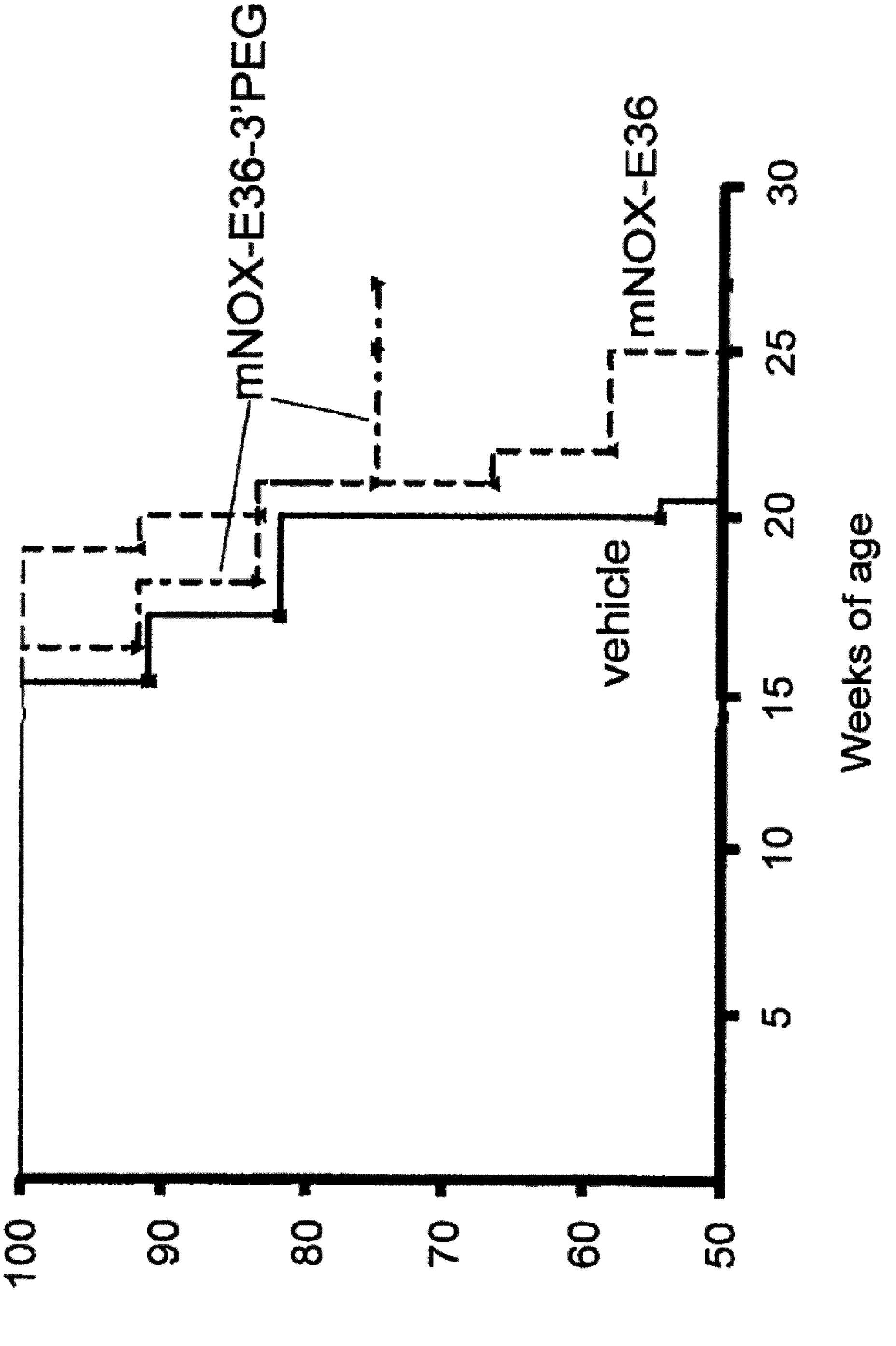
Figure 38:
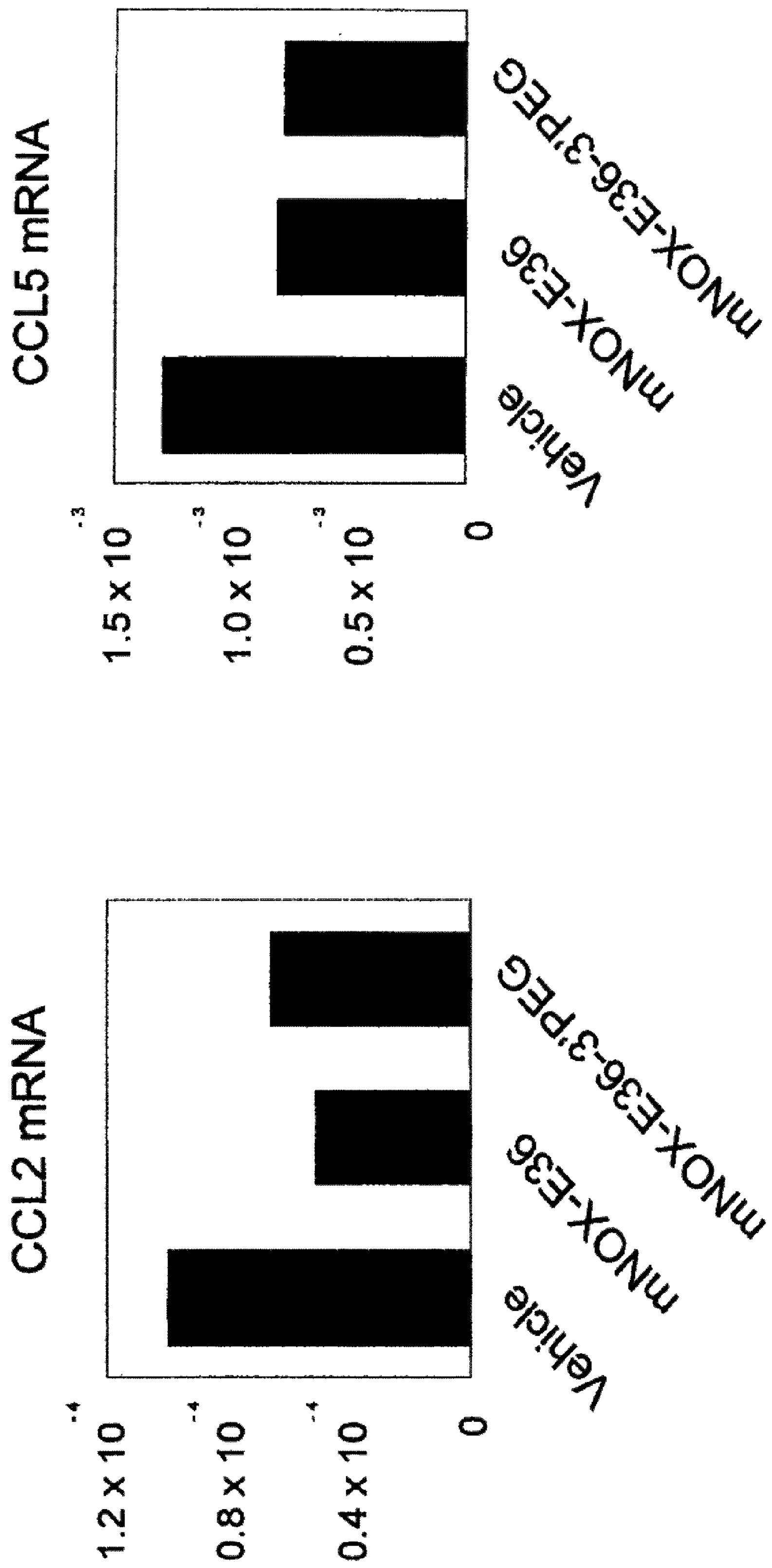
Figure 39:
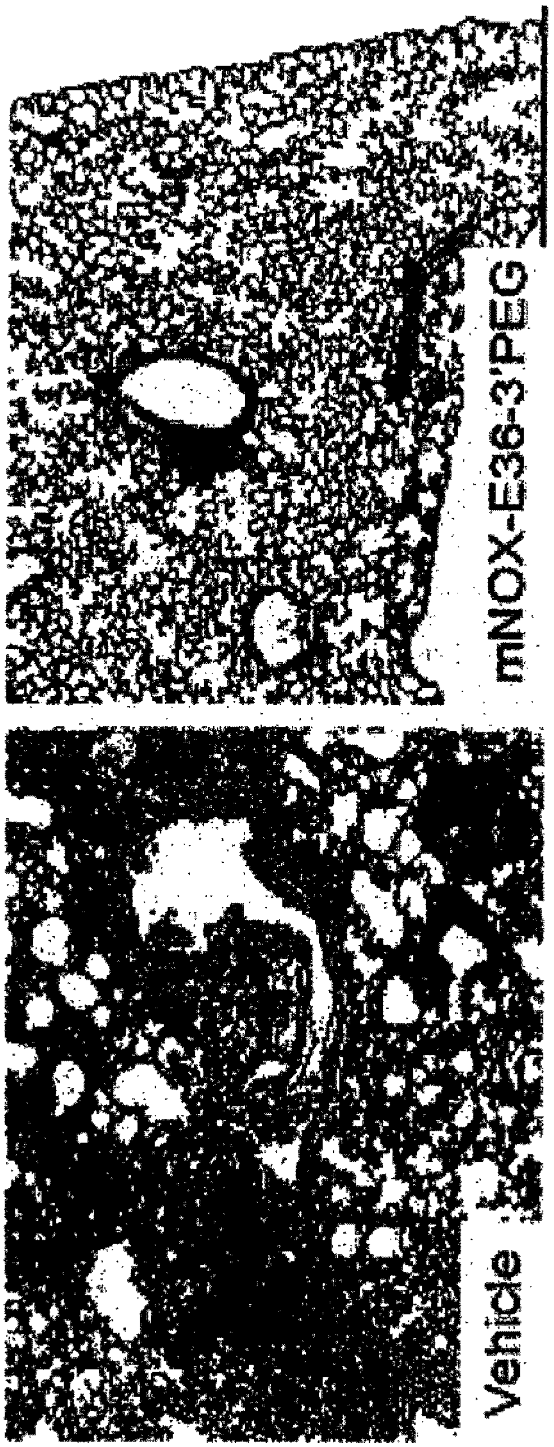
Figure 40:
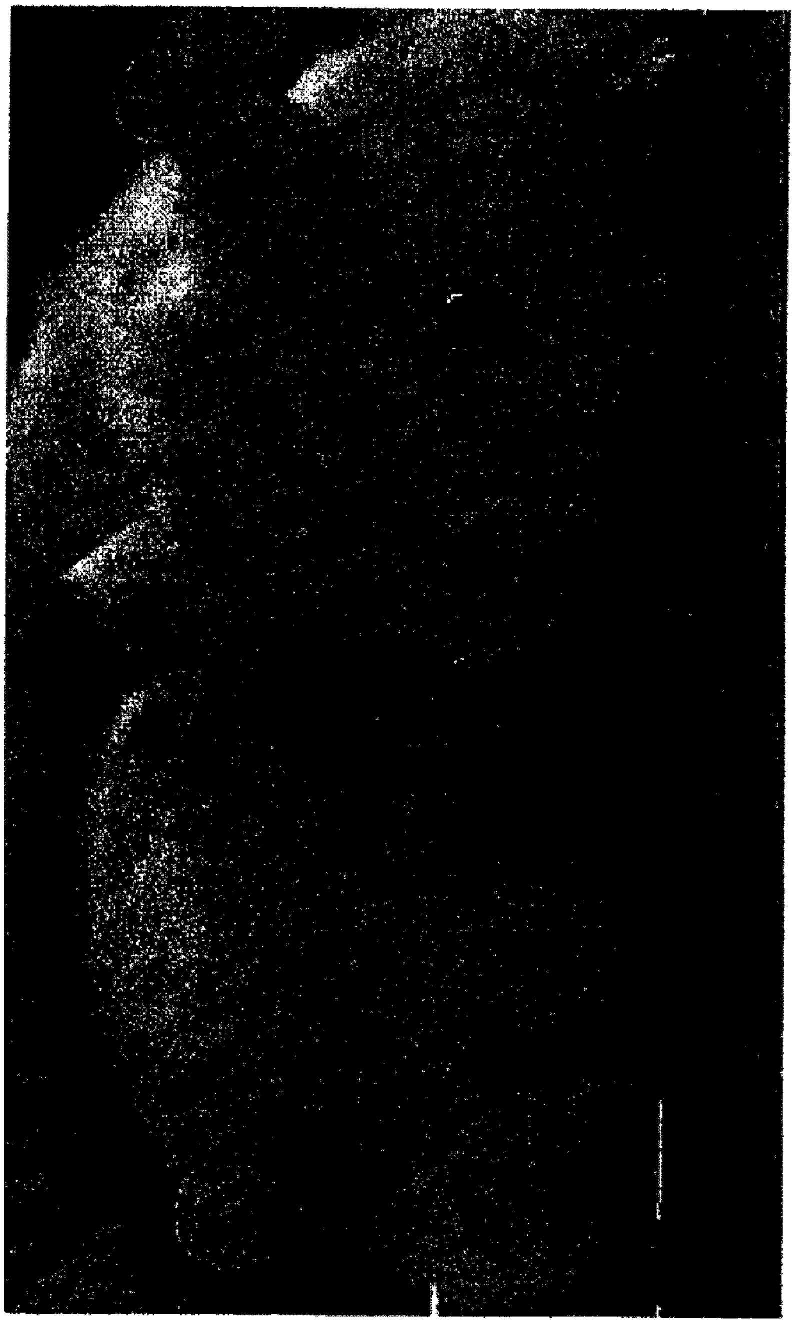
Figure 42:
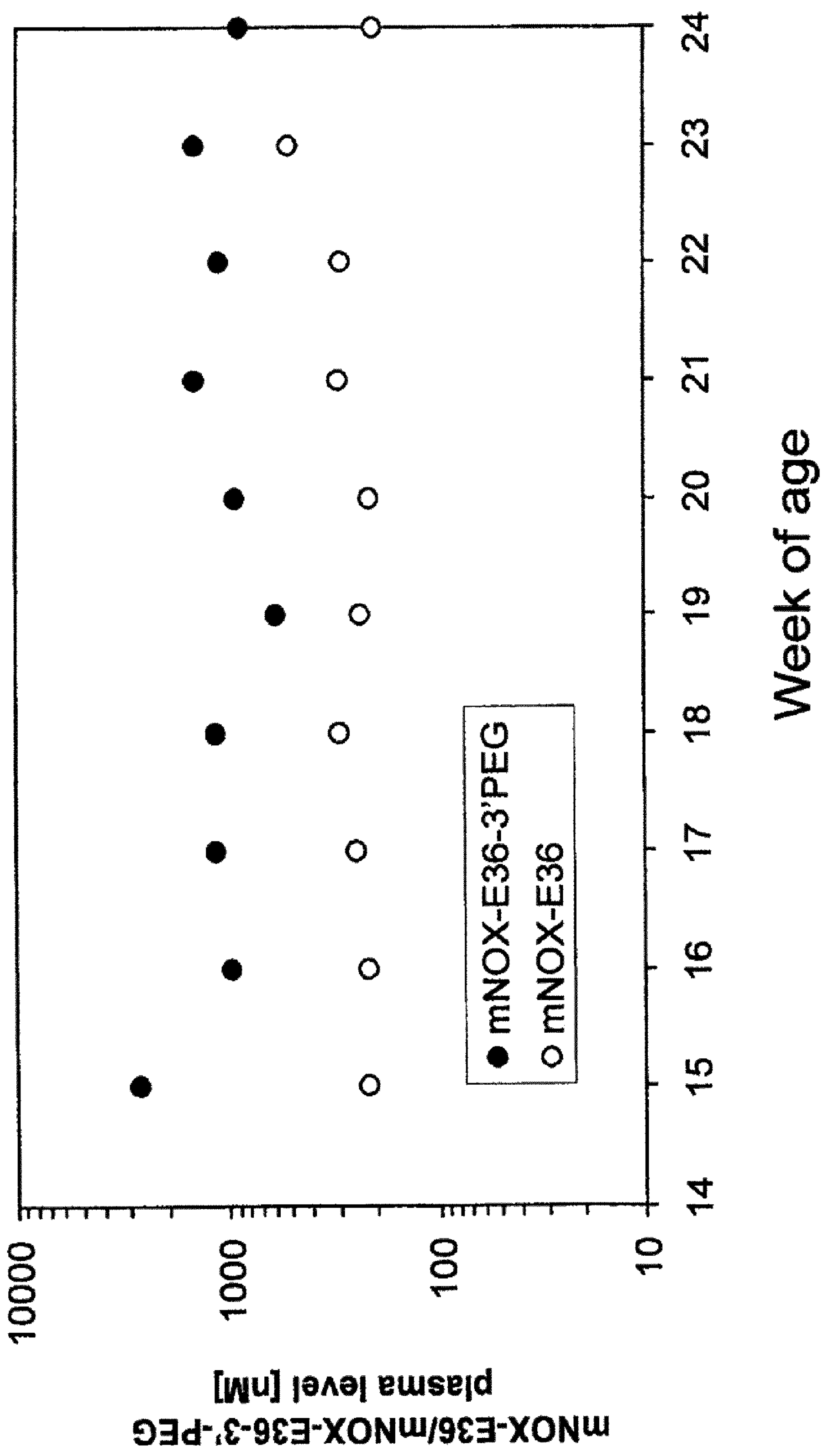
Figure 43:
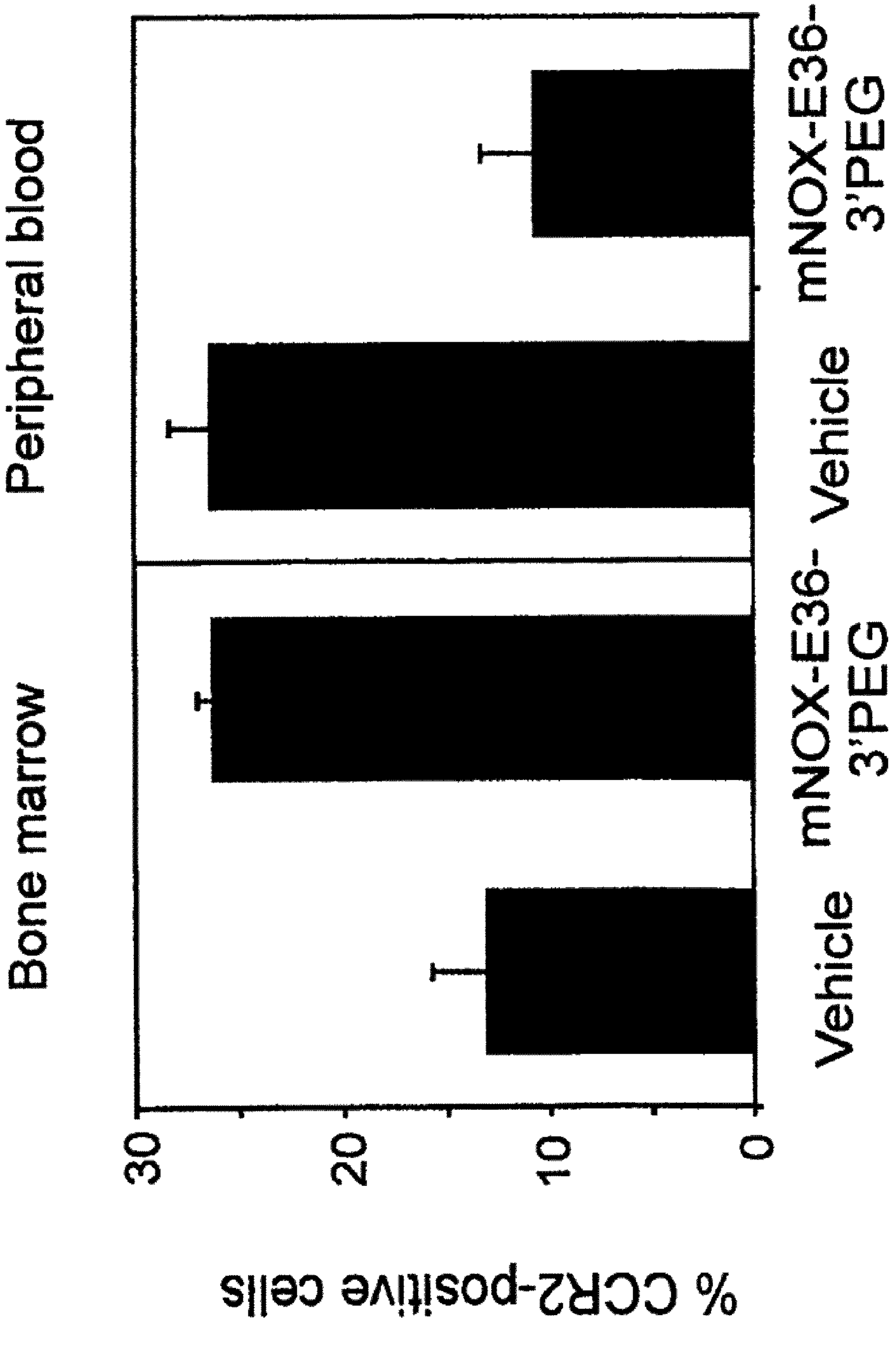
Figure 44:
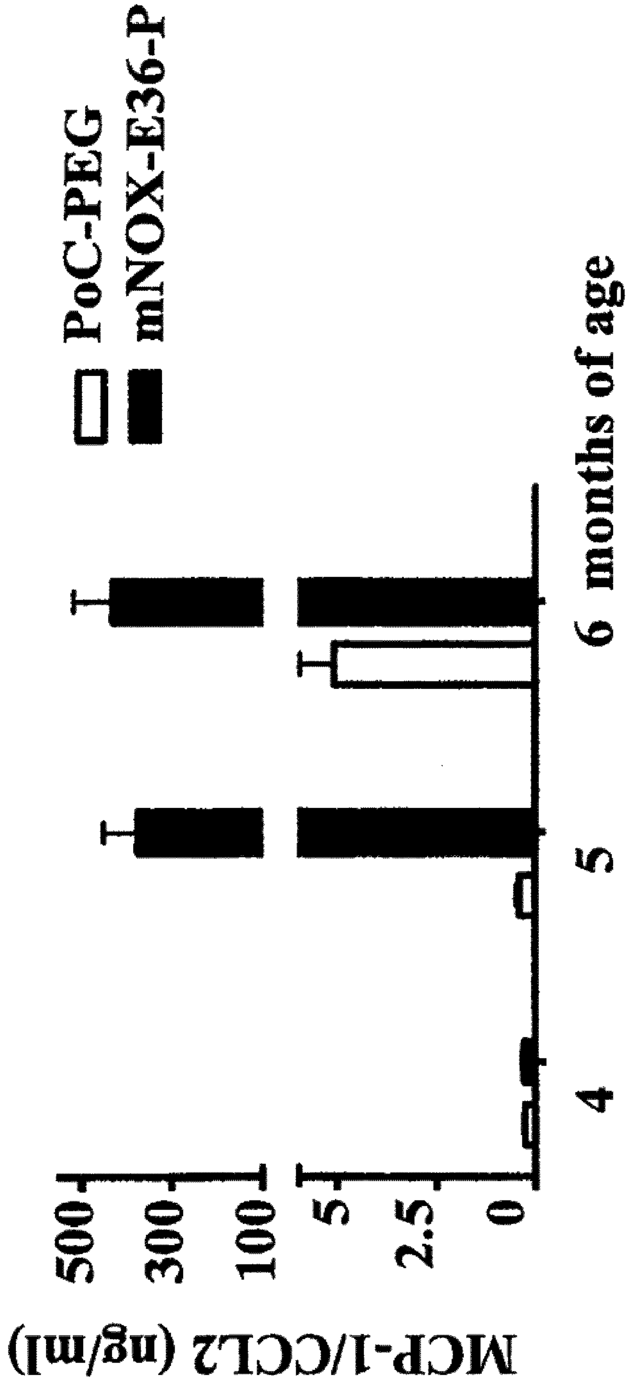
Figure 46:
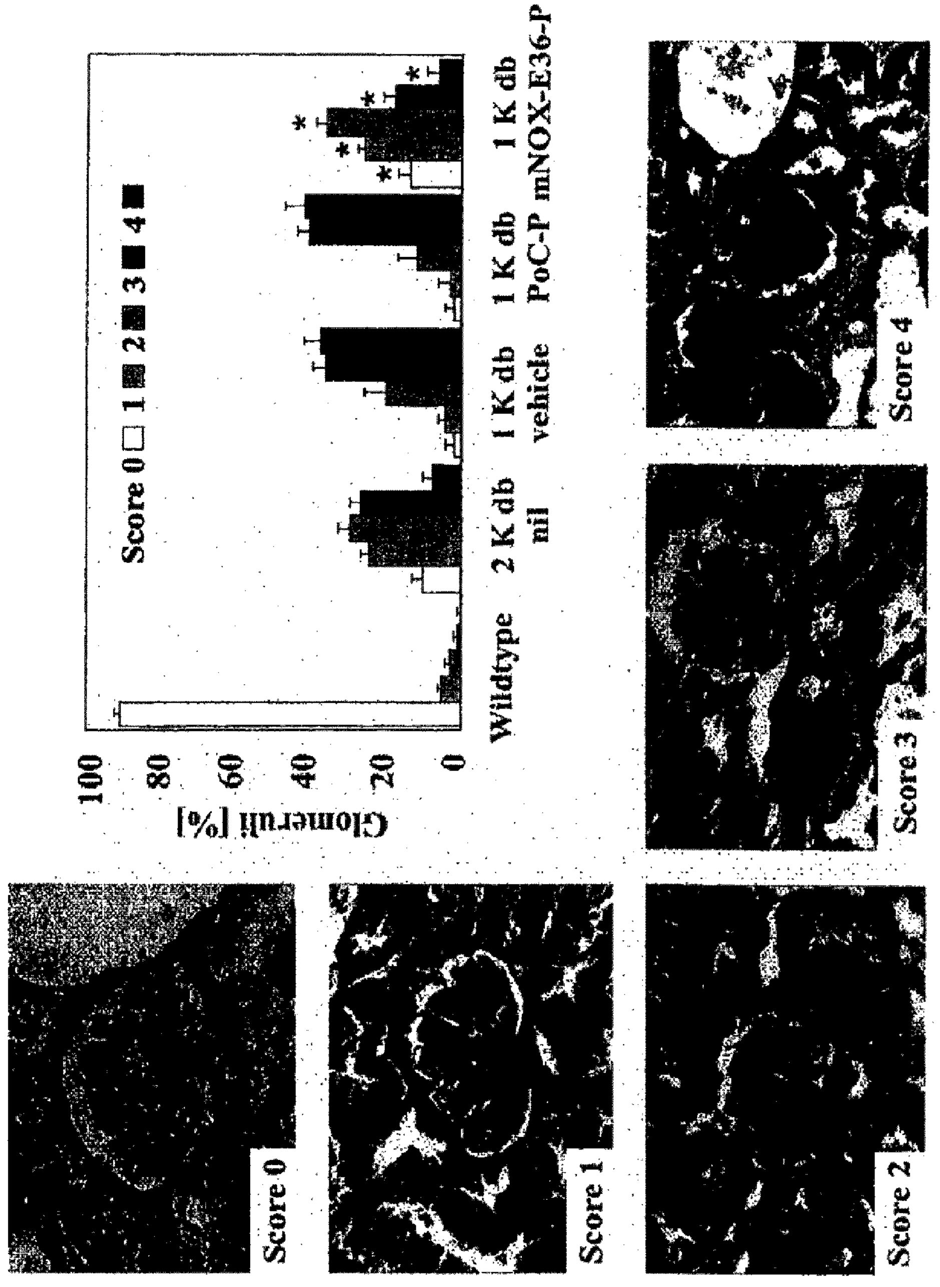
Figure 47:
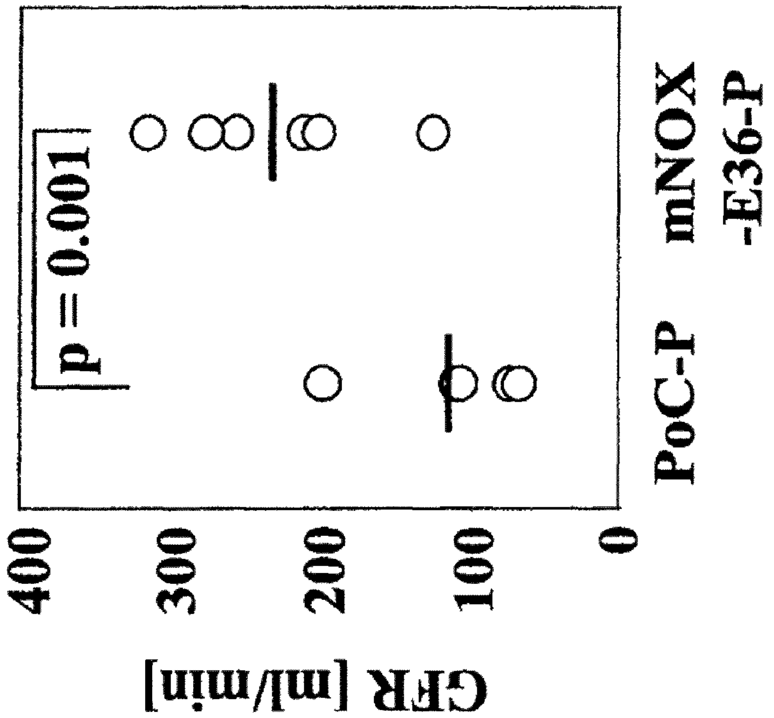
Figure 48:
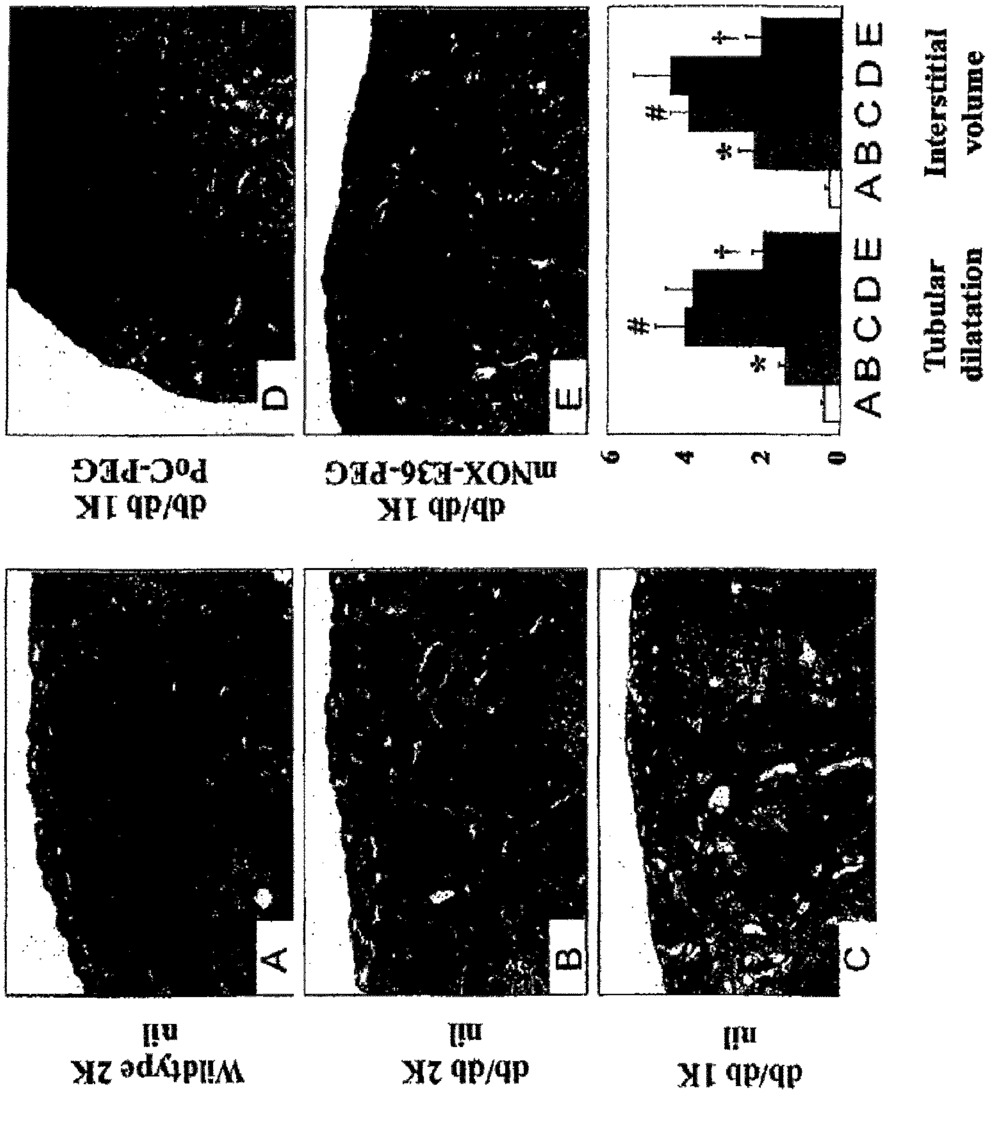
Figure 49:
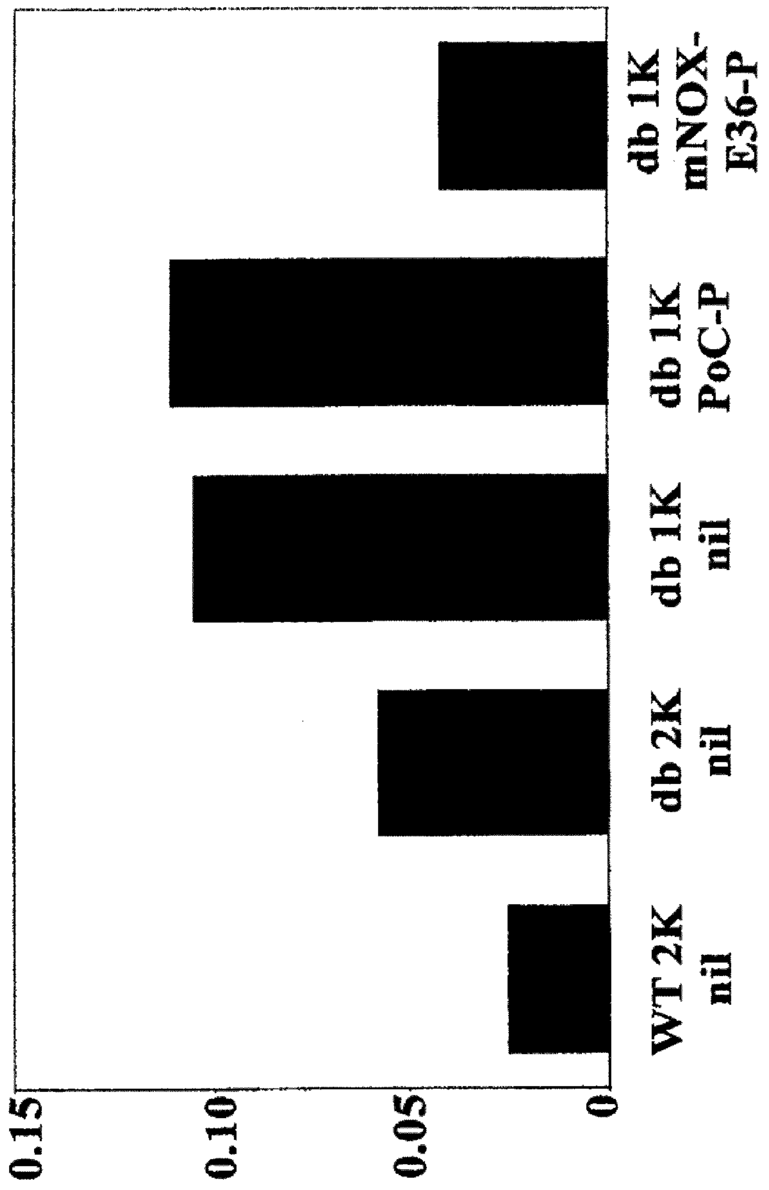
Figure 50:
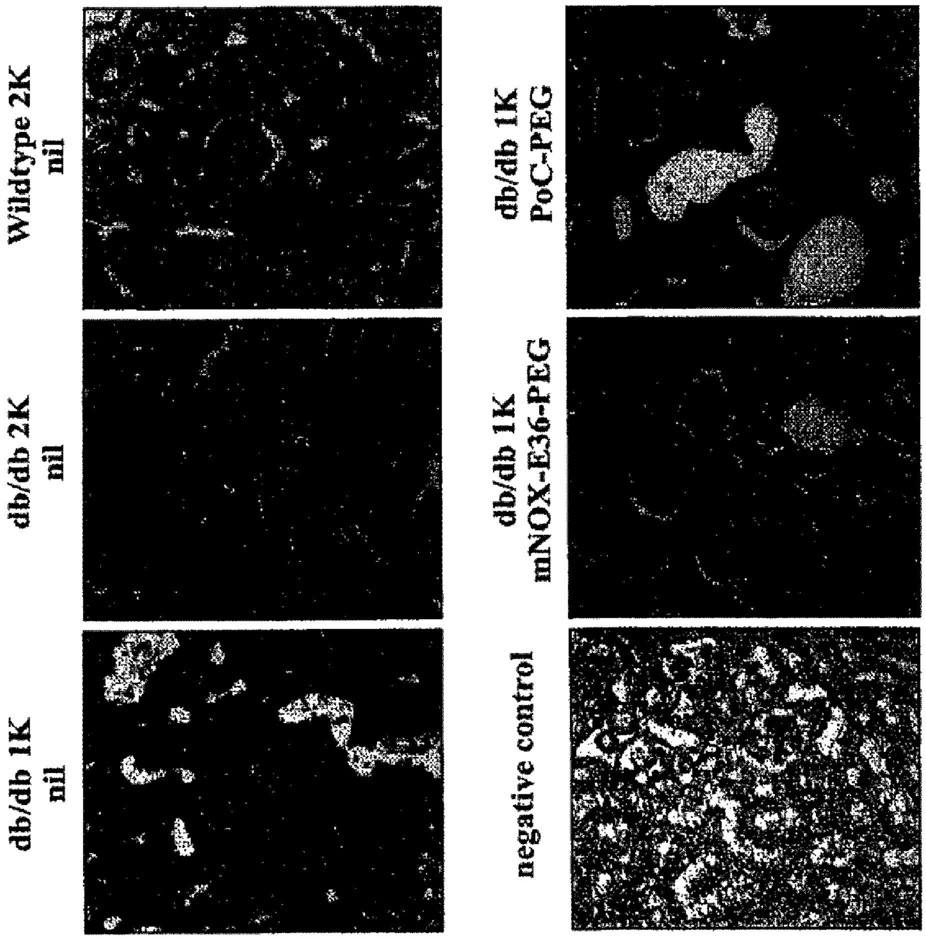
Figure 51:
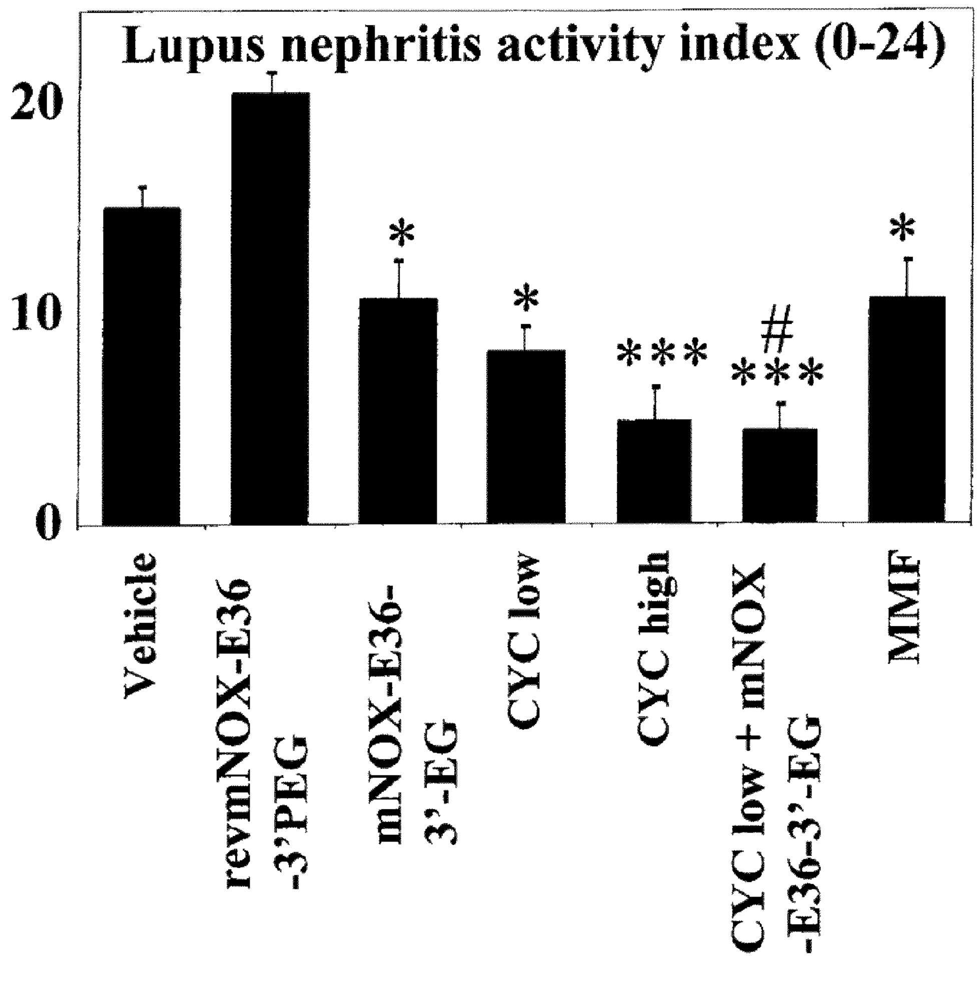
Figure 51:
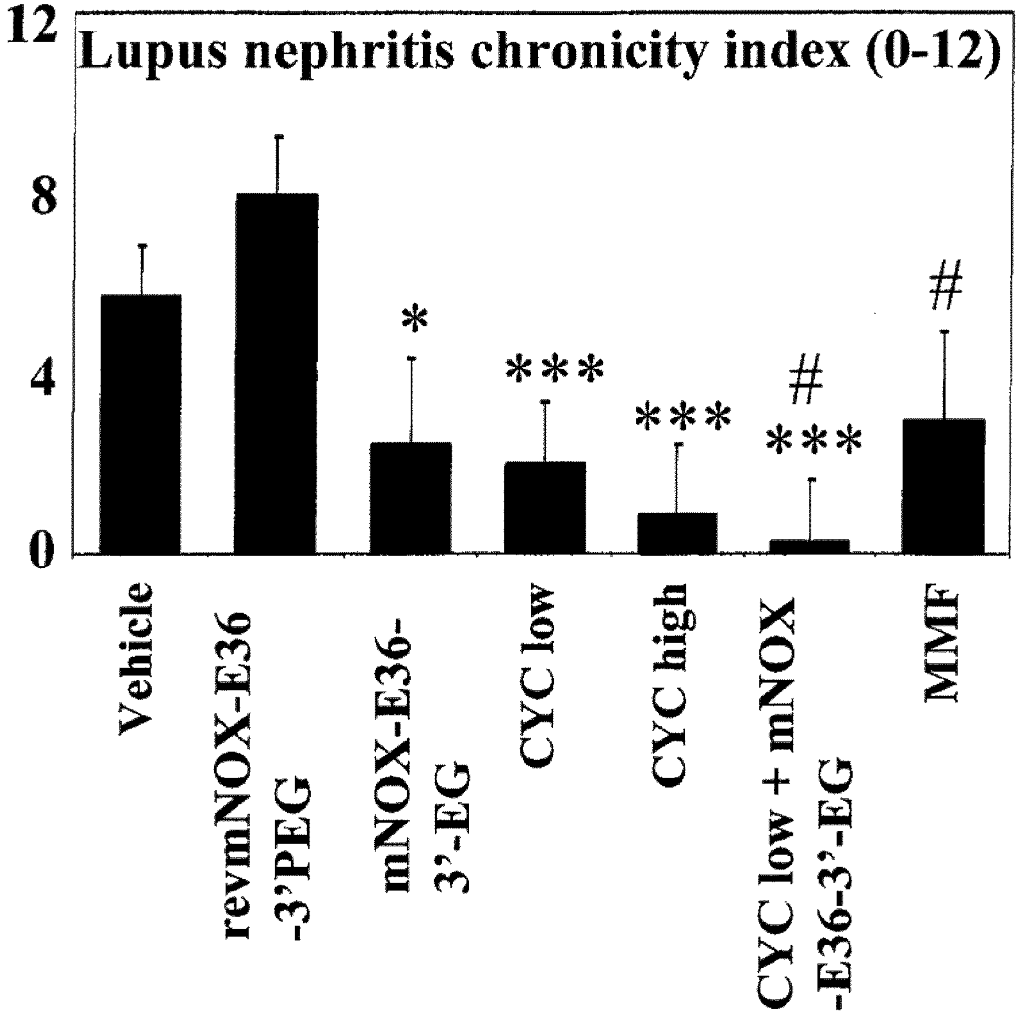
Figure 51:
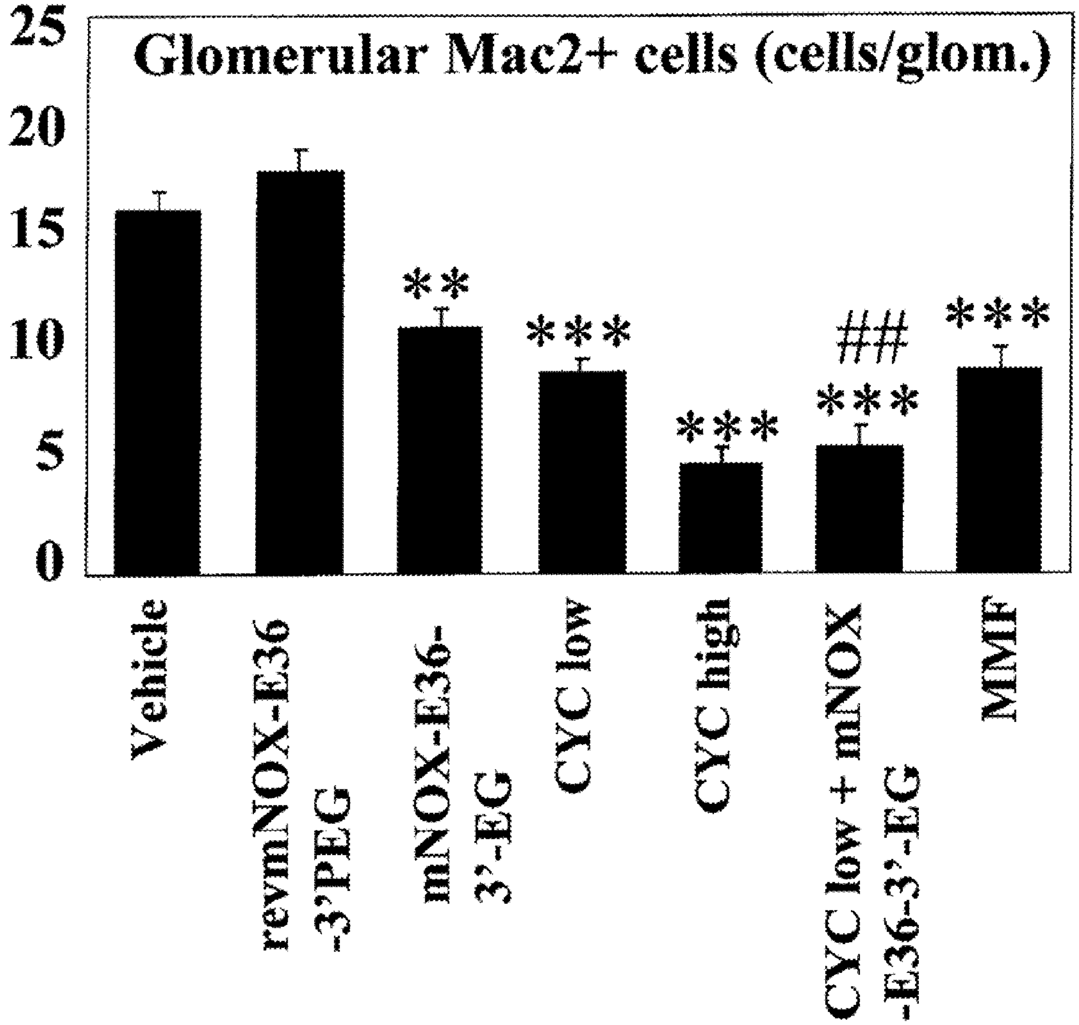
Figure 51:
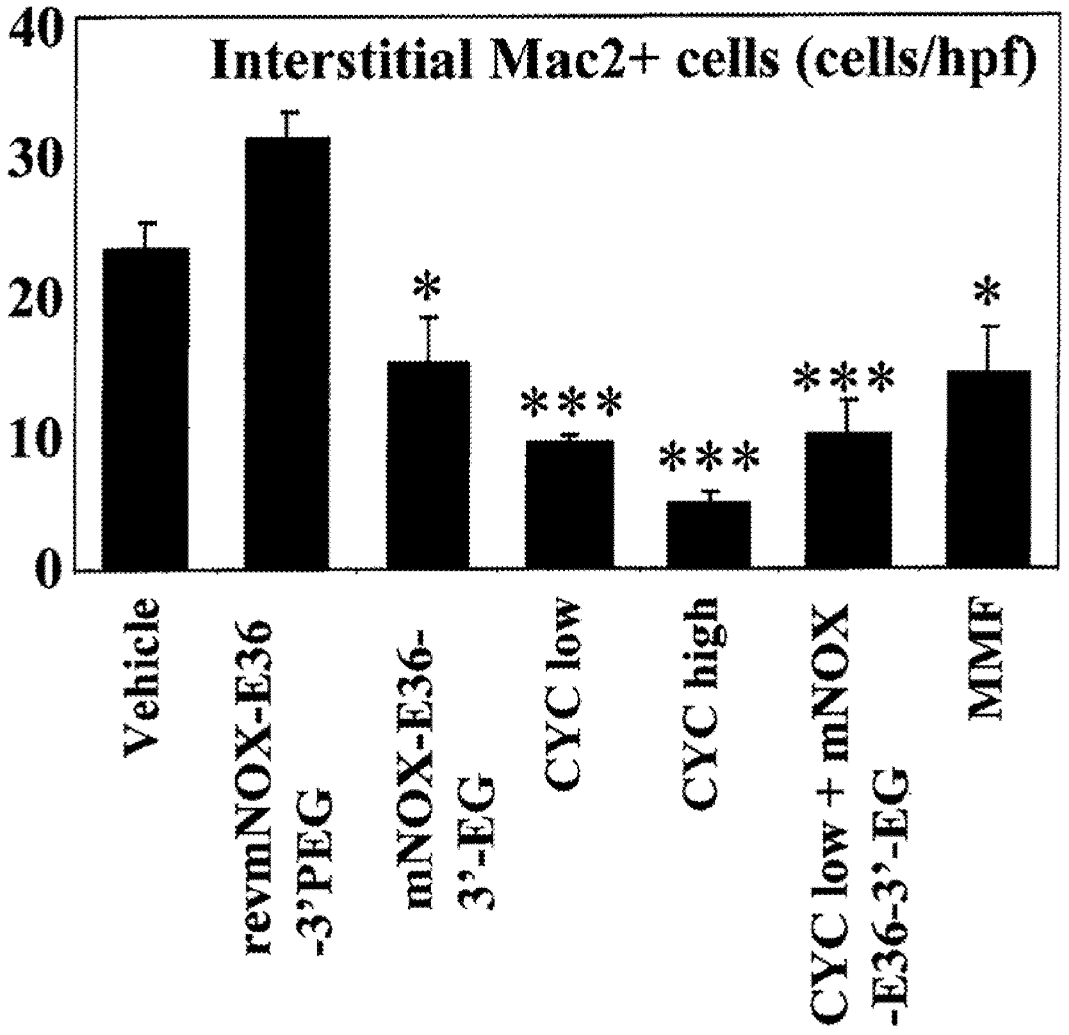
Figure 51:
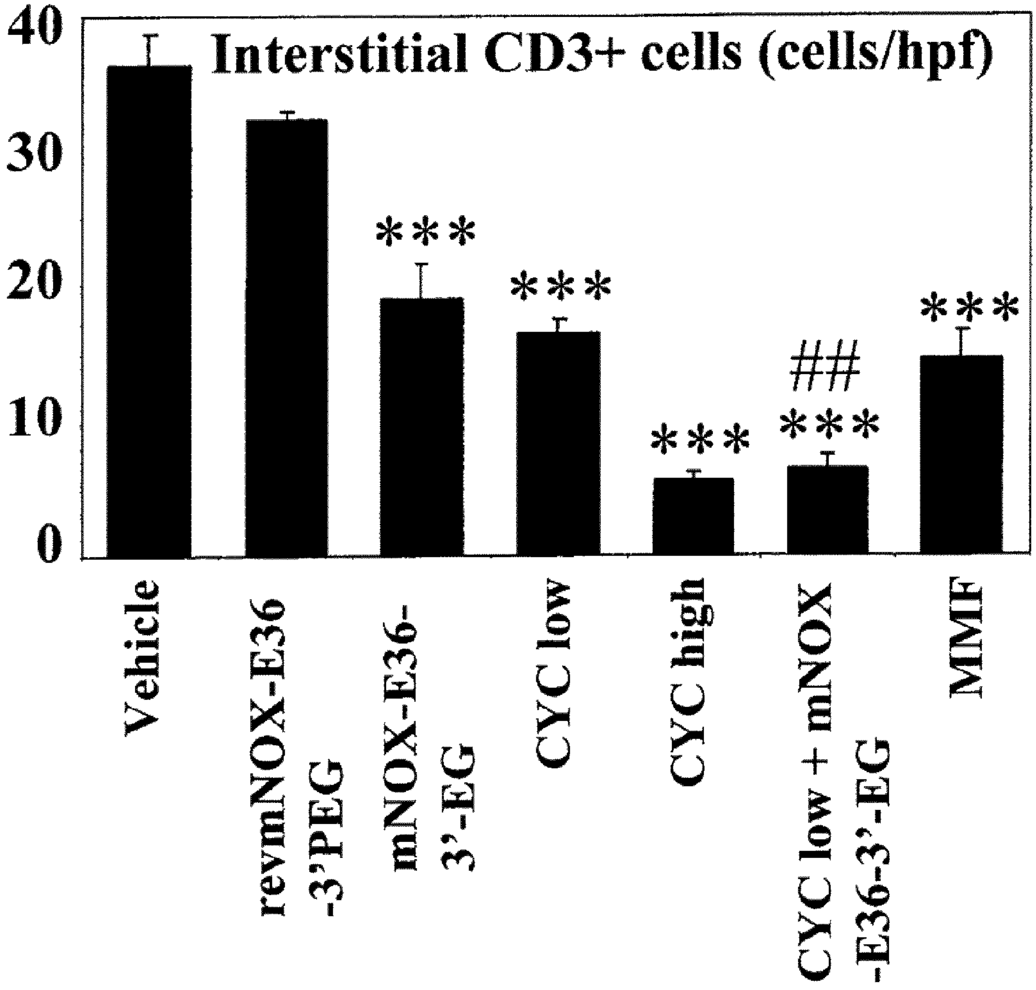
Figure 52:
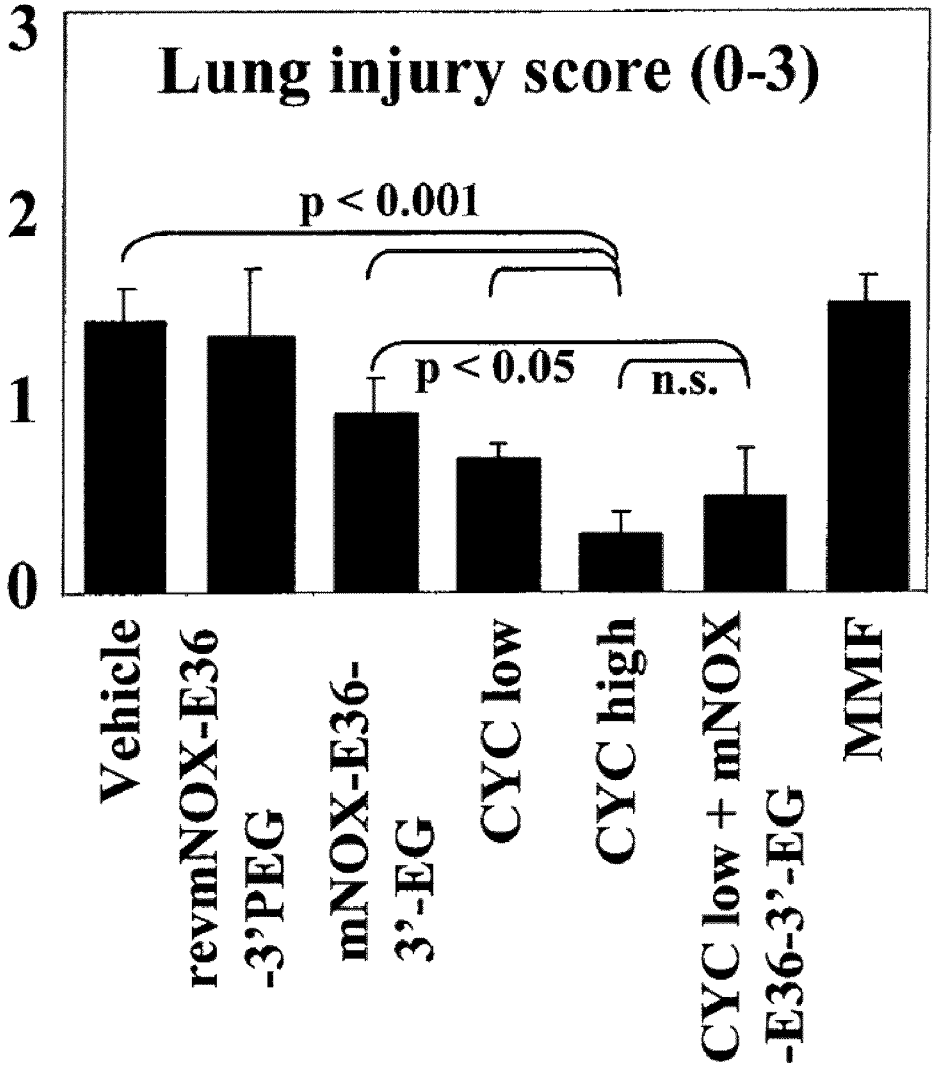
Figure 53:
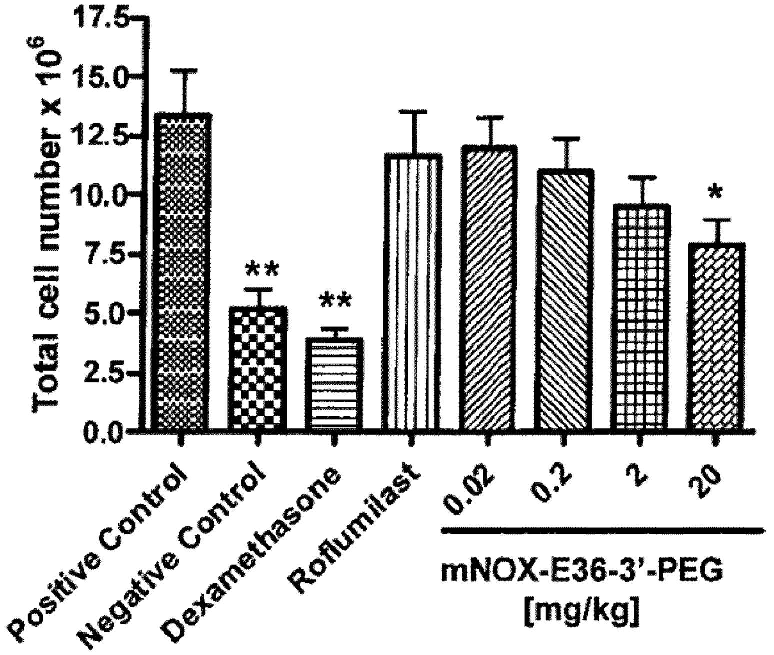
Figure 53:
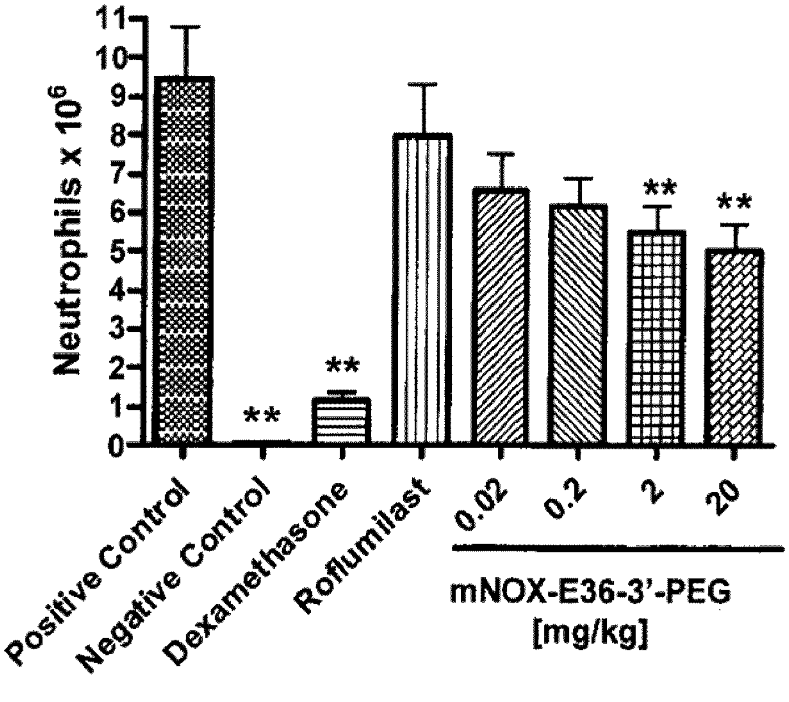
Figure 54:
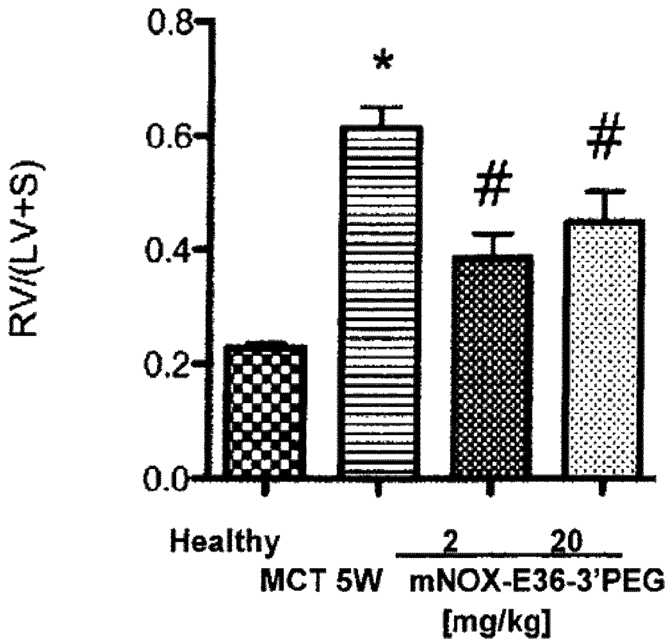
Figure 54:
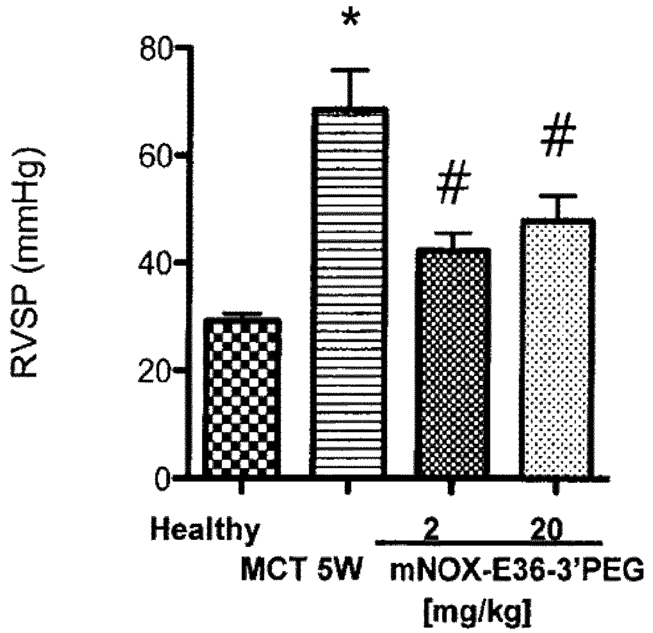

FIG. 5 shows derivatives of RNA ligands 178-D5 and 181-A2(human MCP-1 RNA ligands of sequence motif "Type 3") (FIG. 5 discloses L-RNA sequences as SEQ ID NOS 54-56, 53, 57-61, 295, and 63-73, respectively, in order of appearance, and the corresponding D-RNA sequences as SEQ ID NOS 176-178, 175, 179-183, 296, and 185-195, respectively);

FIG. 6 shows an alignment of sequences of related RNA ligands binding to human MCP-1 indicating the sequence motif ("Type 4") that is in a preferred embodiment in its entirety essential for binding to human MCP-1 (other sequences) (FIG. 6 discloses L-RNA sequences as SEQ ID NOS 74-77, 80-81, 78, 82-83, 79, and 84-86, respectively, in order of appearance, and the corresponding D-RNA sequences as SEQ ID NOS 196-199, 202-203, 200, 204-205, 201, and 206-208, respectively);

FIG. 7 shows a table of sequences of several different RNA ligands binding to human MCP-1 which can not be related to the MCP-1 binding sequence motifs "Type 1A", "Type 1B"; "Type 2", "Type 3" or "Type 4" (FIG. 7 discloses L-RNA sequences as SEQ ID NOS 87-115, respectively, in order of appearance, and the corresponding D-RNA sequences as SEQ ID NOS 209-237, respectively);

FIG. 8 shows alignments of derivatives of RNA ligand 188-A3-001and of 189-G7-001 that bind to murine MCP-1 (FIG. 8 discloses L-RNA sequences as SEQ ID NOS 118-129, respectively, in order of appearance, and the corresponding D-RNA sequences as SEQ ID NOS 240-251, respectively);

FIG. 9 shows the result of a binding analysis of the aptamer D-NOX-E36 to biotinylated human D-MCP-1 at room temperature and 37° C., represented as binding of the aptamer over concentration of biotinylated human D-MCP -1 ;

FIG. 10 shows the result of a binding analysis of the aptamer D-mNOX-E36 to biotinylated murine D-MCP-1 at 37° C., represented as binding of the aptamer over concentration of biotinylated murine D-MCP-1;

FIG. 11 shows MCP-1-induced $Ca^{++}$-release in THP-1 cells, whereas a dose-response curve for human MCP-1 was obtained, indicating a half effective concentration ($EC_{50}$) of approximately 3 nM, represented as difference in fluorescence to blank over concentration of human MCP-1;

FIG. 12 shows the efficacy of Spiegelmer NOX-E36 in a calcium release assay; cells were stimulated with 3 nM human MCP-1 preincubated at 37° C. with various amounts of Spiegelmer NOX-E36, represented as percentage of control over concentration of NOX-E36;

FIG. 13 shows the efficacy of Spiegelmer mNOX-E36 in a calcium release assay; cells were stimulated with 5 nM murine MCP-1 preincubated at 37° C. with various amounts of Spiegelmer mNOX-E36, represented as percentage of control over concentration of mNOX-E36;

FIG. 14 shows the human MCP-1-induced chemotaxis of THP-1 cells whereas after 3 hours migration of THP-1 cells towards various MCP-1 concentrations a dose-response curve for MCP-1 was obtained, represented as X-fold increase compared to control over concentration of human MCP-1;

FIG. 15 shows the efficacy of Spiegelmer NOX-E36 in a chemotaxis assay; cells were allowed to migrate towards 0.5 nM human MCP-1 preincubated at 37° C. with various amounts of Spiegelmer NOX-E36, represented as percentage of control over concentration of Spiegelmer NOX-E36;

FIG. 16 shows the efficacy of Spiegelmer mNOX-E36 in a chemotaxis assay; cells were allowed to migrate towards 0.5 nM murine MCP-1 preincubated at 37° C. with various amounts of Spiegelmer NOX-E36, represented as percentage of control over concentration of Spiegelmer mNOX-E36;

FIG. 17 shows the Biacore 2000 sensorgram indicating the $K_D$ value of Spiegelmer NOX-E-36 binding to human MCP-1 which was immobilized on a PioneerF1 sensor chip by amine coupling procedure, represented as response (RU) over time;

FIG. 18 shows the Biacore 2000 sensorgram indicating binding of Spiegelmer NOX-E36 to human MCP-family proteins (huMCP-1, huMCP-2, huMCP-3) and human eotaxin, which were immobilized by amine coupling procedure on a PioneerF1 and a CM4 sensor chip, respectively, represented as response (RU) over time;

FIG. 19 shows the Biacore 2000 sensorgram indicating binding of Spiegelmer NOX-E36 to MCP-1 from different species (canine MCP-1, monkey MCP-1, human MCP-1, porcine MCP-1, rabbit MCP-1, mouse MCP-1, rat MCP-1) whereas different forms of MCP-1 were immobilized by amine coupling procedure on PioneerF1 and a CM4 sensor chips, respectively, represented as response (RU) over time;

FIG. 20 shows the Biacore 2000 sensorgram indicating the $K_D$ value of Spiegelmer 181-A2-018 binding to human MCP-1 which was immobilized on a CM4 sensor Chip by amine coupling procedure, represented as response (RU) over time;

FIG. 21 shows the Biacore 2000 sensorgram indicating binding of Spiegelmer 181-A2-018 to human MCP-family proteins (huMCP-1, huMCP-2, huMCP-3) and human eotaxin which were immobilized by amine coupling procedure on a PioneerF1 and a CM4 sensor chip, respectively, represented as response (RU) over time;

FIG. 22 shows the Biacore 2000 sensorgram indicating binding of Spiegelmer 181-A2-018 to MCP-1 from different species (canine MCP-1, monkey MCP-1, human MCP-1, porcine MCP-1, rabbit MCP-1, mouse MCP-1, rat MCP-1) whereas different forms of MCP-1 were immobilized by amine coupling procedure on PioneerF1 and a CM4 sensor chips, respectively, represented as response (RU) over time;

FIG. 23 shows a Clustal W alignment of MCP-1 from different mammalian species as well as human MCP-2, MCP-3, and eotaxin (Positions 1-76only of SEQ ID NOS 1, 3, 4, 283, 5, 6, 284, 7-9, 2, and 252, respectively, in order of appearance);

FIG. 24A shows a table summarizing the binding specificity of NOX-E36 and 181-A2-018 regarding MCP-1 from different mammalian species as well as human MCP-2, MCP-3, and eotaxin;

FIG. 24B shows a table summarizing the selectivity of NOX-E36 as determined by Biacore analysis whereby biotinylated NOX-E36 was immobilized on a sensor chip surface and binding of a panel of various CC and CXC chemokines to NOX-E36 was analyzed;

FIG. 24C shows the kinetic analysis of NOX-E36 interacting with chemokines as determined by Biacore analysis whereby the chemokines were immobilized covalently on a CM5 sensor chip surface and various concentrations of the NOX-E36 were injected and NOX-E36s binding behaviour was analyzed using the BiaEvaluation software;

FIG. 24D shows the chemotaxis dose-response curve of THP-1 cell stimulation with MIP-1α with a half-effective concentration of about 0.2 nM;

FIG. 24E shows the Inhibition of MIP-1α induced chemotaxis by NOX-E36. NOX-E36 had no influence on the MIP1a induced chemotaxis of THP-1 cells;

FIG. 25 shows the efficacy of Spiegelmer NOX-E36-3'-PEG in a calcium release assay; cells were stimulated with 3 nM human MCP-1 preincubated at 37° C. with various amounts of Spiegelmer NOX-E36-3'-PEG, represented as percentage of control over concentration of Spiegelmer NOX-E36-3'-PEG;

FIG. 26 shows the efficacy of Spiegelmer NOX-E36-3'-PEG in a chemotaxis assay; cells were allowed to migrate towards 0.5 nM human MCP-1 preincubated at 37° C. with various amounts of Spiegelmer NOX-E36-3'-PEG, represented as percentage of control over concentration of NOX-E36-3'-PEG;

FIG. 27A shows the efficacy of Spiegelmer NOX-E36-5'-PEG in a calcium release assay; cells were stimulated with 3 nM human MCP-1 preincubated at 37° C. with various amounts of Spiegelmer NOX-E36-5'-PEG, represented as percentage of control over concentration of Spiegelmer NOX-E36-5'-PEG;

FIG. 27B shows the efficacy of Spiegelmer NOX-E36-5'-PEG in a chemotaxis assay; cells were allowed to migrate towards 0.5 nM human MCP-1 preincubated at 37° C. with various amounts of Spiegelmer NOX-E36-5'-PEG, represented as percentage of control over concentration of Spiegelmer NOX-E36-5'-PEG;

FIG. 28 shows murine MCP-1-induced Ca++-release in THP-1 cells, whereas a dose-response curve for murine MCP-1 was obtained, indicating a half effective concentration ($EC_{50}$) of approximately 5 nM, represented as difference in fluorescence to blank over concentration of murine MCP-1;

FIG. 29 shows the efficacy of anti-murine MCP-1 Spiegelmer mNOX-E36-3'-PEG in a calcium release assay; cells were stimulated with 3 nM murine MCP-1 preincubated at 37° C. with various amounts of Spiegelmer mNOX-E36-3'-PEG, represented as percentage of control over concentration of Spiegelmer mNOX-E36-3'-PEG;

FIG. 30 shows the murine MCP-1-induced chemotaxis of THP-1 cells whereas after 3 hours migration of THP-1 cells towards various mMCP-1 concentrations a dose-response curve for mMCP-1 was obtained, represented as X-fold increase compared to control over concentration of murine MCP-1;

FIG. 31 shows the efficacy of anti-murine MCP-1 Spiegelmer mNOX-E36-3'-PEG in a chemotaxis assay; cells were allowed to migrate towards 0.5 nM murine MCP-1 preincubated at 37° C. with various amounts of Spiegelmer mNOX-E36-3'-PEG, represented as percentage of control over concentration of anti-murine Spiegelmer mNOX-E36-3'-PEG;

FIG. 32 shows the Biacore 2000 sensorgram indicating the $K_D$ value of aptamer D-mNOX-E36 binding to murine D-MCP-1 which was immobilized on a PioneerF1 sensor chip by amine coupling procedure, represented as response (RU) over time;

FIG. 33 shows the Biacore 2000 sensorgram indicating binding of aptamer D-mNOX-E36 to human D-MCP-1 and murine D-MCP-1 whereas the two different forms of D-MCP-1 were immobilized by amine coupling procedure on PioneerF1 and a CM4 sensor chips, respectively, represented as response (RU) over time;

FIG. 34 shows renal sections of 24-week old $MRL^{lpr/lpr}$ mice, stained with periodic acid Schiff (PAS), antibodies for Mac-2 (macrophages) and CD3 (T cells) as indicated; images are representative for 7-12 mice in each group (original magnification PAS: ×100, PAS inserts: ×400, Mac2: ×400, CD3: ×100;

FIG. 35 shows a table illustrating renal function parameters and histological findings in the different groups of 24-week old $MRL^{lpr/lpr}$ mice;

FIG. 36 shows the quantification of histological changes by morphometry performed on silver stained sections of mice from all groups; A, interstitial volume index; B, tubular dilation index, and C, tubular cell damage index were calculated as percentage of high power field and are expressed as means ±SEM;

FIG. 37 shows the survival of $MRL^{lpr/lpr}$ mice of the various treatment groups as calculated by Kaplan-Meier analysis;

FIG. 38 shows renal mRNA expression for the CC-chemokines CCL2 and CCL5 as determined by real-time RT-PCR using total renal RNA pooled from 5mice of each group whereby RNA levels for each group of mice are expressed per respective 18S rRNA expression;

FIG. 39 shows reduction of lung pathology by treatment with mNOX-E36-3'PEG; lung tissue was prepared from of all groups at age 24 weeks and scored semiquantitatively; treatment with mNOX-E36 and mNOX-E36-3'PEG reduced peribronchiolar inflammation in $MRL^{lpr/lpr}$ mice; mages are representative for 7-11 mice in each group; original magnification ×100;

FIG. 40 shows cutaneous lupus manifestations of $MRL^{lpr/lpr}$ mice at age 24 weeks which typically occur at the facial or neck area (left mouse) which were less common in anti-mCCL2 Spiegelmer-treated mice (right mouse);

FIG. 41 shows serum and histological findings in $MRL^{lpr/lpr}$ mice at age 24 weeks;

FIG. 42 shows the pharmacokinetics of pegylated and unpegylated anti-mCCL2 Spiegelmers in plasma during the study, indicated as plasma concentration of Spiegelmer mNOX-E36 as a function of time;

FIG. 43 shows flow cytometry for CCR2 on bone marrow and peripheral blood in 24 week old vehicle- or mNOX-E36-3'PEG-treated $MRL^{lpr/lpr}$ mice; data are shown as mean percentage of CCR2 positive cells ±SEM in either bone marrow or peripheral blood in 5 mice of each group;

FIG. 44 shows serum CCL2 levels in PoC-PEG- (white bars) and mNOX-E36-3'PEG (mNOX-E36-P)-treated (black bars) 1K db/db mice as determined by ELISA at different time points as indicated; data are means ±SEM; *, $p<0.05$ mNOX-E36-3'PEG (mNOX-E36-P) vs. PoC-PEG;

FIG. 45 shows the infiltrated number of Mac-2 and Ki-67 positive cells in the glomeruli and the interstitium of untreated or POC-PEG or rather mNOX-E36-3'PEG treated db/db mice;

FIG. 46 shows the diabetic glomerulosclerosis in 6 months old db/db mice; renal sections from mice of the different groups were stained with periodic acid Schiff and 15 glomeruli from each renal section were scored for the extent of glomerulosclerosis; images show representative glomeruli graded to the respective scores as indicated, original magnification 400×; the graph illustrates the mean percentage of each score ±SEM from all mice in each group (n=7–10); *, $p<0.05$ for mNOX-E36-3'PEG (mNOX-E36-P) vs. PoC-PEG (PoC-P)-treated 1K db/db mice;

FIG. 47 shows the glomerular filtration rate (GFR) in 6 months old mNOX-E36-3'PEG (mNOX-E36-P)- and PoC-PEG(PoC-P)-treated 1K db/db mice; GFR was determined by FITC-inulin clearance kinetics in the groups of PoC-PEG- and mNOX-E36-3'PEG-treated 1K db/db mice at the end of the study;

FIG. 48 shows tubular atrophy and interstitial volume of 6 months old db/db mice; images of silver-stained renal sections illustrate representative kidneys from the respective groups (original magnification 100×); values represent means ±SEM of the respective morphometric analysis index from 7-10mice in each group; *, $p<0.05$ 2K db/db vs. BKS wild-type mice; #, p 21 0.05 1K vs. 2K db/db mice; †, $p<0.05$ mNOX-E36-3'PEG (mNOX-E36-PEG) - vs. PoC-PEG-treated 1K db/db mice;

FIG. 49 shows renal CCL2 mRNA expression db/db mice as determined by real-time RT-PCR using total renal RNA pooled from 6-10 mice of each group; mRNA levels for each group of mice are expressed per respective 18 S rRNA expression;

FIG. 50 shows spatial CCL2 expression in kidneys of db/db mice as determined by immunostaining; images illustrate representative sections of kidneys from 6 months old mice of the respective groups as indicated (original magnification, 200×);

FIG. 51A-E shows markers of lupus nephritis in MRLpr/Ipr mice after treatment of the MRLIpr/Ipr mice with vehicle, revmNOX-E36-3'-PEG, mNOX-E36-3'-PEG, CYC low, CYC high, CYC low +mNOX-E36-3'-PEG or MMF, whereby the activity index (FIG. 51A) and the chronicity index (FIG. 51 B) for DPLN were determined on PAS stained renal sections as described by Austin et al (Austin et al. 1984); and whereby the mean number of glomerular macrophages (FIG. 51C) in renal sections of 24 weeks old MRLIpr/Ipr mice (Mac2+ cells in 15 glomeruli per section)., numbers of interstitial macrophages (FIG. 51D) or numbers of T cells (FIG. 51E) in renal sections of 24 weeks old MRLIpr/Ipr mice, respectively (Mac2+ or CD3+ cells in 15 high power fields per section) were determined;

FIG. 52 shows the semiquantitative scoring of lung injury from periodic acid Schiff-stained lung sections of 24 weeks old MRLIpr/Ipr mice;

FIG. 53A shows total cell number in the BAL fluid 24 h after LPS challenge ($\times10^6$/animal; mean ±SEM; * $p<0.05$, ** $p<0.01$ vs. positive control group), whereby the animals were treated with vehicle (positive control), dexamethasone, Roflumilast or MCP-1 binding Spiegelmer mNOX-E36-3'-PEG before LPS challenge or vehicle before clean air challenge (negative control);

FIG. 53B shows the absolute number of neutrophils in the BAL fluid 24 h after LPS challenge (mean ±SEM; ** $p<0.01$ vs. positive control group),), whereby the animals were treated with vehicle (positive control), dexamethasone, Roflumilast or MCP-1 binding Spiegelmer mNOX-E36-3'-PEG before LPS challenge or vehicle before clean air challenge (negative control);

FIG. 54A shows right heart hypertrophy of healthy animals or of animals after treatment with MCT/vehicle or MCT/

MCP-1 binding Spiegelmer mNOX-E36-3'-PEG; whereby the readout was right ventricle weight to left ventricle plus septum weight RV/(LV+S);

FIG. 54B shows right ventricular systolic pressure (RSVP [mmHg]) of healthy animals or of animals after treatment with MCT/vehicle or MCT/MCP-1 binding Spiegelmer mNOX-E36-3'-PEG.

EXAMPLE 1

Nucleic Acids That Bind Human MCP-1

Using biotinylated human D-MCP-1 as a target, several nucleic acids that bind to human MCP-1 could be generated the nucleotide sequences of which are depicted in FIGS. 1 through 7. The nucleic acids were characterized on the aptamer, i.e. D-nucleic acid level using competitive or direct pull-down assays with biotinylated human D-MCP-1 (Example 4) or on the Spiegelmer level, i.e. L-nucleic acid with the natural configuration of MCP-1 (L-MCP) by surface plasmon resonance measurement using a Biacore 2000 instrument (Example 7), an in vitro cell culture $Ca^{++}$-release assay (Example 5), or an in vitro chemotaxis assay (Example 6).

The nucleic acid molecules thus generated exhibit different sequence motifs, four main types are defined in FIGS. 1 and 2 (Type 1A/1B), FIG. 3 (Type 2), FIGS. 4 and 5 (Type 3), and FIG. 6 (Type 4). Additional MCP-1 binding nucleic acids which can not be related to each other and to the different sequence motifs described herein, are listed in FIG. 7. For definition of nucleotide sequence motifs, the IUPAC abbreviations for ambiguous nucleotides is used:

| | | |
|---|---|---|
| S | strong | G or C; |
| W | weak | A or U; |
| R | purine | G or A; |
| Y | pyrimidine | C or U; |
| K | keto | G or U; |
| M | imino | A or C; |
| B | not A | C or U or G; |
| D | not C | A or G or U; |
| H | not G | A or C or U; |
| V | not U | A or C or G; |
| N | all | A or G or C or U |

If not indicated to the contrary, any nucleic acid sequence or sequence of stretches and boxes, respectively, is indicated in the 5'→3' direction.

Type 1A MCP-1 Binding Nucleic Acids (FIG. 1)

As depicted in FIG. 1 all sequences of MCP-1 binding nucleic acids of Type 1A comprise several sequences stretches or boxes whereby boxes B1A and B1B are the 5'- and 3' terminal stretches that can hybridize with each other. However, such hybridization is not necessarily given in the molecule as actually present under physiological conditions. Boxes B2, B3, B4, B5 and box B6 are flanked by box B1A and box B1B..

The nucleic acids were characterized on the aptamer level using direct and competitive pull-down assays with biotinylated human D-MCP-1 in order to rank them with respect to their binding behaviour (Example 4). Selected sequences were synthesized as Spiegelmer (Example 3) and were tested using the natural configuration of MCP-1 (L-MCP) in an in vitro cell culture $Ca^{++}$-release assay (Example 5).

The sequences of the defined boxes may be different between the MCP-1 binding nucleic acids of Type 1A which influences the binding affinity to MCP-1. Based on binding analysis of the different MCP-1 binding nucleic acids summarized as Type 1A MCP-1 binding nucleic acids, the boxes B1A, B2, B3, B4, B5, B6 and B1B and their nucleotide sequences as described in the following are individually and more preferably in their entirety essential for binding to MCP-1:

- boxes B1A and B1B are the 5'- and 3' terminal stretches can hybridize with each other;
  - where B1A is AGCRUG, preferably AGCGUG; and
  - where B1B is CRYGCU, preferably CACGCU;
- box B2, which is CCCGGW, preferably CCCGGU;
- box B3, which is GUR, preferably GUG;
- box B4, which is RYA, preferably GUA;
- box B5, which is GGGGGRCGCGAYC, (SEQ ID NO: 292), preferably GGGGGGCGCGACC; (SEQ ID NO: 294);
- box B6, which is UGCAAUAAUG (SEQ ID NO: 293) or URYAWUUG, preferably UACAUUUG;

As depicted in FIG. 1, the nucleic acid molecule referred to as 176-E10trc has the best binding affinity to MCP-1 (as aptamer in the pull-assay with a $K_D$ of 5 nM as well as Spiegelmer with an $IC_{50}$ of 4-5 nM in in vitro cell culture $Ca^{++}$-release assay) and therefore may constitute the optimal sequence and the optimal combination of sequence elements B1A, B2, B3, B4, B5, B6 and B1B.

Type 1B MCP-1 Binding Nucleic Acids (FIG. 2)

As depicted in FIG. 2, all sequences of Type 1B comprise several sequences stretches or boxes whereby boxes B1A and B1B are the 5'- and 3' terminal stretches that can hybridize with each other and boxes B2, B3, B4, B5 and box B6 are flanked by box B1A and box B1B. However, such hybridization is not necessarily given in the molecule as actually present under physiological conditions.

The nucleic acids were characterized on the aptamer level using direct and competitive pull-down assays with biotinylated human D-MCP-1 in order to rank them with respect to their binding behaviour (Example 4). Selected sequences were synthesized as Spiegelmer (Example 3) and were tested using the natural configuration of MCP-1 (L-MCP) in an in vitro cell culture $Ca^{++}$-release assay (Example 5).

The sequences of the defined boxes may be different between the MCP-1 binding nucleic acids of Type 1B which influences the binding affinity to MCP-1. Based on binding analysis of the different MCP-1 binding nucleic acids summarized as Type 1B MCP-1 binding nucleic acids, the boxes B1A, B2, B3, B4, B5, B6 and B1B and their nucleotide sequences as described in the following are individually and more preferably in their entirety essential for binding to MCP-1:

- boxes B1A and B1B that can hybridize with each other;
  - where B1A is AGYRUG, preferably AGCGUG;
  - and where B1B is CAYRCU, preferably CACGCU;
- box B2, which is CCAGCU or CCAGY, preferably CCAGU;
- box B3, which is GUG;
- box B4, which is AUG;

box B5, which is GGGGGGCGCGACC (SEQ ID NO: 294);

box B6, which is CAUUUUA or CAUUUA, preferably CAUUUUA;

As depicted in FIG. 2, the nucleic acid referred to as 176-C9trc has the best binding affinity to MCP-1 (as aptamer in the pull-down assay with a $K_D$ of 5 nM as well as Spiegelmer with an $IC_{50}$ of 4-5 nM in in vitro cell culture $Ca^{++}$-release assay) and therefore may constitute the optimal sequence and the optimal combination of sequence elements B1A, B2, B3, B4, B5, B6 and B1B.

Type 2 MCP-1 Binding Nucleic Acids (FIG. 3)

As depicted in FIG. 3, all sequences of Type 2 comprise several sequences stretches or boxes whereby boxes B1A and B1B are the 5'- and 3' terminal stretches that can hybridize with each other and box B2 is the central sequence element. However, such hybridization is not necessarily given in the molecule as actually present under physiological conditions.

The nucleic acids were characterized on the aptamer level using direct and competitive pull-down assays with biotinylated human D-MCP-1 in order to rank them with respect to their binding behaviour (Example 4). Selected sequences were synthesized as Spiegelmer (Example 3) and were tested using the natural configuration of MCP-1 (L-MCP) in in vitro cell culture $Ca^{++}$-release (Example 5) or in vitro chemotaxis assays (Example 6).

The sequences of the defined boxes may be different between the MCP-1 binding nucleic acids of Type 3 which influences the binding affinity to MCP-1. Based on binding analysis of the different MCP-1 binding nucleic acids summarized as Type 2 MCP-1 binding nucleic acids, the boxes B1A, B2, and B1B and their nucleotide sequences as described in the following are individually and more preferably in their entirety essential for binding to MCP-1:

boxes B1A and B1B, 5'- and 3' terminal stretches that can hybridize with each other; where B1A is ACGCA and B1B is UGCGU, or B1A is CGCA and B1B is UGCG, or B1A is GCA and B1B is UGCG or UGC; preferably B1A is GCA and B1B is UGCG;

box B2, CSUCCCUCACCGGUGCAAGUGAAGCCGYGGCUC (SEQ ID NO: 287), preferably C GUCCCUCACCGGUGCAAGUGAAGCCGUGGCUC (SEQ ID NO: 288)

As depicted in FIG. 3, the nucleic acid referred to as 180-D1-002 as well as the derivatives of 180-D1-002 like 180-D1-011, 180-D1-012, 180-D1-035, and 180-D1-036 (=NOX-E36) have the best binding affinity to MCP-1 as aptamer in the pull-down or competitive pull-down assay with an $K_D$ of <1 nM and therefore may constitute the optimal sequence and the optimal combination of sequence elements B1A, B2, and B1B.

For nucleic acid molecule D-NOX-E36 (D-180-D1-036; SEQ. ID No. 159), a dissociation constant ($K_D$) of 890±65 pM at room temperature (RT) and of 146±13 pM at 37° C. was determined (Example 4; FIG. 9). The respective Spiegelmer NOX-E36 (180-D1-036; SEQ. ID No. 37) exhibited an inhibitory concentration ($IC_{50}$) of 3-4 nM in an in vitro $Ca^{++}$-release assay (Example 5; FIG. 12) and of ca. 0.5 nM in an in vitro chemotaxis assay (Example 6; FIG. 15). For the PEGylated derivatives of NOX-E36, NOX-E36-3'PEG and NOX-E36-5'PEG, $IC_{50}$s of ca. 3 nM were determined in the $Ca^{++}$-release assay (Example 5, FIG. 25 and FIG. 27A) and <1 nM in the chemotaxis assay (Example 6; FIG. 26 and FIG. 27B).

Type 3 MCP-1 Binding Nucleic Acids (FIGS. 4+5)

As depicted in FIGS. 4 and 5, all sequences of Type 3 comprise several sequence stretches or boxes whereby three pairs of boxes are characteristic for Type 3 MCP-1 binding nucleic acids. Both boxes B1A and B1B as well as boxes B2A and B2B as well as boxes B5A and B5B bear the ability to hybridize with each other. However, such hybridization is not necessarily given in the molecule as actually present under physiological conditions. Between these potentially hybridized sequence elements, non-hybridizing nucleotides are located, defined as box B3, box B4 and box B6.

The nucleic acids were characterized on the aptamer level using direct and competitive pull-down assays with biotinylated human D-MCP-1 in order to rank them with respect to their binding behavior (Example 4). Selected sequences were synthesized as Spiegelmer (Example 3) and were tested using the natural configuration of MCP-1 (L-MCP) in in vitro chemotaxis assays (Example 6) or via Biacore measurements (Example 7).

The sequences of the defined boxes may be different between the MCP-1 binding nucleic acids of Type 3 which influences the binding affinity to MCP-1. Based on binding analysis of the different MCP-1 binding nucleic acids summarized as Type 3 MCP-1 binding nucleic acids, the boxes B1A, B2A, B3, B2B, B4, B5A, B6, B5B, B1B and their nucleotide sequences as described in the following are individually and more preferably in their entirety essential for binding to MCP-1:

boxes B1A and B1B 5'- and 3' terminal stretches that can hybridize with each other; where B1A is GURCUGC and B1B is GCAGCAC preferably B1A is GUGCUGC and B1B is GCAGCAC or B1A is GKSYGC and B1B is GCRSMC preferably B1A is GUGCGC and B1B is GCGCAC;

or B1A is KBBSC and B1B is GSVVM preferably B1A is KKSSC and B1B is GSSMM;

or B1A is BNGC and B1B is GCNV; preferably B1A is SNGC and B1B is GCNS; most preferably B1A is GGGC and B1B is GCCC;

boxes B2A and B2B, stretches that can hybridize with each other; where B2A is GKMGU and B2B is ACKMC; preferably B2A is GUAGU and B2B is ACUAC;

box B3, which is KRRAR, preferably UAAAA or GAGAA;

box B4, which is CURYGA or CUWAUGA or CWRMGACW or UGCCAGUG, preferably CAGCGACU or CAACGACU;

B5A and B5B, stretches that can hybridize with each other; where B5A is GGY and B5B is GCYR whereas GCY can hybridize with the nucleotides of B5A; or B5A is CWGC and B5B is GCWG; preferably B5A is GGC and B5B is GCCG;

box B6, which is: YAGA or CKAAU or CCUUUAU preferably UAGA.

As depicted in FIGS. 4 and 5, the nucleic acid referred to as 178-D5 and its derivative 178-D5-030 as well as 181-A2 with its derivatives 181-A2-002, 181-A2-004, 181-A2-005, 181-A2-006, 181-A2-007, 181-A2-017, 181-A2-018, 181-A2-019, 181-A2-020, 181-A2-021, and 181-A2-023 have the best binding affinity to MCP-1. 178-D5 and 178-D5-030 were evaluated as aptamers in direct or competitive pull-down assays (Example 4) with an $K_D$ of approx. 500 pM. In the same experimental set-up, 181-A2 was determined with an $K_D$ of approx. 100 pM. By Biacore analysis (Example 7), the $K_D$ of 181-A2 and its derivatives towards MCP-1 was determined to be 200-300 pM. In $Ca^{++}$ release and chemotaxis assays with cultured cells (Example 5 and 6, respectively), for both 178-D5 and 181-A2, an $IC_{50}$ of approx. 500 pM was measured. Therefore, 178-D5 as well as 181-A2 and their derivatives may constitute the optimal sequence and the optimal combination of sequence elements B1A, B2A, B3, B2B, B4, B5A, B6, B5B and B1B Type 4 MCP-1 Binding Nucleic Acids (FIG. 6)

As depicted in FIG. 6, all sequences of Type 4 comprise several sequences, stretches or boxes whereby boxes B1A and B1B are the 5'- and 3' terminal stretches that can hybridize with each other and box B2 is the central sequence element.

The nucleic acids were characterized on the aptamer level using direct pull-down assays with biotinylated human D-MCP-1 in order to rank them with respect to their binding behavior (Example 4). Selected sequences were synthesized as Spiegelmer (Example 3) and were tested using the natural configuration of MCP-1 (L-MCP) in an in vitro cell culture $Ca^{++}$-release (Example 5) and/or chemotaxis assay (Example 6).

The sequences of the defined boxes may differ among the MCP-1 binding nucleic acids of Type 4 which influences the binding affinity to MCP-1. Based on binding analysis of the different MCP-1 binding nucleic acids summarized as Type 4 MCP-1 binding nucleic acids, the boxes B1A, B2, and B1B and their nucleotide sequences as described in the following are individually and more preferably in their entirety essential for binding to MCP-1:

boxes B1A and B1B, 5'- and 3' terminal stretches that can hybridize with each other;

where B1A is AGCGUGDU and B1B is GNCASGCU; or B1A is GCGCGAG and B1B is CUCGCGUC; or B1A is CSKSUU and B1B is GRSMSG; or B1A is GUGUU and B1B is GRCAC; ; or B1A is UGUU and B1B is GGCA; preferably B1A is CSKSUU and B1B is GRSMSG; ; mostly preferred B1A is CCGCUU and B1B is GGGCGG; ; and box B2, which is AGNDRDGBKGGURGYARGUAAAG (SEQ ID NO: 289) or AGGUGGGUGGUAGUAAGUAAAG (SEQ ID N: 290) or CAGGUGGGUGGUAGAAUGUAAAGA (SEQ ID NO: 291), preferably AGGUGGGUGGUAGUAAGUAAAG (SEQ ID NO: 290)

As depicted in FIG. 6, the nucleic acid referred to as 174-D4-004 and 166-A4-002 have the best binding affinity to MCP-1 (as Spiegelmer with an $IC_{50}$ of 2-5 nM in in vitro cell culture Ca++ release assay) and may, therefore, constitute the optimal sequence and the optimal combination of sequence elements B1A, B2, and B1B.

Additionally, 29 other MCP-1 binding nucleic acids were identified which cannot be described by a combination of nucleotide sequence elements as has been shown for Types 1-4 of MCP-1 binding nucleic acids. These sequences are listed in FIG. 7.

It is to be understood that any of the sequences shown in FIGS. 1 through 7 are nucleic acids according to the present invention, including those truncated forms thereof but also including those extended forms thereof under the proviso, however, that the thus truncated and extended, respectively, nucleic acid molecules are still capable of binding to the target.

EXAMPLE 2

Nucleic Acids that Bind Murine MCP-1

Using biotinylated murine D-MCP-1 as a target, several nucleic acid molecules binding thereto could be generated. The result of a sequence analysis of these nucleic acid molecules can be taken from FIG. 8.

The nucleic acids were characterized on the aptamer level using a pull-down assay using biotinylated murine D-MCP-1 in order to in order to rank them with respect to their binding behavior (Example 4). Selected sequences were synthesized as Spiegelmer (Example 3) and were tested using the natural configuration of MCP-1 (L-MCP) in an in vitro cell culture $Ca^{++}$-release (Example 5) and chemotaxis assay (Example 6).

As depicted in FIG. 8, D-188-A3-001 and D-189-G7-001 and their derivatives bind D-MCP-1 with subnanomolar $K_D$ in the pull-down assay (FIG. 8).

For D-mNOX-E36 (=D-188-A3-007; SEQ. ID No. 244), a dissociation constant ($K_D$) of 0.1-0.2 nM at 37° C. was determined (Example 4; FIG. 10). The respective Spiegelmer mNOX-E36 (188-A3-007; SEQ. ID No. 122) exhibited an inhibitory concentration ($IC_{50}$) of approx. 12 nM in an in vitro $Ca^{++}$-release assay (Example 5; FIG. 13) and of approx. 7 nM in an in vitro chemotaxis assay (Example 6; FIG. 16). For the PEGylated derivative of mNOX-E36, mNOX-E36-3'PEG (SEQ. ID No. 254), $IC_{50}$'s of approx. 8 nM were determined in the $Ca^{++}$-release assay (Example 5, FIG. 29) and approx. 3 nM in the chemotaxis assay (Example 6; FIG. 31).

It is to be understood that any of the sequences shown in FIGS. 1 through 7 are nucleic acids according to the present invention, including those truncated forms thereof but also including those extended forms thereof under the proviso, however, that the thus truncated and extended, respectively, nucleic acid molecules are still capable of binding to the target.

EXAMPLE 3

Synthesis and Derivatization of Aptamers and Spiegelmers

Small Scale Synthesis

Aptamers and Spiegelmers were produced by solid-phase synthesis with an ABI 394 synthesizer (Applied Biosystems, Foster City, Calif., USA) using 2'TBDMS RNA phosphoramidite chemistry (M. J. Damha, K. K. Ogilvie, Methods in Molecular Biology, Vol. 20 Protocols for oligonucleotides and analogs, ed. S. Agrawal, p. 81-114, Humana Press Inc. 1993). rA(N-Bz)-, rC(Ac)-, rG(N-ibu)-, and rU-phosphoramidites in the D- and L-configuration were purchased from ChemGenes, Wilmington, Mass. Aptamers and Spiegelmers were purified by gel electrophoresis.

Large Scale Synthesis Plus Modification

Spiegelmer NOX-E36 was produced by solid-phase synthesis with an ÄktaPilot100 synthesizer (Amersham Biosciences; General Electric Healthcare, Freiburg) using 2'TBDMS RNA phosphoramidite chemistry (M. J. Damha, K. K. Ogilvie, Methods in Molecular Biology, Vol. 20 Protocols for oligonucleotides and analogs, ed. S. Agrawal, p. 81-114, Humana Press Inc. 1993). L-rA(N-Bz)-, L-rC(Ac)-, L-rG(N-ibu)-, and L-rU-phosphoramidites were purchased from ChemGenes, Wilmington, Mass. The 5'-amino-modifier was purchased from American International Chemicals Inc. (Framingham, Mass., USA). Synthesis of the unmodified Spiegelmer was started on L-riboG modified CPG pore size 1000 Å (Link Technology, Glasgow, UK); for the 3'-$NH_2$-modified Spiegelmer, 3'-Aminomodifier-CPG, 1000 Å (ChemGenes, Wilmington, Mass.) was used. For coupling (15 min per cycle), 0.3 M benzylthiotetrazole (CMS-Chemicals, Abingdon, UK) in acetonitrile, and 3.5 equivalents of the respective 0.1 M phosphoramidite solution in acetonitrile was used. An oxidation-capping cycle was used. Further standard solvents and reagents for oligonucleotide synthesis were purchased from Biosolve (Valkenswaard, NL). The Spiegelmer was synthesized DMT-ON; after deprotection, it was purified via preparative RP-HPLC (Wincott F. et al. (1995) *Nucleic Acids Res* 23:2677) using Source15RPC medium (Amersham). The 5'DMT-group was removed with 80% acetic acid (30 min at RT). Subsequently, aqueous 2 M NaOAc solution was added and the Spiegelmer was desalted by tangential-flow filtration using a 5 K regenerated cellulose membrane (Millipore, Bedford, Mass.).

PEGylation of NOX-E36

In order to prolong the Spiegelmer's plasma residence time in vivo, Spiegelmer NOX-E36 was covalently coupled to a 40 kDa polyethylene glycol (PEG) moiety at the 3'-end or 5'-end.

3'-PEGylation of NOX-E36

For PEGylation (for technical details of the method for PEGylation see European patent application EP 1 306 382), the purified 3'-amino modified Spiegelmer was dissolved in a mixture of $H_2O$ (2.5 ml), DMF (5 ml), and buffer A (5 ml; prepared by mixing citric acid.$H_2O$ [7 g], boric acid [3.54 g], phosphoric acid [2.26 ml], and 1 M NaOH [343 ml] and adding $H_2O$ to a final volume of 1 l; pH=8.4 was adjusted with 1 M HCl).

The pH of the Spiegelmer solution was brought to 8.4 with 1 M NaOH. Then, 40 kDa PEG-NHS ester (Nektar Therapeutics, Huntsville, Ala.) was added at 37° C. every 30 min in four portions of 0.6 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), 4 ml buffer A, and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C, 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC. The PEGylated Spiegelmer was desalted by tangential-flow filtration (5 K regenerated cellulose membrane, Millipore, Bedford Mass.).

5'-PEGvlation of NOX-E36

For PEGylation (for technical details of the method for PEGylation see European patent application EP 1 306 382), the purified 5'-amino modified Spiegelmer was dissolved in a mixture of $H_2O$ (2.5 ml), DMF (5 ml), and buffer A (5 ml; prepared by mixing citric acid.$H_2O$ [7 g], boric acid [3.54 g], phosphoric acid [2.26 ml], and 1 M NaOH [343 ml] and adding water to a final volume of 1 l; pH=8.4 was adjusted with 1 M HCl).

The pH of the Spiegelmer solution was brought to 8.4 with 1 M NaOH. Then, 40 kDa PEG-NHS ester (Nektar Therapeutics, Huntsville, Ala.) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C, 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC. The PEGylated Spiegelmer was desalted by tangential-flow filtration (5 K regenerated cellulose membrane, Millipore, Bedford Mass.).

EXAMPLE 4

Determination of Binding Constants (Pull-Down Assay)

Direct Pull-Down Assay

The affinity of aptamers to D-MCP-1 was measured in a pull down assay format at 20 or 37° C., respectively. Aptamers were 5'-phosphate labeled by T4 polynucleotide kinase (Invitrogen, Karlsruhe, Germany) using [γ-32 P]-labeled ATP (Hartmann Analytic, Braunschweig, Germany). The specific radioactivity of labeled aptamers was 200,000-800,000 cpm/pmol. Aptamers were incubated after de- and renaturation at 20 pM concentration at 37° C. in selection buffer (20 mM Tris-HCl pH 7.4; 137 mM NaCl; 5 mM KCl; 1 mM $MgCl_2$; 1 mM $CaCl_2$; 0.1% [w/vol] Tween-20) together with varying amounts of biotinylated D-MCP-1 for 4-12 hours in order to reach equilibrium at low concentrations. Selection buffer was supplemented with 10 μg/ml human serum albumin (Sigma-Aldrich, Steinheim, Germany), and 10 μg/ml yeast RNA (Ambion, Austin, USA) in order to prevent adsorption of binding partners with surfaces of used plasticware or the immobilization matrix. The concentration range of biotinylated D-MCP-1 was set from 8 pM to 100 nM; total reaction volume was 1 ml. Peptide and peptide-aptamer complexes were immobilized on 1.5 μl Streptavidin Ultralink Plus particles (Pierce Biotechnology, Rockford, USA) which had been preequilibrated with selection buffer and resuspended in a total volume of 6 μl. Particles were kept in suspension for 30 min at the respective temperature in a thermonmixer. Immobilized radioactivity was quantified in a scintillation counter after detaching the supernatant and appropriate washing. The percentage of binding was plotted against the concentration of biotinylated D-MCP-1 and dissociation constants were obtained by using software algorithms (GRAFIT; Erithacus Software; Surrey U.K.) assuming a 1:1 stoichiometry.

Competitive Pull-Down Assay

In order to compare different D-MCP-1 binding aptamers, a competitive ranking assay was performed. For this purpose the most affine aptamer available was radioactively labeled (see above) and served as reference. After de- and renaturation it was incubated at 37° C. with biotinylated D-MCP-1 in 1 ml selection buffer at conditions that resulted in around 5-10% binding to the peptide after immobilization and washing on NeutrAvidin agarose or Streptavidin Ultralink Plus (both from Pierce) without competition. An excess of de- and renatured non-labeled D-RNA aptamer variants was added to different concentrations (e.g. 2, 10, and 50 nM) with the labeled reference aptamer to parallel binding reactions. The aptamers to be tested competed with the reference aptamer for target binding, thus decreasing the binding signal in dependence of their binding characteristics. The aptamer that was found most active in this assay could then serve as a new reference for comparative analysis of further aptamer variants.

EXAMPLE 5

Determination of Inhibitory Concentration in a $Ca^{++}$-Release Assay

THP-1-cells (DSMZ, Braunschweig) were cultivated overnight at a cell density of $0.3\times10^6$/ml at 37° C. and 5% $CO_2$ in RPMI 1640 medium with GlutaMAX (Invitrogen) which contained in addition 10% fetal calf serum, 50 units/ml penicillin, 50 μg/ml streptomycin and 50 μM β-mercaptoethanol.

The Spiegelmers were incubated together with recombinant human MCP-1 (Bachem) in Hanks balanced salt solution (HBSS), containing 1 mg/ml bovine serum albumin, 5 mM probenecid and 20 mM HEPES (HBSS+) for 15 to 60 min at 37° C. in a 0.2 ml low profile 96-tube plate ("stimulation solution").

For loading with the calcium indicator dye, cells were centrifuged at 300×g for 5 min, resuspended in 4 ml indicator dye solution (10 μM fluo-4 [Molecular Probes], 0.08% pluronic 127 [Molecular Probes] in HBSS+) and incubated for 60 min at 37° C. Thereafter, 11 ml HBSS+ were added and the cells were centrifuged as above, washed once with 15 ml HBSS+ and then resuspended in HBSS+ to give a cell density of $1.1\times10^6$/ml. 90 μl of this cell suspension were added to each well of a black 96-well plate.

Measurement of fluorescence signals was done at an excitation wavelength of 485 nm and an emission wavelength of 520 nm in a Fluostar Optima multidetection plate reader (BMG). For parallel measurement of several samples, wells of one (perpendicular) row of a 96-well plate were recorded together. First three readings with a time lag of 4 sec were done for determination of the base line. Then the recording was interrupted and the plate was moved from the instrument. Using a multi-channel pipette, 10 μl of the stimulation solution was added to the wells, then the plate was moved into the instrument again and the measurement was continued. In total, 20 recordings with time intervals of 4 seconds were performed.

For each well the difference between maximal fluorescence and base line value was determined and plotted against MCP-1 concentration or, in the experiments on the inhibition of calcium release by Spiegelmers, against concentration of Spiegelmer.

Determination of Half-Maximal Effective Concentration ($EC_{50}$) for Human MCP-1

After stimulation of THP-1 cells with various hMCP-1 concentrations and plotting the difference between the maximal and the baseline signals, a dose-response curve for human MCP-1 was obtained, indicating a half effective concentration ($EC_{50}$) of about 2-4 nM (FIG. 11). This concentration was used for the further experiments on inhibition of $Ca^{++}$-release by Spiegelmers.

Determination of Half-Maximal Effective Concentration ($EC_{50}$) for Murine MCP-1

After stimulation of THP-1 cells with various mMCP-1 concentrations and plotting the difference between the maximal and the baseline signals, a dose-response curve for murine MCP-1 was obtained, indicating a half effective concentration ($EC_{50}$) of about 5 nM (FIG. 28). This concentration was used for the further experiments on inhibition of $Ca^{++}$-release by Spiegelmers.

EXAMPLE 6

Determination of Inhibitory Concentration in a Chemotaxis Assay

THP-1 cells grown as described above were centrifuged, washed once in HBH (HBSS, containing 1 mg/ml bovine serum albumin and 20 mM HEPES) and resuspended at $3\times10^6$ cells/ml. 100 μl of this suspension were added to Transwell inserts with 5 μm pores (Corning, #3421). In the lower compartments MCP-1 was preincubated together with Spiegelmers in various concentrations in 600 μl HBH at 37° C. for 20 to 30 min prior to addition of cells. Cells were allowed to migrate at 37° C. for 3 hours. Thereafter the inserts were removed and 60 μl of 440 μM resazurin (Sigma) in phosphate buffered saline was added to the lower compartments. After incubation at 37° C. for 2.5 hours, fluorescence was measured at an excitation wavelength of 544 nm and an emission wavelength of 590 nm in a Fluostar Optima multidetection plate reader (BMG).

Determination of Half-Maximal Effective Concentration ($EC_{50}$) for Human MCP-1

After 3 hours migration of THP-1 cells towards various human MCP-1 concentrations, a dose-response curve for human MCP-1 was obtained, indicating a maximal effective concentration of about 1 nM and reduced activation at higher concentrations (FIG. 14). For the further experiments on inhibition of chemotaxis by Spiegelmers a MCP-1 concentration of 0.5 nM was used.

Determination of Half-Maximal Effective Concentration ($EC_{50}$) for Murine MCP-1

After 3 hours migration of THP-1 cells towards various murine MCP-1 concentrations, a dose-response curve for murine MCP-1 was obtained, indicating a maximal effective concentration of about 1-3 nM and reduced activation at higher concentrations (FIG. 30). For the further experiments on inhibition of chemotaxis by Spiegelmers a murine MCP-1 concentration of 0.5 nM was used.

EXAMPLE 7

Binding Analysis by Surface Plasmon Resonance Measurement 7.1 Specificity Assessment of NOX-E36, 181-A2-018 and mNOX-E36

The Biacore 2000 instrument (Biacore AB, Uppsala, Sweden) was used to analyze binding of nucleic acids to human MCP-1 and related proteins. When coupling was to be achieved via amine groups, the proteins were dialyzed against water for 1-2 h (Millipore VSWP mixed cellulose esters; pore size, 0.025 μM) to remove interfering amines. PioneerF1 or CM4 sensor chips (Biacore AB) were activated before protein coupling by a 35-μl injection of a 1:1 dilution of 0.4 M NHS and 0.1 M EDC at a flow of 5 μl/min. Chemokine was then injected in concentrations of 0.1-1.5 μg/ml at a flow of 2 μl/min until the instrument's response was in the range of 1000-2000 RU (relative units). Unreacted NHS esters were deactivated by injection of 35 μl ethanolamine hydrochloride solution (pH 8.5) at a flow of 5 μl/min. The sensor chip was primed twice with binding buffer and equilibrated at 10 μl/min for 1-2 hours until the baseline appeared stable. For all proteins, kinetic parameters and dissociation constants were evaluated by a series of Spiegelmer injections at concentrations of 1000, 500, 250, 125, 62.5, 31.25, and 0 nM in selection buffer (Tris-HCl, 20 mM; NaCl, 137 mM; KCl, 5 mM; $CaCl_2$, 1 mM; $MgCl_2$, 1 mM; Tween20, 0.1% [w/v]; pH 7.4). In all experiments, the analysis was performed at 37° C. using the Kinject command defining an association time of 180 and a dissociation time of 360 seconds at a flow of 10 μl/min. Data analysis and calculation of dissociation constants ($K_D$) was done with the BIAevaluation 3.0 software (BIACORE AB, Uppsala, Sweden) using the Langmuir 1:1 stoichiometric fitting algorithm.

7.1.1 NOX-E36 and 181-A2-018 (Human-MCP-1 Specific Nucleic Acids)

Only for human MCP-1 all sensorgrams are depicted (FIGS. 17 and 20, respectively); for the other proteins, only the sensorgram obtained with 125 nM Spiegelmer concentration is shown for sake of clarity (FIGS. 18/19 and 21/22).

Analysis of the NOX-E36•hMCP-1 interaction: recombinant human MCP-1 was immobilized on a PioneerF1 sensor chip following the manufacturer's recommendations (amine coupling procedure) until an instrument response of 1381 RU (relative units) was established. The determined dissociation constant ($K_D$) for NOX-E36 binding to human MCP-1 was ca. 890 pM (FIG. 17).

Analysis of the 181-A2-018•hMCP-1 interaction: recombinant human MCP-1 was immobilized on a CM4 sensor chip following the manufacturer's recommendations (amine coupling procedure) until an instrument response of 3111 RU (relative units) was established. The determined dissociation constant ($K_D$) for 181-A2-018 binding to human MCP-1 was ca. 370 pM (FIG. 20).

To determine the specificity of NOX-E36 and 181-A2-018, various human MCP-1 family proteins as well as human eotaxin were immobilized on a PioneerF1 and a CM4 sensor chip (hMCP-1, 1754 RU; hMCP-2, 1558 RU; hMCP-3, 1290 RU; eotaxin, 1523 RU). Kinetic analysis revealed that NOX-E36 binds to eotaxin and hMCP-2 with dissociation constants ($K_D$) of 5-10 nM; hMCP-3 was not recognized (FIGS. 18 and 24A). 181-A2-018, in contrast, binds eotaxin, hMCP-2 and hMCP-3, but with slightly lower affinity (10-20 nM; FIGS. 21 and 24A).

Interspecies cross-reactivity of NOX-E36 and 181-A2-018 was assessed using amino-coupling immobilized MCP-1 from human (1460 RU), monkey (1218 RU), pig (1428 RU), dog (1224 RU), rabbit (1244 RU), rat (1267 RU), and mouse (1361 RU) on a PioneerF1 and a CM4 sensor chip. Kinetic analysis revealed that NOX-E36 binds to human, monkey, porcine, and canine MCP-1 with comparable dissociation constants ($K_D$) of 0.89-1.2 nM whereas MCP-1 from mouse, rat and rabbit were not recognized (FIGS. 19 and 24A). 181-A2-018 binds to human and monkey MCP-1 with comparable dissociation constants ($K_D$) of 0.5-0.6 nM, whereas porcine, rabbit and canine MCP-1 are bound with much lower affinity. Rat and mouse MCP-1 were not recognized by NOX-A2-018 (FIGS. 22 and 24A).

Sequences as well as degree of homology in percent identical amino acids between the MCP-1 protein from different species and closely related human proteins are depicted in FIG. 23; calculated KD values for NOX-E36 and 181-A2-018 are displayed in tabular format in FIG. 24A.

7.1.2 mNOX-E36 (Murine MCP-1 Specific Nucleic Acid)

To analyze the binding behaviour of mNOX-E36, 3759 RU of synthetic biotinylated murine D-MCP-1 (flow cell 3) and 3326 RU of biotinylated human D-MCP-1 (flow cell 4) were immobilized on a Streptavidin conjugated sensor chip (Biacore AB, Freiburg, Germany), respectively. mNOX-E36 aptamer (D-RNA) solutions of 500, 250, 125, 62.5, 31.25, and 0 nM were injected using the Kinject command defining an association time of 180 sec and a dissociation time of 360 sec. Flow cell 1 was used as buffer and dextran matrix control (Biacore SA-Chip surface) whereas on flow cell 2, an unspecific D-peptide was immobilized to determine unspecific binding of the aptamer. FIG. 32 shows a sensorgram of the D-NOX-E36 kinetic for binding to murine D-MCP-1 with a calculated dissociation constant ($K_D$) of 200-300 pM. mNOX-E36 does not bind human D-MCP-1 (FIG. 33); for sake of clarity, only the sensorgram obtained with 125 nM Spiegelmer is shown.

7.2 Selectivity Assessment of NOX-E36

Selectivity of NOX-E36 was assessed by surface plasmon resonance analysis by immobilizing 5'biotinylated NOX-E36 on a Streptavidin (SA-Chip). 352 RU of NOX-E36 on flow cell (FC) 1 and equal amount of 5'-terminal biotinylated non-functional control Spiegelmer (POC) on FC 2 were immobilized by streptavidin/biotin binding. FC3 was used as surface control to determine unspecific binding to the dextran-SA sensor surface.

100 nM of a panel of human chemokines from all four subgroups (CC, CXC, $CX_3C$, and XC) were injected for 360 s and complexes were allowed to dissociate for 360 s at a flow of 10 μl/min and 37° C. Response units after association (Resp. 1; degree of interaction) and after dissociation (Resp. 2, affinity of interaction) were plotted. After each injection the chip surface was regenerated with a 240 s of 1 M sodium chloride with 0.1% Tween; immobilized Spiegelmers were subsequently allowed to refold for 2 minutes at physiological conditions (running buffer). Injection of each chemokine was repeated 3 times. CXCL1, CXCL2, CXCL6 and CXCL9 showed unspecific binding to ribonucleic acids and chip dextran surface. Specific high-affinity binding to immobilized NOX-E36 could only be detected for CCL2/MCP-1, CCL8/MCP-2, CCL11/eotaxin, CCL3/MIP1α, and CXCL7/NAP-2 (FIG. 24B). The finding that MCP-2 and eotaxin are bound by NOX-E36 is not surprising due to the relatively high homology between these chemokines and MCP-1 of 62 and 70%, for the unexpected positives CCL3/MIP-1α and CXCL7/NAP-2, in vitro tests for functional inhibition have been performed or are currently being established, respectively.

Finally, the kinetic parameters of interaction between NOX-E36 and CCL2/MCP-1, CCL8/MCP-2, CCL11/eotaxin, CCL3/MIP1α, CXCL7/NAP-2, CCL7/MCP-3 and CCL13/MCP-4 were determined in the "inverted" system. Here, the chemokines were immobilized and free NOX-E36 was injected (for the detailed protocol, see 7.1). Kinetic data are summarized in FIG. 24C.

7.3 Assessment of Anti-MIP-1α Functionality In Vitro

Biacore measurements had shown cross reactivity of NOX-E36 with MIP-1α. By employing a functional, cell culture-based in vitro assay it should be checked if mere Biacore binding of NOX-E36 to MIP-1α also translates to functionality, e.g. antagonism.

To achieve this, chemotaxis experiments with THP-1 cells were performed that can be stimulated by MIP-1 α. THP-1 cells grown as described above were centrifuged, washed once in HBH (HBSS, containing 1 mg/ml bovine serum albumin and 20 mM HEPES) and resuspended at $3\times10^6$ cells/ml. 100 µl of this suspension were added to Transwell inserts with 5 µm pores (Corning, #3421), In the lower compartments MIP-1α was preincubated together with Spiegelmers in various concentrations in 600 µl HBH at 37° C. for 20 to 30 min prior to addition of cells. Cells were allowed to migrate at 37° C. for 3 hours. Thereafter the inserts were removed and 60 µl of 440 µM resazurin (Sigma) in phosphate buffered saline was added to the lower compartments. After incubation at 37° C. for 2.5 hours, fluorescence was measured at an excitation wavelength of 544 nm and an emission wavelength of 590 nm in a Fluostar Optima multidetection plate reader (BMG).

After 3 hours migration of THP-1 cells towards various human MIP-1α concentrations, a dose-response curve for human MIP-1α was obtained, indicating a half-maximal effective concentration of about 1 nM and reduced activation at higher concentrations (FIG. 24D). For the further experiments on inhibition of chemotaxis by Spiegelmers a MIP-1α concentration of 0.5 nM was used.

Experiments for determination of chemotaxis inhibition by NOX-E36 were performed with a stimulus of 0.5 nM MIP-1α. It could be clearly shown that NOX-E36 does not inhibit MIP-1α induced chemotaxis up to the highest tested concentration of 1 µM MIP-1α. As positive control, the respective experiment with MCP-1 as stimulus was performed in parallel (FIG. 24E).

EXAMPLE 8

Therapy of Lupus-Like Disease in MRL$^{lpr/lpr}$ Mice with Anti-mMCP-1 Spiegelmer Blocking proinflammatory mediators has become a successful approach for the treatment of chronic inflammation (Steinman 2004). In addition to TNF and interleukins, CC-chemokines are important candidates for specific antagonism because CC-chemokines mediate leukocyte recruitment from the intravascular space to sites of inflammation (Baggiolini 1998, Luster 2005). There is very strong evidence that MCP-1 (=CCL2) and its respective chemokine receptor CCR2 play a crucial role in autoimmune tissue injury such as the clinical manifestations of systemic lupus erythematosus (Gerard & Rollins 2001). For example, MRL$^{lpr/lpr}$ mice deficient either for the Ccl2 or the Ccr2 gene are protected from lupus-like autoimmunity (Perez de Lema 2005, Tesch 1999). Hence, the CCL2/CCR2 axis may represent a promising therapeutic target, e.g. for lupus nephritis. In fact, delayed gene therapy or transfer of transfected cells, both resulting in in situ production of an $NH_2$-truncated MCP-1, markedly reduced autoimmune tissue injury in MRL$^{lpr/lpr}$ mice. However, such experimental approaches cannot be used in humans because of irrepressible antagonist production and tumor formation (Hasegawa 2003, Shimizu 2004). Therefore, it remains necessary to develop novel CCL2 antagonists with favorable pharmacokinetic profiles in vivo. In this example it is shown that blockade of murine CCL2 with the anti-mCCL2 Spiegelmer mNOX-E36 or mNOX-E36-3'PEG would be suitable for the treatment of lupus nephritis and other disease manifestations of systemic lupus erythematosus. Late onset of mCCL2 Spiegelmer therapy effectively improves lupus nephritis, autoimmune peribronchitis, and lupus-like skin disease in MRL$^{lpr/lpr}$ mice, independent of any previous problem associated with therapeutic CCL2/CCR2 blockade.

Animals and Experimental Protocol

Ten week old female MRL$^{lpr/lpr}$mice were obtained from Harlan Winkelmann (Borchen, Germany) and kept under normal housing conditions in a 12 hour light and dark cycle. Water and standard chow (Ssniff, Soest, Germany) were available ad libitum. At age 14 weeks, groups of 12 mice received subcutaneous injections of Spiegelmers in 5% glucose (injection volume, 4 ml/kg) three times per week as follows: mNOX-E36, 1.5 µmol/kg; mNOX-E36-3'PEG, 0.9 µmol/kg; nonfunctional control Spiegelmer PoC (5'-UAAG-GAAACUCGGUCUGAUGCGGU AGCGCUGUGCA-GAGCU-3' (SEQ ID NO: 279)), 1.9 µmol/kg; PoC-PEG, 0.9 µmol/kg; vehicle (5% glucose). The plasma levels of mNOX-E36 and mNOX-E36-3'PEG were determined from blood samples taken weekly from the retroorbital sinus 3 or 24 hours after injection, respectively. Spiegelmer levels in plasma samples were determined by a modification of the sandwich hybridization method as described in Example 8. Mice were sacrificed by cervical dislocation at the end of week 24 of age.

Evaluation of Systemic Lupus

Skin lesions were recorded by a semiquantitative score (Schwarting 2005). The weight ratio of spleen and the bulk of mesenteric lymph nodes to total body weight were calculated as markers of the lupus-associated lymphoproliferative syndrome. Blood and urine samples were collected from each animal at the end of the study period by bleeding from the retro-orbital venous plexus under general anesthesia with inhaled ether. Blood and urine samples were collected from each animal at the end of the study and urine albumin/creatinine ratio and serum dsDNA autoantibody IgG isotype titers were determined as previously described (Pawar 2006). Glomerular filtration rate (GFR) was determined at 24 weeks by clearance kinetics of plasma FITC-inulin (Sigma-Aldrich, Steinheim, Germany) 5, 10, 15, 20, 35, 60, and 90 minutes after a single bolus injection (Qi 2004). Fluorescence was determined with 485 nm excitation and read at 535 nm emission. GFR was calculated based on a two-compartment model using a non-linear regression curve-fitting software (GraphPad Prism, GraphPad Software Inc., San Diego, Calif.). Serum cytokine levels were determined using commercial ELISA kits for IL-6, IL-12p40 (OptEiA, BD Pharmingen), and IFN-α (PBL Biomedical Labs, USA). From all mice, kidneys and lungs were fixed in 10% buffered formalin, processed, and embedded in paraffin. 5-µm sections for silver and periodic acid-Schiff stains were prepared following routine protocols (Anders 2002). The severity of the renal lesions was graded using the indices for activity and chronicity as described for human lupus nephritis (Austin 1984), and morphometry of renal interstitial injury was conducted as previously described (Anders 2002). The severity of the peribronchial inflammation was graded semiquantitatively from 0-4. For immunostaining, sections of formalin-fixed and paraffin-embedded tissues were dewaxed and rehydrated. Endogenous peroxidase was blocked by 3% hydrogen peroxide and antigen retrieval was performed in Antigen Retrieval Solution (Vector, Burlingame, Calif.) in an autoclave oven. Biotin was blocked using the Avidin/Biotin blocking Kit (Vector). Slides were incubated with the primary antibodies for one hour, followed by biotinylated secondary antibodies (anti-rat IgG, Vector), and the ABC reagent (Vector). Slides were washed in phosphate buffered saline between the incubation steps. 3'3'Diaminobenzidine (DAB, Sigma, Taufkirchen, Germany) with metal enhancement was used as detection system, resulting in a black colour product. Methyl green was used as counterstain, slides were dehydrated and mounted in Histomount (Zymed Laboratories, San Francisco, Calif.). The following primary antibodies were used: rat anti-Mac2 (macrophages, Cederlane, Ontario, Canada, 1:50), anti-mouse CD3 (1:100, clone 500A2, BD), anti-mouse $IgG_1$ (1:100, M32015, Caltag Laboratories, Burlingame, Calif., USA), anti-mouse $IgG_{2a}$ (1:100, M32215, Caltag), anti-mouse C3 (1:200, GAM/C3c/FITC, Nordic Immunological Laboratories, Tilburg, Netherlands). Negative controls included incubation with a respective isotype antibody. For quantitative analysis glomerular cells were counted in 15 cortical glomeruli per section. Glomerular Ig and C3c deposits were scored from 0-3 on 15 cortical glomerular sections.

RNA Preparation and Real-Time Quantiative (TaqMan) RT-PCR

Renal tissue from each mouse was snap frozen in liquid nitrogen and stored at −80° C. From each animal, total renal RNA preparation and reverse transcription were performed as described (Anders 2002). Primers and probes were from PE Biosystems, Weiterstadt, Germany. The used primers (300 nM) used for detection of Ccl2, Ccl5 and 18S rRNA, predeveloped TaqMan assay reagent from PE Biosystems.

Flow Cytometry

Total blood and bone marrow samples were obtained from mice of all groups at the end of the study. Flow cytometry was performed using a FACScalibur machine and the previously characterized MC21 anti-mCCR2 antibody (Mack 2001). A biotinylated anti-rat IgG antibody (BD Biosciences) was used for detection. A rat $IgG_{2b}$ (BD Biosciences) was used as isotype control.

Statistical Analysis

Data were expressed as mean±standard error of the mean (SEM). Comparison between groups was performed using univariate ANOVA. Posthoc Bonferroni's correction was used for multiple comparisons. A value of $p<0.05$ was considered to indicate statistical significance.

Sandwich Hybridisation Assay

Amount of Spiegelmer in the samples was quantified by a sandwich hybridisation assay based on an assay as described by Drolet et al. 2000 (Pharm Res 17:1503). Blood samples were collected in parallel to follow the plasma clearance of NOX-E36. Selected tissues were prepared to determine Spiegelmer concentrations.

Hybridisation Plate Preparation

Spiegelmer mNOX-E36 was quantified by using a non-validated sandwich hybridisation assay. Briefly, the mNOX-E36 capture probe (SEQ ID NO:281) was immobilized to white DNA-BIND 96well plates (Corning Costar, Wiesbaden, Germany) at 0.75 mM in 0.5 M sodium phosphate, 1 mM EDTA, pH 8.5 over night at 4° C. Wells were washed twice and blocked with 0.5% w/v BSA in 0.25 M sodium phosphate, 1 mM EDTA, pH 8.5 for 3 h at 37° C., washed again and stored at 4° C. until use. Prior to hybridisation, wells were pre-warmed to 37° C. and washed twice with pre-warmed wash buffer (3×SSC, 0.5% [w/v] sodium dodecyl sarcosinate, pH 7.0; in advance a 20× stock [3 M NaCl, 0.3 M $Na_3$Citrate) is prepared without sodium lauroylsarcosine and diluted accordingly).

Sample Preparation

All samples were assayed in duplicates. Plasma samples were thawed on ice, vortexed and spun down briefly in a cooled tabletop centrifuge. Tissue homogenates were thawed at RT and centrifuged 5 min at maximum speed and RT. Only 5 µl each sample were removed for the assay, and afterwards returned to the freezer for storage. Samples were diluted with hybridisation buffer (8 nM mNOX-E36 detection probe [Seq. ID:282] in wash buffer) at RT according to the following scheme:

| | | |
|---|---|---|
| 1:30 | 5 µl sample + | 145 µl hybridisation buffer |
| 1:300 | 20 µl 1:30 + | 180 µl hybridisation buffer |
| 1:3000 | 20 µl 1:300 + | 180 µl hybridisation buffer |
| 1:30000 | 20 µl 1:3000 + | 180 µl hybridisation buffer |

All sample dilutions were assayed. mNOX-E36 standard was serial diluted to an 8-point calibration curve spanning the 0-4 nM range. No QC samples were prepared and assayed. Calibration standard was identical to that of the in-study samples.

Hybridisation and Detection

Samples were heated for 10 min at 95° C. and cooled to 37° C. Spiegelmer/detection probe complexes were annealed to immobilized capture probes for 30 min at 37° C. Unbound spiegelmers were removed by washing twice with wash buffer and 1×TBST (20 mM Tris-Cl, 137 mM NaCl, 0.1% Tween 20, pH 7.5), respectively. Hybridized complexes were detected by streptavidin alkaline phosphatase diluted 1:5000 in 1×TBST for 1 h at room temperature. To remove unbound conjugate, wells were washed again with 1×TBST and 20 mM Tris-Cl, 1 mM $MgCl_2$, pH 9.8 (twice each). Wells were finally filled with 100 ml CSDP substrate (Applied Biosystems, Darmstadt, Germany) and incubated for 45 min at room temperature. Chemiluminescence was measured on a FLUOstar Optima microplate reader (BMG Labtechnologies, Offenburg, Germany).

Data Analysis

The following assayed sample dilutions were used for quantitative data analysis:

| | |
|---|---|
| rat EDTA plasma | 1:2000 |

The data obtained from the vehicle group (no Spiegelmer was administered) was subtracted as background signal.

The sandwich hybridisation assay as described herein also works in similar fashion for Spiegelmer NOX-36, NOX-E36-5'-PEG and NOX-E36-3'-PEG whereby the respective NOX-E36 capture probe (Seq. ID:255) and the respective NOX-E36 detection probe (Seq. ID:256) has to be used (data not shown).

Results mNOX-E36-3'PEG improves survival and Kidney Disease of $MRL^{lpr/lpr}$ Mice Female $MRL^{lpr/lpr}$ mice develop and subsequentially die from proliferative immune complex glomerulonephritis with striking similarities to diffuse proliferative lupus nephritis in humans. In this therapeutic study design, treated $MRL^{lpr/lpr}$ mice were treated with pegylated and unpegylated anti-mCCL2 Spiegelmer, pegylated and unpegylated control ("PoC")-Spiegelmer or vehicle from week 14 to 24 of age. At this time point vehicle, PoC or PoC-PEG-treated $MRL^{lpr/lpr}$ mice showed diffuse proliferative glomerulonephritis characterized by glomerular macrophage infiltration and a mixed periglomerular and interstitial inflammatory cell infiltrate consisting of glomerular and interstitial Mac2-positive macrophages and interstitial CD3-positive lymphocytes (FIGS. 34 and 35). mNOX-E36-3'PEG improved the activity and chronicity index of lupus nephritis as well as the forementioned markers of renal inflammation (FIG. 35). The unpegylated molecule mNOX-E36 was less effective on the chronicity index and interstitial macrophage and T cell counts (FIG. 35). Advanced chronic kidney disease was further illustrated by tubular atrophy and confluent areas of interstitial fibrosis in vehicle-, PoC-, and PoC-PEG-treated mice (FIG. 34).

Applying morphometry to quantify these changes, it was found that pegylated and unpegylated mNOX-E36 reduced interstitial volume, tubular cell damage, and tubular dilation, all being markers of the severity and prognosis of chronic kidney disease (FIG. 36). mNOX-E36-3'PEG but not unpegylated mNOX-E36 improved 50% mortality (FIG. 37). Thus, mNOX-E36-3'PEG can reduce the number of renal macrophage and T cell infiltrates and improve lupus nephritis and (renal) survival of $MRL^{lpr/lpr}$ mice. In order to study whether treatment with mNOX-E36 and mNOX-E36-3'PEG affects intrarenal inflammation in $MRL^{lpr/lpr}$ mice, real-time RT-PCR was performed to assess the expression levels of the proinflammatory chemokines CCL2 and CCL5 which were previously shown to be progressively upregulated in kidneys of $MRL^{lpr/lpr}$ mice during progression of renal disease (Perez de Lema 2001). Treatment with mNOX-E36 and mNOX-E36-3'PEG from week 14 to 24 of age reduced renal expression of CCL2 and CCL5 mRNA compared to vehicle-treated controls (FIG. 38).

Anti-CCL2 Spiegelmers Reduce Extrarenal Autoimmune Tissue Injury in $MRL^{lpr/lpr}$ mice Skin and lungs are also commonly affected from autoimmune tissue injury in $MRL^{lpr/lpr}$ mice. In vehicle-treated mice autoimmune lung disease was characterized by moderate peribronchiolar and perivascular inflammatory cell infiltrates and skin lesions were observed in 60% of mice (FIGS. 39,40 and 35). mNOX-E36 and mNOX-E36-3'PEG both reduced peribronchial inflammation and skin disease as compared to vehicle-, PoC-, and PoC-PEG-treated $MRL^{lpr/lpr}$ mice, respectively (FIGS. 39, 40 and 35). Hence, the effects of CCL2-specific Spiegelmers are not limited to lupus nephritis but extend to other manifestations of autoimmune tissue injury in $MRL^{lpr/lpr}$ mice.

mNOX-E36 and the Lymphoproliferative Syndrome, dsDNA Autoantibodies, and Serum Cytokine Levels in $MRL^{lpr/lpr}$ Mice Female $MRL^{lpr/lpr}$ mice develop a lymphoproliferative syndrome characterized by massive splenomegaly and bulks of cervical, axillary, inguinal, and mesenteric lymph nodes. mNOX-E36 and mNOX-E36-3'PEG both had no effect on the weight of spleens and lymph nodes in $MRL^{lpr/lpr}$ mice (FIG. 41). Autoimmunity in $MRL^{lpr/lpr}$ mice is characterized by the production of autoantibodies against multiple nuclear antigens including dsDNA. In 24 week old $MRL^{lpr/lpr}$ mice serum dsDNA IgG, $IgG_1$, $IgG_{2a}$, $IgG_{2b}$ autoantibodies were present at high levels. mNOX-E36 and mNOX-E36-3'PEG both had no effect on either of these DNA autoantibodies (FIG. 41). Lupus-like disease in vehicle-treated $MRL^{lpr/lpr}$ mice was characterized by elevated serum levels of IFN-α, IL-12p40, and IL-6. mNOX-E36 and mNOX-E36-3'PEG both had no effect on either of these inflammatory mediators (FIG. 41). Thus, both mNOX-E36 variants do not affect lymphoproliferation, anti-dsDNA IgG production, and serum cytokine levels in $MRL^{lpr/lpr}$ mice.

Plasma levels of mNOX-E36 and MNOX-E36-3'PEG in $MRL^{lpr/lpr}$ mice mNOX-E36 and mNOX-E36-3'PEG plasma levels were determined at weekly intervals in order to monitor drug exposure during progressive kidney disease of $MRL^{lpr/lpr}$ mice. The median plasma levels of mNOX-E36 3 h after injection and mNOX-E36-3'PEG 24 h after injection were approximately 300 nM and 1 μM throughout the study, respectively (FIG. 42). Thus, pegylation increased the plasma levels of mNOX-E36 and the progressive kidney disease of $MRL^{lpr/lpr}$ mice did not modulate the pharmacokinetics of both Spiegelmers.

mNOX-E36-3'PEG Blocks the Emigration of Monocytes from the Bone Marrow

Monocyte emigration from bone marrow during bacterial infection was shown to involve chemokine receptor CCR2 (Serbina 2006), but the role of CCL2 in the context of autoimmunity remains hypothetical. Therefore, the CCR2-positive monocyte population in peripheral blood and bone marrows in mice of mNOX-E36-3'PEG- and vehicle-treated groups of 24 week old $MRL^{lpr/lpr}$ mice was examined. Treatment with mNOX-E36-3'PEG increased the percentage of CCR2 positive cells in the bone marrow from 13% to 26% whereas it reduced this population in the peripheral blood from 26% to 11% (FIG. 43). These data support a role of CCL2 for the evasion of CCR2 positive cells from the bone marrow during autoimmune disease of $MRL^{lpr/lpr}$ mice.

Summary

Applying the Spiegelmer technology, a novel and specific mCCL2 antagonist was created which potently blocks in CCL2 in vitro and in vivo. In fact, late onset of treatment with the CCL2 Spiegelmer markedly improved advanced lupus-like autoimmune tissue injury in $MRL^{lpr/lpr}$ mice. These data support a central role for CCL2 in chronic inflammatory tissue damage and identify CCL2 Spiegelmers as a novel therapeutic for autoimmune tissue injury.

EXAMPLE 9

Therapy of Diabetic Nephropathy in Unilaterally Nephrectomized Diabetic Mice with Anti-mMCP-1 Spiegelmer Diabetic nephropathy remains a leading cause of end-stage renal disease because targeting the angiotensin-dependent pathomechanisms does not always prevent disease progression (Zimmet 2001; Ritz 1999; United States Renal Data System 2004; Svensson 2003). Hence, other treatment strategies are required to add on to the therapeutic armament for diabetic nephropathy.

Data from recent experimental studies relate the progression of diabetic nephropathy to intrarenal inflammation (Galkina 2006; Mora 2005; Meyer 2003; Tuttle 2005). For example, mycophenolate mofetil, methotrexate or irradiation reduces urinary albumin excretion, and glomerulosclerosis in rats with streptozotocin-induced diabetic nephropathy (Yozai 2005; Utimura 2003). Yet, the molecular and cellular mechanisms of intrarenal inflammation in diabetic nephropathy remain poorly characterized. Patients with diabetic nephropathy have increased serum levels of acute phase markers of inflammation but this may not represent intrarenal inflammation (Dalla Vestra 2005; Navarro 2003). Patients with diabetic nephropathy excrete high levels of the CC-chemokine monocyte chemoattractant protein 1 (MCP-1/CCL2) in the urine which may be more specific for intrarenal inflammation (Morii 2003; Tashiro 2002; Takebayashi 2006). In fact, MCP-1/CCL2 is expressed by human mesangial cells exposed to either high glucose concentrations or advanced glycation end products (Ihm 1998; Yamagishi 2002). CCL2 is involved in the complex multistep process of leukocyte recruitment from intravascular to extravascular compartments, i.e. glomeruli and the renal interstitium (Baggiolini 1998). In fact, macrophage infiltrates are a common finding in human and experimental diabetic glomerulosclerosis and tubulointerstitial injury (Bohle 1991; Furuta 1993; Chow 2007). Cc/2-deficient type 1 or type 2 diabetic mice have lower glomerular macrophage counts which are associated with less glomerular injury (Chow 2004; Chow 2006). In these studies the functional role of CCL2 for glomerular pathology of type 1 and type 2 diabetic nephropathy was also demonstrated. Hence, CCL2 may represent a potential therapeutic target for diabetic nephropathy, and suitable CCL2 antagonists with favourable pharmacokinetic profiles should be validated in this disease context. In this example we report the effects of the PEGylated anti-CCL2 Spiegelmer mNOX-E36-3'PEG in type 2 diabetic db/db mice with advanced diabetic nephropathy. We have shown that an anti-CCL2-Spiegelmer would be suitable for the treatment of diabetic nephropathy.

Animals and Experimental Protocol

Male 5 week old C57BLKS db/db or C57BLKS wild-type mice were obtained from Taconic (Ry, Denmark) and housed in filter top cages with a 12 hour dark/light cycle and unlimited access to food and water for the duration of the study. Cages, bedding, nestlets, food, and water were sterilized by autoclaving before use. At the age of 6 weeks uninephrectomy ("1K" mice) or sham surgery ("2K" mice) was performed through a 1 cm flank incision as previously described in db/db and wild-type mice (Bower 1980). In mice of the sham surgery groups the kidney was left in situ. 10 weeks later, at the age of 4 months, 1K db/db mice were divided in two groups that received three times per week subcutaneous injections with either mNOX-E36-3'PEG or PoC-PEG in 5% glucose (dose, 0.9 μmol/kg; injection volume, 1 ml/kg). Treatment was continued for 8 weeks (until the age 6 months) when the animals were sacrificed and the tissues were obtained for histopathological evaluation. All experimental procedures had been approved by the local government authorities.

Evaluation of Diabetic Nephropathy

All immunohistological studies were performed on paraffin-embedded sections as described (Anders 2002). The following antibodies were used as primary antibodies: rat anti-Mac2 (glomerular macrophages, Cederlane, Ontario, Canada, 1:50), anti-Ki-67 (cell proliferation, Dianova, Hamburg, Germany, 1:25). For histopathological evaluation, from each mouse parts of the kidneys were fixed in 10% formalin in phosphate-buffered saline and embedded in paraffin. 3 μm-sections were stained with periodic acid-Schiff reagent or silver following the instructions of the supplier (Bio-Optica, Milano, Italy). Glomerular sclerotic lesions were assessed using a semiquantitative score by a blinded observer as follows: 0=no lesion, 1=<25% sclerotic, 2=25-49% sclerotic, 3=50-74% sclerotic, 4=75-100% sclerotic, respectively. 15 glomeruli were analysed per section. The indices for interstitial volume and tubular dilatation were determined by superimposing a grid of 100 points on 10 non-overlapping cortical fields as described previously (Anders 2002). Interstitial cell counts were determined in 15 high power fields (hpf, 400×) by a blinded observer. RNA preparation and real-time quantitative (TaqMan) RT-PCR was done from deparaffinized glomeruli. After incubation in lysing buffer (10 mM Tris-HCl, 0.1 mM EDTA, 2% SDS and 20 μg/ml proteinase K) for 16 h at 60° C., phenol-chloroform-based RNA extraction was performed. Glomerular RNA was dissolved in 10 μl RNAse free water. Reverse transcription and real time RT-PCR from total organ and glomerular RNA was performed as described (Anders 2002, Cohen 2002). Controls consisting of $ddH_2O$ were negative for target and housekeeper genes. Oligonucleotide primer (300 nM) and probes (100 nM) for mCcl2, Gapdh, and 18 S rRNA were predeveloped TaqMan assay reagents from PE. Primers and probes were from ABI Biosystems, Weiterstadt, Germany. Glomerular filtration rate (GFR) was determined by clearance kinetics of plasma FITC-inulin (Sigma-Aldrich, Steinheim, Germany) 5, 10, 15, 20, 35, 60, and 90 minutes after a single bolus injection (Qi 2004). Fluorescence was determined with 485 nm excitation and read at 535 nm emission. GFR was calculated based on a two-compartment model using a non-linear regression curve-fitting software (GraphPad Prism, GraphPad Software Inc., San Diego, Calif.). All data are presented as mean±SEM. Comparison of groups was performed using ANOVA and post-hoc Bonferroni's correction was used for multiple comparisons. A value of $p<0.05$ was considered to indicate statistical significance.

Results mNOX-E36-3'PEG Reduces Glomerular Macrophage Counts and Global Glomerulosclerosis in Unilaterally Nephrectomized db/db Mice When lack of functional CCL2 is associated with decreased glomerular macrophage recruitment in db/db mice (Chow 2007) and mNOX-E36-3'PEG is able to block CCL2-mediated macrophage recruitment in vitro and in vivo, mNOX-E36-3'PEG should impair renal macrophage recruitment in db/db mice with advanced type 2 diabetic nephropathy. To test this hypothesis, we initiated subcutaneous injections with mNOX-E36-3'PEG or PoC-PEG at age of 4 months in unilaterally nephrectomized ("1K") db/db mice. Treatment was continued for 8 weeks when tissues were collected for the assessment of diabetic nephropathy. During that period, mNOX-E36-3'PEG treatment did not significantly affect white blood or platelet counts, blood glucose levels or body weight which were both markedly elevated in all groups of db/db mice as compared to non-diabetic BLKS mice (data not shown). Interestingly, mNOX-E36-3'PEG increased the serum levels of CCL2 in 1K db/db mice, indicating that the CCL2 antagonist retains CCL2 in the circulation (FIG. 44). Consistent with our hypothesis mNOX-E36-3'PEG significantly reduced the number of glomerular macrophages by 40% as compared to PoC-PEG- or vehicle-treated db/db mice, associated with lower numbers of Ki-67 positive proliferating cells within the glomerulus in mNOX-E36-3'PEG-treated db/db mice (FIG. 45). These findings were associated with a significant improvement of global diabetic glomerulosclerosis in 1K db/db mice (FIG. 46). In fact, mNOX-E36-3'PEG treatment reduced diabetic glomerulosclerosis in 1K db/db mice to the extent of glomerulosclerosis present in age-matched non-nephrectomized ("2K") db/db mice (FIG. 46). These findings show that delayed blockade of CCL2-dependent glomerular macrophage recruitment with mNOX-E36-3'PEG prevents global diabetic glomerulosclerosis in type 2 diabetic db/db mice.

mNOX-E36-3'PEG Improves GFR in 1K db/db Mice

The beneficial effects of mNOX-E36-3'PEG treatment on diabetic glomerulosclerosis in 1K db/db mice should be associated with a better GFR. We analyzed FITC-inulin clearance kinetics as a marker of GFR in db/db mice (Qi 2004). As compared to a normal GFR of about 250 ml/min in db/db mice (Qi 2004), we found a reduced GFR of was 112±23 ml/min in 6 months old 1K db/db mice injected with PoC-PEG (FIG. 47). mNOX-E36-3'PEG treatment significantly improved the GFR to 231±30 ml/min in 1K db/db mice ($p<0.001$) suggesting that blocking CCL2-dependent glomerular macrophage recruitment can also improve renal function in type 2 diabetic mice.

mNOX-E36-3'PEG Reduces Interstitial Macrophage Counts and Tubulointerstitial Injury in 1K db/db Mice Advanced diabetic nephropathy in humans is associated with significant numbers of interstitial macrophages and tubulointerstitial injury (Bohle 1991). In 2K db/db mice interstitial macrophage infiltrates and significant tubulointerstitial injury does not occur before 8 months of age (Chow 2007). Early uninephrectomy accelerates the development of tubulointerstitial pathology in db/db mice (Ninichuk 2005), thus we quantified interstitial macrophages, tubular dilatation and interstitial volume as markers of tubulointerstitial damage in mice of all groups at 6 months of age. At this time point 1K db/db mice revealed increased numbers of interstitial macrophages and significant elevations of tubular dilatation and interstitial volume as compared to 2K db/db mice (FIG. 45, FIG. 48). mNOX-E36-3'PEG treatment reduced the numbers of interstitial macrophages by 53% as well as tubular dilatation and interstitial volume in 1K db/db mice (FIG. 45, FIG. 48). Thus, blocking CCL2-dependent renal macrophage recruitment also prevents tubulointerstitial injury in type 2 diabetic db/db mice.

mNOX-E36-3'PEG Reduces Renal Expression of Ccl2 in 1K db/db Mice

Macrophage infiltrates amplify inflammatory responses in tissue injury, e.g. local CCL2 expression. We therefore hypothesized that the mNOX-E36-3'PEG-related decrease in renal macrophages would be associated with less renal CCL2 expression. We used real-time RT-PCR to quantify the mRNA expression of CCL2 in db/db mice. mNOX-E36-3'PEG reduced the mRNA levels of CCL2 in kidneys of 6 months old 1K db/db mice as compared to age-matched PoC-PEG-treated mice (FIG. 49). To further assess the spatial expression of CCL2 we performed immunostaining for CCL2 protein on renal sections. In 1K db/db mice the expression of CCL2 was markedly enhanced in glomeruli, tubuli, and interstitial cells as compared to 2K db/db or 2K wild-type mice (FIG. 50). mNOX-E36-3'PEG markedly reduced the staining for CCL2 in all these compartments as compared to vehicle- or PoC-PEG-treated 1K db/db mice. These data indicate that blocking CCL2-dependent renal macrophage recruitment with mNOX-E36-3'PEG reduces the local expression of CCL2 in 1K db/db mice.

Summary

The concept that inflammation contributes to the progression of human diabetic nephropathy becomes increasingly accepted (Tuttle 2005), bringing MCP-1/CCL2 as a potential target to treat this disease into the focus. In this example, we have shown that treatment of unilaterally nephrectomized diabetic mice with mNOX-E36-3'PEG reduced the numbers of glomerular (and interstitial) macrophages at 6 months of age, associated with less proliferating glomerular cells. In addition, renal/glomerular expression of CCL2 mRNA was markedly reduced with mNOX-E36-3'PEG treatment. Furthermore, lower numbers of glomerular macrophages and glomerular proliferating cells in the therapy group were associated with protection from global glomerulosclerosis and with a significant improvement of the glomerular filtration rate. The beneficial effects of mNOX-E36-3'PEG on glomerular pathology and renal function in diabetic mice are consistent with those studies that have used other CCL2 antagonists in other models of glomerular injury (Lloyd 1997, Hasegawa 2003, Tang 1996, Wenzel 1997, Fujinaka 1997, Schneider 1999). Remarkably, delayed onset of CCL2 blockade also reduced the numbers of interstitial macrophages being associated with less tubulointerstitial pathology in 1K db/db mice.

Together, these data validate CCL2 as a promising therapeutic target for diabetic nephropathy and suggest that initiating CCL2 blockade with a Spiegelmer—even at an advanced stage of the disease—may still be protective.

EXAMPLE 10 mNOX-E36-3'-PEG Permits Dose Reduction of Cyclophosphamide to Control Diffuse Proliferative Lupus Nephritis and Pneumonitis in MRL$^{lpr/lpr}$ Mice Control of human diffuse proliferative lupus nephritis (abbr. DPLN) requires potent immunosuppression with either cyclophosphamide (abbr. CYC) or mycophenolate mofetil (abbr. MMF). Each of the two drugs is associated with significant morbidity and mortality (Appel 2007). Most serious adverse events and deaths were related to infections due to the unspecific immunosuppressive effects of CYC and MMF (Appel 2007). Novel drugs specifically blocking autoimmune inflammation may allow reducing the toxicity of current treatment protocols either by replacing CYC and MMF or by allowing significant dose reductions when used in combination.

Experimental studies have revealed that MCP-1 and its receptor CCR2 have crucial roles in autoimmune tissue injury such as the manifestations of systemic lupus erythematosus (abbr. SLE) (Gerard 2001); it has for instance been demonstrated that MCP-1 or CCR2-deficient MRL$^{lpr/lpr}$ mice with experimental SLE are protected from DPLN (Perez 2005; Tesch 1999) The beneficial effect of MCP-1 blockade with the anti-mMCP-1 Spiegelmer mNOX-E36-3'-PEG as a monotherapy has already been demonstrated in vivo with female MRL$^{lpr/lpr}$ mice: treatment with mNOX-E36-3'-PEG for 10 weeks starting at an age of 14 weeks significantly improved DPLN as shown in Example 9. Although the therapeutic effect was clearly evident it remained unclear how the efficacy of mNOX-E36-3'-PEG would compare to that of CYC or MMF. In order to assess the hypothesis that therapeutic effects equivalent to full dose CYC—which efficiently suppresses the immune system—could also be reached with a combination of low-dose CYC plus mNOX-E36-3'-PEG, a second in vivo study was performed.

Animals and Experimental Protocol

Seven week old female MRL$^{lpr/lpr}$ mice were obtained from Harlan Winkelmann (Borchen, Germany) and kept under normal housing conditions with a 12 hour light and dark cycle. Water and standard chow (Ssniff, Soest, Germany) were available ad libitum. From an age of 14 weeks, mice were injected for 10 weeks as follows: (A), 5% glucose s.c. (vehicle group); (B), 0.89 μmol/kg the PEGylated control Spiegelmer revmNOX-E36 s.c.; (C), 0.89 μmol/kg mNOX-E36-3'-PEG s.c.; (D), 30 mg/kg/4 weeks CYC i.p. (CYC low); (E), 30 mg kg/week CYC i.p. (CYC high); (F), 0.89 μmol/kg mNOX-E36-3'-PEG plus 30 mg/kg/4 weeks CYC (combination) and (G), 100 mg/kg/day MMF orally (Roche, Mannheim, Germany). All vehicle and Spiegelmer injections were given 3×/week. Mice were sacrificed by cervical dislocation at the end of the 10-week treatment. All experimental procedures were performed according to the German animal care and ethics legislation and were approved by the local government authorities.

Evaluation of Systemic Lupus

The weight ratio of spleen and the bulk of mesenteric lymph nodes to total body weight were calculated as markers of the lupus-associated lymphoproliferative syndrome. Urine albumin/creatinine ratio was determined as previously described (Pawar 2006). From all mice, kidneys and lungs were fixed in 10% buffered formalin, processed, and embedded in paraffin. 5-μm sections for periodic acid-Schiff stain were prepared following routine protocols (Anders 2002). The severity of the renal lesions was graded using the indices for activity and chronicity as described for human lupus nephritis (Austin 1984) The severity of the peribronchial inflammation was graded semiquantitatively from 0-4 by a blinded observer. Immunostaining was performed as previously described (Anders 2002). The following primary antibodies were used: rat anti-Mac2 (macrophages, Cederlane, Ontario, Canada, 1:50), anti-mouse CD3 (1:100, clone 500A2, BD). Negative controls included incubation with a respective isotype antibody. Positive glomerular cells were counted in 15 cortical glomeruli per section. Interstitial cells were counted by high power field (abbr. hpf).

Statistical Analysis

Data were expressed as mean±standard error of the mean (abbr. SEM). Comparison between groups was performed using univariate ANOVA. Posthoc Bonferroni's correction was used for multiple comparisons. A value of $p<0.05$ was considered to indicate statistical significance.

Add-on Therapy with mNOX-E36-3'-PEG Improves the Effects of Monthly CYC on Kidney Disease of $MRL^{lpr/lpr}$ Mice.

Female $MRL^{lpr/lpr}$ mice develop proliferative immune complex glomerulonephritis similar to DPLN in humans. $MRL^{lpr/lpr}$ mice were treated with CYC, MMF, Spiegelmer or vehicle from week 14 to 24 of age. This represents a therapeutic treatment protocol because at 14 weeks of age $MRL^{lpr/lpr}$ mice showed DPLN with an activity score index of 4.1±1.1. At this age major abnormalities of the tubulointerstitial compartment were absent (not shown). After 10 weeks of treatment, vehicle- and control Spiegelmer-treated $MRL^{lpr/lpr}$ mice revealed DPLN associated with glomerular hypercellularity, expansion of glomerular matrix, focal tuft necrosis, and a mixed periglomerular and interstitial inflammatory cell infiltrate. Weekly CYC and monthly CYC plus mNOX-E36-3'-PEG were equally potent in improving the activity and chronicity index of lupus nephritis (FIGS. 51A and 51B). mNOX-E36 and low dose CYC alone as well as MMF were less potent but still significantly improved the activity and chronicity indices of lupus nephritis. Thus, adding mNOX-E36-3'-PEG to a monthly CYC-based regimen is as potent as weekly CYC therapy for DPLN of $MRL^{lpr/lpr}$ mice.

mNOX-E36 and Monthly CYC have Additive Effects on the Reduction of Immune Cell Infiltrates in Kidneys of $MRL^{lpr/lpr}$ Mice.

Immune cell infiltrates contribute to renal damage in lupus nephritis (Vielhauer 2006). and MCP-1 mediates the recruitment of T cells and macrophages to $MRL^{lpr/lpr}$ mice (Tesch 1999). It was therefore hypothesized that the additive effects mNOX-E36-3'-PEG/monthly CYC combination may relate to impaired macrophage and T cell recruitment in $MRL^{lpr/lpr}$ mice. Assessment of the number of glomerular and interstitial macrophages and interstitial T cells (Mac2+ macrophages and CD3+ T cells) by immunostaining revealed that weekly CYC and monthly CYC plus mNOX-E36 were equally potent in reducing the numbers of glomerular as well as interstitial Mac2+ macrophages in kidneys of $MRL^{lpr/lpr}$ mice (FIGS. 51C and 51D). mNOX-E36-3'-PEG and monthly CYC alone as well as MMF were less potent but still significantly reduced the macrophages in both compartments (FIGS. 51C and 51D). The same was found for the numbers of interstitial CD3 positive T cells (FIG. 3E). Thus, the additive effect of mNOX-E36-3'-PEG and monthly CYC on renal pathology of $MRL^{lpr/lpr}$ mice is associated with a significant reduction of interstitial macrophages and T cells as well as of glomerular macrophages which was similar to the effect of weekly CYC.

mNOX-E36-3'-PEG and Monthly CYC have Additive Effects on the Reduction of Lung Injury in $MRL^{lpr/lpr}$ Mice.

Autoimmune peribronchitis is another manifestation of lupus-like systemic autoimmunity in $MRL^{lpr/lpr}$ mice. Weekly CYC was more effective than monthly CYC in controlling lung injury in $MRL^{lpr/lpr}$ mice. However, monthly CYC plus mNOX-E36 were as effective as weekly CYC (FIG. 52). Surprisingly, MMF had no effect of lung injury in $MRL^{lpr/lpr}$ mice.

Summary

The data demonstrate that a combination of mNOX-E36 and low-dose CYC treatment initiated at 14 weeks of age—a time point when autoimmune tissue injury is already established (Tesch 1999; Perez 2001)—is as effective as high dose CYC in suppressing DPLN and lung injury in $MRL^{lpr/lpr}$ mice. In conclusion, inhibition of MCP-1 in combination with CYC allows significant CYC dose reduction which avoids the severe immunotoxic effect of CYC despite equipotent control of autoimmune tissue damage like DPLN. This novel concept may help to reduce the serious and potentially life-threatening CYC toxicity in patients with DPLN and potentially other serious manifestations of autoimmune disease that involve MCP-1 dependent immune cell infiltrates.

EXAMPLE 11

COPD Screening Study—Reduction of Cellular Infiltrate into Lungs by Treatment with MCP-1 Binding Spiegelmer mNOX-E36-3'-PEG The heterogeneous group of chronic respiratory diseases includes chronic bronchitis, chronic obstructive pulmonary disease (abbr. COPD), and asthma. Lung histology from patients affected by COPD and asthma shows a marked airway infiltration of macrophages and granulocytes, principally neutrophils in COPD and eosinophils in asthma. In clinical studies, these inflammatory parameters have been shown to correlate with a reduction in lung function and an exaggerated bronchoconstriction (airway hyperreactivity [abbr. AHR]) to nonspecific stimuli. Few in vivo models emulate the chronic inflammation of COPD, afford the examination of lung function over many days and stimulate the mucus hypersecretion associated with neutrophilia and AHR. A single exposure of rats/humans to lipopolysaccharide (abbr. LPS) has been shown to cause an acute lung neutrophilia and AHR. Inhalation of LPS causes further features analogous to COPD, namely, a progressive decline in lung function, persistent AHR, and a neutrophilic inflammatory cell population in the bronchoalveolar fluid, together with nitric oxide overproduction. Mediators derived from inflammatory cell activation, recruitment, and LPS are thought to induce epithelial proliferation, permeability, and a mucus hypersecretory phenotype.

In the study described in this report, a challenge model using bacterial LPS was used to evaluate a therapeutic effect of MCP-1 binding Spiegelmer mNOX-E36-3'-PEG in LPS induced lung inflammation model in rats. All animals were challenged with LPS for induction of an acute respiratory inflammation. Therapeutic intervention with MCP-1 binding Spiegelmer mNOX-E36-3'-PEG, dexamethasone (pharmacological reference substance 1), and Roflumilast (pharmacological reference substance 2) in different doses was performed.

Dexamethasone is a potent synthetic member of the glucocorticoid class of steroid hormones. It acts as an anti-inflammatory as well as immunosuppressant:

(I), anti-inflammatory: glucocorticoids induce the lipocortin-1 (annexin-1) synthesis, which then binds to cell membranes, preventing the phospholipase A2 from coming into contact with its substrate arachidonic acid. This leads to diminished eicosanoid production. The cyclooxygenase (both COX-1 and COX-2) expression is also suppressed, potentiating the effect. In other words, the two main products in inflammation, prostaglandins and leukotrienes, are inhibited by the action of glucocorticoids. Glucocorticoids also stimulate the lipocortin-1 escaping to the extracellular space, where it binds to the leukocyte membrane receptors and inhibits various inflammatory events: epithelial adhesion, emigration, chemotaxis, phagocytosis, respiratory burst, and the release of various inflammatory mediators (lysosomal enzymes, cytokines, tissue plasminogen activator, chemokines, etc.) from neutrophils, macrophages, and mastocytes.

(II), immunosuppressant: glucocorticoids suppress the cell-mediated immunity. They act by inhibiting many cytokines genes, the most important of which is the IL-2 gene, which in consequence reduces the T cell proliferation. In addition to preventing T cell proliferation, another well known effect is glucocorticoid induced apoptosis. The effect is more prominent in immature T cells that still reside in the thymus, but also affect peripheral T cells. Finally, glucocorticoids suppress the humoral immunity, causing B cells to express smaller amounts of IL-2 and of IL-2 receptors. This diminishes both B cell clone expansion and antibody synthesis. The diminished amounts of IL-2 also cause fewer T lymphocyte cells to be activated.

Roflumilast is a drug which acts as a selective, long-acting inhibitor of the phosphodiesterase enzyme PDE-4. It has antiinflammatory effects and is under development as an orally administered drug for the treatment of inflammatory conditions of the lungs such as asthma, chronic obstructive pulmonary disease and emphysema. While roflumilast was found to be effective in clinical trials, it produced several dose-limiting side effects including nausea, diarrhea and headache, and development is continuing in an attempt to minimise the incidence of side effects while retaining clinical efficacy.

Animals and Husbandry

Male Sprague Dawley rats were used in this study as well established model of LPS-induced inflammation. The rats were supplied at an age of 5 weeks (ca. 80-110 g) by Harlan Winkelmann, Borchen, Germany and were at start of the study at an age of 7 weeks. Animals were housed in Makrolon® (polycarbonate) cages (two rats per cage) and were maintained under conventional laboratory conditions. Cages and softwood bedding material (Ssniff 3/4, Soest, Germany) were changed twice a week. The temperature and the relative humidity of the animal room were monitored electronically and recorded on a continuous basis. The limits were set at 22±2° C. for the temperature and 55±15% for relative humidity. A 12-hour light/dark cycle was used for lighting controlled by an automatic timing device. As diet a commercial chow in pellet form was used (Ssniff R/M-H V1534, Ssniff-Spezialdiäten, Soest, Germany). Diet and drinking water (Stadtwerke Hannover) were available ad libitum.

Two weeks were allowed for the animals to adjust and become acclimatized to the environment of the facilities before the randomization and the first sensitization. The animals used in the study did not show any signs of decline of their health conditions. All animals were observed in their cages daily.

Materials

MCP-1 Binding Spiegelmer mNOX-E36-3'PEG

Vehicle for mNOX-E36-3'-PEG: 5% glucose solution for injection purposes

LPS: Lipopolysaccharide from *Escherichia coli* 0111:B4 (Sigma/Aldrich, Batch No. 76K4085). The working solution was prepared freshly on application day.

Pharmacological reference substance (1): Dexamethasone dihydrogenphosphat sodium, Ratiopharm Batch No. H22416 4 mg/mL solution. The stock solution was stored after opening in a refrigerator for 7 days. The working solution was prepared freshly on every application day.

Pharmacological reference substance (2): Roflumilast (selective PDE4 inhibitor, Batch No. K429927). The working solution was prepared freshly on application day.

Vehicle for dexamethasone: Dulbecco's Phosphate Buffered Saline (abbr. DPBS)-0.0095 M (PO4) without Ca++ and Mg++

Conduct of the Study

All animals were weighed and randomized prior to their first sensitization: in consideration of their weight they were distributed evenly to groups of ten animals each. After distribution in groups the mean values and the standard deviation of the mean body weights (±SD) were checked and were below 20% within each group as well as between groups. The body weights of the animals were measured and documented individually.

On day 1 of the study, the LPS challenge was performed by inhalation resulting in a deposited dose of approximately 2.93 μg LPS. The animals of the positive and negative control groups were treated i.v. with vehicle (5% glucose) one hour before LPS challenge (positive control) or clean air sham challenge (negative control). Animals in pharmacological control (1) received 2 mg/kg dexamethasone 18 and 1 hour before LPS challenge i.p.; those in pharmacological control (2) received 600 μg Roflumilast per animal intragastrically. The treatment using MCP-1 binding Spiegelmer mNOX-E36-3'-PEG was done in four different doses by intravenous injection one hour before LPS challenge (0.02 mg/kg; 0.2 mg/kg; 2 mg/kg; 20 mg/kg).

24 hours after challenge, the animals were sacrificed painlessly with an overdose of pentobarbital sodium and bronchoalveolar lavage (abbr. BAL) was collected. The lungs of the animals were lavaged five times, each time with 5.0 ml ice cold 0.9% NaCl. For evaluation of the BAL, the supernatant of the first lavage was aliquoted after sedimentation of the cells by centrifugation. After that, cells from all lavages were pooled and centrifuged immediately after collection (10 min at 1,200 U/min). The cells were resuspended in 1 mL PBS and counted automatically in a CasyÒ cell counter. Cytospots were prepared and stained according to Pappenheim to evaluate differential cell counts. The inflammatory status in lungs was analyzed including the numbers of macrophages/monocytes, neutrophils, eosinophils and lymphocytes by counting a total number of 400 cells per cytospot.

Statistical Methods

To test for significant differences between groups, non-parametric tests were used. For multiple comparison (>two groups), ANOVA test and non-parametric Dunnett test were performed. Differences with $p<0.05$ were considered significant.

Results

The total cell number in the BAL was significantly decreased in the negative control group compared to the positive control group as expected. The treatment with 20 mg/kg MCP-1 binding Spiegelmer mNOX-E36-3'-PEG resulted in a significantly decreased total cell number by 41% of the positive control group in the BAL. The treatment using dexamethasone induced a 71% reduction of the cell number, whereas Roflumilast did not show any significant effect (see FIG. 53A).

The inhalative LPS challenge induced an inflammation in the lung represented by a neutrophilia of 71.8% neutrophil granulocytes in the BAL. The lung lavage fluid of untreated animals in the negative control group did not contain any neutrophil granulocytes. The treatment using Dexamethasone and 2 or 20 mg/kg MCP-1 binding Spiegelmer mNOX-E36-3'-PEG resulted in a significantly diminished number of neutrophils. Already 2 mg/kg mNOX-E36-3'-PEG decreased the number of neutrophils by ca. 42% and 20 mg/kg mNOX-E36-3'-PEG resulted in a neutrophil decrease of ca. 48%. Roflumilast treatment did not influence the absolute and relative amount of neutrophils in bronchoalveolar lavage compared to the positive control group (see FIG. 53B).

Conclusion

The results for differential cell counts in BAL confirmed positively the induction of an acute LPS induced inflammation response in the lungs. Therapeutic treatment of LPS challenged rats with dexamethasone was shown to prevent the inflammation response after exposure to LPS significantly. A significant therapeutic effect was also obtained for animals treated with MCP-1 binding Spiegelmer mNOX-E36-3'-PEG. Based on the data as shown herein, MCP-1 binding Spiegelmers have the potential to be used in the therapy of chronic respiratory diseases, preferably COPD, alone or in combination therapy. Preferably in combination therapy with dexamethasone. Combination therapy of MCP-1 binding Spiegelmers with dexamethasone takes the advantage of two independent mode-of-actions in order to treat chronic respiratory diseases such as COPD.

EXAMPLE 12

Effects of the MCP-1 Binding Spiegelmer mNOX-E36 in Experimental Pulmonary Hypertension The study as described herein was done in order to determine the effects of MCP-1 binding Spiegelmer in NOX-E36-3'-PEG on hemodynamics and remodeling in an established model of monocrotaline induced pulmonary hypertension in rats.

Pulmonary arterial hypertension (abbr. PAH) is defined by an elevation of mean pulmonary arterial pressure ≧20 mmHg at rest, vascular remodelling and right ventricular hypertrophy. Idiopathic PAH, also known as primary pulmonary hypertension (abbr. PPH), often presents in young women leading to death from right heart failure within 3 years, without treatment. Key to the severity of the disease is the pulmonary vascular remodelling, characterized by proliferation and migration of pulmonary artery smooth muscle cells (abbr. PASMCs). Neointimal lesions can also be observed in advanced stages of PAH, as a consequence of endothelial cell proliferation. The pathologies observed are potentially self perpetuating, with a concurrent dysregulation of growth factors and inflammatory mediators playing a role in disease progression.

Monocrotaline as Rodent Model of Pulmonary Hypertension

This model successfully predicted the clinical effectiveness of all modern treatments for clinical pulmonary hypertension, including prostanoids, phosphodiesterase inhibitors and endothelin receptor antagonists. In addition, it provides opportunities for both prevention and reversal studies of PAH. In the monocrotaline model, rats are given a single subcutaneous injection of the pyrrolizidine alkaloid toxin monocrotaline. The toxin produces an inflammatory pulmonary vasculopathy resulting in marked pulmonary hypertension after 3-4 weeks. Readouts for this model include right ventricular pressure, systemic pressure, right ventricle/left ventricle+septum weight ratio (RV/[LV+S]) and pulmonary vascular remodeling.

Animals

Adult male Sprague Dawley rats (300-350 g body weight) were obtained from Charles River Laboratories (Sulzfeld, Germany). The experiments were performed in accordance with the National Institutes of Health Guidelines on the Use of Laboratory Animals.

Experimental Protocol

In-life procedure: Monocrotaline (abbr. MCT; Sigma, Deishofen) was dissolved in 1 M HCl, adjusted to pH 7.4 with 1 M NaOH and administered as a single subcutaneous injection in a dose of 60 mg/kg body mass as described. Control rats received an equal volume of isotonic saline.

For chronic intervention studies, MCT injected rats were randomized to receive either 5% glucose as placebo (n=10) or MCP-1 binding Spiegelmer mNOX-E36-3'-PEG (n=10 for both doses of 2 and 20 mg/kg, respectively) by subcutaneous injections 3 times per week. Treatment was initiated 3 weeks after injection of MCT—a time point when pulmonary hypertension is expected to be fully established. Animals were treated for the duration of further 2 weeks, i.e. six injections in total. On day 35, haemodynamic parameters were determined and tissue was prepared.

Haemodynamics: For measurement of hemodynamic parameters, rats were anaesthetized. Afterwards, rats received an i.m. injection of atropine (250 μg/kg body mass) to minimize vasovagal side-effects during the preparation. The rats were tracheotomized and ventilated with a frequency of 60/min. Positive end expiratory pressure was set at 1 cm H2O. The left carotid artery was cannulated for arterial pressure monitoring, and a right heart catheter was inserted through the right jugular vein for measurement of right ventricular pressure with fluid filled force transducers.

Tissue preparation: After exsanguination, the lungs were flushed with isotonic saline at a constant pressure of 22 cm H2O via the pulmonary artery. The right lung was ligated at the hilus, shock frozen in liquid nitrogen, and stored at −80° C.; the left lobe was perfused for 5 minutes with Zamboni's fixative at a pressure of 22 cm H2O via the pulmonary artery. The tissue was fixed in Formalin (4%) for 12 hours at 4° C. and then transferred into 0.1 M phosphate buffer.

Right heart hypertrophy assessment: In order to assess right ventricular hypertrophy, the heart was removed and dissected. The ratio of the right ventricle weight to left ventricle plus septum weight RV/(LV+S) was calculated.

Statistical Analysis

All data are given as mean±SEM. Differences between groups were assessed by ANOVA and Student-Newman-Keuls post-hoc test for multiple comparisons.

Results

As expected, the MCT/placebo-treated animals showed a dramatic and statistically significant increase in right heart hypertrophy in comparison with healthy animals. Whereas the MCT/placebo-treated animals exhibited an RV/(LV+S) of ca. 0.61, healthy rats had only ca. 0.23. Administration of MCP-1 binding Spiegelmer mNOX-E36-3'-PEG instead of placebo resulted in MCT-treated animals to a significantly reduced right heart hypertrophy of ca. 0.39 for 2 mg/kg and ca. 0.45 for 20 mg/kg mNOX-E36 (see FIG. 54A).

In line with the right heart hypertrophy, the measured right ventricular systolic pressure in MCT/placebo-treated rats was increased to 69 mmHg (healthy animals, 29 mmHg). Treatment with MCP-1 binding Spiegelmer mNOX-E36-3'-PEG instead of placebo resulted in significantly reduced right ventricular systolic pressure of ca. 46 mmHg for 2 mg/kg and ca. 49 mmHg for 20 mg/kg mNOX-E36-3'PEG (FIG. 54B).

Conclusion

The results for right heart hypertrophy and right ventricular systolic pressure in MCT/placebo treated animals confirmed positively the induction of pulmonary arterial hypertension by MCT. Administration of MCP-1 binding Spiegelmer mNOX-E36-3'-PEG to MCT-treated rats significantly prevented both right heart hypertrophy and right ventricular systolic pressure. Hence, MCP-1 binding Spiegelmers are promising agents for the treatment of pulmonary hypertension.

REFERENCES

The complete bibliographic data of the documents recited herein the disclosure of which is incorporated by reference is, if not indicated to the contrary, as follows.

Akahoshi T, Wada C, Endo H, Hirota K, Hosaka S, Takagishi K, Kondo H, Kashiwazaki S, Matsushima K (1993). Expression of monocyte chemotactic and activating factor in rheumatoid arthritis. Regulation of its production in synovial cells by interleukin-1 and tumor necrosis factor. *Arthritis Rheum.* 36:762

Alam R, York J, Moyars M, Stafford S, Grant J A, Lee J, Forsythe P, Sim T, Ida N (1996). Increased MCP-1, RANTES, and MIP-1α in bronchoalveolar lavage fluid of allergic asthmatic patients. *Am. J. Respir. Crit. Care Med.* 153:1398

Altschul S F, Gish W, Miller W, Myers E W, Lipman D J (1990), Basic local alignment search tool. *J Mol Biol.* 215(3):403-10.

Altschul S F, Madden T L, Schaffer A A, Zhang J, Zhang Z, Miller W, Lipman D J (1997). Gapped BLAST and PSI-BLAST: a new generation of protein database search programs. *Nucleic Acids Res.* Sep 1; 25(17):3389-402.

Amann B, Tinzmann R, Angelkort B (2003). ACE inhibitors improve diabetic nephropathy through suppression of renal MCP-1. *Diabetes Care* 26:2421

Anders H J, Vielhauer V, Frink M, Linde Y, Cohen CD, Blattner S M, Kretzler M, Strutz F, Mack M, Grone H J, Onuffer J, Horuk R, Nelson P J, Schlöndorff D (2002). A chemokine receptor CCR-1 antagonist reduces renal fibrosis after unilateral ureter ligation. *J. Clin. Invest.* 109:251

Anders H J, Vielhauer V, Schlöndorff D (2003). Chemokines and chemokine receptors are involved in the resolution or progression of renal disease. *Kidney Int.* 63:401

Appel G, Dooley M A, Ginzler E M, Isenberg D, Jayne D, Solomons N, Wolfs D. (2007). Mycophenolate mofetil compared with intravenous cyclophosphamide as induction therapy for lupus nephritis: Aspreva Lupus Management Study (ALMS) results. *J Am Soc Nephrol* 18: SA-FC057 [abstract]

Aurup H Tuschl T, Benseler F, Ludwig J, Eckstein F. (1994). Oligonucleotide duplexes containing 2'-amino-2'-deoxycytidines: thermal stability and chemical reactivity. *Nucleic Acids Res* 22:20

Austin H A 3rd, Muenz L R, Joyce K M, Antonovych T T, Balow J E (1984). Diffuse proliferative lupus nephritis: identification of specific pathologic features affecting renal outcome. *Kidney Int.* 25:689

Austin H A III, Klippel J H, Balow J E, et al. Therapy of lupus nephritis: controlled trial of prednisone and cytotoxic drugs. (1986) *N Engl J Med* 314:614-619.

Baggiolini M (1998). Chemokines and leukocyte traffic. *Nature* 392:565

Baggiolini M, Dewald B, Moser B. (1994). Interleukin-8 and related chemotactic cytokines—CXC and CC chemokines. *Adv. Immunol* 55:97

Banba N, Nakamura T, Matsumura M, Kuroda H, Hattori Y, Kasai K (2000). Possible relationship of monocyte chemoattractant protein-1 with diabetic nephropathy. *Kidney Int.* 58:684

Banisor I, Leist T P, Kalman B (2005). Involvement of β-chemokines in the development of inflammatory demyelination. *J. Neuroinflammation* 2:7

Bazan J F, Bacon K B, Hardiman G, Wang W, Soo K, Rossi D, Greaves D R, Zlotnik A, Schall T J (1997). A new class of membrane-bound chemokine with a CX3C motif. *Nature* 385:640

Berkhout T A (1997). *J Biol Chem* 272:16404

Bohle A, Wehrmann M, Bogenschutz O, Batz C, Muller C A, Muller G A (1991). The pathogenesis of chronic renal failure in diabetic nephropathy. Investigation of 488 cases of diabetic glomerulosclerosis. *Pathol. Res. Pract.* 187:251

Boring L, Gosling J, Chensue S W, Kunkel S L, Farese RV Jr, Broxmeyer H E, Charo I F (1997). Impaired monocyte migration and reduced type 1 (Th1) cytokine responses in C-C chemokine receptor 2 knockout mice. *J. Clin. Invest.* 100:2552

Boring L, Gosling J, Cleary M, Charo I F (1998). Decreased lesion formation in CCR2−/− mice reveals a role for chemokines in the initiation of atherosclerosis. *Nature* 394:894

Boring L, Gosling J, Monteclaro F S, Lusis A J, Tsou C L, Charo I F (1996). Molecular cloning and functional expression of murine JE (monocyte chemoattractant protein 1) and murine macrophage inflammatory protein 1alpha receptors: evidence for two closely linked C-C chemokine receptors on chromosome 9. *J. Biol. Chem.* 271:7551

Bossink A W, Paemen L, Jansen P M, Hack C E, Thijs L G, Van Damme J (1995). Plasma levels of the chemokines monocyte chemotactic proteins-1 and -2 are elevated in human sepsis. *Blood* 86:3841

Boumpas D T, Austin H A III, Fessler B J, Balow J E, Klippel J H, Lockshin M D. Systemic lupus erythematosus: emerging concepts (1995). Part I. Renal, neuropsychiatric, cardiovascular, pulmonary, and hematologic disease. Ann Intern Med 122:940-950.

Boumpas D T, Austin H A III, Vaughn E M, et al. (1992) Controlled trial of pulse methylprednisolone versus two regimens of pulse cyclophosphamide in severe lupus nephritis. *Lancet* 340:741-745.

Bower G, Brown D M, Steffes M W, Vernier R L, Mauer S M (1980). Studies of the glomerular mesangium and the juxtaglomerular apparatus in the genetically diabetic mouse. *Lab. Intvest.* 43:333

Charo I F, Myers S J, Herman A, Franci C, Connolly A J, Coughlin S R (1994). Molecular cloning and functional expression of two monocyte chemoattractant protein 1 receptors reveals alternative splicing of the carboxyl-terminal tails. *Proc. Natl Acad. Sci. USA* 91:2752

Chow F, Ozols E, Nikolic-Paterson D J, Atkins R C, Tesch G H (2004). Macrophages in mouse type 2 diabetic nephropathy: Correlation with diabetic state and progressive renal injury. *Kidney Int.* 65:116

Chow F Y, Nikolic-Paterson D J, Ma F Y, Ozols E, Rollins B J, Tesch G H (2007). Monocyte chemoattractant protein-1-induced tissue inflammation is critical for the development of renal injury but not type 2 diabetes in obese db/db mice. *Diabetologica* 50:471

Chow F Y, Nikolic-Paterson D J, Ozols E, Atkins R C, Rollin B J, Tesch G H (2006). Monocyte chemoattractant protein-1 promotes the development of diabetic renal injury in streptozotocin-treated mice. *Kidney Int.* 69:73

Cockwell P, Howie A J, Adu D, Savage C O (1998). In situ analysis of C-C chemokine mRNA in human glomerulonephritis. *Kidney Int.* 54:827

Cohen C D, Gröne H J, Gröne E F, Nelson P J, Schlöndoroff D, Kretzler M (2002). Laser microdissection and gene expression analysis on formaldehyde-fixed archival tissue. *Kidney Int.* 61:125

Cummins L L Owens S R, Risen L M, Lesnik E A, Freier S M, McGee D, Guinosso C J, Cook P D. (1995). Characterization of fully 2'-modified oligoribonucleotide hetero- and homoduplex hybridization and nuclease sensitivity. *Nucleic Acids Res* 23:2019

Dalla Vestra M, Mussap M, Gallina P, Bruseghin M, Cernigoi A M, Saller A, Plebani M, Fioretto P (2005). Acute-phase markers of inflammation and glomerular structure in patients with type 2 diabetes. *J. Am. Soc. Nephrol.* 16 Suppl 1:S78

Dawson J, Miltz W, Mir A K, Wiessner C (2003). Targeting monocyte chemoattractant protein-1 signalling in disease. *Expert Opin. Ther. Targets* 7:35

De Bleecker J L, De Paepe B, Vanwalleghem I E, Schroder J M (2002). Differential expression of chemokines in inflammatory myopathies. *Neurology* 58:1779

De Boer W I, Sont J K, van Schadewijk A, Stolk J, van Krieken J H, Hiemstra P S. (2000) Monocyte chemoattractant protein 1, interleukin 8, and chronic airways inflammation in COPD (2000) *J Pathol.* 190(5):619-26

Dooley M A, Cosio F G, Nachman P H, et al. Mycophenolate mofetil therapy in lupus nephritis: clinical observations. (1999) *J Am Soc Nephrol* 10:833-839.

Drolet D W, Nelson J, Tucker C E, Zack P M, Nixon K, Bolin R, Judkins M B, Farmer J A, Wolf J L, Gill S C, Bendele R A (2000). Pharmacokinetics and safety of an anti-vascular endothelial growth factor aptamer (NX1838) following injection into the vitreous humor of rhesus monkeys. *Pharm. Res.* 17:1503

Eaton B E, Gold L, Hicke B J, Janjic N, Jucker F M, Sebosta D P, Tarasow T M, Willis M C, Zichi D A (1997). *Bioorg Med Chem* 5:1087

Eaton B E, Gold L, Zichi D A. (1995). Let's get specific: the relationship between specificity and affinity. *Chem Biol* 2:633

Economou E, Tousoulis D, Katinioti A, Stefanadis C, Trikas A, Pitsavos C, Tentolouris C, Toutouza MG, Toutouzas P (2001). Chemokines in patients with ischaemic heart disease and the effect of coronary angioplasty. *Int. J. Cardiol.* 80:55

Egashira K, Zhao Q, Kataoka C, Ohtani K, Usui M, Charo I F, Nishida K, Inoue S, Katoh M, Ichiki T, Takeshita A (2002). Importance of monocyte chemoattractant protein-1 pathway in neointimal hyperplasia after periarterial injury in mice and monkeys. *Circ. Res.* 90:1167

Fujinaka H, Yamamoto T, Takeya M, Feng L, Kawasaki K, Yaoita E, Kondo D, Wilson C B, Uchiyama M, Kihara I (1997). Suppression of anti-glomerular basement membrane nephritis by administration of anti-monocyte chemoattractant protein-1 antibody in WKY rats. *J. Am. Soc. Nephrol.* 8:1174

Furuichi K, Wada T, Iwata Y, Kitagawa K, Kobayashi K-I, Hashimoto H, Ishiwata Y, Tomosugi N, Mukaida N, Matsushima K, Egashira K, Yokoyama H (2003). Gene therapy expressing amino-terminal truncated monocyte chemoattractant protein-1 prevents renal ischemia-reperfusion injury. *J. Am. Soc. Nephrol.* 14:1066

Furuta T, Saito T, Ootaka T, Soma J, Obara K, Abe K, Yoshinaga K (1993). The role of macrophages in diabetic glomerulosclerosis. *Am. J. Kidney Dis.* 21:480

Galasso J M, Liu Y, Szaflarski J, Warren J S, Silverstein F S (2000). Monocyte chemoattractant protein-1 is a mediator of acute excitotoxic injury in neonatal rat brain. *Neuroscience* 101:737

Galkina E, Ley K (2006). Leukocyte recruitment and vascular injury in diabetic nephropathy. *J. Am. Soc. Nephrol.* 17:368-377

Gao J L, Kuhns D B, Tiffany H L, McDermott D, Li X, Francke U, Murphy P M (1993). Structure and functional expression of the human macrophage inflammatory protein 1 alpha/RANTES receptor. *J. Exp. Med.* 177:1421

Garcia-Zepeda E A, Combadiere C, Rothenberg M E, Sarafi M N, Lavigne F, Hamid Q, Murphy P M, Luster A D (1996). Human monocyte chemoattractant protein (MCP)-4 is a novel CC chemokine with activities on monocytes, eosinophils, and basophils induced in allergic and nonallergic inflammation that signals through the CC chemokine receptors (CCR)-2 and -3. *J. Immunol.* 157: 5613

Gaubitz M, Schorat A, Schotte H, Kern P, Domschke W. (1999) Mycophenolate mofetil for the treatment of systemic lupus erythematosus: an open pilot trial. *Lupus* 8:731-736.

Gerard C, Rollins, B J(2001). Chemokines and disease. Nat. Immunol. 2:108

Gong X, Gong W, Kuhns D B, Ben-Baruch A, Howard O M, Wang J M (1997). Monocyte chemotactic protein-2 (MCP-2) uses CCR1 and CCR2B as its functional receptors. *J. Biol. Chem.* 272:11682

Gonzalo J A, Lloyd C M, Wen D, Albar J P, Wells T N C, Proudfoot A, Martinez-A C, Dorf M, Bjerke T, Coyle A J, Gutierrez-Ramos J C (1998). The coordinated action of CC chemokines in the lung orchestrates allergic inflammation and airway hyperresponsiveness. *J. Exp. Med.* 188:157

Gordillo G M, Onat D, Stockinger M, Roy S, Atalay M, Beck F M, Sen C K (2004). A key angiogenic role of monocyte chemoattractant protein-1 in hemangioendothelioma proliferation. Am. J. Physiol. Cell Physiol. 287:C866

Gourley M F, Austin H A III, Scott D, et al. (1996) Methylprednisolone and cyclophosphamide, alone or in combination, in patients with lupus nephritis. *Ann Intern Med* 125: 549-557.

Green L S et al. (1995). *Chem Biol* 2:683

Handel T M, Domaille P J (1996). Heteronuclear (1H, 13C, 15N) NMR assignments and solution structure of the monocyte chemoattractant protein-1 (MCP-1) dimer. *Biochemistry* 35:6569

Harigai M, Hara M, Yoshimura T, Leonard E J, Inoue K, Kashiwazaki S (1993). Monocyte chemoattractant protein-1 (MCP-1) in inflammatory joint diseases and its involvement in the cytokine network of rheumatoid synovium. *Clin. Immunol. Immunopathol.* 69:83

Hasegawa H, Kohno M, Sasaki M, Inoue A, Ito M R, Terada M, Hieshima K, Maruyama H, Miyazaki J, Yoshie O, Nose M, Fujita S (2003). Antagonist of monocyte chemoattractant protein 1 ameliorates the initiation and progression of lupus nephritis and renal vasculitis in MRL/lpr mice. *Arthritis Rheum.* 48:2555

Hatano S, Strasser R (1975). Primary pulmonary hypertension. *Geneva: World Heath Organization.*

Heath H, Qin S, Rao P, Wu L, LaRosa G, Kassam N, Ponath P D, Mackay C R. (1997). Chemokine receptor usage by human eosinophils. The importance of CCR3 demonstrated using an antagonistic monoclonal antibody. *J Clin Invest* 99:178

Holdsworth S R, Kitching A R, Tipping P G (2000). Chemokines as therapeutic targets in renal disease. *Curr. Opin. Nephrol. Hypetens.* 9:505

Holgate S T, Bodey K S, Janezic A, Frew A J, Kaplan A P, Teran L M (1997). Release of RANTES, MIP-1α, and MCP-1 into asthmatic airways following endobronchial allergen challenge. *Am. J. Respir. Crit. Care Med.* 156: 1377

Hopkins N, McLoughlin P (2002) The structural basis of pulmonary hypertension in chronic lung disease: remodelling, rarefaction or angiogenesis? *J. Anal.* 201(4):335-48.

Hosaka S, Akahoshi T, Wada C, Kondo H. (1994). Expression of the chemokine superfamily in rheumatoid arthritis. *Clin Exp Immunol* 97:451

Huang D R, Wang J, Kivisakk P, Rollins B J, Ransohoff R M (2001). Absence of monocyte chemoattractant protein 1 in mice leads to decreased local macrophage recruitment and antigen-specific T helper cell type 1 immune response in experimental autoimmune encephalomyelitis. *J. Exp. Med.* 193:713

Hulkower K, Brosnan C F, Aquino D A, Cammer W, Kulshrestha S, Guida M P, Rapoport D A, Berman J W (1993). Expression of CSF-1, c-fins, and MCP-1 in the central nervous system of rats with experimental allergic encephalomyelitis. *J. Immunol.* 150:2525

Humbert M, Ying S, Corrigan C, Menz G, Barkans J, Pfister R, Meng Q, Van Damme J, Opdenakker G, Durham S R, Kay A B (1997). Bronchial mucosal expression of the genes encoding chemokines RANTES and MCP-3 in symptomatic atopic and nonatopic asthmatics: relationship to the eosinophil-active cytokines interleukin (IL)-5, granulocyte macrophage-colony-stimulating factor, and IL-3. *Am J Respir Cell Mol Biol* 16:1

Ihm C G, Park J K, Hong S P, Lee T W, Cho B S, Kim M J, Cha D R, Ha H (1998). A high glucose concentration stimulates the expression of monocyte chemotactic peptide 1 in human mesangial cells. *Nephron* 79:33

Ioannidis J P A, Boki K A, Katsorida E M, et al. (2000) Remission, relapse, and re-remission of proliferative lupus nephritis treated with cyclophosphamide. *Kidney Int* 57:258-264.

Itoh T, Nagaya N, Ishibashi-Ueda H, Kyotani S, Oya H, Sakamaki F, Kimura H, Nakanishi N (2006), Increased plasma monocyte chemoattractant protein-1 level in idiopathic pulmonary arterial hypertension, *Respirology.* 11(2):158-63.

Iyonaga K, Takeya M, Saita N, Sakamoto O, Yoshimura T, Ando M, Takahashi K (1994). Monocyte chemoattractant protein-1 in idiopathic pulmonary fibrosis and other interstitial lung diseases. *Hum. Pathol.* 25:455.

Johrer K, Zelle-Rieser C, Perathoner A, Moser P, Hager M, Ramoner R, Gander H, Holtl L, Bartsch G, Greil R, Thurnher M (2005). Up-regulation of functional chemokine receptor CCR3 in human renal cell carcinoma. *Clin Cancer Res* 11:2459

Jolicoeur C, Lemay A, Akoum A (2001). Comparative effect of danazol and a GnRH agonist on monocyte chemotactic protein-1 expression by endometriotic cells. *Am. J. Reprod. Immunol.* 45:86

Jose P J, Griffiths-Johnson D A, Collins P D, Walsh D T, Moqbel R, Totty N F, Truong O, Hsuan J J, Williams T J (1994). Eotaxin: a potent eosinophil chemoattractant cytokine detected in a guinea pig model of allergic airways inflammation. *J. Exp. Med.* 179:881

Kaburagi Y, Shimada Y, Nagaoka T, Hasegawa M, Takoehara K, Sato S (2001). Enhanced production of CC-chemokines (RANTES, MCP-1, MIP-1α, MIP-1β, and eotaxin) in patients with atopic dermatitis. *Arch. Dermatol. Res.* 293: 350

Karim M Y, Alba P, Cuadrado M J, et al. (2002) Mycophenolate mofetil for systemic lupus erythematosus refractory to other immunosuppressive agents. *Rheumatology* (*Oxford*) 41:876-882.

Kawasaki A M et al. (1993). *J Med Chem* 36:831

Kennedy K J, Strieter R M, Kunkel S L, Lukacs N W, Karpus W J (1998). Acute and relapsing experimental autoimmune encephalomyelitis are regulated by differential expression of the CC chemokines macrophage inflammatory protein-1α and monocyte chemotactic protein-1. *J. Neuroimmunol.* 91:98

Kim J S, Gautam S C, Chopp M, Zaloga C, Jones M L, Ward P A, Welch K M (1995). Expression of monocyte chemoattractant protein-1 and macrophage inflammatory protein-1 after focal cerebral ischemia in the rat. *J. Neuroimmunol.* 56:127

Kingdon E J, McLean A G, Psimenou E, et al. (2001) The safety and efficacy of MMF in lupus nephritis: a pilot study. *Lupus* 10:606-611.

Kitamoto S, Egashira K (2003). Anti-monocyte chemoattractant protein-1 gene therapy for cardiovascular diseases. *Expert Rev. Cardiovasc. Ther.* 1:393

Kleinhans M, Tun-Kyi A, Gilliet M, Kadin M E, Dummer R, Burg G, and Nestle F O (2003). Functional expression of the eotaxin receptor CCR3 in CD30+ cutaneous T-cell lymphoma. *Blood* 101:1487

Ko F W, Lau C Y, Leung T F, Wong G W, Lam C W, Hui D S (2006) Exhaled breath condensate levels of 8-isoprostane, growth related oncogene alpha and monocyte chemoattractant protein-1 in patients with chronic obstructive pulmonary disease. *Respir Med.* 100(4):630-8.

Koch A E, Kunkel S L, Harlow L A, Johnson B, Evanoff H L, Haines G K, Burdick M D, Pope R M, Strieter R M (1992). Enhanced production of monocyte chemoattractant protein-1 in rheumatoid arthritis. *J. Clin. Invest.* 90:772

Korbet S M, Lewis E J, Schwartz M M, Reichlin M, Evans J, Rohde R D. (2000) Factors predictive of outcome in severe lupus nephritis. *Am J Kidney Dis* 35:904-914.

Kouno J, Nagai H, Nagahata T, Onda M, Yamaguchi H., Adachi K, Takahashi H, Teramoto A, and Emi M (2004). Up-regulation of CC chemokine, CCL3L1, and receptors, CCR3, CCR5 in human glioblastoma that promotes cell growth. *J Neurooncol* 70:301

Kurihara T, Warr G, Loy J, Bravo R (1997). Defects in macrophage recruitment and host defense in mice lacking the CCR2 chemokine receptor. *J. Exp. Med.* 186:1757

Kusser W (2000). Chemically modified nucleic acid aptamers for in vitro selections: evolving evolution. *J Biotechnol* 74:27-38

Kuziel W A, Morgan S J, Dawson T C, Griffin S, Smithies O, Ley K, Maeda N (1997). Severe reduction in leukocyte adhesion and monocyte extravasation in mice deficient in CC chemokine receptor 2. *Proc. Natl Acad. Sci. USA* 94:12053

Lehman T J, Sherry D D, Wagner-Weiner L, et al. (1989) Intermittent intravenous cyclophosphamide therapy for lupus nephritis. *J Pediatr* 114:1055-1060.

Lesnik E A, Guinosso C J, Kawasaki A M, Sasmor H, Zounes M, Cummins L L, Ecker D J, Cook P D, Freier S M. (1993). Oligodeoxynucleotides containing 2'-O-modified adenosine: synthesis and effects on stability of DNA:RNA duplexes. *Biochemistry* 32:7832

Lloyd C M, Minto A W, Dorf M E, Proudfoot A, Wells T N C, Salant D J, Gutierrez-Ramos J C (1997). RANTES and monocyte chemoattractant protein-1 (MCP-1) play an important role in the inflammatory phase of crescentic nephritis, but only MCP-1 is involved in crescent formation and interstitial fibrosis. *J. Exp. Med.* 185:1371
Lu B B, Rutledge B J, Gu L, Fiorillo J, Lukacs N W, Kunkel S L, North R, Gerard C, Rollins B J (1998). Abnormalities in monocyte recruitment and cytokine expression in monocyte chemoattractant protein-1 deficient mice. *J. Exp. Med.* 187:601
Lubkowski J, Bujacz G, Boque L, Domaille P J, Handel T M, Wlodawer A (1997). The structure of MCP-1 in two crystal forms provides a rare example of variable quaternary interactions. *Nat Struct Biol* 4:64
Mack M, Cihak J, Simonis C, Luckow B, Proudfoot A E, Plachy J, Bruhl H, Frink M, Anders H J, Vielhauer V, Pfirstinger J, Stangassinger M, Schlöndorff D (2001). Expression and characterization of the chemokine receptors CCR2 and CCR5 in mice. *J. Immunol.* 166:4697
Martinelli R, Sabroe I, LaRosa G, Williams T J, Pease J E. The CC chemokine eotaxin (CCL11) is a partial agonist of CC chemokine receptor 2b. *J Biol Chem* 276:42957
Matsushima K, Morishita K, Yoshimura T, Lavu S, Kobayashi Y, Lew W, Appella E, Kung H F, Leonard E J, Oppenheim J J (1989). Molecular cloning of a human monocyte-derived neutrophil chemotactic factor (MDNCF) and the induction of MDNCF mRNA by interleukin 1 and tumor necrosis factor. *J. Exp. Med.* 167:1883
McGinnis S, Madden T L (2004). BLAST: at the core of a powerful and diverse set of sequence analysis tools. *Nucleic Acids Res.* 32(Web Server issue):W20-5.
Meyer T W (2003). Immunosuppression for diabetic glomerular disease? *Kidney Int.* 63:377
Miller L E et al. (1993). *J Physiol* 469:213
Miller M D, Krangel M S (1992). Biology and biochemistry of the chemokines: a family of chemotactic and inflammatory cytokines. *Crit. Rev. Immunol.* 12:17
Mok C C, Ying K Y, Tang S, et al. Predictors and outcome of renal flares after successful cyclophosphamide treatment for diffuse proliferative lupus glomerulonephritis. (2004) *Arthritis Rheum* 50:2559-2568.
Mora C, Navarro J F (2005). The role of inflammation as a pathogenic factor in the development of renal disease in diabetes. *Curr. Diab. Rep.* 5:399
Morii T, Fujita H, Narita T, Shimotomai T, Fujishima H, Yoshioka N, Imai H, Kakei M, Ito S (2003). Association of monocyte chemoattractant protein-1 with renal tubular damage in diabetic nephropathy. *J. Diabetes Complications* 17:11
Murphy P M, Baggiolini M, Charo I F, Hebert C A, Horuk R, Matsushima K, Miller L H, Oppenheim J J, Power C A (2000). International union of pharmacology. XXII. Nomenclature for chemokine receptors. *Pharmacol. Rev.* 52:145
Myers S J, Wong L M, Charo I F (1995). Signal transduction and ligand specificity of the human monocyte chemoattractant protein-1 receptor in transfected embryonic kidney cells. *J. Biol. Chem.* 270:5786
Nakamura H, Weiss S T, Israel E, Luster A D, Drazen J M, Lilly C M (1999). Eotaxin and impaired lung function in asthma. *Am J Respir Crit Care Med* 160:1952
Nakazawa T, Hisatomi T, Nakazawa C, Noda K, Maruyama K, She H, Matsubara A, Miyahara S, Nakao S, Yin Y, Benowitz L, Hafezi-Moghadam A, Miller J W (2007). Monocyte chemoattractant protein 1 mediated retinal detachment-induced photoreceptor apoptosis. *Proc Natl. Acad. Sci. USA* 104:2425
Navarro I F, Mora C, Maca M, Garca J (2003). Inflammatory parameters are independently associated with urinary albumin in type 2 diabetes mellitus. *Am. J. Kidney Dis.* 42:53
Needleman & Wunsch (1970), A general method applicable to the search for similarities in the amino acid sequence of two proteins. J Mol Biol. 48(3):443-53.
Nelken N A, Coughlin S R, Gordon D, Wilcox J N (1991). Monocyte chemoattractant protein-1 in human atheromatous plaques. *J. Clin. Invest.* 88:1121
Neote K, DiGregorio D, Mak J Y, Horuk R, Schall T J (1993). Molecular cloning, functional expression, and signaling characteristics of a C-C chemokine receptor. *Cell* 72:415
Ninichuk V, Gross O, Reichel C, Khandoga A, Pawar R D, Ciubar R, Segerer S, Belemezova E, Radomska E, Luckow B, de Lema G P, Murphy P M, Gao J L, Henger A, Kretzler M, Horuk R, Weber M, Krombach F, Schlondorff D, Anders H J (2005). Delayed chemokine receptor 1 blockade prolongs survival in collagen 4A3-deficient mice with Alport disease. *J. Am. Soc. Nephrol.* 16:977
Ogata H, Takeya M, Yoshimura T, Takagi K, Takahashi K (1997). The role of monocyte chemoattractant protein-1 (MCP-1) in the pathogenesis of collagen-induced arthritis in rats. J. Pathol. 182:106
Okuno T, Andoh A, Bamba S, Araki Y, Fujiyama Y, Fujiyama M, Bamba T (2002). Interleukin-1β and tumor necrosis factor-α induce chemokine and matrix metalloproteinase gene expression in human colonic subepithelial myofibroblasts. Scand. *J. Gastroenterol.* 37:317
Oppenheim J J, Zachariae C O, Mukaida N, Matsushima K (1991). Properties of the novel proinflammatory supergene "intercrine" cytokine family. *Annu. Rev. Immunol.* 9:617
Pawar R D, Patole P S, Zecher D, Segerer S, Kretzler M, Schlöndorff D, Anders H J (2006). Toll-like receptor-7 modulates immune complex glomerulonephritis. *J. Am. Soc. Nephrol.* 17:141
Pearson & Lipman (1988), Improved tools for biological sequence comparison. Proc. Nat'l. Acad. Sci. USA 85: 2444
Peinado V I, Pizarro S, Barberà J A. Pulmonary Vascular Involvement in COPD (2008) *Chest.* 134:808-814
Perez de Lema G, Maier H, Franz T J, Escribese M, Chilla m S, Segerer S, Camarasa N, Schmid H, Banas B, Kalaydjiev S, Busch D H, Pfeffer K, Mampaso F, Schlöndorff D, Luckow B (2005). Chemokine receptor CCR2 deficiency reduces renal disease and prolongs survival in MRL/lpr lupus-prone mice. *J. Am. Soc. Nephrol.* 16:3592
Perez de Lema G, Maier H, Nieto E, Vielhauer V, Luckow B, Mampaso F, Schlöndorff D (2001). Chemokine expression precedes inflammatory cell infiltration and chemokine receptor and cytokine expression during the initiation of murine lupus nephritis. *J. Am. Soc. Nephrol.* 12:1369
Ponath P D, Qin S, Post T W, Wang J, Wu L, Gerard N P, Newman W, Gerard C, Mackay C R (1996b). Molecular cloning and characterization of a human eotaxin receptor expressed selectively on eosinophils. *J. Exp. Med.* 183: 2437
Ponath P D, Qin S, Ringler D J, Clark-Lewis I, Wang J, Kassam N, Smith H, Shi X, Gonzalo J A, Newman W, Gutierrez-Ramos J C, Mackay C R (1996a). Cloning of the human eosinophil chemoattractant, eotaxin. Expression, receptor binding, and functional properties suggest a mechanism for the selective recruitment of eosinophils. *J. Clin. Invest.* 97:604
Power C A, Meyer A, Nemeth K, Bacon K B, Hoogewerf A J, Proudfoot A E, Wells T N (1995). Molecular cloning and functional expression of a novel CC chemokine receptor cDNA from a human basophilic cell line. *J. Biol. Chem.* 270:19495

Qi Z, Whitt I, Mehta A, Jin J, Zhao M, Harris R C, Fogo A B, Breyer M D (2004). Serial determination of glomerular filtration rate in conscious mice using FITC-inulin clearance. *Am. J. Physiol. Renal Physiol.* 286:F590

Qin S, LaRosa G, Campbell J J, Smith-Heath H, Kassam N, Shi X, Zeng L, Buthcher E C, Mackay C R (1996). Expression of monocyte chemoattractant protein-1 and interleukin-8 receptors on subsets of T cells: correlation with transendothelial chemotactic potential. *Eur. J. Immunol.* 26:640

Ransohoff R M, Hamilton T A, Tani M, Stoler M H, Shick H E, Major J A, Estes M L, Thomas D M, Tuohy V K. (1993). Astrocyte expression of mRNA encoding cytokines IP-10 and JE/MCP-1 in experimental autoimmune encephalomyelitis *FASEB J* 7:592

Raport C J, Gosling J, Schweickart V L, Gray P W, Charo I F (1996). Molecular cloning and functional characterization of a novel human CC chemokine receptor (CCR5) for RANTES, MIP-1β, and MIP-1α. *J. Biol. Chem.* 271:17161

Ritz E, Rychlik I, Locatelli F, Halimi S (1999). End-stage renal failure in type 2 diabetes: A medical catastrophe of worldwide dimensions. *Am. J. Kidney Dis.* 34:795-808

Rollins B J (1996). Monocyte chemoattractant protein 1: a potential regulator of monocyte recruitment in inflammatory disease. *Mol. Med. Today* 2:198

Rollins B J, Stier P, Ernst T, Wong G G (1989). The human homolog of the JE gene encodes a monocyte secretory protein. *Mol. Cell Biol.* 9:4687

Rovin B H, Rumancik M, Tan L, Dickerson J (1994). Glomerular expression of monocyte chemoattractant protein-1 in experimental and human glomerulonephritis. *Lab. Invest.* 71:536

Rubin L J (1997) Primary pulmonary hypertension. *N Engl J Med.* 336(2): 111-7

Ruffing N, Sullivan N, et al. (1998). CCR5 has an expanded ligand-binding repertoire and is the primary receptor used by MCP-2 on activated T cells. *Cell Immunol* 189:160

Salcedo R, Ponce M L, Young H A, Wasserman K, Ward J M, Keinman H K, Oppenheim J J, Murphy W J (2000). Human endothelial cells express CCR2 and respond to MCP-1: direct role of MCP-1 in angiogenesis and tumor progression. *Blood* 96:34

Samson M, Labbe O, Mollereau C, Vassart G, Parmentier M (1996). Molecular cloning and functional expression of a new human CC-chemokine receptor gene. *Biochemistry* 35:3362

Schall T J, Bacon K B (1994). Chemokines, leukocyte trafficking, and inflammation. *Curr. Opin. Immunol.* 6:865

Schneider A, Panzer U, Zahner G, Wenzel U, Wolf G, Thaiss F, Helmchen U, Stahl R A (1999). Monocyte chemoattractant protein-1 mediates collagen deposition in experimental glomerulonephritis by transforming growth factor-beta. *Kidney Int.* 56:135

Schwarting A, Paul K, Tschirner S, Menke J, Hansen T, Brenner W, Kelly V R, Relle M, Galle P R (2005). Interferon-beta: a therapeutic for autoimmune lupus in MRL-Faslpr mice. *J. Am. Soc. Nephrol.* 16:3264

Schwartz C J, Valente A J, Sprague E A (1993). A modern view of atherogenesis. *Am. J. Cardiol.* 71:9B Segerer S, Nelson P J, Schlöndorff D (2000). Chemokines, chemokine receptors, and renal disease: from basic science to pathophysiologic and therapeutic studies. *J. Am. Soc. Nephrol.* 11:152

Shimizu S, Nakashima H, Masutani K, Inoue Y, Miyake K, Akahoshi M, Tanaka Y, Egashira K, Hirakata H, Otsuka T, Harada M (2004). Anti-monocyte chemoattractant protein-1 gene therapy attenuates nephritis in MRL/lpr mice. *Rheumatology* (*Oxford*) 43:1121

Simonneau G, Galiè N, Rubin L J, et al (2004). Clinical classification of pulmonary hypertension". *J. Am. Coll. Cardiol.* 43 (12 Suppl S): 5S-12S.

Smith & Waterman (1981), *Adv. Appl. Math.* 2: 482

Springer T A (1995). Traffic signals on endothelium for lymphocyte recirculation and leukocyte emigration. *Annu. Rev. Physiol.* 57:827

Steinberg A D, Steinberg S C. Long-term preservation of renal function in patients with lupus nephritis receiving treatment that includes cyclophosphamide versus those treated with prednisone only. (1991) *Arthritis Rheum* 34:945-950.

Steinman L (2004). Immune therapy for autoimmune diseases. *Science* 305:212

Svensson M, Sundkvist G, Arnqvist H J, Bjork E, Blohme G, Bolinder J, Henricsson M, Nystrom L, Torffvit O, Waernbaum I, Ostman J, Eriksson J W (2003). Signs of nephropathy may occur early in young adults with diabetes despite modern diabetes management: Results from the nationwide population-based Diabetes Incidence Study in Sweden (DISS). *Diabetes Care* 26:2903

Takebayashi K, Matsumoto S, Aso Y, Inukai T (2006). Association between circulating monocyte chemoattractant protein-1 and urinary albumin excretion in nonobese Type 2 diabetic patients. *J. Diabetes Complications* 20:98

Takeya M, Yoshimura T, Leonard E J, Takahashi K (1993). Detection of monocyte chemoattractant protein-1 in human atherosclerotic lesions by an anti-monocyte chemoattractant protein-1 monoclonal antibody. *Hum. Pathol.* 24:534

Tang W W, Qi M, Warren J S (1996). Monocyte chemoattractant protein 1 mediates glomerular macrophage infiltration in anti-GBM Ab GN. *Kidney Int.* 50:665

Tashiro K, Koyanagi I, Saitoh A, Shimizu, A, Shike T, Ishiguro C, Koizumi M, Funabiki K, Horikoshi S, Shirato I, Tomino Y (2002). Urinary levels of monocyte chemoattractant protein-1 (MCP-1) and interleukin-8 (IL-8), and renal injuries in patients with type 2 diabetic nephropathy. *J. Clin. Lab. Anal.* 16:1

Tesch G H, Maifert S, Schwarting A, Rollins B J, Kelley V R (1999). Monocyte chemoattractant protein I-dependent leukocytic infiltrates are responsible for autoimmune disease in MRL-Fas(lpr) mice. *J. Exp. Med.* 190:1813

Torres F (2007) Systematic review of randomised, double-blind clinical trials of oral agents conducted in patients with pulmonary arterial hypertension. *Int J Clin Pract.* 61(10): 1756-65.

Traves S L, Culpitt S V, Russell R E, Barnes P J, Donnelly L E (2002) Increased levels of the chemokines GROalpha and MCP-1 in sputum samples from patients with COPD. Thorax. 57(7):590-5.

Tuaillon N, Shen de F, Berger R B, Lu B, Rollins B J, Chan C C (2002). MCP-1 expression in endotoxin-induced uveitis. *Invest. Ophthalmol. Vis. Sci.* 43:1493

Tuttle K R (2005). Linking metabolism and immunology: diabetic nephropathy is an inflammatory disease. *J. Am. Soc. Nephrol.* 16:1537

Uguccioni M, Mackay C R et al. (1997). High expression of the chemokine receptor CCR3 in human blood basophils. Role in activation by eotaxin, MCP-4, and other chemokines. *J Clin Invest* 100:1137

United States Renal Data System (2004). Annual data report: Incidence and prevalence 2004. *Am. J. Kidney Dis.* 45:S77

Utimura R, Fujihara C K, Mattar A L, Malheiros D M, Noronha I L, Zatz R (2003). Mycophenolate mofetil prevents the development of glomerular injury in experimental diabetes. *Kidney Int.* 63:209

Valeri A, Radhakrishnan J, Estes D, et al. (1994) Intravenous pulse cyclophosphamide treatment of severe lupus nephritis: a prospective five-year study. *Clin Nephrol* 42:71-78.

Van Riper G, Siciliano S, Fischer P A, Meurer R, Springer M S, Rosen H (1993). Characterization and species distribution of high affinity GTP-coupled receptors for human rantes and monocyte chemoattractant protein 1. *J. Exp. Med.* 177:851

Venkatesan N et al. (2003). *Curr Med Chem* 10:1973

Vestergaard C, Just H, Baumgartner Nielsen J, Thestrup-Pedersen K, Deleuran M (2004). Expression of CCR2 on monocytes and macrophages in chronically inflamed skin in atopic dermatitis and psoriasis. *Acta Derm. Venereol.* 84:353

Viedt C, Orth S R (2002). Monocyte chemoattractant protein-1 (MCP-1) in the kidney: does it more than simply attract monocytes? *Nephrol. Dial. Transplant.* 17:2043

Vielhauer V, Anders H J (2006). Blockade of chemokine-mediated tissue injury in lupus nephritis. *Endocr Metab Immune Disord Drug Targets.* 6(4):313-21.

Voelkel N F, Tuder R M. (1995) Cellular and molecular mechanisms in the pathogenesis of severe pulmonary hypertension (1995) *Eur Respir J.* 8(12):2129-38.

Wada T, Furuichi K, Segada-Takaeda C, Ahimizu M, Sakai N, Takeda S I, Takasawa K, Kida H, Kobayashi K I, Mukaida N, Ohmoto Y, Matsushima K, Yokoyama H (1999). MIP-1α and MCP-1 contribute to crescents and interstitial lesions in human crescentic glomerulonephritis. *Kidney Int.* 56:995

Wada T, Yokoyama H, Furuichi K, Kobayashi K I, Harada K, Naruto M, Su S B, Akiyama M, Mukaida N, Matsushima K (1996). Intervention of crescentic glomerulonephritis by antibodies to monocyte chemotactic and activating factor (MCAF/MCP-1). *FASEB J.* 10:1418

Wada T, Yokoyama H, Matsushima K, Kobayashi K I (2001). Chemokines in renal diseases. *Int. Immunopharmacol.* 1:637

Wang X, Yue T L, Barone F C, Feuerstein G Z (1995). Monocyte chemoattractant protein-1 messenger RNA expression in rat ischemic cortex. *Stroke* 26:661

Wenzel U, Schneider A, Valente A J, Abboud H E, Thaiss F, Helmchen U M, Stahl R A (1997). Monocyte chemoattractant protein-1 mediates monocyte/macrophage influx in anti-thymocyte antibody-induced glomerulonephritis. *Kidney Int.* 51:770

Yamagishi S, Inagaki Y, Okamoto T, Amano S, Koga K, Takeuchi M, Makita Z (2002). Advanced glycation end product-induced apoptosis and overexpression of vascular endothelial growth factor and monocyte chemoattractant protein-1 in human-cultured mesangial cells. *J. Biol. Chem.* 277:20309

Ying S, Meng Q, Zeibecoglou K, Robinson D S, Macfarlane A, Humbert M, Kay A B (1999). Eosinophil chemotactic chemokines (eotaxin, eotaxin-2, RANTES, monocyte chemoattractant protein-3 (MCP-3), and MCP-4), and C-C chemokine receptor 3 expression in bronchial biopsies from atopic and nonatopic (Intrinsic) asthmatics. *J Immunol* 163:6321

Ying S, Robinson D S, Meng Q, Rottman J, Kennedy R, Ringler D J, Mackay C R, Daugherty B L, Springer M S, Durham S R, Williams T J, Kay A B (1997). Enhanced expression of eotaxin and CCR3 mRNA and protein in atopic asthma. Association with airway hyperresponsiveness and predominant co-localization of eotaxin mRNA to bronchial epithelial and endothelial cells. Eur J Immunol 27:3507

Yla-Herttuala S, Lipton B A, Rosenfeld M E, Sarkioja T, Yoshimura T, Leonard E J, Witztum J L, Steinberg D (1991). Expression of monocyte chemoattractant protein 1 in macrophage-rich areas of human and rabbit atherosclerotic lesions. *Proc. Natl Acad. Sci. USA* 88:5252

Yoshimura T, Robinson E A, Tanaka S, Appella E, Leonard E J (1989). Purification and amino acid analysis of two human monocyte chemoattractants produced by phytohemagglutinin-stimulated human blood mononuclear leukocytes. *J. Immunol.* 142:1956

Yozai K, Shikata K, Sasaki M, Tone A, Ohga S, Usui H, Okada S, Wada J, Nagase R, Ogawa D, Shikata Y, Makino H (2005). Methotrexate prevents renal injury in experimental diabetic rats via anti-inflammatory actions. J. Am. Soc. Nephrol. 16:3326

Zimmet P, Alberti K G, Shaw J (2001). Global and societal implications of the diabetes epidemic. *Nature* 414:782

The features of the present invention disclosed in the specification, the claims and/or the drawings may both separately and in any combination thereof be material for realizing the invention in various forms thereof.

---

The invention claimed is:

1. A treatment composition comprising two active agents consisting of (1) an L nucleic acid comprising SEQ ID NO:37 or a homolog thereof with at least 85% homology thereto and (2) a cyclophosphamide.

2. The composition of claim 1, wherein SEQ ID NO:37 or homolog thereof binds monkey MCP-1, horse MCP-1, rabbit MCP-1, bovine MCP-1, canine MCP-1, porcine MCP-1 or human MCP-1.

3. The composition according to claim 1, wherein SEQ ID NO:37 or homoloq thereof binds a human MCP-1.

4. The composition according to claim 1, wherein SEQ ID NO:37 or homolog thereof binds the amino acid sequence according to SEQ ID NO:1.

5. The composition according to claim 1, wherein SEQ ID NO:37 or homolog thereof comprises a modification.

6. The composition according to claim 5, wherein the modification is selected from the group consisting of a HES moiety, a PEG moiety, a biodegradable modification and combinations thereof.

7. The composition according to claim 6, wherein the PEG moiety comprises a straight or branched PEG.

8. The composition according to claim 6, wherein the modification is a HES moiety.

9. The composition according to claim of 5, wherein the modification is coupled to SEQ ID NO:37 or homolog thereof via a linker.

10. The composition of claim 6, wherein said PEG moiety is at the 5' terminus of SEQ ID NO:37 or homolog thereof.

11. The composition of claim 6, wherein said PEG moiety is at the 3' terminus of SEQ ID NO:37 or homolog thereof.

12. The composition of claim 6, wherein said PEG moiety is from about 2 kD to about 200 kD.

13. The composition of claim 6, wherein said PEG moiety is from about 40 kD to about 120 kD.

14. The composition of claim 1, wherein said active agents are contained in a single vessel.

* * * * *

UNITED STATES PATENT AND TRADEMARK OFFICE

CERTIFICATE OF CORRECTION

PATENT NO. : 8,367,629 B2
APPLICATION NO. : 12/325180
DATED : February 5, 2013
INVENTOR(S) : Werner Purschke et al.

It is certified that error appears in the above-identified patent and that said Letters Patent is hereby corrected as shown below:

In the Claims

Claim 1, line 4, following, ‘cyclophosphamide’, please insert, -- or a mycophenolate mofetil --.

Signed and Sealed this
Twenty-second Day of October, 2013

Teresa Stanek Rea
*Deputy Director of the United States Patent and Trademark Office*

UNITED STATES PATENT AND TRADEMARK OFFICE

CERTIFICATE OF CORRECTION

PATENT NO. : 8,367,629 B2
APPLICATION NO. : 12/325180
DATED : February 5, 2013
INVENTOR(S) : Werner Purschke et al.

It is certified that error appears in the above-identified patent and that said Letters Patent is hereby corrected as shown below:

In the Claims

Column 227, line 12, Claim 1, following, 'cyclophosphamide', please insert, -- or a mycophenolate mofetil --.

This certificate supersedes the Certificate of Correction issued October 22, 2013.

Signed and Sealed this
Nineteenth Day of November, 2013

Teresa Stanek Rea
*Deputy Director of the United States Patent and Trademark Office*